(12) United States Patent
Arron et al.

(10) Patent No.: US 11,226,341 B2
(45) Date of Patent: Jan. 18, 2022

(54) METHOD OF TREATING ASTHMA USING AN IL-13 ANTIBODY

(71) Applicant: GENENTECH, INC., South San Francisco, CA (US)

(72) Inventors: Joseph R. Arron, San Mateo, CA (US); Richard W. Erickson, Castro Valley, CA (US); Michelle Freemer, Mill Valley, CA (US); Meredith Hazen, Belmont, CA (US); Guiquan Jia, Foster City, CA (US); John G. Matthews, San Francisco, CA (US); Wendy Putnam, Belmont, CA (US); Heleen Scheerens, Menlo Park, CA (US); Yanan Zheng, Redwood City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/992,115

(22) Filed: May 29, 2018

(65) Prior Publication Data

US 2019/0120854 A1  Apr. 25, 2019

Related U.S. Application Data

(62) Division of application No. 14/021,947, filed on Sep. 9, 2013, now Pat. No. 9,995,755, which is a division of application No. 13/328,830, filed on Dec. 16, 2011, now abandoned.

(60) Provisional application No. 61/557,295, filed on Nov. 8, 2011, provisional application No. 61/574,485, filed on Aug. 2, 2011, provisional application No. 61/484,650, filed on May 10, 2011, provisional application No. 61/465,425, filed on Mar. 18, 2011, provisional application No. 61/459,760, filed on Dec. 16, 2010.

(51) Int. Cl.
| | | |
|---|---|---|
| *A61K 39/395* | (2006.01) | |
| *G01N 33/68* | (2006.01) | |
| *C07K 16/28* | (2006.01) | |
| *C07K 16/24* | (2006.01) | |
| *C07K 16/18* | (2006.01) | |
| *A61K 31/522* | (2006.01) | |
| *A61K 31/573* | (2006.01) | |
| *A61K 45/06* | (2006.01) | |

(52) U.S. Cl.
CPC ....... *G01N 33/6884* (2013.01); *A61K 31/522* (2013.01); *A61K 31/573* (2013.01); *A61K 39/3955* (2013.01); *A61K 39/39566* (2013.01); *A61K 45/06* (2013.01); *C07K 16/18* (2013.01); *C07K 16/244* (2013.01); *C07K 16/28* (2013.01); *G01N 33/6887* (2013.01); *G01N 33/6893* (2013.01); *G01N 2333/475* (2013.01); *G01N 2800/122* (2013.01); *G01N 2800/52* (2013.01)

(58) Field of Classification Search
CPC ............. A61K 39/3955; A61K 39/395; G01N 2800/122; A61P 11/06
See application file for complete search history.

(56) References Cited

U.S. PATENT DOCUMENTS

| | | |
|---|---|---|
| 4,578,349 A | 3/1986 | Schaffel |
| 4,676,980 A | 6/1987 | Segal et al. |
| 4,737,456 A | 4/1988 | Weng et al. |
| 4,816,567 A | 3/1989 | Cabilly et al. |
| 4,818,709 A | 4/1989 | Primus et al. |
| 5,047,507 A | 9/1991 | Buchegger et al. |
| 5,122,599 A | 6/1992 | Barnett et al. |
| 5,208,020 A | 5/1993 | Chari et al. |
| 5,231,009 A | 7/1993 | Barnett et al. |
| 5,274,087 A | 12/1993 | Barnett et al. |
| 5,416,064 A | 5/1995 | Chari et al. |
| 5,500,362 A | 3/1996 | Robinson et al. |
| 5,571,710 A | 11/1996 | Barnett et al. |
| 5,571,894 A | 11/1996 | Wels et al. |
| 5,587,458 A | 12/1996 | King et al. |
| 5,596,072 A | 1/1997 | Culpepper et al. |
| 5,624,821 A | 4/1997 | Winter et al. |
| 5,635,483 A | 6/1997 | Pettit et al. |
| 5,648,237 A | 7/1997 | Carter |
| 5,648,260 A | 7/1997 | Winter et al. |
| 5,712,374 A | 1/1998 | Kuntsmann et al. |
| 5,714,586 A | 2/1998 | Kuntsmann et al. |
| 5,731,168 A | 3/1998 | Carter et al. |
| 5,739,116 A | 4/1998 | Hamann et al. |
| 5,750,373 A | 5/1998 | Garrard et al. |

(Continued)

FOREIGN PATENT DOCUMENTS

| | | |
|---|---|---|
| EP | 0346710 | 9/1991 |
| EP | 0263933 | 10/1993 |

(Continued)

OTHER PUBLICATIONS

Prenner B.M. Role of long-acting beta2-adrenergic agonists in asthma management based on updated asthma guidelines. Curr Opin Pulm Med. Jan. 2008;14(1):57-63.*

(Continued)

*Primary Examiner* — Dong Jiang
(74) *Attorney, Agent, or Firm* — McNeill Baur PLLC

(57) ABSTRACT

Methods of diagnosing and treating disorders related to TH2 inhibition, including but not limited to asthma, are provided. Also provided are methods of selecting or identifying patients for treatment with certain therapeutic agents that are TH2 pathway inhibitors.

27 Claims, 25 Drawing Sheets

Specification includes a Sequence Listing.

(56) References Cited

U.S. PATENT DOCUMENTS

| | | |
|---|---|---|
| 5,756,664 A | 5/1998 | Amann et al. |
| 5,767,285 A | 6/1998 | Hamann et al. |
| 5,770,429 A | 6/1998 | Lonberg et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,789,199 A | 8/1998 | Joly et al. |
| 5,821,377 A | 10/1998 | Buysch et al. |
| 5,840,523 A | 11/1998 | Simmons et al. |
| 5,843,761 A | 12/1998 | Barnett et al. |
| 5,869,046 A | 2/1999 | Presta et al. |
| 5,872,235 A | 2/1999 | Chen et al. |
| 5,877,296 A | 3/1999 | Hamann et al. |
| 5,959,177 A | 9/1999 | Hein et al. |
| 6,013,772 A | 1/2000 | Barnett et al. |
| 6,022,958 A | 2/2000 | Barnett et al. |
| 6,040,498 A | 3/2000 | Stomp et al. |
| 6,075,181 A | 6/2000 | Kucherlapati et al. |
| 6,150,584 A | 11/2000 | Kucherlapati et al. |
| 6,171,586 B1 | 1/2001 | Lam et al. |
| 6,194,551 B1 | 2/2001 | Idusogie et al. |
| 6,248,516 B1 | 6/2001 | Winter et al. |
| 6,267,958 B1 | 7/2001 | Andya et al. |
| 6,268,482 B1 | 7/2001 | Cerretti |
| 6,342,581 B1 | 1/2002 | Barnett et al. |
| 6,342,583 B1 | 1/2002 | Barnett et al. |
| 6,417,429 B1 | 7/2002 | Hein et al. |
| 6,420,548 B1 | 7/2002 | Vezina et al. |
| 6,468,528 B1 | 10/2002 | Mak et al. |
| 6,518,061 B1 | 2/2003 | Puri et al. |
| 6,518,063 B1 | 2/2003 | Ducy et al. |
| 6,602,684 B1 | 8/2003 | Umana et al. |
| 6,630,579 B2 | 10/2003 | Chari et al. |
| 6,737,056 B1 | 5/2004 | Presta |
| 6,911,530 B1 | 6/2005 | Willson et al. |
| 6,946,292 B2 | 9/2005 | Kanda et al. |
| 6,982,321 B2 | 1/2006 | Winter |
| 7,026,139 B2 | 4/2006 | Yang |
| 7,041,870 B2 | 5/2006 | Tomizuka et al. |
| 7,064,191 B2 | 6/2006 | Shinkawa et al. |
| 7,087,409 B2 | 8/2006 | Barbas et al. |
| 7,087,727 B2 | 8/2006 | Chen et al. |
| 7,125,978 B1 | 10/2006 | Vezina et al. |
| 7,189,826 B2 | 3/2007 | Rodman |
| 7,312,024 B2 | 12/2007 | Mak et al. |
| 7,332,581 B2 | 2/2008 | Presta |
| 7,361,740 B2 | 4/2008 | Hinton et al. |
| 7,371,826 B2 | 5/2008 | Presta |
| 7,390,882 B2 | 6/2008 | Cairns et al. |
| 7,498,298 B2 | 3/2009 | Doronina et al. |
| 7,501,121 B2 | 3/2009 | Tchistiakova et al. |
| 7,521,541 B2 | 4/2009 | Eigenbrot et al. |
| 7,527,791 B2 | 5/2009 | Adams et al. |
| 7,585,500 B2 | 9/2009 | Foltz et al. |
| 7,585,953 B2 | 9/2009 | Chen et al. |
| 7,601,505 B2 | 10/2009 | Monahan et al. |
| 7,615,213 B2 | 11/2009 | Kasaian et al. |
| 7,674,459 B2 | 3/2010 | Fung et al. |
| 7,676,337 B2 | 3/2010 | Akao et al. |
| 7,691,568 B2 | 4/2010 | Niwa et al. |
| 7,749,504 B2 | 7/2010 | Cairns et al. |
| 7,749,753 B2 | 7/2010 | Kanda et al. |
| 7,785,903 B2 | 8/2010 | Bond |
| 7,803,915 B2 | 9/2010 | Cairns et al. |
| 7,807,788 B2 | 10/2010 | Ashman et al. |
| 7,816,511 B2 | 10/2010 | Kawashima et al. |
| 7,871,607 B2 | 1/2011 | Bookbinder et al. |
| 7,985,840 B2 | 7/2011 | Fuh et al. |
| 8,017,119 B2 | 9/2011 | Taniyama et al. |
| 8,067,199 B2 | 11/2011 | Fung et al. |
| 8,088,618 B2 | 1/2012 | Fung et al. |
| 8,318,160 B2 | 11/2012 | Fung et al. |
| 8,372,957 B2 | 2/2013 | Taniyama |
| 8,394,379 B2 | 3/2013 | Imboden et al. |
| 8,420,310 B2 | 4/2013 | Lzuhara |
| 8,679,490 B2 | 3/2014 | Dennis et al. |
| 9,347,954 B2 | 5/2016 | Lzuhara |
| 2003/0152956 A1 | 8/2003 | Ohtani et al. |
| 2003/0157108 A1 | 8/2003 | Presta |
| 2004/0002112 A1 | 1/2004 | Mann et al. |
| 2004/0093621 A1 | 5/2004 | Shitara et al. |
| 2004/0110704 A1 | 6/2004 | Yamane et al. |
| 2004/0132140 A1 | 7/2004 | Satoh et al. |
| 2005/0070514 A1 | 3/2005 | Rapeport |
| 2005/0079574 A1 | 4/2005 | Bond |
| 2005/0107595 A1 | 5/2005 | Cairns et al. |
| 2005/0112129 A1 | 5/2005 | Phillips |
| 2005/0123546 A1 | 6/2005 | Umana et al. |
| 2005/0208496 A1 | 9/2005 | Ohtani et al. |
| 2006/0025576 A1 | 2/2006 | Miller et al. |
| 2006/0073133 A1 | 4/2006 | Kikly et al. |
| 2006/0104968 A1 | 5/2006 | Bookbinder et al. |
| 2006/0140948 A1* | 6/2006 | Foltz .................. A61P 13/12 424/145.1 |
| 2006/0154278 A1 | 7/2006 | Brody et al. |
| 2006/0228763 A1 | 10/2006 | Chen et al. |
| 2007/0048326 A1 | 3/2007 | Cairns et al. |
| 2007/0061900 A1 | 3/2007 | Murphy et al. |
| 2007/0117126 A1 | 5/2007 | Sidhu et al. |
| 2007/0237764 A1 | 10/2007 | Birtalan et al. |
| 2007/0275925 A1 | 11/2007 | Woodruff et al. |
| 2007/0292936 A1 | 12/2007 | Barthelemy et al. |
| 2008/0069820 A1 | 3/2008 | Fuh et al. |
| 2009/0023208 A1 | 1/2009 | Thomson et al. |
| 2009/0028793 A1 | 1/2009 | Neri et al. |
| 2009/0035314 A1 | 2/2009 | Kim et al. |
| 2009/0047277 A1 | 2/2009 | Reed et al. |
| 2009/0068195 A1 | 3/2009 | Vugmeyster |
| 2009/0214523 A1 | 8/2009 | Fung et al. |
| 2010/0098692 A1 | 4/2010 | Theuer et al. |
| 2010/0111965 A1 | 5/2010 | Johnson et al. |
| 2011/0123530 A1 | 5/2011 | Arron et al. |
| 2012/0156194 A1 | 6/2012 | Arron et al. |
| 2012/0156203 A1 | 6/2012 | Fung et al. |
| 2012/0164144 A1 | 6/2012 | Fung et al. |
| 2012/0214971 A1 | 8/2012 | Fung et al. |
| 2012/0219977 A1 | 8/2012 | Garnero |
| 2014/0044645 A1 | 2/2014 | Arron et al. |
| 2014/0044702 A1 | 2/2014 | Arron et al. |

FOREIGN PATENT DOCUMENTS

| | | |
|---|---|---|
| EP | 0404097 | 9/1996 |
| EP | 0425235 | 9/1996 |
| EP | 0562508 | 6/1998 |
| EP | 1270595 A1 | 3/2001 |
| EP | 1327681 A1 | 10/2001 |
| EP | 1347051 A1 | 9/2003 |
| EP | 1394274 A2 | 3/2004 |
| EP | 1646656 A2 | 7/2004 |
| EP | 1442995 | 8/2004 |
| EP | 1978034 A1 | 10/2008 |
| EP | 2000545 | 12/2008 |
| JP | 2007505314 A | 3/2007 |
| JP | 2010096748 A | 4/2010 |
| WO | WO 1993001161 A1 | 1/1993 |
| WO | WO 1993008829 A1 | 5/1993 |
| WO | WO 1993016185 A2 | 8/1993 |
| WO | WO 1993016185 A3 | 8/1993 |
| WO | WO 1994004680 | 3/1994 |
| WO | WO 1994029351 A2 | 12/1994 |
| WO | WO 1994029351 A3 | 12/1994 |
| WO | WO 1997030087 A1 | 8/1997 |
| WO | WO 1998058964 A1 | 12/1998 |
| WO | WO 1999022764 A1 | 5/1999 |
| WO | WO 1999051642 A1 | 10/1999 |
| WO | WO 2000061739 A1 | 10/2000 |
| WO | WO 2001029246 A1 | 4/2001 |
| WO | WO 200220055 A1 | 3/2002 |
| WO | WO 200231140 A1 | 4/2002 |
| WO | WO 2002052006 A1 | 4/2002 |
| WO | WO 2002055100 | 7/2002 |
| WO | WO 2002055200 A1 | 7/2002 |

(56) References Cited

FOREIGN PATENT DOCUMENTS

| WO | WO 2003000113 A2 | 1/2003 |
| --- | --- | --- |
| WO | WO 2003011878 A2 | 2/2003 |
| WO | WO 2003011878 A3 | 2/2003 |
| WO | WO 2003016471 A2 | 2/2003 |
| WO | WO 2003016471 A3 | 2/2003 |
| WO | WO 2003018635 A1 | 3/2003 |
| WO | WO 2003021261 A2 | 3/2003 |
| WO | WO 2003021261 A3 | 3/2003 |
| WO | WO 2003086451 | 4/2003 |
| WO | WO 2003035847 A2 | 5/2003 |
| WO | WO 2003072827 A1 | 9/2003 |
| WO | WO 2003084570 A1 | 10/2003 |
| WO | WO 2003085107 A1 | 10/2003 |
| WO | WO 2003085119 A1 | 10/2003 |
| WO | WO 2003086458 A1 | 10/2003 |
| WO | WO 2004006495 A1 | 1/2004 |
| WO | WO 2004056312 A2 | 7/2004 |
| WO | WO 2004056312 A3 | 7/2004 |
| WO | WO 2004106495 A2 | 12/2004 |
| WO | WO 2004106495 A3 | 12/2004 |
| WO | WO 2004112829 A2 | 12/2004 |
| WO | WO 2004112829 A3 | 12/2004 |
| WO | WO 2005007699 A2 | 1/2005 |
| WO | WO 2005007699 A3 | 1/2005 |
| WO | WO 2005007699 A8 | 1/2005 |
| WO | WO 2005019471 A2 | 3/2005 |
| WO | WO 2005019471 A3 | 3/2005 |
| WO | WO 2005025417 A1 | 3/2005 |
| WO | WO 2005035586 A1 | 4/2005 |
| WO | WO 2005035778 A1 | 4/2005 |
| WO | WO 2005053742 A1 | 6/2005 |
| WO | WO 200562972 A2 | 7/2005 |
| WO | WO 200562972 A3 | 7/2005 |
| WO | WO 2005062967 A2 | 7/2005 |
| WO | WO 2005100402 A1 | 10/2005 |
| WO | WO 2006003407 A2 | 1/2006 |
| WO | WO 2006003407 A3 | 1/2006 |
| WO | WO 2006029879 A2 | 3/2006 |
| WO | WO 2006029879 A3 | 3/2006 |
| WO | WO 2006044908 A2 | 4/2006 |
| WO | WO 2006044908 A3 | 4/2006 |
| WO | WO 2006085938 A2 | 7/2006 |
| WO | WO 2006085938 A3 | 7/2006 |
| WO | WO 2007036745 A2 | 4/2007 |
| WO | WO 2007036745 A3 | 4/2007 |
| WO | WO 2007045477 A2 | 4/2007 |
| WO | WO 2007045477 A3 | 4/2007 |
| WO | WO 2007045477 A8 | 4/2007 |
| WO | WO 2007077934 A1 | 7/2007 |
| WO | WO 2007080174 A2 | 7/2007 |
| WO | WO 2007080174 A3 | 7/2007 |
| WO | WO 2007082068 A2 | 7/2007 |
| WO | WO 2007082068 A3 | 7/2007 |
| WO | WO 2007096142 A2 | 8/2007 |
| WO | WO 2007096142 A3 | 8/2007 |
| WO | WO 2008016356 A2 | 2/2008 |
| WO | WO 2008016356 A3 | 2/2008 |
| WO | WO 2008077546 A1 | 7/2008 |
| WO | WO 2008086395 A2 | 7/2008 |
| WO | WO 2008086395 A3 | 7/2008 |
| WO | WO 2008116149 A2 | 9/2008 |
| WO | WO 2008116149 A3 | 9/2008 |
| WO | WO 2008127271 A2 | 10/2008 |
| WO | WO 2008127271 A3 | 10/2008 |
| WO | WO 2008134724 A2 | 11/2008 |
| WO | WO 2008134724 A3 | 11/2008 |
| WO | WO 2008140455 A1 | 11/2008 |
| WO | WO 2009009775 A1 | 1/2009 |
| WO | WO 2009089004 A1 | 7/2009 |
| WO | WO 2009124090 A1 | 10/2009 |
| WO | WO 2009001940 A1 | 12/2009 |
| WO | WO 2010007701 A1 | 1/2010 |
| WO | WO 2010073119 A1 | 7/2010 |
| WO | WO 2013035799 A1 | 3/2013 |

OTHER PUBLICATIONS

Wang et al. Fixed dosing versus body size-based dosing of monoclonal antibodies in adult clinical trials. J Clin Pharmacol. Sep. 2009;49(9):1012-24.*
Dimov et al., 2010, "Immunomodulators for asthma," Allergy Asthma Immunol Res., 2(4):228-234.
"A Study of Lebrikizumab (MILR1444A) In Adult Patients with Asthma Who Are Inadequately Controlled on Inhaled Corticosteroids (MILLY)," at http://clinicaltrials.gov/archive/NCT00930163/2010_06_08 [Accessed May 20, 2014].
"Lebrikizumab," WHO Drug Information 23(2): 154-155 (2009).
"Mepolizumab: 240563, anti-IL5 monoclonal antibody—GlaxoSmithKline, anti-interleukin-5 monoclonal antibody—GlaxoSmithKline SB 240563," Drugs R D, 9(2):125-130 (2008).
"Monoclonal Anti-Human IL 13 Antibody," R&D Systems, Inc. Catalog [on-line], Oct. 2002 [retrieved on Oct. 14, 2002], Retrieved from the Internet:< URL: http://www.rndsystems.com.asp.search. asp?ucategory=3&factors=IL%2D13>.
Abbas et al., Cellular and Molecular Immunology, Philadelphia, Pa. W.B. Saunders Co., pp. 54 (1991).
Adamko et al., "The rise of the phoenix: The expanding role of the eosinophil in health and disease" Allergy 60:13-22 (2005).
Almagro et al., "Humanization of antibodies," Frontiers In Bioscience 13:1619-1633 (2008).
Anderson, G-P, "Endotyping asthma: new insights into key pathogenic mechanisms in a complex, heterogeneous disease" Lancet 372:1107-1119 (2008).
Arguelles et al., "Inflammatory bronchial polyps associated with asthma" Arch Intern Med 143(3):570-571 (1983).
Arron, "Challenges in Biomarker Development," presented at Exploratory Clinical Development Worrld Americas Conference, Philadelphia, Pennsylvania, USA. (2008).
Arron et al., "Peripheral biomarkers of an IL-13 induced bronchial epithelial gene signature in asthma," J Allergy Clin Immunol (Abstract), S74:271 (2009).
Assarian et al., "Inflammatory fibroid polyp of the ileum," Hum Pathol 16(3):311-312 (1985).
Atanes et al., "Idiopathic eosinophilic synovitis—Case report and review of the literature," Scand J Rheumatol 25(3):183-185 (1996).
Baca et al., "Antibody humanization using monovalent phage display," J Biol Chem 272(16):10678-10684 (1997).
Bachert et al., "Total and specific IgE in nasal polyps is related to local eosinophilic inflammation," J Allergy Clin Immunol 107:607-614 (2001).
Ballesta et al., "Carcinoembryonic antigen in staging and follow-up of patients with solid tumors," Tumor Biol 16:32-41 (1995).
Baril et al., "Periostin promotes invasiveness and resistance of pancreatic cancer cells to hypoxia-induced cell death: role of the $\beta_4$ integrin and the PI3κ pathway," Oncogene 26:2082-2094 (2007).
Barnes, P-J., "The cytokine network in asthma and chronic obstructive pulmonary disease," J Clin Invest 118(11):3546-3556 (2008).
Bateman et al., "Can guideline-defined asthma control be achieved," Am J Respir Crit Care Med 170:836-844 (2004).
Beauchemin et al., "Isolation and characterization of full-length functional cDNA clones for human carcinoembryonic antigen," Mol Cell Biol 7(9):3221-3230 (1987).
Beavil et al., "Bent domain structure of recombinant human IgE-Fc in solution by X-ray and neutron scattering in conjunction with an automated curve fitting procedure," Biochem 34:14449-14461 (1995).
Ben et al., "Circulating levels of periostin may help identify patients with more aggressive colorectal cancer," Int J Oncol 34:821-828 (2009).
Benchimol et al., "Carcinoembryonic antigen, a human tumor marker, functions as an intercellular adhesion molecule," Cell 57:327-334 (1989).
Berry et al., "Evidence of a role of tumor necrosis factor α in refractory asthma," N Engl J Med 354:697-708 (2006).
Berry et al., "Pathological features and inhaled corticosteroid response of eosinophilic and non-eosinophilic asthma," Thorax 62:1043-1049 (2007).

(56) References Cited

OTHER PUBLICATIONS

Berry et al., "Sputum and bronchial submucosal IL-13 expression in asthma and eosinophilic bronchitiss," J Allergy Clin Inmmunol 114:1106-1109 (2004).
Blanchard et al., "Inhibition of human interleukin-13-induced respiratory and oesophageal inflammation by anti-human-interleukin-13 antibody (CAT-354)," Clin Exp Allergy, 35(8):1096-1103 (2005).
Blanchard et al., "IL-13 involvement in eosinophilic esophagitis: transcriptome analysis and reversibility with glucocorticoids," J Allergy Clin Immunol 120:1292-1300 (2007).
Blanchard et al., "Periostin facilitates eosinophil tissue infiltration in allergic lung and esophageal responses," Mucosal Immunol 1(4):289-296 (2008).
Blease et al., "Therapeutic effect of IL-13 immunoneutralization during chronic experimental fungal asthma," J. Immunol, 165:5219-5224 (2001).
Boerner et al., "Production of antigen-specific human monoclonal antibodies from in vitro-primed human splenocytes," J Immunol 147(1):86-95 (1991).
Bost et al., "In vivo treatment with anti-interleukin-13 antibodies significantly reduces the humoral immune response against an oral immunogen in mice," Immunology, vol. 87(4):633-641 (1996).
Bouros et al., "Histopathologic subsets of fibrosing alveolitis in patients with systemic sclerosis and their relationship to outcome," Am J Respir Crit Care Med 165:1581-1586 (2002).
Boushey et al., "Daily versus as-needed corticosteroids for mild persistent asthma," N Engl J Med, 352(15):1519-1528 (2005).
Bousquet et al., "Uniform definition of asthma severity, control, and exacerbations: Document presented for the World Health Organization Consultation on Severe Asthma," J Allergy Clin Immunol 126:926-938 (2010).
Brennan et al., "Preparation of bispecific antibodies by chemical recombination of monoclonal immunoglobulin G $_1$ fragments," Science 229(4708):81-83 (1985).
Brightling et al., "Comparison of airway immunopathology of eosinophilic bronchitis and asthma," Thorax 58:528-532 (2003).
Brodeur et al. Monoclonal Antibody Production Techniques and Applications Lawrence B Schook, New York:Marcel Dekker, Inc., 55-63 (1987).
Brueggmann et al., "Comparison of the effector functions of human immunoglobulins using a matched set of chimeric antibodies," J. Exp. Med 166:1351-1361 (1987).
Caldas et al., "Humanization of the anti-CD18 antibody 6-7: an unexpected effect of a framework residue in binding to antigen," Mol Immunol, 39(15), 941-952 (2003).
Calderon et al., "T-cell cytokine profiles are altered in childhood asthma exacerbation," Respirology 14:264-269 (2009).
Campbell et al., "Allergic humans are hypo-responsive to CXCR3 chemokines in a Th1 immunity-promoting loop," FASEB Journal, 18(2):329-331 (2003).
Carter et al., "Humanization of an Anti-p185 $^{HER2}$ Antibody For Human Cancer Therapy," Proc Natl Acad Sci USA, 89(10):4285-4289 (1992).
Casset et al., "A peptide mimetic of an anti-CD4 monoclonal antibody by rational design," Biochem Biophys res—Commun 307(1), 198-205 (2003).
Chanez et al., "Severe asthma in adults: What are the important questions," J Allergy Clin Immunol 119(6):1337-1348 (2007).
Chang, "The pharmacological basis of anti-IgE therapy," Nat Biotechnol 18:157-162 (2000).
Chari et al., "Immunoconjugates containing novel maytansinoids: Promising anticancer drugs," Cancer Res 52:127-131 (1992).
Charlton, K-A-, "Expression and isolation of recombinant antibody fragments in E-coli," Method Molec Biol 248:245-254 (2003).
Chen et al., "Eosinophilic vasculitis in connective tissue disease," J Am Acad Dermatol, 35(2 Pt 1), 173-182 (1996).
Chen et al., "Selection and analysis of an optimized anti-VEGF antibody: Crystal structure of an affinity-matured Fab in complex with antigen," J Mol Biol 293:865-881 (1999).

Cheng et al., "Anti-interleukin-9 antibody treatment inhibits airway inflammation and hyperreactivity in mouse asthma model," Am J Respir Crit Care Med 166:409-416 (2002).
Chibana et al., "IL-13 indued increases in nitrite levels are primarily driven by incrases in inducible nitric oxide synthase as compared with effects on arginases in human primary bronchial epithelial cells," Clin Exp Allergy 38:936-946 (2008).
Chien et al., "Significant structural and functional change of an antigen-binding site by a distant amino acid substitution: proposal of a structural mechanism," Proc Natl Acad Sci, 86(14), 5532-5536 (1989).
Chowdhury, "Engineering hot spots for affinity enhancement of antibodies," Methods Molec Biol 207:179-196 (2008).
Choy et al., "Gene expression patterns of Th2 inflammation and intercellular communication in asthmatic airways," J Immunol 186:1861-1869 (2011).
Chu et al., "Expression and activation of 15-lipoxygenase pathway in severe asthma: relationship to eosinophilic phenotype and collagen deposition," Clin Exp Allergy 32:1558-1565 (2002).
Chupp et al., "A Chitinase-like protein in the lung and circulation of patients with severe asthma," New Engl J Med 357:2016-2027 (Nov. 15, 2007).
Cimerman et al., "Serum cystatin C, a potent inhibitor of cysteine proteinases, is elevated in athmatic patients," Clin Chim Acta 300:83-95 (2000).
Clackson et al., "Making antibody fragments using phage display libraries," Nature, 352(6336), 624-628 (1991).
Clynes et al., "Fc receptors are required in passive and active immunity to melanoma," P Natl Acad Sci USA, 95(2):652-656 (1998).
Corren et al., "Lebrikizumab Treatment in Adults with Asthma," N Engl J Med, 365:1088-98 (2011).
Corren et al., "A randomized, controlled, phase 2 study of AMG 317, an IL-4Rα antagonist, in patients with asthma," Am J Resp Crit Care Med, 181(8):788-96 (2010).
Coutu et al., "Periostin, a member of a novel family of vitamin K-dependent proteins, is expressed by mesenchymal stromal cells," J Biol Chem 283(26):17991-18001 (2008).
Cowan et al., "Effects of steroid therapy on inflammatory cell subtypes in asthma," Thorax, 65(5):384-390 (2010).
Cragg et al., "Antibody specificity controls in vivo effector mechanisms of anti-CD20 reagents," Blood 103(7):2738-2743 (2004).
Cragg et al., "Complement-mediated lysis by anti-CD20 mAb correlates with segregation into lipid rafts," Blood 101(3):1045-1052 (2003).
Cunningham et al., "High-resolution epitope mapping of hGH-receptor interactions by alanine-scanning mutagenesis," Science 244:1081-1085 (Jun. 2, 1989).
Dall'Acqua et al., "Antibody humanization by framework shuffling," Methods, 36(1):43-60 (2005).
De Filippis et al., "Cannabinomimetic control of mast cell mediator release: new perspective in chronic inflammation," J Neuroendocrinology 20(Suppl 1):20-25 (2008).
De Pascalis et al., "Grafting of "abbreviated complementarity-determining regions containing specificity-determining residues essential for ligand contact to engineer a less immunogenic humanized monoclonal antibody," J Immunol, 169(6), 3076-3084 (2002).
Deschryver-Kecskemeti et al., "Perineural and intraneural inflammatory infiltrates in the intestines of patients with systemic connective-tissue disease," Arch Pathol Lab Med 113(4):394-398 (1989).
Dolganov et al., "A novel method of gene transcript profiling in airway biopsy homogenates reveals increased expression of a Na+—K+—Cl⁻ cotransporter (NKCC1) in asthmatic subjects," Genome Res 11:1473-1483 (2001).
Douwes et al., "Non-eosinophilic asthma: importance and possible mechanisms," Thorax, 57:643-648 (2002).
drugs.com. Azmacort [online] [accessed May 20, 2014]. http://web.archive.org/web/20100508071843/http://www.drugs.com/azmacort.html.
D'Silva et al., "Changing pattern of sputum cell counts during successive exacerbations of airway disease," Respir Med, 101:2217-2220 (2007).

(56) References Cited

OTHER PUBLICATIONS

Dubowchik et al., "Doxorubicin immunoconjugates containing bivalent, lysosomally-cleavable dipeptide linkages," Bioorg Med Chem Lett, 12:1529-1532 (2002).
Duncan et al., "The binding site for Clq on IgG," Nature, 322:738-740 (1988).
Dweik et al., "Use of exhaled nitric oxide measurement to identify a reactive, at risk phenotype among patients with asthma," Am J Respir Crit Care Med, 181:1033-1041 (2010).
Eisen et al., "Cluster analysis and display of genome-wide expression patterns," Proc Natl Acad Sci USA, 95:14863-14868 (1998).
Engineer et al., "Bullous pemphigoid: Interaction of interleukin 5, anti-basement membrane zone antibodies and eosinophils—A preliminary observation," Cytokine, 13(1):32-38 (2001).
Extended European Search Report dated Apr. 25, 2014 in connection with PCT/US2011/065410.
Fahy, "Eosinophilic and neutrophilic inflammation in asthma," Proc Am Thorac Soc, 6:256-259 (2009).
Fahy, "Identifying clinical phenotypes of asthma," Am J Respir Crit Care Med, 181:296-297 (2010).
Falanga et al., "Frequency, levels, and significance of blood eosinophilia in systemic sclerosis, localized scleroderma, and eosinophilic fasciitis," J Am Acad Dermatol, 17(4):648-656 (1987).
Fellouse et al., "Synthetic antibodies from a four-ammo-acid code: A dominant role for tyrosine in antigen recognition," P Natl Acad Sci USA, 101(34):12467-12472 (2004).
Feltelius et al., "Raised circulating levels of the eosinophil cationic protein in ankylosing spondylitis: relation with the inflammatory activity and the influence of sulphasalazine treatment," Ann Rheum Dis, 46:403-407 (1987).
Ferrando et al., "Applying stereology to measure thickness of the basement membrane zone in bronchial biopsy specimens," J Allergy Clin Immunol, 112(6):1243-1245 (2003).
Finkelman et al., "Suppressive effect of IL-4 on IL-13-induced genes in mouse lung," J Immunol, 174:4630-4638 (2005).
Fixman et al., "Basic mechanisms of development of airway structural changes in asthma," Eur Resp J, 29(2):379-389 (2007).
Flatman et al., "Process analytics for purification of monoclonal antibodies," J Chromatography, 848:79-87 (2007).
Flood-Page et al., "A study to evaluate safety and efficacy of mepolizumab in patients with moderate persistent asthma," Am J Respir Crit Care Med, 176:1062-1071 (2007).
Flood-Page et al., "Eosinophil's role remains uncertain as anti-interleukin-5 only partially depletes numbers in asthmatic airway," Am J Respir Crit Care Med, 167:199-204 (2003).
Galli et al., "The development of allergic inflammation," Nature, 454:445-454 (2008).
Gauvreau et al., "Effects of interleukin-13 blockade on allergen-induced airway responses in mild atopic asthma," Am J Respir Crit Care Med, 183:1007-1014 (2011).
Gazzano-Santoro et al., "A non-radiactive complement-dependent cytotoxicity assay for anti-CD20 monoclonal antibody," J Immunol Methods, 202:163-171 (1997).
Geha, R S, "Human IgE," J Allergy Clin Immunol, 74(2):109-120 (1984).
Genebank Accession No. NP.002179 (Apr. 7, 2003) Interleukin 13 Precursor (*Homo sapiens*) http://www.ncbi-nlm-nih.gov/protein-26787978?sat=24&satkey=4532247.
Gentleman et al., "Bioconductor: open software development for computational biology and bioinformatics," Genome Biol, 5 (2004).
George et al., "Differential effects of anti-beta2-glycoprotein I antibodies on endothelial cells and on the manifestations of experimental antiphospholipid syndrome," Circulation, 97(9), 900-906 (1995).
Gerngross, T-U, "Advances in the production of human therapeutic proteins in yeasts and filamentous fungi," Nat Biotech, 22(11):1409-1414 (2004).
Gibson, P-G-, "Inflammatory phenotypes in adult asthma: clinical applications," Clin Respir J, 3:198-206 (2009).

Giusti et al., 1987, "Somatic diversification of S107 from an antiphosphocholine to an anti-DNA autoantibody is due to a single base change in its heavy chain variable region," Proc Natl Acad Sci, 84(9), 2926-2930 (1987).
Gold et al., "Specific carcinoembryonic antigens of the human digestive system," J Exp Med, 122:467-481 (1965).
Gonlugur et al., "Non-allergic eosinophilic inflammation," Immunol Invest, 35:29-45 (2006).
Gordon, S, "Alternative activation of macrophages," Nat Rev Immunol, 3:23-35 (2003).
Gould et al., "The biology of IgE and the basis of allergic disease," Annu Rev Immunol, 21:579-628 (2003).
Graham et al., "Characteristics of a human cell line transformed by DNA from human adenovirus type 5," J Gen Virol, 36(1):59-72 (1977).
Green et al., "Asthma exacerbations and sputum eosinophil counts: a randomised controlled tria,l", Lancet, 360:1715-1721 (2002).
Griffith et al., "Human anti-self antibodies with high specificity from phage display libraries," Embo J, 12(2):725-734 (1993).
Gruber et al., "Efficient tumor cell lysis mediated by a bispecific single chain antibody expressed in *Escherichia coli*," J Immunol, 152:5368-5374 (1994).
Grunig et al., "Requirement of IL-13 independently of IL-4 in experimental asthma," Science, 282:2261-2263 (1998).
Gussow et al., "Humanization of monoclonal antibodies," Methods Enzymol, 203:99-121 (1991).
Guyer et al., "Immunoglobulin binding by mouse intestinal epithelial cell receptors," J Immunol, 117(2):587-593 (1976).
Hahn et al., "Inhibition of the IL-4-IL-13 receptor system prevents allergic sensitization without affecting established allergy in a mouse model for allergic asthma," J Allergy Clin Immunol, 111:1361-1369 (2003).
Hakonarson et al., "Profiling of genes expressed in peripheral blood mononuclear cells predicts glucocorticoid sensitivity in asthma patients," Proc Natl Acad Sci USA, 102(41):14789-14794 (2005).
Haldar et al., "Mepolizumab and exacerbations of refractory eosinophilic asthma," New Engl J Med, 360:973-984 (2009).
Haldar et al., "Noneosinophilic asthma: A distinct clinical and pathologic phenotype," J Allergy Clin Immunol, 119:1043-1052 (2007).
Hammarstrom et al., "Antigenic sites in carcinoembryonic antigen," Cancer Res, 49:4852-4858 (1989).
Hammarstrom, "The carcinoembryonic antigen (CEA) family: structures, suggested functions and expression in normal and malignant tissues," Sem Cancer Biol, 9:67-81 (1999).
Hanania et al., 2015, "Lebrikizumab in moderate-to-severe asthma: pooled data from two randomized placebo-controlled studies." Online publication (10.1136/thoraxjnl-2014-206719) with Supplemental data. Downloaded from http://thorax.bmj.com. Published by group.bmj.com.
Harlow et al., Antibodies: A Laboratory Manual, Cold Spring Harbor:Cold Spring Harbor Press (1988).
Hart et al., "Preclinical efficacy and safety of mepolizumab (SB-240563), a humanized monoclonal antibody to IL-5, in cynomolgus monkeys," J Allergy Clin Immunol, 108(2):250-257 (2001).
Hart et al., "Preclinical efficacy and safety of pascolizumab (SB 240683): a humanized anti-interleukin-4 antibody with therapeutic potential in asthma," Clin Exp Immunol, 130(1):93-100 (2002).
Hayashi et al., "T helper 1 cells stimulated with ovalbumin and IL-18 induce airway hyperresponsiveness and lung fibrosis by IFN-γ and IL-13 production," P Natl Acad Sci USA, 104(37):14765-14770 (2007).
Hellstrom et al., "Antitumor effects of L6, an IgG2a antibody that reacts with most human carcinomas," P Natl Acad Sci USA, 83:7059-7063 (1986).
Hellstrom et al., "Strong antitumor activities of IgG3 antibodies to a human melanoma-associated ganglioside," P Natl Acad Sci USA, 82:1499-1502 (1985).
Hernnas et al., "Eosinophil cationic protein alters proteoglycan metabolism in human lung fibroblast cultures," Eur J Cell Biol, 59(2):352-363 (1992).
Hershey, G K, "IL-13 receptors and signaling pathways: an evolving web," J Allergy Clin Immunol, 111:677-690 (2003).

(56) References Cited

OTHER PUBLICATIONS

Hirose et al., "GS143, an IkappaBubiquitination inhibitor, inhibitsallergic airway inflammation in mice," Biochemical and Biophysical Researchcommunications, 374(3):507-511 (2008), XP023783847.
Hoersch et al., "Periostin shows increased evolutionary plasticity in its alternatively spliced region," BMC Evol Biol, 10(30):1-19 (2010).
Hogan et al., "Cellular and molecular mechanisms involved in the regulation of eosinophil traffickingin vivo," Medicinal Research Reviews, 16(5):407-432 (1996), XP055111993.
Holgate et al., "Treatment strategies for allergy and asthma," Nat Rev Immunol, 8:218-230 (2008).
Holgate, "Epithelium dysfunction in asthma," J Allergy Clin Immunol, 120:1233-1244 (2007).
Holgate, "Pathogenesis of asthma," Clin Exp Allergy, 38:872-897 (2008).
Holliger et al., "Diabodies: Small bivalent and bispecific antibody fragments," Pnatl Acad Sci USA, 90:6444-6448 (1993).
Holm et al., "Functional mapping and single chain construction of the anti-cytokeratin 8 monoclonal antibody TSI," Mol Immunol, 44(6), 1075-1084 (2007).
HOOGENBOOM and WINTER, "By-passing immunisation—Human antibodies from synthetic repertoires of germline $V_H$ gene segments rearranged in vitro," J Mol Biol, 227(2):381-388 (1992).
Hoogenboom, H-, "Overview of antibody phage-display technology and its applications," Methods Mol Biol 178:1-37 (2002).
Horiuchi et al., "Identification and characterization of a novel protein, periostin, with restricted expression to periosteum and periodontal ligament and increased expression by transforming growth factor β," J Bone Miner Res, 14(7):1239-1249 (1999).
Hudson et al., "Engineered antibodies," Nature Medicine, 9(1):129-134 (2003).
Humbert et al., "Elevated expression of messenger ribonucleic acid encoding IL-13 in the bronchial mucosa of atopic and nonatopic subjects with asthma" J Allergy Clin Immunol, 99:657-665 (1997).
Hyun-Shiek Yeum et al., "Fritillaria cirrhosa, Anemarrhena asphodeloides, Lee-Mo-Tang and Cyclosporine a Inhibit Ovalbumin-Induced Eosinophil Accumulation and Th2-Mediated Bronchial Hyperresponsiveness in a Murine Model of Asthma," Basic & Clinical Pharmacology & Toxicology, 100(3):205-213 (2007), XP055111935.
Iba et al., 1998, "Changes in the specificity of antibodies against steroid antigens by introduction of mutations into complementarity-determining regions of the V(H) domain," Protein Eng, 11(5), 361-70 (1998).
Idusogie et al., "Mapping of the C1q binding site on Rituxan, a chimeric antibody with a human IgG1 Fc," J Immunol, 164:4178-4184 (2000).
Innes et al., "Epithelial mucin stores are increased in the large airways of smokers with airflow obstruction," Chest, 130:1102-1108 (2006).
Ishizaka et al., "Antigenic structure of γE-globulin and reaginic antibody," J Immunol 99(5):849-858 (1967).
Ishizaka et al., "Identification of γE-antibodies as a carrier of reaginic activity," J Immunol, 99(6):1187-1198 (1967).
Izuhara et al., "Clarification of the pathogenesis and development of clinical examination for allergic diseases" Japanese J Clin Pathol (Article in Japanese, English abstract provided), 55(4):369-374 (2007).
Izuhara et al., "Microarray-based identification of novel biomarkers in asthma" Allergol Int, 55(4):361-367 (2006).
Jeffrey et al., "Dipeptide-based highly potent doxorubicin antibody conjugates" Bioorganic Med Chem Letters, 16:358-362 (2006).
Jia et al., "Peripheral Biomarkers of an IL-13 Induced Bronchial Epithelial Gene Signature in Asthma, Abstract # 271", presented at American Academy of Allergy, Asthma, and Immunology Conference, Mar. 2009, Washington, DC, USA.
Jia et al., "Peripheral Biomarkers of an IL-13 Induced Bronchial Epithelial Gene Signature in Asthma", presented at Keystone Symposium, Jan. 2009, Keystone, Colorado, USA.
Jia et al., "Periostin is a systemic biomarker of eosinophilic airway inflammation in asthmatic patients," J Allergy Clin Immunol, 130:647-654 (2012).
Jiang et al., "A novel peptide isolated from a phage display peptide library with trastuzumab can mimic antigen epitope of HER-2," J Biol Chem, 280(6), 4656-4662 (2005).
Juniper et al., "Identifying 'well-controlled' and 'not well-controlled' asthma using the asthma control questionnaire," Respir Med, 100:616-621 (2006).
Juniper et al., "Measuring asthma control," Am J Respir Crit Care Med, 162:1330-1334 (2000).
Kabat et al. Sequences of Proteins of Immunological Interest Fifth edition,NIH Publication, 91-3242 (1991).
Kam et al., "Carbon nanotubes as multifunctional biological transporters and near-infrared agents for selective cancer cell destruction," P Natl Acad Sci USA, 102(33):11600-11605 (2005).
Kanda et al., "Comparison of cell lines for stable production of fucose-negative antibodies with enhanced ADCC," Biotechnol Bioeng, 94(4):680-688 (2006).
Kapp et al., "Interleukin 13 is secreted by and stimulates the growth of Hodgkin and Reed-Sternberg cells," J Exp Med, 189(12):1939-1945 (1999).
Kashmiri et al., "SDR grafting a new approach to antibody humanization," Methods, 36:25-34 (2005).
Kelly-Welch et al., "Interleukin-4 and interleukin-13 signaling connections maps," Science, 300:1527-1528 (2003).
Kettleborough et al., "Humanization of a mouse monoclonal antibody by CDR-grafting: the importance of framework residues on loop conformation," Protein Eng, 4(7), 773-83 (1991).
Kim et al., "Localization of the site of the murine IgG1 molecule that is involved in binding to the murine intestinal Fc receptor," Eur J Immunol, 24:2429-2434 (1994).
Kim et al., "Persistent activation of an innate immune response translates respiratory viral infection into chronic lung disease," Nat Med, 14(6):633-640 (2008).
Kindt et al. Kuby Immunology 6th ed edition, N.Y.:W.H. Freeman and Co, p. 91 (2007).
King et al., "Monoclonal antibody conjugates of doxorubicin prepared with branched peptide linkers: Inhibition of aggregation by methoxytriethyleneglycol chains," J Med Chem, 45:4336-4343 (2002).
Kirkham et al., "Heterogeneity of airways mucus: variations in the amounts and glycoforms of the major oligomeric mucins MUC5AC and MUC5B," Biochem J 361:537-546 (2002).
Klimka et al., "Human anti-CD30 recombinant antibodies by guided phage antibody selection using cell panning," BR J Cancer, 83(2):252-260 (2000).
Komiya et al., "Concerted expression of eotaxin-1, eotaxin-2, and eotaxin-3 in human bronchial epithelial cells," Cell Immunol, 225:91-100 (2003).
Kostelny et al., "Formation of a bispecific antibody by the use of leucine zippers," J Immunol, 148(5):1547-1553 (1992).
Kozbor et al., "A human hybrid myeloma for production of human monoclonal antibodies," J Immunol, 133(6):3001-3005 (1984).
Kratz et al., "Prodrugs of anthracyclines in cancer chemotherapy," Curr Med Chem, 13:477-523 (2006).
Krupsky et al., "Wegener's granulomatosis with peripheral eosinophilia—Atypical variant of a classic disease," Chest, 104(4):1290-1292 (1993).
Kruzynska-Frejtag et al., "Periostin is expressed within the developing teeth at the sites of epithelial-mesenchymal interaction," Dev Dyn, 229:857-868 (2004).
Kudlacz et al., "Functional effects of eotaxin are selectively upregulated on IL-5 transgenic mouse eosinophils," Inflammation, 26:111-119 (2002).
Kudo et al., "Periostin promotes invasion and anchorage-independent growth in the metastatic process of head and neck cancer," Cancer Res, 66:6928-6935 (2006).
Kuperman et al., "Dissecting asthma using focused transgenic modeling and functional genomics," J Allergy Clin Immunol, 116:305-311 (2005).

(56) References Cited

OTHER PUBLICATIONS

Kuroki et al., "Reaction profiles of seven enzyme immunoassay kits for carcinoembryonic antigen (CEA) analyzed with purified preparation of CEA and related normal antigens," Clin Biochem, 25:29-35 (1992).
Lakhanpal et al., "Eosinophilic fasciitis: Clinical spectrum and therapeutic response in 52 cases," Semin Arthritis Rheum, 17(4):221-231 (1988).
Lanier et al., "Omalizumab for the treatment of exacerbations in children with inadequately controlled allergic (IgE-mediated) asthma", J Allergy Clin Immunol, 124(6):1210-1216 (2009).
Lauder & McKenzie, "Measurement of Interleukin-13," Current Protocols in Immunology, Unit 6-18, Supplement 46, 6-18-1-6-18-6, John Wiley & Sons, Inc., New York (2001).
Leckie et al., "Effects of an interleukin-5 blocking monoclonal antibody on eosinophils, airway hyper-responsiveness, and the late asthmatic response," Lancet, 356(9248), 2144-2148 (2000).
Lee et al., "Bivalent antibody phage display mimics natural immunoglobulin," J Immunol Methods, 284(1-2):119-132 (2004).
Lee et al., "High-affinity human antibodies from phage-displayed synthetic Fab libraries with a single framework scaffold," J Mol Biol 340(5):1073-1093 (2004).
Lee et al., "Serum levels of interleukins (IL).4, IL-5, IL-13, and interferon-γ in acute asthma," J Asthma 38(8):665-671 (2001).
Lemiere et al., "Airway inflammation assessed by invasive and noninvasive means in severe asthma: eosinophilic and noneosinophilic phenotypes," J Allergy Clin Immunol 118:1033-1039 (2006).
Leung et al., "Dysregulation of interleukin 4, interleukin 5, and interferon γ gene expression in steroid-resistant asthma," J Exp Med, 181:33-40 (1995).
Li et al., "Human antibodies for immunotherapy development generated via a human B cell hybridoma technology," P Natl Acad Sci USA, 103(10):3557-62 (2006).
Li et al., "Optimization of humanized IgGs in glycoengineered Pichia pastoris," Nat Biotechnol, 24(2):210-215 (2006).
Li et al., "Refractory periorbital edema in a 29-year-old man," Ann Allergy 69(2):101-105 (1992).
Liao et al., "Combined detection of serum tumor markers for differential diagnosis of solid lesions located at the pancreatic head," Hepatobiliary Pancreat Dis Int., 6(6):641-645 (2007).
Lindahl et al., "Newly identified proteins in human nasal and bronchoalveolar lavage fluids: potential biomedical and clinical applications," Electrophoresis, 20:3670-3676 (1999).
Litvin et al., "Expression and function of periostin-isoforms in bone," J Cell Biochem, 92:1044-1061 (2004).
Litvin et al., "Periostin family of proteins: therapeutic targets for heart disease," Anat Rec A Discov Mol Cell Evol Biol., 287(2):1205-12 (2005).
Liu et al., "Immune cell transcriptome datasets reveal novel leukocyte subset-specific genes and genes associated with allergic processes," J Allergy Clin Immunol, 118:496-503 (2006).
Lode et al., "Targeted therapy with a novel enediyene antibiotic calicheamicin $\theta^I_1$ effectively suppresses growth and dissemination of liver metastases in a syngeneic model of murine neuroblastoma," Cancer Res, 58:2925-2928 (1998).
Lonberg, "Fully human antibodies from transgenic mouse and phage display platforms," Current Opin Immunol, 20:450-459 (2008).
Lonberg, "Human antibodies from transgenic animals," Nat Biotechnol, 23(9):1117-1125 (2005).
MacCallum et al., "Antibody-antigen interactions: contact analysis and binding site topography," J Mol Biol, 262(5), 732-745 (1996).
Maeda et al., "Concentrations of carcinoembryonic antigen in serum and bronchoalveolar lavage fluid of asthmatic patients with mucoid impaction," Nihon Kokyuki Gakkai Zasshi (in English Abstract), 42(12):988-993 (2004).
Mariuzza et al., "The structural basis of antigen-antibody recognition," Annu Rev Biophys Biophys Chem, 16,139-159 (1987).
Marks et al., "By-passing immunization—Human antibodies from V-gene libraries displayed on phage" J Mol Biol, 222:581-597 (1991).
Marks et al., *Methods Mol Biol, Antibody Engineering* "Selection of human antibodies from phage display libraries" Benny K. C. Lo, Humana Press, 248:161-176 (2004).
Martin et al., "A link between chronic asthma and chronic infection," J Allergy Clin Immunol, 107:595-601 (2001).
Martin et al., "The predicting response to inhaled corticosteroid efficacy (PRICE) trial," Allergy Clin Immunol, 119:73-80 (2007).
Mather et al., "Culture of testicular cells in hormone-supplemented serum-free medium," Ann Ny Acad Sci, 383:44-68 (1982).
Mather, "Establishment and characterization of two distinct mouse testicular epithelial cell Lines," Biol Reprod, 23:243-252 (1980).
McCafferty et al., "Phage antibodies: filamentous phage displaying antibody variable domains," Nature, 348:552-554 (1990).
McKenzie et al., "Interleukin 13, a T-cell-derived cytokine that regulates human monocyte and B-cell function," Proc Natl Acad Sci USA, 90:3735-3739 (1993).
McKinley et al., "$T_H17$ cells mediate steroid-resistant airway inflammation and airway hyperresponsiveness in mice," J Immunol, 181:4089-4097 (2008).
Miller et al., "Standardisation of spirometry," Eur Respir J, 26:319-338 (2005).
Milstein et al., "Hybrid hybridomas and their use in immunohistochemistry," Nature, 305:537-540 (1983).
Miossec, P-, "Cytokines and the pathophysiology of bone erosions in rheumatoid arthritis," J Clin Rheumatol 3(Suppl 2):S81-S83 (1997).
Miranda et al., "Distinguishing severe asthma phenotypes: Role of age at onset and eosinophilic inflammation," J Allergy Clin Immunol, 113:101-108 (2004).
Modrek et al., 2008, "Gene Expression Signatures in Bronchial Epithelium Define Distinct Molecular Subtypes of Asthma," Abstract # 2669, presented at American Thoracic Society Conference, May 2008, Toronto, Ontario, Canada (2008).
Moore et al., "Identification of asthma phenotypes using cluster analysis in the severe asthma research program," Am J Respir Crit Care Med, 181:315-323 (2010).
Morris, G-E- (ed-), *Methods In Molec Biol* "Epitope Mapping Protocols," Totowa, NJ:Humana Press, 66 (1996).
Morrison et al., "Chimeric human antibody molecules: Mouse antigen-binding domains with human constant region domains," P Natl Acad Sci USA, 81:6851-6855 (1984).
Munitz et al., "Eosinophils: 'new' roles for 'old' cells," Allergy, 59:268-275 (2004).
Nagy et al., "Stability of cytotoxic luteinizing hormone-releasing hormone conjugate (AN-152) containing doxorubicin 14-O-hemiglutarate in mouse and human serum in vitro: implications for the design of preclinical studies," P Natl Acad Sci USA, 97(2):829-34 (2000).
Nair et al., "Mepolizumab for prednisone-dependent asthma with sputum eosinophili,a" New Engl J Med, 360(10):985-993 (2009).
Nair et al., "Nitric oxide in exhaled breath is poorly correlated to sputum eosinophils in patients with prednisone-dependent asthma," J Allergy Clin Immunol, 126(2):404-406 (2009).
Nakajima et al., "Identification of granulocyte subtype-selective receptors and ion channels by using a high-density oligonucleotide probe array," J Allergy Clin Immunol, 113:528-535 (2004).
Nakanishi et al., "Role of gob-5 in mucus overproduction and airway hyperresponsiveness in asthma," Proc Natl Acad Sci USA, 98(9):5175-5180 (2001).
Neumaier et al., "Characterization of a cDNA clone for the non-specific cross-reacting antigen (NCA) and a comparison of NCA and carcinoembryonic antigen," J Biol Chem, 263(7):3202-3207 (1988).
Ni, "Research progress and future perspectives in antibodomics and antibodomic drugs," Xiandai Mianyixue (Abstract only), 26(4):265-168 (2006).
Nielsen et al., "Assessment of IgE allergen specificity among latex-allergic health care workers: review of IgE-binding components of various latex extracts," Ann Allergy Asthma Immunol 85:489-494 (2000).

(56) References Cited

OTHER PUBLICATIONS

Niven et al., "Effectiveness of Omalizumab in Patients with Inadequately Controlled Severe Persistent Allergic Asthma: an Open-Label Study," Respier. Med., 102(10):1371-1378 (2008).
Noonan et al., 2013, "Dose-ranging study of lebrikizumab in asthmatic patients not receiving inhaled steroids." J Allergy Clin Immunol. 132(3):567-574.
Norris et al., "Periostin promotes a fibroblastic lineage pathway in atrioventricular valve progenitor cells," Dev Dyn, 238:1052-1063 (2009).
Norris et al., "Periostin regulates collagen fibrillogenesis and the biomechanical properties of connective tissues," J Cell Biochem, 101:695-711 (2007).
Ohno et al., "Antigen-binding specificities of antibodies are primarily determined by seven residues of VH," Proc Natl Acad Sci USA, 82(9),2945-2949 (1985).
Okamoto et al., 2011, "Periostin, a matrix protein, is a novel biomarker for idiopathic interstitial pneumonias," Eur. Respir. J. 37:1119-1127.
Okazaki et al., "Fucose depletion from human IgG1 oligosaccharide enhances binding enthalpy and association rate between IgG1 and FycγRIIIa," J Molec Biol, 336:1239-1249 (2004).
Oku et al., "Periostin and bone marrow fibrosis," Int J Hematol, 88:57-63 (2008).
Oldhoff et al., "Anti-IL-5 recombinant humanized monoclonal antibody (Mepolizumab) for the treatment of atopic dermatitis," Allergy, 60:693-696 (2005).
Ordonez et al., "Mild and moderate asthma is associated with airway goblet cell hyperplasia and abnormalities in mucin gene expression," Am J Respir Crit Care Med, 163:517-523 (2001).
Osbourn et al., "From rodent reagents to human therapeutics using antibody guided selection," Methods, 36:61-68 (2005).
Oshima et al., "Characterization of a powerful high affinity antagonist that inhibits biological activities of human interleukin-13," J Biol Chem,276(18):15185-15191 (2001).
Padlan, "A possible procedure for reducing the immunogenicity of antibody variable domains while preserving their ligand-binding properties," Mol Immunol, 28(4-4):489-498 (1991).
Pahl et al., 2002, "Regulation of IL-13 synthesis in human lymphocytes: implications for asthma therapy," British J of Pharmacology, 135(8), 1915-1926 (2002).
Pavord et al., "Airway inflammation in patients with asthma with high-fixed or low-fixed plus as-needed budesonide-formoterol," J Allergy Clin Immunol, 123(Suppl 1088e1-e7):1083-1089 (2009).
Pavord et al., "Non-eosinophilic corticosteroid unresponsive asthma," Lancet, 353:2213-2214 (1999).
Pavord et al., "The use of exhaled nitric oxide in the management of asthma," J Asthma, 45:523-531 (2008).
PCT International Search Report dated Jul. 2, 2012 in connection with PCT/US2011/065410.
Pelers-Golden, M, "The alveolar macrophage: The forgotten cell in Asthma," Am J Respir Cell Mol Biol, 31:3-7 (2004).
Petkova et al., "Enhanced half-life of genetically engineered human IgG1 antibodies in a humanized FcRn mouse model: potential application in humorally mediated autoimmune disease," Int Immunol, 18(12):1759-69 (2006).
Plager et al., "Gene transcription changes in asthmatic chronic rhinosinusitis with nasal polyps and comparison to those in atopic dermatitis," PLoS One, 5(Suppl 411450):1-9 (2010).
Pluckthun, The Pharmacology of Monoclonal Antibodies: Handbook of Pharmacology "Antibodies from *Escherichia coli*," (Chapter 11), Rosenberg and Moore, eds., Berlin:Springer-Verlag, 113:269-315 (1994).
Portolano et al., "Lack of promiscuity in autoantigen-specific H and L chain combinations as revealed by human H and L chain Roulette," J Immunol, 150(3):880-887 (1993).
Presta et al., "Humanization of an antibody directed against IgE," J Immunol, 151(5):2623-2632 (1993).
Presta et al., "Humanization of an Anti-Vascular Endothelial Growth Factor Monoclonal Antibody for the Therapy of Solid Tumors and Other Disorders," Cancer Res, 57(20):4593-4599 (1997).
Puglisi et al., "Expression of periostin in human breast cance,r" J Clin Pathol, 61:494-498 (2008).
Queen et al., "A humanized antibody that binds to the interleukin 2 receptor," P Natl Acad Sci USA, 86(24):10029-10033 (1989).
Rasmussen et al., "Manufacture of recombinant polyclonal antibodies," Biotechnol, 29(6):845-852 (2007).
Ravetch and Kinet, "Fc receptors," Ann Rev Immunol, 9:457-492 (1991).
Ray et al., "Uteroglobin suppresses SCCA gene expression associated with allergic asthma," J Biol Chem, 280(11):9761-9764 (2005).
Reed et al., "The role of protease activation of inflammation in allergic respiratory diseases," J Allergy Clin Imunol, 114:997-1008 (2004).
Riechmann et al., "Reshaping human antibodies for therapy," Nature, 332:323-327 (1988).
Riemer et al., "Matching of trastuzumab (Herceptin) epitope mimics onto the surface of Her-2-neu—a new method of epitope definition," Mol Immunol, 42(9), 1121-1124 (2005).
Ripka et al., "Two Chinese hamster ovary glycosylation mutants affected in the conversion of GDP-mannose to GDP-fucose," Arch Biochem Biophys, 249(2):533-545 (1986).
Roche et al., "Subepithelial fibrosis in the bronchi of asthmatics," Lancet, 1(8637):520-4 (1989).
Rosok et al., "A combinatorial library strategy for the rapid humanization of anticarcinoma BR96 Fab," J Biol Chem, 271(37):22611-22618 (1996).
Rudikoff et al., "Single amino acid substitution altering antigen-binding specificity," Proc Natl Acad Sci USA, 79(6), 1979-1983 (1982).
Rzany et al., "Histopathological and epidemiological characteristics of patients with erythema exudativum multiforme major, Stevens-Johnson syndrome and toxic epidermal necrolysis," Br J Dermatol, 135:6-11 (1996).
Sabatini et al., "Tissue distribution of RNAs for cystatins, histatins, statherin, and proline-rich salivary proteins in humans and macaques," J Dent Res. 68(7):1138-45 (1989).
Saha et al., "Increased sputum and bronchial biopsy IL-13 expression in severe asthma," J Allergy Clin Immunol 121:685-691 (2008).
Saldanha, A J, "Java Treeview extensible visualization of microarray data," Bioinformatics, 20(17):3246-3248 (2004).
Sanz et al., "Serum eosinophil peroxidase (EPO) levels in asthmatic patients," Allergy, 52:417-422 (1997).
Sasaki et al., "Expression of Periostin, homologous with an insect cell adhesion molecule, as a prognostic marker in non-small cell lung cancers," Jpn-J Cancer Res, 92(8):869-873 (2001).
Sasaki et al., "Elevated serum periostin levels in patients with bone metastases from breast but not lung cancer," Breast Cancer Research Treatment, 77:245-252 (2003).
Sasaki et al., "Serum level of the periostin, a homologue of an insect cell adhesion molecule, as a prognostic marker in nonsmall cell lung carcinomas," Cancer 92(4):843-848 (2001).
Scheerens et al., 2013, "The effects of lebrikizumab in patients with mild asthma following whole lung allergen challenge." Clin. & Experi. Allergy 44:38-46.
Schildbach et al., "Modulation of antibody affinity by a non-contact residue," Protein Sci, 2(2), 206-14 (1993).
Seibold et al., "Chitotriosidase is the primary active chitinase in the human lung and is modulated by genotype and smoking habit," J Allergy Clin Immunol, 122:944-950 (2008).
Sekiya et al., "Increased levels of a TH2-type CC chemokine thymus and activation-regulated chemokine (TRAC) in serum and induced sputum of asthmatics," Allergy, 57:173-177 (2002).
Shaw et al., "The use of exhaled nitric oxide to guide asthma management," Am J Respir Crit Care Med 176:231-237 (2007).
Shields et al., "High resolution mapping of the binding site on human IgG1 for FcγRI, FcγRII, FcγRIII, and FcRn and design of IgG1 variants with improved binding to the FcγR," J Biol Chem, 276(9):6591-6604 (2001).
Shively et al., "CEA-related antigens: molecular biology and clinical Significance," Crit Rev Olcol Hematol, 2(4):355-399 (1985).

(56) References Cited

OTHER PUBLICATIONS

Sidhu et al., "Phage-displayed antibody libraries of synthetic heavy chain complementarity determining regions," J Mol Biol, 338:299-310 (2004).
Sidhu et al., "Roles of epithelial cell-derived periostin in TGF-β activation, collagen production, and collagen gel elasticity in asthma," P Natl Acad Sci USA, 107(32):14170-14175 (2010).
Silkoff et al., "Exhaled nitric oxide identifies the persistent eosinophilic phenotype in severe refractory asthma," J Allergy Clin Immunol, 116:1249-1255 (2005).
Simpson et al., "Inflammatory subtypes in asthma: Assessment and identification using induced sputurm," Respir, 11:54-61 (2006).
Sims et al., "A Humanized CD18 Antibody Can Block Function Without Cell Destruction," J Immunol 151(4):2296-2308 (1993).
Singapore Search Report dated Jan. 15, 2014 in connection with Application No. 201304043.1.
Singer et al., "Gens and Genoms", Moscow, Mir., 1,63 (1998) [in Russian with English translation].
Singh et al., "A phase 1 study evaluating the pharmacokinetics, safety and tolerability of repeat dosing with a human IL-13 antibody (CAT-354) in subjects with asthma," BMC Pulm Med, 10:3 (1-8); 10-1186-1471-2466-10-3 (2010).
Siriwardena et al., "Periostin is frequently overexpressed and enhances invasion and angiogenesis in oral cancer," Br J Cancer, 95:1396-1403 (2006).
Skinnider et al., "Signal transducer and activator of transcription 6 is frequently activated in Hodgkin and Reed-Sternberg cells of Hodgkin lymphoma" Blood, 99(2):618-626 (2002).
Skinnider et al., "The role of interleukin 13 in classical Hodgkin lymphoma," Lenk Lymphoma, 43(6):1203-1210 (2002).
Stankovic et al., "Gene expression profiling of nasal polyps associated with chronic sinusitis and aspirin-sensitive asthma," Laryngoscope, 118:881-889 (2008).
Storey et al., "Statistical significance for genomewide studies," Proc Natl Acad Sci USA, 100(16):9440-9445 (2003).
Sullivan et al., "An evaluation of the cost-effectiveness of omalizumab for the treatment of severe allergic asthma", Allergy, 63(6):670-684 (2008).
Suresh et al., "Measurement of IL-13-induced iNOS-derived gas phase nitric oxide in human bronchial epithelial cells," Am J Respir Cell Mol Biol, 37:97-104 (2007).
Sutton et al., "The human IgE netork," Nature, 366:421-428 (1993).
Takatsu et al., "IL-5 and eosinophilia," Curr Opin Immunol, 20:288-294 (2008).
Takayama et al., "Periostin: A novel component of subepithelial fibrosis of bronchial asthma downstream of IL-4 and IL-13 signals," J Allergy Clin Immunol, 118:98-104 (2006).
Takeshita et al., "Osteoblast-specific factor 2: cloning of a putative bone adhesion protein with homology with the insect protein fasciclin I," Biochem J, 294:271-278 (1993).
Tezuka et al., "Isolation of mouse and human cDNA clones encoding a protein expressed specifically in osteoblasts and brain tissues," Biochem Biophys Res Comm, 173(1):246-251 (1990).
Thompson et al., "Mutants of interleukin 13 with altered reactivity toward interleukin 13 receptors," J Biol Chem, 274(42), 29944-29950 (1999).
Tilman et al., "Human periostin gene expression in normal tissues, tumors and melanoma: evidences for periostin production by both stromal and melanoma cells," Mol Cancer, 6(80):1-13 (2007).
Torgov et al., "Generation of an intensely potent anthracycline by a monoclonal antibody-β-galactosidase conjugate," Bioconjugate Chem, 16:717-721 (2005).
Traunecker et al., "Bispecific single chain molecules (Janusins) target cytotoxic lymphocytes on HIV infected cells," EMBO J, 10(12):3655-3659 (1991).
Trieu et al., "Inhibition of Hodgkin Lymphoma cell line growth using an adenovirus expressing the soluble IL-13 decoy receptor(sll-13 Ralpha2)," Blood (Abstract #2272, American Society of Hematology 44th annual meeting, Philadelphia, Pennsylvania, USA), 100(11):578a-579a (2002).
Truyen et al., "Evaluation of airway inflammation by quantitative Th1-Th2 cytokine mRNA measurement in sputum of asthma patients," Thorax, 61:202-208 (2006).
Tsarbopoulos et al., "Mass spectrometric mapping of disulfide bonds in recombinant human interleukin-13," J-Mass-Spectrom, vol. 35(3):446-453 (2000).
Tsuburai et al., "Case of eosinophilic bronchitis and bronchiolitis associated with increased level of serum CEA in asthmatics," Nihon Kokyuki Gakkai Zasshi (Article in Japanese) English abstract provided, 1 printed page [retrieved on Mar. 7, 2013], retrieved from the Internet (URL:www-ncbi-nlm-nih-gov-pubmed-17087343), 44(10):742-748 (2006).
Tutt et al., "Trispecific F(ab') $_3$ derivatives that use cooperative signaling via the TCR-CD3 complex and CD2 to activate and redirect resting cytotoxic T cells," J Immunol 147(1):60-69 (Jul. 1991).
Ultsch et al., "Structural Basis of Signaling Blockade by Anti-IL-13 Antibody Lebrikizumab," J Mol Biol, 425(8), 1330-1339 (2013).
Ultsch et al., "Structural basis of signaling blockade by anti-IL-13 antibody lebrikizumab," J Mol Biol (http://dx-doi-org-10-1016-j-jmb-2013-01-024), (2013).
Urlaub et al., "Isolation of chinese hamster cell mutants deficient in dihydrofolate reductase activity," P Natl Acad Sci USA, 77(7):4216-4220 (1980).
Vajdos et al., "Comprehensive functional maps of the antigen-binding site of an anti-Erb antibody obtained with shotgun scanning mutagenesis," J Mol Biol, 320(2), 415-428 (2002).
Van Der Pouw Kraan et al., "Human IL-13 production is negatively influenced by CD3 engagement—enhancement of IL-13 production by cyclosporine A1," J. Immunol, 156(5):1818-1823 (1996).
Van Dijk et al., "Human antibodies as next generation therapeutics," Curr Opin Chem Biol, 5(4):368-374 (2001).
Vancheri et al., "Human Lung Fibroblast-derived granulocyte-macrophage colony stimulating factor (GM-CSF) mediates eosinophil survival in vitro," Am J Respir Cell Mol Biol, 1:289-295 (1989).
Varga et al., "Eosinophilia-myalgia syndrome, eosinophilic fasciitis, and related fibrosing disorders," Curr Opin Rheumatol, 9(6):562-570 (1997).
Venkayya et al., "The Th2 lymphocyte products IL-4 and IL-13 rapidly induce airway hyperresponsiveness through direct effects on resident airway cells," Am J Respir Cell Mol Biol, 26(2), 202-208 (2002).
Vignola et al., "Airway inflammation in mild intermittent and in persistent asthma," Am J Respir Crit Care Med, 157:403-409 (1998).
Vitetta et al., "Redesigning Nature's Poisons to Create Anti-Tumor Reagents," Science, 238:1098-1104 (1987).
Vollmers and Brandlein, "Death by stress: natural IgM-induced Apoptosis," Methods Find Exp Clin Pharmacol, 27(3):185-191 (2005).
Vollmers and Brandlein, "The 'early birds': Natural IgM antibodies and immune surveillance," Histol Histopathol, 20:927-937 (2005).
Walsh, G-M, "Emerging drugs for asthma," Expert Opin Emerging Drugs, 13(4):643-653 (2008).
Walter et al., "Critical role for 1IL-13 in the development of Aallergen-induced airway hyperreactivity," The Journal of Immunology, The American Association of Immunologists, US, 167(8): 4668-4675 (2001), XP002542096.
Wan et al., "The crystal structure of IgE Fc reveals an asymmetrically bent conformation," Nat Immunol, 3(7):681-686 (2002).
Wang et al., "Fixed dosing versus body size-based dosing of monoclonal antibodies in adult clinical trials", J Clin Pharmacol., 49(9):1012-1024 (2009).
Wardlaw et al., "Multi-dimensional phenotyping: Towards a new taxonomy for airway disease," Clin Exp Allergy, 35:1254-1262 (2005).
Warner et al., "Proline-rich proteins are present in serous cells of submucosal glands in the respiratory tract," Am Rev Respir Dis, 130(1):115-8 (1984).
Weibel et al., "How much is there really? Why stereology is essential in lung morphometry," J Appl Physiol, 102:459-467 (2007).

(56) References Cited

OTHER PUBLICATIONS

Wenzel et al., "Bronchoscopic evaluation of severe asthma. Persistent inflammation associated with high dose glucocorticoids," Am J Respir Crit Care Med., 156:737-743 (1997).
Wenzel et al., "Asthma: defining of the persistent adult phenotypes," Lancet, 368:804-813 (2006).
Wenzel et al., "Effect of an interleukin-4 variant on late phase asthmatic response to allergen challenge in asthmatic patients: results of two phase 2a studies," Lancet, 370:1422-1431 (2007).
Wenzel et al., "Evidence that severe asthma can be divided pathologically into two inflammatory subtypes with distinct physiologic and clinical characteristics," Am J Respir Crit Care Med, 160:1001-1008(1999).
Wills-Karp et al., "Interleukin-13: central mediator of allergic asthma," Science, 282:2258-2261 (1998).
Winkler et al., "Changing the antigen binding specificity by single point mutations of an anti-p24 (HIV-1) antibody," J Immunol, 165(8), 4505-4514 (2000).
Winpenny et al., "The CLCA gene family: Putative therapeutic target for respiratory diseases," Inflammation & Allergy-Drug Targets, 8:146-160 (2009).
Winter et al., "Making antibodies by phage display technology," Annu Rev Immunol, 12:433-455 (1994).
Woodruff et al., "Gene Expression Signatures in Bronchial Epithelium Define Distinct Molecular Subtypes of Asthma," presented at Bay Area Clinical Research Symposium, Oct. 2008, San Francisco, California, USA (2008).
Woodruff et al., "Gene Expression Signatures in Bronchial Epithelium Define Distinct Molecular Subtypes of Asthma," presented at Keystone Symposium, Jan. 2009, Keystone, Colorado, USA (2009).
Woodruff et al., "Genome-wide profiling identifies epithelial cell genes associated with asthma and with treatment response to corticosteroids," PNAS, 104(40):15858-15863 (2007).
Woodruff et al., "A distinctive alveolar macrophage activation state induced by cigarette smoking," Am J Respir Crit Care Med, 172:1383-1392 (2005).
Woodruff et al., "Genome-wide profiling identifies epithelial cell genes associated with asthma and with treatment response to corticosteroids," P Natl Acad Sci USA, 104:15858-15863 (2007).
Woodruff et al., "T-helper type 2-driven inflammation defines major subphenotypes of asthma," Am J Respir Crit Care Med, 180:388-395 (2009).
Wright and Morrison, "Effect of glycosylation on antibody function: Implications for genetic engineering," Trends Biotechnol 15:26-32 (1997).
Wu et al., "Humanization of a murine monoclonal antibody by simultaneous optimization of framework and CDR residues," J Mol Biol, 294(1), 151-162 (1999).
Wynn, T A, "IL-13 effector functions," Annu-Rev Immunol, 21:425-456 (2003).
Yamane-Ohnuki et al., "Establishment of FUT8 knockout Chinese hamster ovary cells: an ideal host cell line for producing completely defucosylated antibodies with enhanced antibody-dependent cellular cytotoxicity," Biotechnol Bioeng, 87(5):614-622 (2004).
Yang et al., "Anti-IL-13 monoclonal antibody inhibits airway hyperresponsiveness, inflammation and airway remodeling," Cytokine, 28(6), 224-232 (2004).
Yang et al., "Therapeutic dosing with Anti-Interleukin-13 Monoclonal Antibody Inhibits Asthma Progression in Mice," J Pharmacol Exp Ther, 313(1), 8-15 (2005).
Yazaki et al., "Expression of recombinant antibodies in mammalian cell lines," Methods Molec Biol, 248:255-268 (2004).
Yetiser et al., "Eosinophilic granuloma of the bilateral temporal bone," Int J Pediatr Otorhinolaryngol, 62:169-173 (2002).
Yuyama et al., "Analysis of novel disease-related genes in bronchial asthma," Cytokine, 19(6):287-296 (2002).
Zhang et al., "Identification of monoclonal antibodies against IL-6," Molecular Cardiology of China, 3(3), 152-156 (2003).
Zhou et al., "Characterization of a calcium-activated chloride channel as a shared target of Th2 cytokine pathways and its potential involvement in asthma," Am J Respir Cell Mol Biol, 25:486-491 (2001).
Zhu et al., "Periostin-like-factor in osteogenesis," J Cell Physiol, 218:584-592 (2009).
Zimmermann et al., "Chemokines in asthma: cooperative interaction between chemokines and IL-13," J Allergy Clin Immunol, 111:227-242 (2003).
Zimmermann et al., "Expression and regulation of small proline-rich protein 2 in allergic inflammation," Am J Respir Cell Mol Biol, 32:428-435 (2005).
Zimmermann et al., "Isolation and characterization of cDNA clones encoding the human carcinoembryonic antigen reveal a highly conserved repeating structure," Proc Natl Acad-Sci USA, 84:2960-2964 (1987).
Tan et al., "Serum Periostin Levels in Adults of Chinese Descent: An Observational Study", Allergy, Asthma & Clinical Immunology, vol. 14, No. 87, 2018, pp. 1-9.
Izuhara et al., "Roles of Periostin in Respiratory Disorders", American Journal of Respiratory and Critical Care Medicine, vol. 193, No. 9, May 1, 2016, pp. 949-956.
Johansson et al., "Serum Periostin is Associated with Type 2 Immunity in Severe Asthma", J. Allergy Clin. Immunol., vol. 137, No. 6, Jun. 2016, pp. 1904-1907.
Simpson et al., "Periostin Levels and Eosinophilic Inflammation in Poorly-Controlled Asthma", BMC Pulmonary Medicine, vol. 16, No. 67, 2016, pp. 1-7.
James et al., "Serum Periostin Relates to Type-2 Inflammation and Lung Function in Asthma: Data from the Large Population-Based Cohort Swedish GA(2)LEN", Allergy, vol. 72, 2017, pp. 1753-1760.
Semprini et al., "Type 2 Biomarkers and Prediction of Future Exacerbations and Lung Function Decline in Adult Asthma", J. Allergy Clin. Immunol. Pract., vol. 6, No. 6, Nov.-Dec. 2018, pp. 1982-1988.
Semprini et al., "Change in Biomarkers of Type-2 Inflammation Following Severe Exacerbations of Asthma", Thorax, vol. 74, 2019, pp. 95-98.
Busby et al., "Change in Type-2 Biomarkers and Related Cytokines with Prednisone in Uncontrolled Severe Oral Corticosteriod Dependent Asthmatics: An Interventional Open-Label Study", Thorax, vol. 0, 2019, pp. 1-4.
Hanania et al., "Efficacy and Safety of Lebrikizumab in Patients with Uncontrolled Asthma (Lavolta I and Lavolta II): Replicate, Phase 3, Randomised, Double-Blind, Placebo-Controlled Trials", Lancet Respir. Med., vol. 4, 2016, pp. 781-796.
Bai et al., Novel Isoforms of Periostin Expressed in the Human Thyroid, Jpn Clin Med. 2010; 1: 13-20.
Jakubke H.D. et al., Amino acids, peptides, proteins, M: Mir, 1985, pp. 92-94.
Bhakta et al., "Human asthma phenotypes: from the clinic, to cytokines, and back again," Immunol Rev.; Jul. 2011; 242(1): 220-32.

* cited by examiner

|  | Lebrikizumab (N = 88) | Placebo (N = 92) |
|---|---|---|
| Age (Years) | 45 (11) | 44 (13) |
| Gender (Female) | 61% | 65% |
| Race (White) | 86% | 86% |
| IL-13 Signature Surrogate Positive | 57% | 50% |
| IgE Median | 173 | 211 |
| Eosinophils | 0.2 (0.2) | 0.3 (0.2) |
| Periostin High | 41% | 51% |
| Weight | 87 (20) | 85 (19) |
| FEV1 % Predicted | 65 (11) | 67 (10) |
| LABA Use (YES) | 77.3% | 80.4% |
| High Dose ICS (≥500 mcg FP) | 51% | 63% |
| Never Smokers | 81% | 86% |
| Skin Test (Positive) | 86% (n=59) | 88% (n=60) |
| ACQ | 2.5 (0.9) | 2.6 (0.9) |
| FeNO | 30.0 (24.7) | 29.3 (27.6) |
| Eczema (Yes) | 6.8% | 18.5% |
| Allergic Rhinitis (Yes) | 76% | 75% |
| %Reversibility | 22.0 (18.3) | 18.1 (11.7) |

*FIG. 6*

| Time | 12 Weeks (95% CI) | | | 24 Weeks (95% CI) | | |
|---|---|---|---|---|---|---|
| Treatment Group | Lebrikizumab | Placebo | Lebrikizumab-Placebo | Lebrikizumab | Placebo | Lebrikizumab-Placebo |
| All Subjects N = 180 | 9.1% | 3.2% | 5.9% (0.9%, 10.9%) | 8.2% | 3.5% | 4.8% (0.3%, 9.3%) |
| IL-13 Signature + N = 96 | 9.0% | 2.8% | 6.2% (-0.2%, 12.6%) | 9.2% | 2.4% | 6.8% (0.5%, 13.1%) |
| IL-13 Signature - N = 84 | 9.1% | 3.5% | 5.6% (-2.4%, 13.5%) | 7.0% | 4.5% | 2.5% (-4.4%, 9.3%) |
| Periostin High (≥ Median) N = 83 | 11.8% | 1.8% | 10.0% (2.5%, 17.5%) | 8.2% | 2.2% | 6.1% (-1.4%, 13.6%) |
| Periostin Low (< Median) N = 97 | 7.2% | 4.6% | 2.5% (-4.1%, 9.2%) | 8.3% | 4.8% | 3.5% (-2.2%, 9.1%) |

FIG. 7

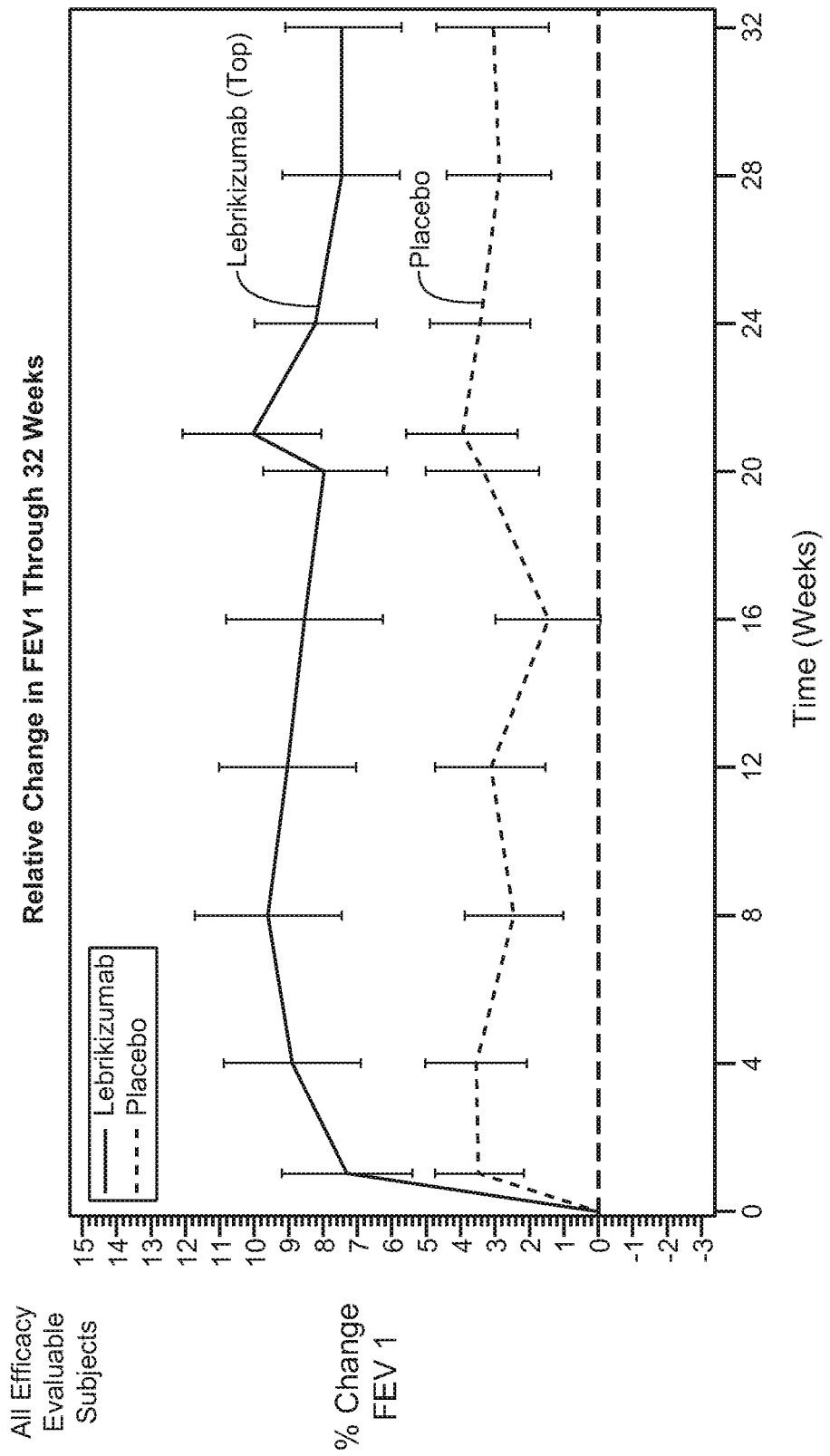

| Group | Rate Reduction in Exacerbations Over 24 Weeks (95% CI) p Value | Rate Reduction in *Severe* Exacerbations Over 24 Weeks (95% CI) p Value |
|---|---|---|
| All Patients (n = 180) | 37% (-22%, 67%) p = 0.17 | 51% (-33%, 82%) p = 0.16 |
| Periostin High* (n = 83) | 61% (-6%, 86%) p = 0.07 | 84% (14%, 97%) p = 0.03 |
| Periostin Low* (n = 97) | 25% (-73%, 68%) p = 0.50 | 9% (-228%, 75%) p = 0.89 |

*Defined by ≥ median periostin in all subjects.

|  | Lebrikizumab n = 106 | Placebo n = 112 | All n = 218 |
|---|---|---|---|
| Any Adverse Event | 79 (74.5%) | 87 (77.7%) | 166 (76.1%) |
| All SAEs | 4 (3.8%) | 6 (5.4%) | 10 (4.6%) |
| SAEs Related to Study Drug | 0 | 0 | 0 |
| Discontinuations Due to AEs | 5 (4.7%) | 3 (2.7%) | 8 (3.7%) |
| Mild AEs | 58 (54.7%) | 66 (58.9%) | 124 (56.9%) |
|    Mild Related AEs | 12 (11.3%) | 11 (9.8%) | 23 (10.6%) |
| Moderate AEs | 51 (48.1%) | 58 (51.8%) | 109 (50.0%) |
|    Moderate Related AEs | 9 (8.5%) | 7 (6.3%) | 16 (7.3%) |
| Severe AEs | 15 (14.2%) | 20 (17.9%) | 35 (16.1%) |
|    Severe Related AEs | 5 (4.7%) | 3 (2.7%) | 8 (3.7%) |
| Deaths | 0 | 0 | 0 |
| Pregnancies | 0 | 0 | 0 |
| Malignancies | 0 | 1 | 1 |

[1] n = Number of subjects with at least one event

|  | | Placebo | ebrikizumab | Δ | p-value |
|---|---|---|---|---|---|
| 1 Week | Periostin-LOW | -2.3% | -5.9% | -3.6% | 0.2 |
|  | Periostin-HIGH | -8.1% | -14.9% | -6.8% | 0.0006 |
|  | TOTAL | -5.4% | -9.8% | -4.4% | 0.003 |
|  | | Placebo | Lebrikizumab | Δ | p-value |
| 4 Weeks | Periostin-LOW | -4.0% | -6.5% | -2.5% | 0.6 |
|  | Periostin-HIGH | -7.1% | -17.2% | -10.1% | <0.0001 |
|  | TOTAL | -4.9% | -10.5% | -5.6% | 0.005 |
|  | | Placebo | Lebrikizumab | Δ | p-value |
| 12 Weeks | Periostin-LOW | -4.9% | -7.1% | -2.2% | 0.6 |
|  | Periostin-HIGH | -3.9% | -19.2% | -15.3% | <0.0001 |
|  | TOTAL | -4.6% | -12.3% | -7.7% | 0.0006 |
|  | | Placebo | Lebrikizumab | Δ | p-value |
| 24 Weeks | Periostin-LOW | -2.6% | -6.7% | -4.1% | 0.2 |
|  | Periostin-HIGH | -6.0% | -16.5% | -10.5% | 0.0003 |
|  | TOTAL | -4.6% | -10.7% | -6.1% | 0.002 |
|  | | Placebo | Lebrikizumab | Δ | p-value |
| 32 Weeks | Periostin-LOW | +0.3% | -3.0% | -3.3% | 0.02 |
|  | Periostin-HIGH | -7.4% | -14.1% | -6.7% | 0.009 |
|  | TOTAL | -2.2% | -8.9% | -6.7% | 0.005 |

*FIG. 19*

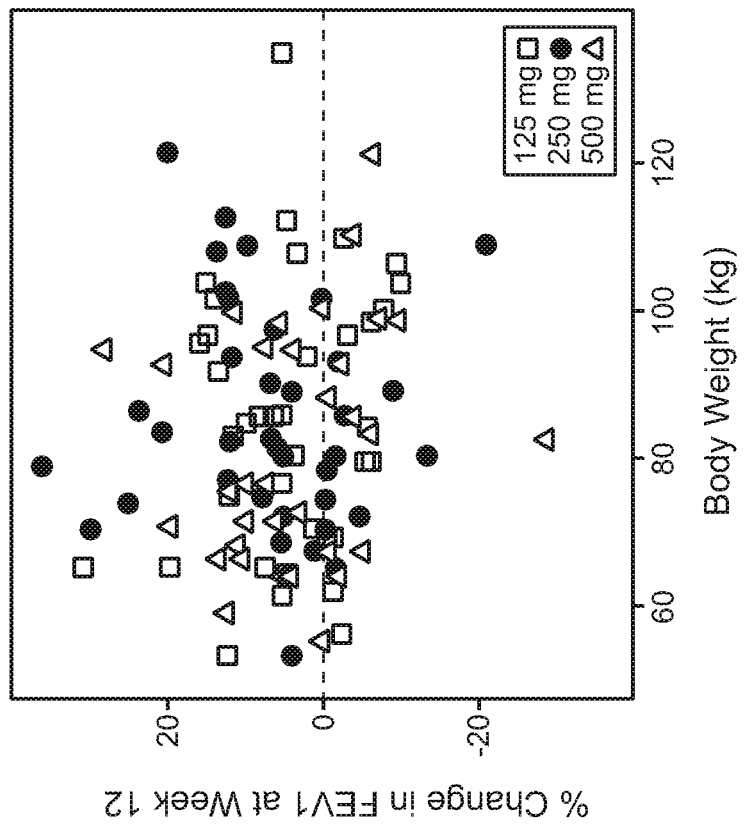
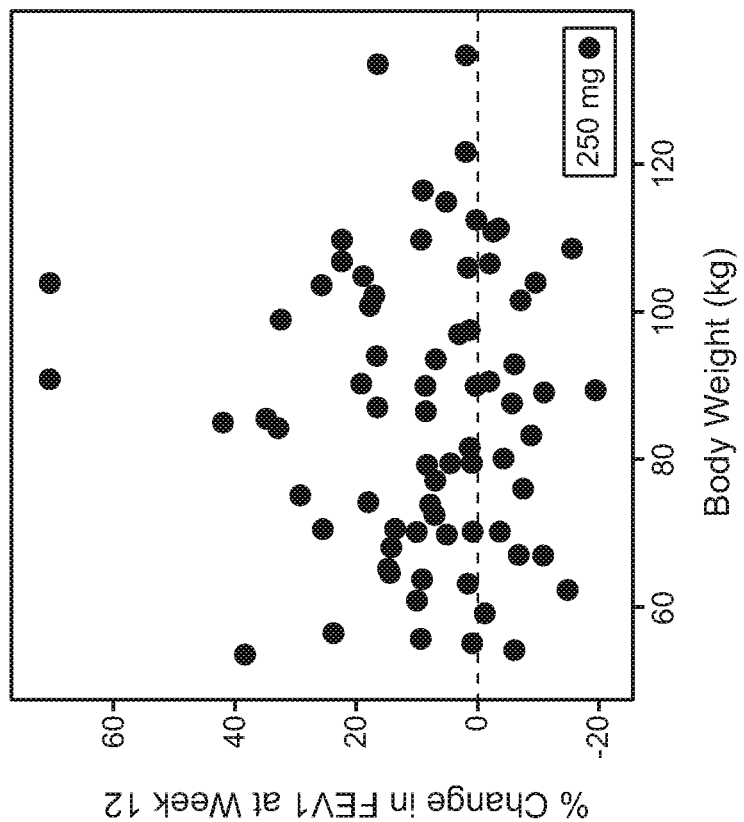
FIG. 20A
FIG. 20B

METHOD OF TREATING ASTHMA USING AN IL-13 ANTIBODY

CROSS REFERENCE TO RELATED APPLICATIONS

This application is a divisional of U.S. application Ser. No. 14/021,947, filed Sep. 9, 2013, now U.S. Pat. No. 9,995,755, which is a divisional of U.S. application Ser. No. 13/328,830, filed Dec. 16, 2011, now abandoned, which claims the benefit priority of provisional U.S. Application No. 61/459,760 filed Dec. 16, 2010, provisional U.S. Application No. 61/465,425 filed Mar. 18, 2011, provisional U.S. Application No. 61/484,650 filed May 10, 2011, provisional U.S. Application No. 61/574,485 filed Aug. 2, 2011, and provisional U.S. Application No. 61/557,295 filed Nov. 8, 2011, all of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on May 29, 2018, is named 12279_7955_999_SEQLIST.txt and is 73,217 bytes in size.

FIELD

Methods of diagnosing and treating disorders related to TH2 inhibition, including but not limited to asthma, are provided. Also provided are methods of selecting or identifying patients for treatment with certain therapeutic agents that are TH2 pathway inhibitors.

BACKGROUND

Asthma is a complex disease with increasing worldwide incidence. Among other events, eosinophilic inflammation has been reported in the airways of asthma patients. The pathophysiology of the disease is characterized by variable airflow obstruction, airway inflammation, mucus hypersecretion, and subepithelial fibrosis. Clinically, patients may present with cough, wheezing, and shortness of breath. While many patients are adequately treated with currently available therapies, some patients with asthma have persistent disease despite the use of current therapies.

A plethora of drugs are on the market or in development for treating asthma. One of the numerous targets for asthma therapy is IL-13. IL-13 is a pleiotropic TH2 cytokine produced by activated T cells, NKT cells, basophils, eosinophils, and mast cells, and it has been strongly implicated in the pathogenesis of asthma in preclinical models. Despite the many links between IL-13, IL-14 and asthma in the literature, many IL13 and/or IL14 antagonists therapies have had disappointing results in the clinic. Currently, no IL-13 or IL-14 antagonist therapy has been approved for use in asthma. Furthermore, moderate to severe asthmatic patients continue to lack good, alternative treatment options. Thus, there is a need to identify better therapies for treating asthma and improved methods for understanding how to treat asthma patients.

All references cited herein, including patent applications and publications, are incorporated by reference in their entirety for any purpose.

SUMMARY

This application provides therapeutic agents for inhibiting the TH2 pathway and better methods of using the same. This application also provides better methods for diagnosing disease for use in treating the disease optionally with the TH2 pathway inhibitor.

The methods of treatment and diagnosis as provided herein can be applied to patients suffering from asthma, eosinophilic disorder, respiratory disorders, IL-13 mediated disorder and/or IgE-mediated disorder, or symptoms related to those disorders. Patients suffering from asthma-like symptoms, include patients that have not been diagnosed with asthma may be treated according to the methods provided herein.

According to one embodiment, a patient treated according to the methods provided herein suffers from asthma, an eosinophilic disorder, a respiratory disorder, an IL-13 mediated disorder and/or an IgE-mediated disorder, or symptoms related to those disorders, and does not have cancer or a neoplasm. According to another embodiment, the patient treated according to the methods provided herein is suffering from asthma, eosinophilic disorder, respiratory disorders, IL-13 mediated disorder and/or IgE-mediated disorder, or symptoms related to those disorders, and is 12 years old or older, 18 years old or older or 19 years old or older, or between 12-17 years old or between 18-75 years old.

In one embodiment, a patient treated with a TH2 pathway inhibitor according to this invention is also treated with one, two, three or more therapeutic agents. In one embodiment, the patient is an asthma patient. According to one embodiment, the patient is treated with the TH2 pathway inhibitor and one, two, three or more therapeutic agents, wherein at least one therapeutic agent, other than the TH2 inhibitor, is a corticosteroid, a leukotriene antagonist, a LABA, a corticosteroid/LABA combination composition, a theophylline, cromolyn sodium, nedocromil sodium, omalizumab, a LAMA, a MABA, a 5-Lipoxygenase Activating Protein (FLAP) inhibitor, or an enzyme PDE-4 inhibitor. According to one aspect of the invention, a TH2 pathway inhibitor is administered to an asthma patient diagnosed as EIP status, wherein the diagnosis comprises the use of an EID assay (alone or in combination with other assays) to determine the EIP status. In one further embodiment, the asthma patient is uncontrolled on a corticosteroid prior to the treatment. In another embodiment, the asthma patient is also being treated with a second controller. In one embodiment, the second controller is a corticosteroid, a LABA or a leukotriene antagonist. In a further embodiment, the asthma patient is suffering from moderate to severe asthma. Thus, in one embodiment, the patient to be treated with the TH2 pathway inhibitor is a moderate to severe asthma patient who is uncontrolled on a corticosteroid prior to treatment with the TH2 pathway inhibitor, and then is treated with the TH2 pathway inhibitor and one, two, three or more controllers. In one embodiment, at least one of the controllers is a corticosteroid. In a further embodiment, such patient is treated with a TH2 pathway inhibitor, a corticosteroid and another controller. In another embodiment, the patient is suffering from mild asthma but is not being treated with a corticosteroid. It should be understood that the therapeutic agents may have different treatment cycles as compared with the TH2 inhibitor and, consequently can be administered at different times compared to the TH2 inhibitor as a part of the patient's treatment. Therefore, according to one embodiment, a method of treatment according to this invention comprises the steps of administering to a patient a TH2 pathway inhibitory and optionally, administering at least one, two or three additional therapeutic agents. In one embodiment, the TH2 pathway inhibitor is present in a composition with another therapeutic agent. In another embodiment, the TH2 pathway inhibitor is not present in a composition with another therapeutic agent.

According to another embodiment, the invention comprises a method for treating asthma comprising administering an anti-IL-13 antibody comprising a VH comprising SEQ ID NO:9 and VL comprising SEQ ID NO:10 or an anti-IL13 antibody comprising HVRH1, HVRH2, HVRH3, HVRL1, HVRL2, and HVRL3, the respective HVRs having the amino acid sequence of SEQ ID NO.: 11, SEQ ID NO.: 12, SEQ ID NO.: 13, SEQ ID NO.: 14, SEQ ID NO.: 15, and SEQ ID NO.: 16 as a flat dose. In one embodiment an anti-IL13 antibody comprising a VH comprising SEQ ID NO:9 and VL comprising SEQ ID NO:10 is administered as a 125-1000 mg flat dose (i.e., not weight dependent), by subcutaneous injection or by intravenous injection, at a frequency of time selected from: every 2 weeks, every 3 weeks, and every 4 weeks. In one embodiment an anti-IL13 antibody comprising HVRH1, HVRH2, HVRH3, HVRL1, HVRL2, and HVRL3, the respective HVRs having the amino acid sequence of SEQ ID NO.: 11, SEQ ID NO.: 12, SEQ ID NO.: 13, SEQ ID NO.: 14, SEQ ID NO.: 15, and SEQ ID NO.: 16 is administered as a 125-1000 mg flat dose (i.e., not weight dependent), by subcutaneous injection or by intravenous injection, at a frequency of time selected from: every 2 weeks, every 3 weeks, and every 4 weeks. In one embodiment, the anti-IL13 antibody is lebrikizumab, which is administered as a 125-1000 mg flat dose (i.e., not weight dependent), by subcutaneous injection or by intravenous injection, at a frequency of time selected from: every 2 weeks, every 3 weeks, and every 4 weeks. In another embodiment, the patient is diagnosed with EIP status using a Total Periostin Assay to determine EIP status.

According to another embodiment, an antibody comprising a VH comprising SEQ ID NO:9 and VL comprising SEQ ID NO:10 is administered to treat asthma in a therapeutically effective amount sufficient to reduce the rate of exacerbations of the patient over time or improve FEV1. In yet another embodiment, the invention comprises a method for treating asthma comprising administering an anti-IL-13 antibody comprising a VH comprising SEQ ID NO:9 and VL comprising SEQ ID NO:10 or an anti-IL13 antibody comprising HVRH1, HVRH2, HVRH3, HVRL1, HVRL2, and HVRL3, the respective HVRs having the amino acid sequence of SEQ ID NO.: 11, SEQ ID NO.: 12, SEQ ID NO.: 13, SEQ ID NO.: 14, SEQ ID NO.: 15, and SEQ ID NO.: 16 as a flat dose (i.e., not weight dependent) of 37.5 mg, or a flat dose of 125 mg, or a flat dose of 250 mg. In certain embodiments, the dose is administered by subcutaneous injection once every 4 weeks for a period of time. In certain embodiments, the period of time is 6 months, one year, two years, five years, ten years, 15 years, 20 years, or the lifetime of the patient. In certain embodiments, the asthma is severe asthma and the patient is inadequately controlled or uncontrolled on inhaled corticosteroids plus a second controller medication. In another embodiment, the patient is diagnosed with EIP status using a Total Periostin Assay to determine EIP status and the patient is selected for treatment with an anti-IL13 antibody as described above. In another embodiment, the method comprises treating an asthma patient with an anti-IL13 antibody as described above where the patient was previously diagnosed with EIP status using a Total Periostin Assay to determine EIP status. In one embodiment, the asthma patient is age 18 or older. In one embodiment, the asthma patient is age 12 to 17 and the anti-IL13 is administered in as a flat dose of 250 mg or a flat dose of 125 mg. In one embodiment, the asthma patient is age 6 to 11 and the anti-IL13 antibody is administered in as a flat dose of 125 mg or a flat dose of 62.5 mg.

The present invention provides a periostin assay. In one embodiment, the periostin assay is a Total Periostin Assay. In another embodiment, the Total Periostin Assay comprises the use of one or more of the anti-periostin antibodies of this invention to bind to the Total Periostin in a biological sample obtained from a patient. In yet another embodiment of this invention, the biological sample is serum obtained from whole blood. In one embodiment, the biological sample is obtained from an asthma patient. In a further embodiment, the asthma patient is a moderate to severe asthma patient. In yet a further embodiment the moderate to severe asthma patient is uncontrolled on a corticosteroid and optionally, is being treated with one, two, three or more controllers.

The anti-periostin assays and antibody assays disclosed herein can be used for other diseases in which periostin is elevated such as idiopathic pulmonary fibrosis (IPF), non-specific interstitial pneumonia (NSIP), and cancer.

The present invention provides a therapeutic agent that is a TH2 pathway inhibitor for use in treating asthma or a respiratory disorder in a patient, wherein the patient expresses elevated levels of total periostin. In one embodiment, the target for inhibition in the TH2 pathway is selected from: IL-9, IL-5, IL-13, IL-4, OX40L, TSLP, IL-25, IL-33 and IgE; and receptors such as: IL-9 receptor, IL-5 receptor, IL-4receptor alpha, IL-13receptoralpha1 and IL-13receptoralpha2, OX40, TSLP-R, IL-7Ralpha (a co-receptor for TSLP), IL17RB (receptor for IL-25), ST2 (receptor for IL-33), CCR3, CCR4, CRTH2, FcepsilonRI and FcepsilonRII/CD23 (receptors for IgE). In one embodiment, the patient to be treated according to the methods of the present invention is suffering from mild to severe asthma, optionally moderate to severe asthma, and whose asthma is uncontrolled on a corticosteroid. In a further embodiment, the serum level of Total Periostin in the moderate to severe asthmatic patient who is uncontrolled on a corticosteroid is greater than 20 ng/ml, 21 ng/ml, 22 ng/ml, 23 ng/ml, 24 ng/ml or 25 ng/ml in a E4 Assay. In yet a further embodiment, the patient to be treated additionally has elevated expression levels of any one, combination or all CEA, TARC (CCL17) and MCP-4 (CCL13) mRNAs or proteins. In yet a further embodiment, the patient to be treated in addition to having elevated expression levels of periostin as described herein, has a $FE_{NO}$ level greater than 21 ppb, or greater than 35 ppb.

The present invention provides the use of a therapeutic agent that binds a TH2 induced asthma pathway target in the preparation of a medicament for the treatment of a patient having asthma or a respiratory disorder, wherein the patient expresses elevated levels of total periostin, and wherein the target is IL-9, IL-5, IL-13, IL-4, OX40L, TSLP, IL-25, IL-33 and IgE; and receptors such as: IL-9 receptor, IL-5 receptor, IL-4receptor alpha, IL-13receptoralpha1 and IL-13receptoralpha2, OX40, TSLP-R, IL-7Ralpha (a co-receptor for TSLP), IL17RB (receptor for IL-25), ST2 (receptor for IL-33), CCR3, CCR4, CRTH2, FcepsilonRI or FcepsilonRII/CD23 (receptors for IgE). In one embodiment, the patient is EIP. According to one embodiment, the patient was determined to have EIP by using an assay according to this invention, in yet another embodiment, the assay is a Total Periostin Assay. In another embodiment, the assay measures the level of Total Periostin in a biological sample obtained from the patient. In one embodiment, the assay measures the level of Total Periostin protein in the serum sample obtained from the patient.

The present invention comprises a kit or article for manufacture for diagnosing an asthma subtype in a patient comprising:

(1) determining the levels of Total Periostin in a serum sample obtained from the patient and optionally the protein expressions levels for one or more proteins selected from TARC and MCP-4; and (2) instructions for measuring the expression levels of the Total Periostin and optionally the TARC and/or MCP-4 proteins in the serum sample, wherein the elevated expression levels of any one, combination or all of said proteins is indicative of the asthma subtype.

In yet another embodiment, methods of identifying an asthma patient or a respiratory disorder patient who is likely to be responsive to treatment with a TH2 Pathway Inhibitor are provided. In certain embodiments, the methods comprise determining whether the patient is Eosinophilic Inflammation Positive (EIP) using an Eosinophilic Inflammation Diagnostic Assay (EIDA), wherein the EIP status indicates that the patient is likely to be responsive to treatment with a TH2 Pathway Inhibitor.

In another embodiment, methods of identifying an asthma patient or a respiratory disorder patient who is likely to suffer from severe exacerbations are provided. In certain embodiments, the methods comprise determining whether the patient is EIP using an EIDA, wherein the EIP status indicates that the patient is likely to suffer from an increase in severe exacerbations.

In yet still another embodiment, methods of identifying an asthma patient or a respiratory disorder patient who is less likely to be responsive to treatment with a TH2 Pathway Inhibitor are provided. In certain embodiments, the methods comprise determining whether the patient is Eosinophilic Inflammation Negative (EIN) using an EIDA, wherein the EIN status indicates that the patient is less likely to be responsive to treatment with the TH2 Pathway Inhibitor.

In another embodiment, methods of monitoring an asthma patient being treated with a TH2 Pathway inhibitor are provided. In certain embodiments, the methods comprise determining whether the patient is EIP or EIN using an EIDA. In one embodiment, the method comprises determining a treatment regimen for the TH2 Pathway Inhibitor. In one embodiment, the determination of EIP indicates continuing therapy with the TH2 Pathway Inhibitor and the determination of EIN indicates discontinuing therapy with the TH2 Pathway Inhibitor.

In certain embodiments, the EIDA used in methods described above comprises the steps of: (a) determining the amount of Total Periostin in a sample obtained from an asthma patient; (b) comparing the amount of Total Periostin determined in step (a) to a reference amount; and (c) stratifying said patient into the category of responder or non-responder based on the comparison obtained in step (b). In certain embodiments, the Total Periostin is serum periostin, which periostin is a measured using an immunoassay. In certain embodiments, the immunoassay is a sandwich immunoassay. In certain embodiments, the sandwich immunoassay is performed by an Elecsys® analyzer (Roche Diagnostics GmbH). In certain embodiments, the sandwich immunoassay is an E4 Assay. In one embodiment, the reference amount for EIP is 23 ng/ml greater when using the E4 Assay in step (a). In one embodiment, the reference amount for EIP is 50 ng/ml or greater when using the Elecsys® analyzer in step (a). In one embodiment, the reference amount for EIN is 21 ng/ml or lower when using the E4 Assay in step (a). In one embodiment, the reference amount for EIN is 48 ng/ml or lower when using the Elecsys® analyzer in step (a).

In certain embodiments, the patient according to the methods described above is suffering from moderate to severe asthma. In certain embodiments, the asthma or respiratory disorder is uncontrolled on a corticosteroid. In certain embodiments, the corticosteroid is an inhaled corticosteroid. In certain embodiments, the inhaled corticosteroid is Qvar®, Pulmicort®, Symbicort®, Aerobid®, Flovent®, Flonase®, Advair® or Azmacort®. In one embodiment, the patient is also being treated with a second controller. In certain embodiments, the second controller is a long acting bronchial dilator (LABD). In certain embodiments, the LABD is a long-acting beta-2 agonist (LABA) leukotriene receptor antagonist (LTRA), long-acting muscarinic antagonist (LAMA), theophylline, or oral corticosteroids (OCS). In certain embodiments, the LABD is Symbicort®, Advair®, Brovana®, Foradil®, Perforomist™ or Serevent®.

In certain embodiments, the TH2 Pathway Inhibitor according to the methods above inhibits the target ITK, BTK, IL-9 (e.g., MEDI-528), IL-5 (e.g., Mepolizumab, CAS No. 196078-29-2; resilizumab), IL-13 (e.g., IMA-026, IMA-638 (also referred to as, anrukinzumab, INN No. 910649-32-0; QAX-576; IL4/IL13 trap), tralokinumab (also referred to as CAT-354, CAS No. 1044515-88-9); AER-001, ABT-308 (also referred to as humanized 13C5.5 antibody), IL-4 (e.g., AER-001, IL4/IL13 trap), OX40L, TSLP, IL-25, IL-33 and IgE (e.g., XOLAIR, QGE-031; MEDI-4212); and receptors such as: IL-9 receptor, IL-5 receptor (e.g., MEDI-563 (benralizumab, CAS No. 1044511-01-4), IL-4receptor alpha (e.g., AMG-317, AIR-645), IL-13receptoralpha1 (e.g., R-1671) and IL-13receptoralpha2, OX40, TSLP-R, IL-7Ralpha (a co-receptor for TSLP), IL17RB (receptor for IL-25), ST2 (receptor for IL-33), CCR3, CCR4, CRTH2 (e.g., AMG-853, AP768, AP-761, MLN6095, ACT129968), FcepsilonRI, FcepsilonRII/CD23 (receptors for IgE), Flap (e.g., GSK2190915), Syk kinase (R-343, PF3526299); CCR4 (AMG-761), TLR9 (QAX-935), or is a multi-cytokine inhibitor of CCR3, IL5, IL3, GM-CSF (e.g., TPI ASM8). In certain embodiments, the TH2 Pathway Inhibitor is an anti-IL13/IL4 pathway inhibitor or an anti IgE binding agent. In certain embodiments, the TH2 Pathway Inhibitor is an anti-anti-IL-13 antibody. In certain embodiments, the anti-IL-13 antibody is an antibody comprising a VH comprising SEQ ID NO:9 and VL comprising SEQ ID NO:10, an anti-IL13 antibody comprising HVRH1, HVRH2, HVRH3, HVRL1, HVRL2, and HVRL3, the respective HVRs having the amino acid sequence of SEQ ID NO.: 11, SEQ ID NO.: 12, SEQ ID NO.: 13, SEQ ID NO.: 14, SEQ ID NO.: 15, and SEQ ID NO.: 16 or lebrikizumab. In certain embodiments, the anti-IL-13 antibody is a bispecific antibody that also binds IL-4. In certain embodiments, the TH2 Pathway Inhibitor is an anti-IgE antibody. In certain embodiments, the anti-IgE antibody is (i) the XOLAIR® antibody, (ii) anti-M1' antibody comprising a variable heavy chain and a variable light chain, wherein the variable heavy chain is SEQ ID NO:24 and the variable light chain SEQ ID NO:25 or (iii) an anti-M1' antibody comprising a variable heavy chain and a variable light chain, wherein the variable heavy chain further comprises an HVR-H1, HVR-H2 and HVR-H3, and the variable light chain further comprises and HVR-L1, HVR, L2 and HVR-L3 and: (a) the HVR-H1 is residues 26-35 of SEQ ID NO:24, [GFTFSDYGIA]; (b) the HVR-H2 is residues 49-66 of SEQ ID NO:24, [AFISDLAY-TIYYADTVTG]; (c) the HVR-H3 is residues 97-106 of SEQ ID NO:24, [ARDNWDAMDY]; (d) the HVR-L1 is residues 24-39 of SEQ ID NO:25, [RSSQSLVHNNAN- TYLH]; (e) the HVR-L2 is residues 55-61 of SEQ NO:25, [KVSNRFS]; (f) the HVR-L3 is residues 94-102 of SEQ ID NO:25 [SQNTLVPWT].

In another aspect, uses of a kit for detecting Total Periostin in a sample obtained from an asthma patient for stratifying/classifying asthma patients into likely responders and non-responders for therapeutic treatment with a TH2 Pathway Inhibitor. In certain embodiments, the Total Periostin is detected using an EIDA, which EIDA comprises the steps of: (a) determining the amount of Total Periostin in a sample obtained from an asthma patient; (b) comparing the amount of Total Periostin determined in step (a) to a reference amount; and (c) stratifying said patient into the category of responder or non-responder based on the comparison obtained in step (b). In certain embodiments, the Total Periostin is serum periostin, which periostin is a measured using an immunoassay. In certain embodiments, the immunoassay is a sandwich immunoassay. In certain embodiments, the sandwich immunoassay is performed by an Elecsys® analyzer (Roche Diagnostics GmbH). In certain embodiments, the sandwich immunoassay is an E4 Assay. In one embodiment, the reference amount for EIP is 23 ng/ml greater when using the E4 Assay in step (a). In one embodiment, the reference amount for EIP is 50 ng/ml or greater when using the Elecsys® analyzer in step (a).

In certain embodiments, the patient according to the uses described in the paragraph above is suffering from moderate to severe asthma. In certain embodiments, the asthma or respiratory disorder is uncontrolled on a corticosteroid. In certain embodiments, the corticosteroid is an inhaled corticosteroid. In certain embodiments, the inhaled corticosteroid is Qvar®, Pulmicort®, Symbicort®, Aerobid®, Flovent®, Flonase®, Advair® or Azmacort®. In one embodiment, the patient is also being treated with a second controller. In certain embodiments, the second controller is a long acting bronchial dilator (LABD). In certain embodiments, the LABD is a long-acting beta-2 agonist (LABA), leukotriene receptor antagonist (LTRA), long-acting muscarinic antagonist (LAMA), theophylline, or oral corticosteroids (OCS). In certain embodiments, the LABD is Symbicort®, Advair® Brovana®, Foradil®, Perforomist™ or Serevent®.

In certain embodiments, the TH2 Pathway Inhibitor according to the uses above inhibits the target ITK, BTK, IL-9 (e.g., MEDI-528), IL-5 (e.g., Mepolizumab, CAS No. 196078-29-2; resilizumab), IL-13 (e.g., IMA-026, IMA-638 (also referred to as, anrukinzumab, INN No. 910649-32-0; QAX-576; IL4/IL13 trap), tralokinumab (also referred to as CAT-354, CAS No. 1044515-88-9); AER-001, ABT-308 (also referred to as humanized 13C5.5 antibody), IL-4 (e.g., AER-001, IL4/IL13 trap), OX40L, TSLP, IL-25, IL-33 and IgE (e.g., XOLAIR, QGE-031; MEDI-4212); and receptors such as: IL-9 receptor, IL-5 receptor (e.g., MEDI-563 (benralizumab, CAS No. 1044511-01-4), IL-4receptor alpha (e.g., AMG-317, AIR-645), IL-13receptoralpha1 (e.g., R-1671) and IL-13receptoralpha2, OX40, TSLP-R, IL-7Ralpha (a co-receptor for TSLP), IL17RB (receptor for IL-25), ST2 (receptor for IL-33), CCR3, CCR4, CRTH2 (e.g., AMG-853, AP768, AP-761, MLN6095, ACT129968), FcepsilonRI, FcepsilonRII/CD23 (receptors for IgE), Flap (e.g., GSK2190915), Syk kinase (R-343, PF3526299); CCR4 (AMG-761), TLR9 (QAX-935) or is a multi-cytokine inhibitor of CCR3, IL5, IL3, GM-CSF (e.g., TPI ASM8). In certain embodiments, the TH2 Pathway Inhibitor is an anti-IL13/IL4 pathway inhibitor or an anti IgE binding agent. In certain embodiments, the TH2 Pathway Inhibitor is an anti-anti-IL-13 antibody. In certain embodiments, the anti-IL-13 antibody is an antibody comprising a VH comprising SEQ ID NO:9 and VL comprising SEQ ID NO:10, an anti-IL13 antibody comprising HVRH1, HVRH2, HVRH3, HVRL1, HVRL2, and HVRL3, the respective HVRs having the amino acid sequence of SEQ ID NO.: 11, SEQ ID NO.: 12, SEQ ID NO.: 13, SEQ ID NO.: 14, SEQ ID NO.: 15, and SEQ ID NO.: 16 or lebrikizumab. In certain embodiments, the anti-IL-13 antibody is a bispecific antibody that also binds IL-4. In certain embodiments, the TH2 Pathway Inhibitor is an anti-IgE antibody. In certain embodiments, the anti-IgE antibody is (i) the XOLAIR® antibody, (ii) anti-M1' antibody comprising a variable heavy chain and a variable light chain, wherein the variable heavy chain is SEQ ID NO:24 and the variable light chain is SEQ ID NO:25 or (iii) an anti-M1' antibody comprising a variable heavy chain and a variable light chain, wherein the variable heavy chain further comprises an HVR-H1, HVR-H2 and HVR-H3, and the variable light chain further comprises and HVR-L1, HVR, L2 and HVR-L3 and: (a) the HVR-H1 is residues 26-35 of SEQ ID NO:24, [GFTFSDYGIA]; (b) the HVR-H2 is residues 49-66 of SEQ ID NO:24, [AFISDLAY-TIYYADTVTG]; (c) the HVR-H3 is residues 97-106 of SEQ ID NO:24, [ARDNWDAMDY]; (d) the HVR-L1 is residues 24-39 of SEQ ID NO:25, [RSSQSLVHNNAN-TYLH]; (e) the HVR-L2 is residues 55-61 of SEQ ID NO:25, [KVSNRFS]; (f) the HVR-L3 is residues 94-102 of SEQ ID NO:25 [SQNTLVPWT].

In yet another aspect, kits for measuring the Total Periostin in a biological sample obtained from an asthma patient or a patient suffering from a respiratory disorder are provided, wherein the kit comprises a first nucleic acid molecule that hybridizes to a second nucleic acid molecule, wherein the second nucleic acid molecule encodes Total Periostin or a portion thereof, or the kit comprises an antibody that binds to Total Periostin. In certain embodiments, the kit comprises a package insert containing information describing the uses provided above.

In still yet another aspect, kits for diagnosing an asthma subtype in a patient are provided, the kits comprising: (1) determining the levels of Total Periostin in a serum sample obtained from the patient and optionally the protein expressions levels in the serum sample for one or more proteins selected from TARC and MCP-4; and (2) instructions for measuring the levels of the Total Periostin and optionally TARC and/or MCP-4 in the serum sample, wherein the elevated expression levels of any one, combination or all of said proteins is indicative of the asthma subtype. In certain embodiments, the kit further comprises a package insert for determining whether an asthma patient or respiratory disorder patient is EIP or EIN. In certain embodiments, the kit further comprises a package insert for determining whether an asthma patient is likely to respond to a TH2 Pathway Inhibitor. In certain embodiments, the kit further comprises a package insert containing information describing any of the uses provided above. In certain embodiments, the kit further comprises an empty container to hold a biological sample. In certain embodiments, the kit comprises two anti-periostin antibodies for use in an immunoassay for determining Total Periostin levels.

In another aspect, methods of treating an asthma or a respiratory disorder comprising administering an anti-IL-13 antibody comprising HVRH1, HVRH2, HVRH3, HVRL1, HVRL2, and HVRL3, the respective HVRs having the amino acid sequence of SEQ ID NO.: 11, SEQ ID NO.: 12, SEQ ID NO.: 13, SEQ ID NO.: 14, SEQ ID NO.: 15, and SEQ ID NO.: 16 to a patient suffering from asthma or a respiratory disorder in a 125-500 mg flat dose every 2-8 weeks, in certain embodiments, the patient is suffering from moderate to severe asthma. In certain embodiments, the asthma or respiratory disorder is uncontrolled on a corticosteroid. In certain embodiments, the asthma or respiratory disorder is uncontrolled on an inhaled corticosteroid. In certain embodiments, the asthma or respiratory disorder is uncontrolled on a total daily dose of at least 500 mcg fluticasone propionate (FP). In certain embodiments, the corticosteroid is an inhaled corticosteroid is Qvar®, Pulmicort®, Symbicort®, Aerobid®, Flovent®, Flonase®, Advair®, Azmacort®. In certain embodiments, the patient is being treated with a second controller. In certain embodiments, the patient is continuing to be treated with a corticosteroid, optionally an inhaled corticosteroid, during the treatment with the anti-IL13 antibody. In certain embodiments, the patient is continuing to be treated with a second controller during the treatment with the anti-IL-13 antibody. In certain embodiments, the second controller is a long acting bronchial dilator. In certain embodiments, the long acting bronchial dilator is a LABA, LTRA, LAMA, theophylline, or OCS. In certain embodiments, the patient has been determined to be EIP. In certain embodiments, the patient has been determined to be EIP using a kit a described above. In certain embodiments, the patient has been determined to be EIP using a method as described above. In certain embodiments, the patient is administered a flat dose of 125 mg or 250 mg every four weeks. In certain embodiments, the patient is 18 years or older, or the patient is 12-17 years old or 12 years old and older, or the patient is 6-11 years old or 6 years old and older.

In certain embodiments, the anti-IL-13 antibody is administered subcutaneously. In certain embodiments, the anti-IL-13 antibody is administered using a prefilled syringe or autoinjector device. In certain embodiments, the asthma patient to be treated according to the methods above is 18 years old or older and has serum periostin at ≥50 ng/mL and is uncontrolled on an inhaled corticosteroid and a second controller medication. In certain embodiments, the serum periostin is measured using an immunoassay, which immunoassay is selected from Elecsys® periostin assay and E4 Assay. In certain embodiments, the serum periostin is measured using a kit as described above. In certain embodiments, the anti-IL-13 antibody is an antibody comprising a VH comprising SEQ ID NO:9 and a VL comprising SEQ ID NO:10. In certain embodiments, the anti-IL-13 antibody is lebrikizumab. In certain embodiments, the asthma patient to be treated according to the methods described above is 12 years old and above and uncontrolled on an inhaled corticosteroid and a second controller medication.

In yet another aspect, methods of treating asthma or a respiratory disease comprising administering a therapeutically effective amount of lebrikizumab to the patient are provided, in certain embodiments, the treatment results in a relative improvement in FEV1 of greater than 5% compared to before treatment with lebrikizumab. In certain embodiments, the relative improvement in FEV1 is greater than 8% compared to before treatment with lebrikizumab. In certain embodiments, the treatment results in a reduction in severe exacerbations.

In still another aspect, methods of treating of a patient suffering from asthma or a respiratory disease comprising administering a TH2 Pathway Inhibitor to the patient diagnosed as EIP are provided. In certain embodiments, the methods comprise the step of diagnosing the patient as EIP using a Total Periostin assay. In certain embodiments, the methods further comprise the step of retreating the patient with the TH2 Pathway Inhibitor if the patient is determined to be EIP. In certain embodiments, serum from the patient is used to determine whether the patient is EIP.

In certain embodiments, the EIP status determined according to the methods above uses an EIDA comprising the steps of: (a) determining the amount of Total Periostin in a sample obtained from the patient; (b) comparing the amount of Total Periostin determined in step (a) to a reference amount; and (c) stratifying said patient into the category of responder or non-responder based on the comparison obtained in step (b). In certain embodiments, the Total Periostin is serum periostin, which periostin is a measured using an immunoassay. In certain embodiments, the immunoassay is a sandwich immunoassay. In certain embodiments, the sandwich immunoassay is performed by an Elecsys® analyzer (Roche Diagnostics GmbH). In certain embodiments, the sandwich immunoassay is an E4 Assay. In one embodiment, the reference amount for EIP is 23 ng/ml greater when using the E4 Assay in step (a). In one embodiment, the reference amount for EIP is 50 ng/ml or greater when using the Elecsys® analyzer in step (a).

In certain embodiments, the patient according to the methods described above is suffering from moderate to severe asthma. In certain embodiments, the asthma or respiratory disorder is uncontrolled on a corticosteroid. In certain embodiments, the corticosteroid is an inhaled corticosteroid. In certain embodiments, the inhaled corticosteroid is Qvar®, Pulmicort®, Symbicort®, Aerobid®, Flovent®, Flonase®, Advair® or Azmacort®. In one embodiment, the patient is also being treated with a second controller. In certain embodiments, the second controller is a long acting bronchial dilator (LABD). In certain embodiments, the LABD is a long-acting beta-2 agonist (LABA), leukotriene receptor antagonist (LTRA), long-acting muscarinic antagonist (LAMA), theophylline, or oral corticosteroids (OCS). In certain embodiments, the LABD is Symbicort®, Advair®, Brovana®, Foradil®, Peroromist™ or Serevent®).

In certain embodiments, the TH2 Pathway Inhibitor according to the methods above inhibits the target ITK, BTK, IL-9 (e.g., MEDI-528), IL-5 (e.g., Mepolizumab, CAS No. 196078-29-2; resilizumab), IL-13 (e.g., IMA-026, IMA-638 (also referred to as, anrukinzumab, INN No. 910649-32-0; QAX-576; IL4/IL13 trap), tralokinumab (also referred to as CAT-354, CAS No. 1044515-88-9); AER-001, ABT-308 (also referred to as humanized 13C5.5 antibody), IL-4 (e.g., AER-001, IL4/IL13 trap), OX40L, TSLP, IL-25, IL-33 and IgE (e.g., XOLAIR®, QGE-031; MEDI-4212); and receptors such as: IL-9 receptor, IL-5 receptor (e.g., MEDI-56 3 (benralizumab, CAS No. 1044511-01-4), IL-4receptor alpha (e.g., AMG-317, AIR-645), IL-13receptoralpha1 (e.g., R-1671) and IL-13receptoralpha2, OX40, TSLP-R, IL-7Ralpha (a co-receptor for TSLP), IL17RB (receptor for IL-25), ST2 (receptor for IL-33), CCR3, CCR4, CRTH2 (e.g., AMG-853, AP768, AP-761, MLN6095, ACT129968), FcepsilonRI, FcepsilonRII/CD23 (receptors for IgE), Flap (e.g., GSK2190915), Syk kinase (R-343, PF3526299); CCR4 (AMG-761), TLR9 (QAX-935), or is a multi-cytokine inhibitor of CCR3, IL5, IL3, GM-CSF (e.g., TPI ASM8). In certain embodiments, the TH2 Pathway Inhibitor is an anti-IL13/IL4 pathway inhibitor or an anti IgE binding agent. In certain embodiments, the TH2 Pathway Inhibitor is an anti-anti-IL-13 antibody. In certain embodiments, the anti-IL-13 antibody is an antibody comprising a VH comprising SEQ ID NO:9 and VL comprising SEQ ID NO:10, an anti-IL13 antibody comprising HVRH1, HVRH2, HVRH3, HVRL1, HVRL2, and HVRL3, the respective HVRs having the amino acid sequence of SEQ ID NO.: 11, SEQ ID NO.: 12, SEQ ID NO.: 13, SEQ ID NO.: 14, SEQ ID NO.: 15, and SEQ ID NO.: 16 or lebrikizumab. In certain embodiments, the anti-IL-13 antibody is a bispecific antibody that also binds IL-4.

In certain embodiments, the TH2 Pathway Inhibitor is an anti-IgE antibody. In certain embodiments, the anti-IgE antibody is (i) the XOLAIR® antibody, (ii) anti-M1' antibody comprising a variable heavy chain and a variable light chain, wherein the variable heavy chain is SEQ ID NO:24 and the variable light chain is SEQ ID NO:25 or (iii) an anti-M1' antibody comprising a variable heavy chain and a variable light chain, wherein the variable heavy chain further comprises an HVR-H1, HVR-H2 and HVR-H3, and the variable light chain further comprises and HVR-L1, HVR, L2 and HVR-L3 and: (a) the HVR-H1 is residues 26-35 of SEQ ID NO:24, [GFTFSDYGIA]; (b) the HVR-H2 is residues 49-66 of SEQ ID NO:24, [AFISDLAYTIYY-ADTVTG]; (c) the HVR-H3 is residues 97-106 of SEQ ID NO:24, [ARDNWDAMDY]; (d) the HVR-L1 is residues 24-39 of SEQ ID NO:25, [RSSQSLVHNNANTYLH]; (e) the HVR-L2 is residues 55-61 of SEQ ID NO:25, [KVSNRFS]; (f) the HVR-L3 is residues 94-102 of SEQ ID NO:25 [SQNTLVPWT].

In another aspect, methods for evaluating adverse events in a patient associated with treatment of asthma with lebrikizumab are provided. In certain embodiments, the methods comprise the steps of monitoring the number and/or severity of events that are exacerbations, community-acquired pneumonia, anaphylaxis, musculoskeletal pains, musculoskeletal disorders, connective tissue pains or connective tissue disorders. In certain embodiments, the musculoskeletal or connective tissue disorder is arthralgia, back pain, pain in extremity, myalgia, neck pain, arthritis, bone development abnormalities, bursitis, costochondritis, exostosis flank pain, musculoskeletal chest pain, musculoskeletal pain, pain in jaw or tendinitis.

In yet another aspect, anti-periostin antibodies are provided. In certain embodiments, the anti-periostin antibody comprises the HVR sequences of SEQ ID NO:1 and the HVR sequences of SEQ ID NO:2. In certain embodiments, the anti-periostin antibody comprises the sequences of SEQ ID NO:1 and SEQ ID NO:2. In certain embodiments, the anti-periostin antibody comprises the HVR sequences of SEQ ID NO:3 and the HVR sequences of SEQ ID NO:4. In certain embodiments, the anti-periostin antibody comprises the sequences of SEQ ID NO:3 and SEQ ID NO:4. In certain embodiments, Total Periostin Assays comprising the use of the above anti-periostin antibodies are provided.

BRIEF DESCRIPTION OF THE DRAWINGS

(FIG. 3C) Reductions in IgE, CCL13, and CCL17 at Week 13 in individual patients relative to baseline levels of those markers.

FIG. 6 provides the baseline characteristics of patients participating in the asthma trial of Example 2.

FIG. 7 provides results from the asthma trial of Example 2.

FIGS. 8A-8B provide FEV1 results from the asthma trial of Example 2 for all efficacy evaluable subjects (FIG. 8A) and for periostin high subjects only (FIG. 8B).

(FIG. 14A) correlation between visit 1 and visit 2; (FIG. 14B) correlation between visit 1 and visit 3; (FIG. 14C) correlation between visit 2 and visit 3; (FIG. 14D) correlation between visit 1 and the mean serum periostin level across all visits; (FIG. 14E) correlation between visit 2 and the mean serum periostin level across all visits; and (FIG. 14F) correlation between visit 3 and the mean serum periostin level across all visits.

(FIG. 15A) Asthmatics with >3% sputum eosinophils had significantly elevated $FE_{NO}$ compared to asthmatics with <3% sputum eosinophils (p<0.001 by Wilcoxon rank-sum test). (FIG. 15B) Asthmatics with >22 eosinophils/mm2 total bronchial tissue had a trend for elevated $FE_{NO}$ compared to asthmatics with <22 eosinophils/mm2 total bronchial tissue (p=0.07 by Wilcoxon rank-sum test). (FIG. 15C) A composite airway eosinophil score where 0=sputum eosinophils <3% AND tissue ("Bx") eosinophils <22/mm2; 1=EITHER sputum eosinophils >3% OR tissue eosinophils >22/mm2 (exclusive); 2=BOTH sputum eosinophils >3% AND tissue eosinophils >22/mm2 demonstrated a strong positive trend for increasing $FE_{NO}$ levels with increasing composite airway eosinophil score (p=0.001 by logistic regression). Serum periostin status is indicated as in the legends. (FIG. 15D) Serum periostin and $FE_{NO}$ were both elevated in most subjects with elevated sputum or tissue eosinophils, but subsets of subjects had elevation of only periostin or $FE_{NO}$. Most subjects lacking elevated sputum AND tissue eosinophils exhibited low serum periostin and low $FE_{NO}$. (FIG. 15E) Receiver operating characteristic (ROC) curve analysis of the sensitivity and specificity of serum periostin, $FE_{NO}$, blood eosinophils, and serum IgE for composite airway eosinophil status. AUC=area under the curve.

FIG. 19 shows the percent change in median periostin levels over time in placebo and lebrikizumab-treated patients as described in Example 2.

FIGS. 20A-20B show the correlation between % change in FEV1 at week 12 and body weight for individuals in the Phase II study described in Example 2 (FIG. 20A) and the Phase II study described in Example 3 (FIG. 20B) as described in Example 6.

DETAILED DESCRIPTION

Figure 1:
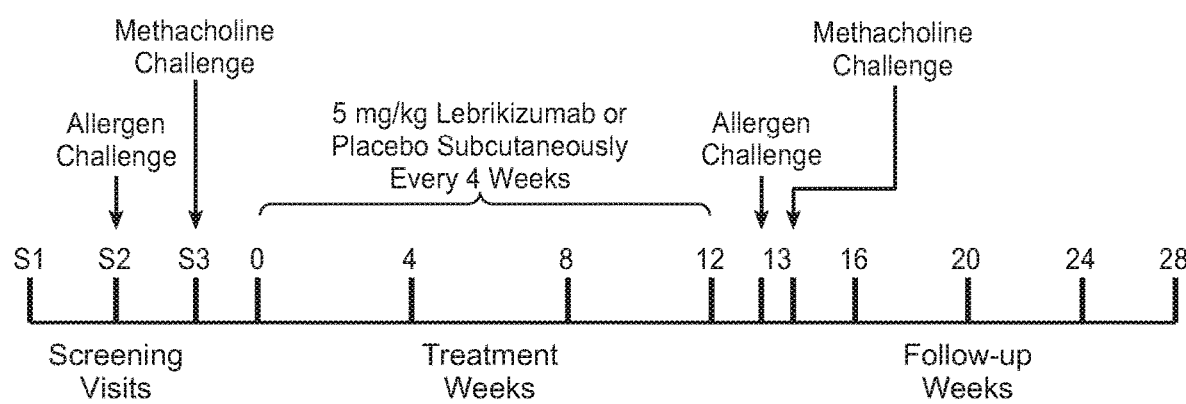
FIG. 1 provides a schematic of the allergen challenge trial described in Example 1.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

Certain Definitions

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

As used in this specification and the appended claims, the singular forms "a," "an" and "the" include plural referents unless the context clearly dictates otherwise. Thus, for example, reference to "a protein" or an "antibody" includes a plurality of proteins or antibodies, respectively; reference to "a cell" includes mixtures of cells, and the like.

The term "Total Periostin" as used herein refers to at least isoforms 1, 2, 3 and 4 of periostin. Human periostin isoforms 1, 2, 3 and 4 are known in the art as comprising the following amino acid sequences: NP_006466.2 (SEQ ID NO:19); NP_001129406.1 (SEQ ID NO:20), NP_001129407.1 (SEQ ID NO:21), and NP_001129408.1 (SEQ ID NO:22), respectively, according to the NCBI database. In addition, applicants have detected an additional form of periostin. This new isoform is referred to herein as "isoform 5" and has been partially sequenced. Isoform 5 comprises the amino acid sequence of SEQ ID NO:23. In one embodiment, the isoforms of periostin are human periostins. In a further embodiment, the term Total Periostin includes isoform 5 of human periostin in addition to isoforms 1-4. In another embodiment, Total Periostin is Total Serum Periostin or Total Plasma Periostin (i.e., Total Periostin from a serum sample obtained from whole blood or a plasma sample obtained from whole blood, respectively, the whole blood obtained from a patient).

The term "Total Periostin Assay" refers to an assay that measures the levels of Total Periostin in a biological sample. In one embodiment, the Total Periostin levels are measured using anti-periostin antibodies. In another embodiment, the anti-periostin antibodies are the anti-periostin antibodies described herein. In another example, the Total Periostin Levels are measured using one or more nucleic acid sequences antisense to mRNA encoding periostin isoforms 1-4. In yet another example, the Total Periostin Assay is the assay described in Example 4 ("Example 4 Assay" or "E4 Assay"). In one embodiment, the Total Periostin Assay comprises the use of (1) an antibody comprising the sequences SEQ ID NO:1 and SEQ ID NO:2 (the "25D4" antibody) and/or an antibody comprising the sequences of SEQ ID NO:3 and SEQ ID NO:4 (the "23B9" antibody) to bind periostin in a biological sample, (2) an antibody comprising the variable region sequences SEQ ID NO:1 and SEQ NO:2 and/or an antibody comprising the variable region sequences of SEQ ID NO:3 and SEQ ID NO:4 to bind periostin in a biological sample, (3) an antibody comprising the HVR sequences of SEQ ID NO:1 and SEQ ID NO:2 and/or an antibody comprising the HVR sequences of SEQ ID NO:3 and SEQ ID NO:4 to bind periostin in a biological sample, (4) an antibody comprising the HVR sequences that are 95% or more identical to the HVR sequences of SEQ ID NO:1 and SEQ ID NO:2 and/or an antibody comprising HVR sequences that are 95% or more identical to the HVR sequences of SEQ ID NO:3 and SEQ ID NO:4.

As used herein, "Eosinophilic Inflammation Diagnostic Assay," abbreviated "EIDA" is an assay that diagnoses a patient having eosinophilic inflammation in the body or TH2 pathway inflammation in the body by measuring levels of an eosinophilic inflammation marker in a biological sample from a patient, wherein the marker is selected from the group consisting of Periostin mRNA levels or Periostin protein levels, iNOS mRNA levels or iNOS protein levels or $FE_{NO}$ levels or CCL26 mRNA or CCL26 protein levels, serpinB2 mRNA levels or serpinB2 protein levels, serpinB4 mRNA levels or serpinB4 protein levels, CST1 mRNA levels or CST1 protein levels, CST2 mRNA levels or CST2 protein levels, CST4 mRNA levels or CST4 protein levels. In one embodiment, Total Periostin serum or plasma levels are measured. Highly effective examples of assays include, but are not limited to, the example described in Example 4 below (also referred to as the E4 Assay), or other periostin assays that measure serum or plasma levels of Total Periostin in a biological sample. Two or more assays can be conducted to make a diagnosis of eosinophilic inflammation in a patient. In one embodiment, the EID assay comprises a Total Periostin Assay in combination with a $FE_{NO}$ assay. In another embodiment, the EID assay comprises a Total Periostin Assay+/−$FE_{NO}$ Levels assay in combination with an assay measuring the levels of any one or combination of the following markers: CST1, CST2, CCL26, CLCA1, PRR4, PRB4, SERPINB2, CEACAM5, iNOS, SERPINB4, CST4, and SERPINB10.

The term "periostin antibody" or "anti-periostin antibody" refers to an antibody that binds to an isoform of periostin. In one embodiment, the periostin is human periostin. In one embodiment, the antibody comprises the sequences SEQ ID NO:1 and SEQ ID NO:2 (the "25D4" antibody) or comprises the sequences of SEQ ID NO:3 and SEQ ID NO:4 (the "23B9" antibody). In another embodiment, the antibody comprises the variable region sequences of SEQ ID NO:1 and SEQ ID NO:2 or comprises the variable region sequences of SEQ ID NO:3 and SEQ ID NO:4. In another embodiment, the antibody comprising the HVR sequences of SEQ ID NO:1 and SEQ ID NO:2 or the HVR sequences of SEQ ID NO:3 and SEQ ID NO: In another embodiment, the antibody comprises the HVR sequences that are 95% or more identical to the HVR sequences of SEQ ID NO:1 and SEQ ID NO:2 and/or an antibody comprising HVR sequences that are 95% or more identical to the HVR sequences of SEQ ID NO:3 and SEQ ID NO:4.

Eosinophilic Inflammation Positive (EIP) Patient or Status: refers to a patient who, if a serum or plasma sample from that patient had been tested for serum or plasma periostin levels, respectively, using the E4 Assay (Example 4), would have Total Serum Periostin levels of 20 ng/ml or higher (Eosinophilic Positive). According to one embodiment, the Total Periostin levels in a patient who is EIP can be selected from the group consisting of 21 ng/ml or higher, 22 ng/ml or higher, 23 ng/ml or higher, 24 ng/ml or higher, 25 ng/ml or higher, 26 ng/ml or higher, 27 ng/ml or higher, 28 ng/ml or higher, 29 ng/ml or higher, 30 ng/ml or higher, 31 ng/ml or higher, 32 ng/ml or higher, 33 ng/ml or higher, 34 ng/ml or higher, 35 ng/ml or higher, 36 ng/ml or higher, 37 ng/ml or higher, 38 ng/ml or higher, 39 ng/ml or higher, 40 ng/ml or higher, 41 ng/ml or higher, 42 ng/ml or higher, 43 ng/ml or higher, 44 ng/ml or higher, 45 ng/ml or higher, 46 ng/ml or higher, 47 ng/ml or higher, 48 ng/ml or higher, 49 ng/ml or higher, 50 ng/ml or higher, 51 ng/ml or higher, 52 ng/ml or higher, 53 ng/ml or higher, 54 ng/ml or higher, 55 ng/ml or higher, 56 ng/ml or higher, 57 ng/ml or higher, 58 ng/ml or higher, 59 ng/ml or higher, 60 ng/ml or higher, 61 ng/ml or higher, 62 ng/ml or higher, 63 ng/ml or higher, 64 ng/ml or higher, 65 ng/ml or higher, 66 ng/ml or higher, 67 ng/ml or higher, 68 ng/ml or higher, 69 ng/ml or higher and 70 ng/ml or higher in the serum or plasma. It should be understood that the EIP Status represents the state of the patient, and is not dependent on the type of assay used to determine the status. Thus, other Eosinophilic Inflammation Diagnostic Assays, including other periostin assays such as the Elecsys® periostin assay shown in Example 7, can be used or developed to be used to test for Eosinophilic Inflammation Positive status.

Eosinophilic Inflammation Negative (EIN) Patient or Status refers to a patient who, if a serum or plasma sample from that patient had been tested for serum or plasma periostin levels, respectively, using the E4 Assay, would have Total Serum Periostin levels less than 20 ng/ml. It should be understood that the EIN Status represents the state of the patient, and is not dependent on the type of assay used to determine the status. Thus, other Eosinophilic Inflammation Diagnostic Assays, including other periostin assays such as the Elecsys® periostin assay shown in Example 7, can be used or developed to be used to test for Eosinophilic Inflammation Negative status.

The term "biological sample" as used herein includes, but is not limited to, blood, serum, plasma, sputum, tissue biopsies (e.g., lung samples), and nasal samples including nasal swabs or nasal polyps.

$FE_{NO}$ assay refers to an assay that measures $FE_{NO}$ (fractional exhaled nitric oxide) levels. Such levels can be evaluated using, e.g., a hand-held portable device, NIOX MINO (Aerocrine, Solna, Sweden), in accordance with guidelines published by the American Thoracic Society (ATS) in 2005. $FE_{NO}$ may be noted in other similar ways, e.g., FeNO or FENO, and it should be understood that all such similar variations have the same meaning.

Age of Patients to be tested or treated according to the methods provided herein include: all ages. In one embodiment, the ages are 18+ years old. In another embodiment, the ages are 12+ years old. In yet another embodiment, the ages are 2+ years old. In one embodiment, the ages are 18-75 year olds, 12-75 year olds or 2-75 year olds.

Asthma is a complex disorder characterized by variable and recurring symptoms, reversible airflow obstruction (e.g., by bronchodilator) and bronchial hyperresponsiveness which may or may not be associated with underlying inflammation. Examples of asthma include aspirin sensitive/exacerbated asthma, atopic asthma, severe asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids and other asthmas as mentioned in J Allergy Clin Immunol (2010) 126(5):926-938.

Eosinophilic Disorder means: a disorder associated with excess eosinophil numbers in which atypical symptoms may manifest due to the levels or activity of eosinophils locally or systemically in the body. Disorders associated with excess eosinophil numbers or activity include but are not limited to, asthma (including aspirin sensitive asthma), atopic asthma, atopic dermatitis, allergic rhinitis (including seasonal allergic rhinitis), non-allergic rhinitis, asthma, severe asthma, chronic eosinophilic pneumonia, allergic bronchopulmonary aspergillosis, coeliac disease, Churg-Strauss syndrome (Periarteritis nodosa plus atopy), eosinophilic myalgia syndrome, hypereosinophilic syndrome, oedematous reactions including episodic angiodema, helminth infections, where eosinophils may have a protective role, onchocercal dermatitis and Eosinophil-Associated Gastrointestinal Disorders, including but not limited to, eosinophilic esophagitis, eosinophilic gastritis, eosinophilic gastroenteritis, eosinophilic enteritis and eosinophilic colitis, nasal micropolyposis and polyposis, aspirin intolerance, asthma and obstructive sleep apnoea. Eosinophil-derived secretory products have also been associated with the promotion of angiogenesis and connective tissue formation in tumors and the fibrotic responses seen in conditions such as chronic asthma, Crohn's disease, scleroderma and endomyocardial fibrosis (Munitz A, Levi-Schaffer F. Allergy 2004; 59: 268-75, Adamko et al. Allergy 2005; 60: 13-22, Oldhoff, et al. Allergy 2005; 60: 693-6). Other examples include cancer (e.g., glioblastoma (such as glioblastoma multiforme), non-Hodgkin's lymphoma (NHL)), atopic dermatitis, allergic rhinitis, asthma, fibrosis, inflammatory bowel disease, pulmonary fibrosis (including idiopathic pulmonary fibrosis (IPF) and pulmonary fibrosis secondary to sclerosis), COPD, hepatic fibrosis.

IL-13 mediated disorder means a disorder associated with excess IL-13 levels or activity in which atypical symptoms may manifest due to the levels or activity of IL-13 locally and/or systemically in the body. Examples of IL-13 mediated disorders include: cancers (e.g., non-Hodgkin's lymphoma, glioblastoma), atopic dermatitis, allergic rhinitis, asthma, fibrosis, inflammatory bowel disease (e.g., Crohn's disease), lung inflammatory disorders (e.g., pulmonary fibrosis such as IPF), COPD, hepatic fibrosis.

IL-4 mediated disorder means: a disorder associated with excess IL4 levels or activity in which atypical symptoms may manifest due to the levels or activity of IL4 locally and/or systemically in the body. Examples of IL4 mediated disorders include: cancers (e.g., non-Hodgkin's lymphoma, glioblastoma), atopic dermatitis, allergic rhinitis, asthma, fibrosis, inflammatory bowel disease (e.g., Crohn's disease), lung inflammatory disorders (e.g., pulmonary fibrosis such as IPF), COPD, hepatic fibrosis.

IL-5 mediated disorder means: a disorder associated with excess IL5 levels or activity in which atypical symptoms may manifest due to the levels or activity of IL5 locally and/or systemically in the body. Examples of IL5 mediated disorders include: cancers (e.g., non-Hodgkin's lymphoma, glioblastoma), atopic dermatitis, allergic rhinitis, asthma, fibrosis, inflammatory bowel disease (e.g., Crohn's disease), lung inflammatory disorders (e.g., pulmonary fibrosis such as IPF), COPD, hepatic fibrosis.

IL-9 mediated disorder means: a disorder associated with excess IL9 levels or activity in which atypical symptoms may manifest due to the levels or activity of IL9 locally and/or systemically in the body. Examples of IL9 mediated disorders include: cancers (e.g., non-Hodgkin's lymphoma, glioblastoma), atopic dermatitis, allergic rhinitis, asthma, fibrosis, inflammatory bowel disease (e.g., Crohn's disease), lung inflammatory disorders (e.g., pulmonary fibrosis such as IPF), COPD, hepatic fibrosis.

TSLP mediated disorder means: a disorder associated with excess TSLP levels or activity in which atypical symptoms may manifest due to the levels or activity of TSLP locally and/or systemically in the body. Examples of TSLP mediated disorders include: cancers (e.g., non-Hodgkin's lymphoma, glioblastoma), atopic dermatitis, allergic rhinitis, asthma, fibrosis, inflammatory bowel disease (e.g., Crohn's disease), lung inflammatory disorders (e.g., pulmonary fibrosis such as IPF), COPD, hepatic fibrosis.

IgE-mediated disorder means: a disorder associated with excess IgE levels or activity in which atypical symptoms may manifest due to levels of IgE locally and/or systemically in the body. Such disorders include, asthma, atopic dermatitis, allergic rhinitis, fibrosis (e.g., pulmonary fibrosis, such as IPF)

Asthma-Like Symptom includes a symptom selected from the group consisting of shortness of breath, cough (changes in sputum production and/or sputum quality and/or cough frequency), wheezing, chest tightness, bronchioconstriction and nocturnal awakenings ascribed to one of the symptoms above or a combination of these symptoms (Juniper et al (2000) Am. J. Respir. Crit. Care Med., 162(4), 1330-1334.).

The term "respiratory disorder" include, but is not limited to asthma (e.g., allergic and non-allergic asthma (e.g., due to infection, e.g., with respiratory syncytial virus (RSV), e.g., in younger children)); bronchitis (e.g., chronic bronchitis); chronic obstructive pulmonary disease (COPD) (e.g., emphysema (e.g., cigarette-induced emphysema); conditions involving airway inflammation, eosinophilia, fibrosis and excess mucus production, e.g., cystic fibrosis, pulmonary fibrosis, and allergic rhinitis. Examples of diseases that can be characterized by airway inflammation, excessive airway secretion, and airway obstruction include asthma, chronic bronchitis, bronchiectasis, and cystic fibrosis.

Exacerbations (commonly referred to as asthma attacks or acute asthma) are episodes of new or progressive increase in shortness of breath, cough (changes in sputum production and/or sputum quality and/or cough frequency), wheezing, chest tightness, nocturnal awakenings ascribed to one of the symptoms above or a combination of these symptoms. Exacerbations are often characterized by decreases in expiratory airflow (PEF or FEV1). However, PEF variability does not usually increase during an exacerbation, although it may do so leading up to or during the recovery from an exacerbation. The severity of exacerbations ranges from mild to life-threatening and can be evaluated based on both symptoms and lung function. Severe asthma exacerbations as described herein include exacerbations that result in any one or combination of the following hospitalization for asthma treatment, high corticosteroid use (e.g., quadrupling the total daily corticosteroid dose or a total daily dose of greater or equal to 500 micrograms of FP or equivalent for three consecutive days or more), or oral/parenteral corticosteroid use.

A TH2 pathway inhibitor is an agent that inhibits the TH2 pathway.

Examples of a TH2 pathway inhibitor include inhibitors of the activity of any one of the targets selected from the group consisting of: ITK, BTK, IL-9 (e.g., MEDI-528), IL-5 (e.g., Mepolizumab, CAS No. 196078-29-2; resilizumab), IL-13 (e.g., IMA-026, IMA-638 (also referred to as, anrukinzumab, INN No. 910649-32-0; QAX-576; IL4/IL13 trap), tralokinumab (also referred to as CAT-354, CAS No. 1044515-88-9); AER-001, ABT-308 (also referred to as humanized 13C5.5 antibody), IL-4 (e.g., AER-001, IL4/IL13 trap), OX40L, TSLP, IL-25, IL-33 and IgE (e.g., XOLAIR, QGE-031; MEDI-4212); and receptors such as: IL-9 receptor, IL-5 receptor (e.g., MEDI-563 (benralizumab, CAS No. 1044511-01-4), IL-4receptor alpha (e.g., AMG-317, AIR-645), IL-13receptoralpha1 (e.g., R-1671) and IL-13receptoralpha2, OX40, TSLP-R, IL-7Ralpha (a co-receptor for TSLP), IL17RB (receptor for IL-25), ST2 (receptor for IL-33), CCR3, CCR4, CRTH2 (e.g., AMG-853, AP768, AP-761, MLN6095, ACT129968), FcepsilonRI, FcepsilonRII/CD23 (receptors for IgE), Flap (e.g., GSK2190915), Syk kinase (R-343, PF3526299); CCR4 (AMG-761), TLR9 (QAX-935) and multi-cytokine inhibitor of CCR3, IL5, IL3, GM-CSF (e.g., TPI ASM8). Examples of inhibitors of the aforementioned targets are disclosed in, for example, WO2008/086395; WO2006/085938; U.S. Pat. Nos. 7,615,213; 7,501,121; WO2006/085938; WO 2007/080174; U.S. Pat. No. 7,807,788; WO2005007699; WO2007036745; WO2009/009775; WO2007/082068; WO2010/073119; WO2007/045477; WO2008/1134724; US2009/0047277; and WO2008/127,271).

A therapeutic agent a provided herein includes an agent that can bind to the target identified herein above, such as a polypeptide(s) (e.g., an antibody, an immunoadhesin or a peptibody), an aptamer or a small molecule that can bind to a protein or a nucleic acid molecule that can bind to a nucleic acid molecule encoding a target identified herein (i.e., siRNA).

"An anti-IL13/IL4 pathway inhibitor" refers to a therapeutic agent that inhibits IL-13 and/or IL-4 signaling. Examples of an anti-IL13/IL4 pathway inhibitors includes inhibitors of the interaction of IL13 and/or IL4 with its receptor(s), such inhibitors include, but are not limited to, anti-IL13 binding agents, anti-IL4 binding agents, anti-IL3/IL4 bispecific binding agents, anti-IL4receptoralpha binding agents, anti-IL13receptoralpha1 binding agents and anti-IL13 receptoralpha2 binding agents. Single domain antibodies that can bind IL13, IL4, (including bispecific antibody with a single domain binding IL13 and a single domain binding IL4), IL-13Ralpha1, IL-13Ralpha2 or IL-4Ralpha are specifically included as inhibitors. It should be understood that molecules that can bind more than one target are included.

"Anti-IL4 binding agents" refers to agent that binds to human IL-4. Such binding agents can include a small molecule, an aptamer or a polypeptide. Such polypeptide can include, but is not limited to, a polypeptide(s) selected from the group consisting of an immunoadhesin, an antibody, a peptibody and a peptide. According to one embodiment, the binding agent binds to a human IL-4 sequence with an affinity between 1 uM-1 pM. Specific examples of anti-IL4 binding agents can include soluble IL4Receptor alpha (e.g., extracellular domain of IL4Receptor fused to a human Fc region), anti-IL4 antibody, and soluble IL13receptoralpha1 (e.g., extracellular domain of IL13receptoralpha1 fused to a human Fc region).

"Anti-IL4receptoralpha binding agents" refers to an agent that binds to human IL4 receptoralpha. Such binding agents can include a small molecule, an aptamer or a polypeptide. Such polypeptide can include, but is not limited to, a polypeptide(s) selected from the group consisting of an immunoadhesin, an antibody, a peptibody and a peptide. According to one embodiment, the binding agent binds to a human IL4 receptor alpha sequence with an affinity between 1 uM-1 pM. Specific examples of anti-IL4 receptoralpha binding agents can include anti-IL4 receptor alpha antibodies.

"Anti-IL13 binding agent" refers to agent that binds to human IL13. Such binding agents can include a small molecule, aptamer or a polypeptide. Such polypeptide can include, but is not limited to, a polypeptide(s) selected from the group consisting of an immunoadhesin, an antibody, a peptibody and a peptide. According to one embodiment, the binding agent binds to a human IL-13 sequence with an affinity between 1 uM-1 pM. Specific examples of anti-IL-13 binding agents can include anti-IL-13 antibodies, soluble IL-13receptoralpha2 fused to a human Fc, soluble IL4receptoralpha fused to a human Fc, soluble IL-13 receptoralpha fused to a human Fc. According to one embodiment, the anti-IL13 antibody comprises (1) a HVRH1 comprising the amino acid sequence SEQ ID NO 11, (2) HVRH2 comprising the amino acid sequence SEQ ID NO:12, (3) HVRH3 comprising the amino acid sequence SEQ ID NO:13, (4) HVRL1 comprising the amino acid sequence SEQ ID NO:14, (5) HVRL2 comprising the amino acid sequence SEQ ID NO:15, and (6) HVRL3 comprising the amino acid sequence SEQ ID NO:16. In another embodiment, the anti-IL-13 antibody comprises a VH domain comprising the amino acid sequence SEQ ID NO:9 and a VL domain comprising the amino acid sequence SEQ ID NO:10. According to one embodiment, the antibody is an IgG1 antibody. According to another embodiment, the antibody is an IgG4 antibody. According to one embodiment, the IgG4 antibody comprises a S228P mutation in its constant domain.

Anti-IL13receptoralpha1 binding agents" refers to an agent that specifically binds to human IL13 receptoralpha1. Such binding agents can include a small molecule, aptamer or a polypeptide. Such polypeptide can include, but is not limited to, a polypeptide(s) selected from the group consisting of an immunoadhesin, an antibody, a peptibody and a peptide. According to one embodiment, the binding agent binds to a human IL-13 receptor alpha1 sequence with an affinity between 1 uM-1 pM. Specific examples of anti-IL13 receptoralpha1 binding agents can include anti-IL13 receptor alpha1 antibodies.

"Anti-IL13receptoralpha2 binding agents" refers to an agent that specifically binds to human IL13 receptoralpha2. Such binding agents can include a small molecule, an aptamer or a polypeptide. Such polypeptide can include, but is not limited to, a polypeptide(s) selected from the group consisting of an immunoadhesin, an antibody, a peptibody and a peptide. According to one embodiment, the binding agent binds to a human IL-13 receptor alpha2 sequence with an affinity between 1 uM-1 pM. Specific examples of anti-IL13 receptoralpha2 binding agents can include anti-IL13 receptor alpha2 antibodies.

"Anti IgE binding agents" refers to an agent that specifically binds to human IgE. Such binding agents can include a small molecule, an aptamer or a polypeptide. Such polypeptide can include, but is not limited to, a polypeptide(s) selected from the group consisting of an immunoadhesin, an antibody, a peptibody and a peptide. According to one embodiment, the anti-IgE antibody comprises a VL sequence comprising the amino acid sequence of SEQ ID NO:17 and a VH sequence comprising the amino acid sequence SEQ ID NO:18.

"Anti-M1' binding agents" refers to an agent that specifically binds to the membrane proximal M1' region of surface expressed IgE on B cells. Such binding agents can include a small molecule, an aptamer or a polypeptide. Such polypeptide can include, but is not limited to, a polypeptide(s) selected from the group consisting of an immunoadhesin, an antibody, a peptibody and a peptide. According to one embodiment, the anti-IgE antibody comprises an antibody described in WO2008/116149 or a variant thereof. According to another embodiment, the anti-M1' antibody comprises a variable heavy chain and a variable light chain, wherein the variable heavy chain is SEQ ID NO:24 and the variable light chain is SEQ ID NO:25. According to another embodiment, An anti-IgE/M1' antibody comprising a variable heavy chain and a variable light chain, wherein the variable heavy chain further comprises an HVR-H1, HVR-H2 and HVR-H3, and the variable light chain further comprises and HVR-L1, HVR, L2 and HVR-L3 and: (a) the HVR-H1 is residues 26-35 of SEQ ID NO:24, [GFTFSDYGIA]; (b) the HVR-H2 is residues 49-66 of SEQ ID NO:24, [AFISDLAYTIYYADTVTG]; (c) the HVR-H3 is residues 97-106 of SEQ ID NO:24, [ARDNWDAMDY]; (d) the HVR-L1 is residues 24-39 of SEQ ID NO:25, [RSSQSLVHNNANTYLH]; (e) the HVR-L2 is residues 55-61 of SEQ ID NO:25, [KVSNRFS]; (f) the HVR-L3 is residues 94-102 of SEQ ID NO:25. [SQNTLVPWT].

The term "small molecule" refers to an organic molecule having a molecular weight between 50 Daltons to 2500 Daltons.

The term "antibody" is used in the broadest sense and specifically covers, for example, monoclonal antibodies, polyclonal antibodies, antibodies with polyepitopic specificity, single chain antibodies, multi-specific antibodies and fragments of antibodies. Such antibodies can be chimeric, humanized, human and synthetic. Such antibodies and methods of generating them are described in more detail below.

The term "uncontrolled" or "uncontrollable" refers to the inadequacy of a treatment regimen to minimize a symptom of a disease. As used herein, the term "uncontrolled" and "inadequately controlled" can be used interchangeably and are meant to refer to the same state. The control status of a patient can be determined by the attending physician based on a number of factors including the patient's clinical history, responsiveness to treatment and level of current treatment prescribed. For example, a physician may consider factors such as FEV1<75% predicted or personal best, frequency of need for a SABA in the past 2-4 weeks (e.g., greater than or equal two doses/week), nocturnal awakenings/symptoms in the past 2-4 weeks (e.g., less than or equal to 2 nights/week), limitations on activity in the past 2-4 weeks, daytime symptoms in the past 2-4 weeks The term "therapeutic agent" refers to any agent that is used to treat a disease.

The term "controller" or "preventor" refers to any therapeutic agent that is used to control asthma inflammation.

Examples of controllers include corticosteroids, leukotriene receptor antagonists (e.g., inhibit the synthesis or activity of leukotrienes such as montelukast, zileuton, pranlukast, zafirlukast), LABAs, corticosteroid/LABA combination compositions, theophylline (including aminophylline), cromolyn sodium, nedocromil sodium, omalizumab, LAMAs, MABA (e.g, bifunctional muscarinic antagonist-beta2 Agonist), 5-Lipoxygenase Activating Protein (FLAP) inhibitors, and enzyme PDE-4 inhibitor (e.g., rotlumilast). A "second controller" typically refers to a controller that is not the same as the first controller.

The term "corticosteroid sparing" or "CS" means the decrease in frequency and/or amount, or the elimination of, corticosteroid used to treat a disease in a patient taking corticosteroids for the treatment of the disease due to the administration of another therapeutic agent. A "CS agent" refers to a therapeutic agent that can cause CS in a patient taking a corticosteroid.

The term "corticosteroid" includes, but is not limited to fluticasone (including fluticasone propionate (FP)), beclometasone, budesonide, ciclesonide, mometasone, flunisolide betamethasone and triamcinolone. "Inhalable corticosteroid" means a corticosteroid that is suitable for delivery by inhalation. Exemplary inhalable corticosteroids are fluticasone, beclomethasone dipropionate, budenoside, mometasone furoate, ciclesonide, flunisolide, triamcinolone acetonide and any other corticosteroid currently available or becoming available in the future. Examples of corticosteroids that can be inhaled and are combined with a long-acting beta2-agonist include, but are not limited to: budesonide/formoterol and fluticasone/salmeterol.

Examples of corticosteroid/LABA combination drugs include fluticasone furoate/vilanterol trifenatate and indacaterol/mometasone.

The term "LABA" means long-acting beta-2 agonist, which agonist includes, for example, salmeterol, formoterol, bambuterol, albuterol, indacaterol, arformoterol and clenbuterol.

The term "LAMA" means long-acting muscarinic antagonist, which agonists include: tiotropium.

Examples of LABA/LAMA combinations include, but are not limited to: olodaterol tiotropium (Boehringer Ingelheim's) and indacaterol glycopyrronium (Novartis)

The term "SABA" means short-acting beta-2 agonists, which agonists include, but are not limited to, salbutamol, levosalbutamol, fenoterol, terbutaline, pirbuterol, procaterol, bitolterol, rimiterol, carbuterol, tulobuterol and reproterol Leukotriene receptor antagonists (sometimes referred to as a leukast) (LTRA) are drugs that inhibit leukotrienes. Examples of leukotriene inhibitors include montelukast, zileuton, pranlukast, and zafirlukast.

The term "FEV1" refers to the volume of air exhaled in the first second of a forced expiration. It is a measure of airway obstruction. Provocative concentration of methacholine required to induce a 20% decline in FEV1 (PC20) is a measure of airway hyperresponsiveness. FEV1 may be noted in other similar ways, e.g., $FEV_1$, and it should be understood that all such similar variations have the same meaning.

The term "relative change in FEV1"=(FEV1 at week 12 of treatment–FEV1 prior to start of treatment) divided by FEV1

The term "mild asthma" refers to a patient generally experiencing symptoms or exacerbations less than two times a week, nocturnal symptoms less than two times a month, and is asymptomatic between exacerbations. Mild, intermittent asthma is often treated as needed with the following: inhaled bronchodilators (short-acting inhaled beta2-agonists): avoidance of known triggers; annual influenza vaccination; pneumococcal vaccination every 6 to 10 years, and in some cases, an inhaled beta2-agonist, cromolyn, or nedocromil prior to exposure to identified triggers. If the patient has an increasing need for short-acting beta2-agonist (e.g., uses short-acting beta2-agonist more than three to four times in 1 day for an acute exacerbation or uses more than one canister a month for symptoms), the patient may require a stepup in therapy.

The term "moderate asthma" generally refers to asthma in which the patient experiences exacerbations more than two times a week and the exacerbations affect sleep and activity; the patient has nighttime awakenings due to asthma more than two times a month; the patient has chronic asthma symptoms that require short-acting inhaled beta2-agonist daily or every other day; and the patient's pretreatment baseline PEF or FEV1 is 60 to 80 percent predicted and PEF variability is 20 to 30 percent.

The term "severe asthma" generally refers to asthma in which the patient has almost continuous symptoms, frequent exacerbations, frequent nighttime awakenings due to the asthma, limited activities, PEF or FEV1 baseline less than 60 percent predicted, and PEF variability of 20 to 30 percent.

Examples of rescue medications include albuterol, ventolin and others.

"Resistant" refers to a disease that demonstrates little or no clinically significant improvement after treatment with a therapeutic agent. For example, asthma which requires treatment with high dose ICS (e.g., quadrupling the total daily corticosteroid dose or a total daily dose of greater or equal to 500 micrograms of FP (or equivalent) for at least three consecutive days or more, or systemic corticosteroid for a two week trial to establish if asthma remains uncontrolled or FEV1 does not improve is often considered severe refractory asthma.

A therapeutic agent as provided herein can be administered by any suitable means, including parenteral, subcutaneous, intraperitoneal, intrapulmonary, and intranasal. Parenteral infusions include intramuscular, intravenous, intraarterial, intraperitoneal, or subcutaneous administration. In one embodiment, the therapeutic agent is inhaled. According to another embodiment, the dosing is given by injections, e.g., intravenous or subcutaneous injections. In yet another embodiment, the therapeutic agent is administered using a syringe (e.g., prefilled or not) or an autoinjector.

For the prevention or treatment of disease, the appropriate dosage of a therapeutic agent may depend on the type of disease to be treated, the severity and course of the disease, whether the therapeutic agent is administered for preventive or therapeutic purposes, previous therapy, the patient's clinical history and response to the therapeutic agent, and the discretion of the attending physician. The therapeutic agent is suitably administered to the patient at one time or over a series of treatments. The therapeutic agent composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

Dosing for lebrikizumab, for eosinophilic diseases (including asthma) and for treating other diseases using TH2 therapies: lebrikizumab can be administered 0.1 mg/kg to 100 mg/kg of the patient's body weight. In one embodiment, the dosage administered to a patient is between 0.1 mg/kg and 20 mg/kg of the patient's body weight. In another embodiment, the dose is 1 mg/kg to 10 mg/kg of the patient's body weight.

In an alternative embodiment, lebrikizumab can be administered as a flat dose. In one embodiment lebrikizumab is administered in as a 125-1000 mg flat dose (i.e., not weight dependent), by subcutaneous injection or by intravenous injection, at a frequency of time selected from the group consisting of: every 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 1 month, 2 months, 3 month or 4 months. In another embodiment, if the patient is overweight, lebrikizumab can be administered, e.g., 125-250 mg at a frequency of 3 times per month. In one embodiment, the lebrikizumab is administered as a flat dose of 125 mg, 250 mg or 500 mg every 4 weeks. In another embodiment, the lebrikizumab is administered in a patient >40 kg as a flat dose of 37.5 mg, 125 mg, 250 mg or 500 mg every 4 weeks.

In one embodiment, the patient is 18 years of age or older. In one embodiment, the asthma patient is age 12 to 17 and lebrikizumab is administered in as a flat dose of 250 mg or a flat dose of 125 mg. In one embodiment, the asthma patient is age 6 to 11 and lebrikizumab is administered in as a flat dose of 125 mg.

"Patient response" or "response" (and grammatical variations thereof) can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e. reduction, slowing down or complete stopping) of disease spread; (6) decrease of auto-immune response, which may, but does not have to, result in the regression or ablation of the disease lesion; (7) relief, to some extent, of one or more symptoms associated with the disorder; (8) increase in the length of disease-free presentation following treatment; and/or (9) decreased mortality at a given point of time following treatment.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair antibody and antigen binding arm). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-target antibody" and "an antibody that binds to target" refer to an antibody that is capable of binding the target with sufficient affinity such that the antibody is useful as a diagnostic and/or therapeutic agent in targeting the target. In one embodiment, the extent of binding of an anti-target antibody to an unrelated, non-target protein is less than about 10% of the binding of the antibody to target as measured, e.g., by a radioimmunoassay (RIA) or biacore assay. In certain embodiments, an antibody that binds to a target has a dissociation constant (Kd) of $\leq 1$ µM, $\leq 100$ nM, $\leq 10$ nM, $\leq 1$ nM, $\leq 0.1$ nM, $\leq 0.01$ nM, or $\leq 0.001$ nM (e.g. 10-8 M or less, e.g. from 10-8 M to 10-13 M, e.g., from 10-9 M to 10-13 M). In certain embodiments, an anti-target antibody binds to an epitope of a target that is conserved among different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and µ, respectively.

The term "cytotoxic agent" as used herein refers to a substance that inhibits or prevents a cellular function and/or causes cell death or destruction. Cytotoxic agents include, but are not limited to, radioactive isotopes (e.g., At211, I131, I125, Y90, Re186, Re188, Sm153, Bi212, P32, Pb212 and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter typically being of highest sequence variability and/or involved in antigen recognition. An HVR region as used herein comprise any number of residues located within positions 24-36 (for HVRL1), 46-56 (for HVRL2), 89-97 (for HVRL3), 26-35B (for HVRH1), 47-65 (for HVRH2), and 93-102 (for HVRH3).

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-target antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used according to the methods provided herein may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products. The term "package insert" is also used to refer to instructions customarily included in commercial packages of diagnostic products that contain information about the intended use, test principle, preparation and handling of reagents, specimen collection and preparation, calibration of the assay and the assay procedure, performance and precision data such as sensitivity and specificity of the assay.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length attic sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "target," as used herein, refers to any native molecule from any vertebrate source, including mammals such as primates (e.g. humans) and rodents (e.g., mice and rats), unless otherwise indicated. The term encompasses "full-length," unprocessed target as well as any form of target that results from processing in the cell. The term also encompasses naturally occurring variants of targets, e.g., splice variants or allelic variants.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W.H. Freeman and Co., page 91 (2007).) A single VH VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

Compositions and Methods

In one aspect, the invention is based, in part, on new diagnostic assays and better methods of treatment. In certain embodiments, antibodies that bind periostin are provided. Antibodies of the invention are useful, e.g., for the diagnosis or treatment of asthma and other diseases.

Exemplary Antibodies

Anti-Periostin Antibodies

In one aspect, the invention provides isolated antibodies that bind to periostin. In certain embodiments, an anti-periostin antibody that can bind to isoforms 1-4 of human periostin with good affinity.

In one embodiment, the antibody comprises the sequences SEQ ID NO:1 and SEQ ID NO:2 (the "25D4" antibody) or comprises the sequences of SEQ ID NO:3 and SEQ ID NO:4 (the "23B9" antibody). In another embodiment, the antibody comprises the variable region sequences SEQ ID NO:1 and SEQ ID NO:2 or comprises the variable region sequences of SEQ ID NO:3 and SEQ ID NO:4. In another embodiment, the antibody comprising the HVR sequences of SEQ ID NO:1 and SEQ ID NO:2 or the HVR sequences of SEQ ID NO:3 and SEQ ID NO:4: In another embodiment, the antibody comprises the HVR sequences that are 95% or more identical to the HVR sequences of SEQ ID NO:1 and SEQ ID NO:2 and/or an antibody comprising HVR sequences that are 95% or more identical to the HVR sequences of SEQ NO:3 and SEQ ID NO:4.

In any of the above, embodiments, an anti-periostin antibody can be humanized. In one embodiment, an anti-periostin antibody comprises HVRs as in any of the above embodiments, and further comprises an acceptor human framework, e.g. a human immunoglobulin framework or a human consensus framework.

In another aspect, an anti-periostin antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:1. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-periostin antibody comprising that sequence retains the ability to bind to periostin. In certain embodiments, a total of 1 to 10 amino acids have been substituted, inserted and/or deleted in SEQ ID NO:1. In certain embodiments, substitutions, insertions, or deletions occur in regions outside the HVRs (i.e., in the FRs). Optionally, the anti-periostin antibody comprises the VH sequence in SEQ ID NO:1, including post-translational modifications of that sequence.

In another aspect, an anti-periostin antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:2. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-periostin antibody comprising that sequence retains the ability to bind to periostin. In certain embodiments, a total of 1 to 10 amino acids have been substituted, inserted and/or deleted in SEQ ID NO:2. In certain embodiments, the substitutions, insertions, or deletions occur in regions outside the HVRs (i.e., in the FRs). Optionally, the anti-periostin antibody comprises the VL sequence in SEQ ID NO:2, including post-translational modifications of that sequence.

In another aspect, an anti-periostin antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:3. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-periostin antibody comprising that sequence retains the ability to bind to periostin. In certain embodiments, a total of 1 to 10 amino acids have been substituted, inserted and/or deleted in SEQ ID NO:3. In certain embodiments, substitutions, insertions, or deletions occur in regions outside the HVRs (i.e., in the FRs). Optionally, the anti-periostin antibody comprises the VH sequence in SEQ ID NO:3, including post-translational modifications of that sequence.

In another aspect, an anti-periostin antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:2. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-periostin antibody comprising that sequence retains the ability to bind to periostin. In certain embodiments, a total of 1 to 10 amino acids have been substituted, inserted and/or deleted in SEQ ID NO:4. In certain embodiments, the substitutions, insertions, or deletions occur in regions outside the HVRs (i.e., in the FRs). Optionally, the anti-periostin antibody comprises the VL sequence in SEQ ID NO:4, including post-translational modifications of that sequence.

In another aspect, an anti-periostin antibody is provided, wherein the antibody comprises a VH as in any of the embodiments provided above, and a VL as in any of the embodiments provided above.

In a further aspect, the invention provides an antibody that binds to the same epitope as an anti-periostin antibody provided herein. For example, in certain embodiments, an antibody is provided that binds to the same epitope as an anti-periostin antibody comprising a VH sequence of SEQ ID NO:1 and a VL sequence of SEQ ID NO:2. For example, in certain embodiments, an antibody is provided that binds to the same epitope as an anti-periostin antibody comprising a VH sequence of SEQ ID NO:3 and a VL sequence of SEQ ID NO:4.

In a further aspect of the invention, an anti-periostin antibody according to any of the above embodiments is a monoclonal antibody, including a chimeric, humanized or human antibody. In one embodiment, an anti-periostin antibody is an antibody fragment, e.g., a Fv, Fab, Fab', scFv, diabody, or F(ab')2 fragment. In another embodiment, the antibody is a full length antibody, e.g., an intact IgG1 or IgG4 antibody or other antibody class or isotype as defined herein. In another embodiment, the antibody is a bispecific antibody.

In a further aspect, an anti-periostin antibody according to any of the above embodiments may incorporate any of the features, singly or in combination, as described in Sections 1-7 below:

Anti-IL13 Antibodies

In one aspect, the invention provides isolated antibodies that bind to human IL-13.

In one embodiment, the anti-IL13 antibody comprises a HVR-L1 comprising amino acid sequence SEQ ID NO:14; an HVR-L2 comprising amino acid sequence SEQ ID NO:15; an HVR-L3 comprising amino acid sequence SEQ ID NO: 16; an HVR-H1 comprising amino acid sequence SEQ ID NO:11; an HVR-H2 comprising amino acid sequence SEQ ID NO: 12; and an HVR-H3 comprising amino acid sequence SEQ ID NO: 13.

In another embodiment, the antibody comprises the variable region sequences SEQ ID NO:9 and SEQ ID NO:10.

In any of the above embodiments, an anti-IL-13 antibody can be humanized. In one embodiment, an anti-IL-13 antibody comprises HVRs as in any of the above embodiments, and further comprises an acceptor human framework, e.g. a human immunoglobulin framework or a human consensus framework.

In another aspect, an anti-IL-13 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:9. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-IL-13 antibody comprising that sequence retains the ability to bind to human IL-13. In certain embodiments, a total of 1 to 10 amino acids have been substituted, altered inserted and/or deleted in SEQ ID NO:9. In certain embodiments, substitutions, insertions, or deletions occur in regions outside the HVRs (i.e., in the FRs). Optionally, the anti-IL13 antibody comprises the VH sequence in SEQ ID NO:9, including post-translational modifications of that sequence.

In another aspect, an anti-IL-13 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:10. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-IL-13 antibody comprising that sequence retains the ability to bind to IL-13. In certain embodiments, a total of 1 to 10 amino acids have been substituted, inserted and/or deleted in SEQ ID NO:10. In certain embodiments, the substitutions, insertions, or deletions occur in regions outside the HVRs (i.e., in the FRs). Optionally, the anti-IL-13 antibody comprises the VL sequence in SEQ ID NO:10, including post-translational modifications of that sequence.

In yet another embodiment, the anti-IL-13 antibody comprises a VL region having at least 90%, 91%, 92%, 93%, 94%, 95%, 96%, 97%, 98%, 99%, or 100% sequence identity to the amino acid sequence of SEQ ID NO:10 and a VH region having at least 90%, 91%, 92%, 93%, 94%, 95%, 96%, 97%, 98%, 99%, or 100% sequence identity to the amino acid sequence of SEQ ID NO:9. In yet a further embodiment, the anti-IL-13 antibody comprises a HVR-L1 comprising amino acid sequence SEQ ID NO:14; an HVR-L2 comprising amino acid sequence SEQ ID NO:15; an HVR-L3 comprising amino acid sequence SEQ ID NO: 16; an HVR-H1 comprising amino acid sequence SEQ ID NO:11; an HVR-H2 comprising amino acid sequence SEQ ID NO: 12; and an HVR-H3 comprising amino acid sequence SEQ ID NO: 13.

In another aspect, an anti-IL-13 antibody is provided, wherein the antibody comprises a VH as in any of the embodiments provided above, and a VL as in any of the embodiments provided above.

In a further aspect, the invention provides an antibody that binds to the same epitope as an anti-IL-13 antibody provided herein. For example, in certain embodiments, an antibody is provided that binds to the same epitope as or can by competitively inhibited by an anti-IL-13 antibody comprising a VH sequence of SEQ ID NO:9 and a VL sequence of SEQ ID NO:10.

In a further aspect of the invention, an anti-IL-13 antibody according to any of the above embodiment can be a monoclonal antibody, including a chimeric, humanized or human antibody. In one embodiment, an anti-IL13 antibody is an antibody fragment, e.g., a Fv, Fab, Fab', scFv, diabody, or F(ab')2 fragment. In another embodiment, the antibody is a full length antibody, e.g., an intact IgG1 or IgG4 antibody or other antibody class or isotype as defined herein. According to another embodiment, the antibody is a bispecific antibody. In one embodiment, the bispecific antibody comprises the HVRs or comprises the VH and VL regions described above.

In a further aspect, an anti-IL-13 antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g. 10-8 M or less, e.g. from 10-8 M to 10-13 M, e.g., from 10-9 M to 10-13 M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of (125I)-labeled antigen in the presence of a titration series of unlabeled antigen, then capturing bound antigen with an anti-Fab antibody-coated plate (see, e.g., Chen et al., J. Mol. Biol. 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [125I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 ml/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates (kon) and dissociation rates (koff) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio koff/kon. See, e.g., Chen et al., J. Mol. Biol. 293:865-881 (1999). If the on-rate exceeds 106 M-1 s-1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson et al. Nat. Med. 9:129-134 (2003). For a review of scFv fragments, see, e.g., Pluckthün, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. E. coli or phage) as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol. 147: 86 (1991). Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Methods Histology and Histopathology, 20(3): 927-937 (2005) and Vollmers and Brandlein, Methods and Findings in Experimental and Clinical Pharmacology, 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178: 1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., Immunol. Methods 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for IL-13 and the other is for any other antigen. In certain embodiments, bispecific antibodies may bind to two different epitopes of IL-13. Bispecific antibodies may also be used to localize cytotoxic agents to cells. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bispecific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g. Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to IL-13 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Conservative Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the patent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.) US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249: 533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcRIII only, whereas monocytes express FcRI, FcRII and FcRIII. FcR expression on hematopoietic cells is summarized in Table 3 on page 464 of Ravetch and Kinet, Annu. Rev. Immunol 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); U.S. Pat. No. 5,821,337 (see Bruggemann, M. et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half life determinations can also be performed using methods known in the art (see, e.g., Petkova, S. B. et al., Int'l. Immunol. 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to it stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Recombinant Methods and Compositions

Antibodies may be produced using recombinant methods and compositions, e.g., as described in U.S. Pat. No. 4,816,567. In one embodiment, isolated nucleic acid encoding an anti-periostin antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-periostin antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-periostin antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gemgross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (19771); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

Assays

Anti-periostin antibodies provided herein may be identified, screened for, or characterized for their physical/chemical properties and/or biological activities by various assays known in the art.

Binding Assays and other Assays

In one aspect, an antibody of the invention is tested for its antigen binding activity, e.g., by known methods such as ELISA, Western blot, etc.

In another aspect, competition assays may be used to identify an antibody that competes with IL-13 or periostin for binding to IL13 or periostin, respectively. In certain embodiments, such a competing antibody binds to the same epitope (e.g., a linear or a conformational epitope) that is bound by lebrikizumab or another anti-IL13 antibody specified herein or anti-periostin antibody specified herein. Detailed exemplary methods for mapping an epitope to which an antibody binds are provided in Morris (1996) "Epitope Mapping Protocols," in Methods in Molecular Biology vol. 66 (Humana Press, Totowa, N.J.).

In an exemplary competition assay, immobilized periostin is incubated in a solution comprising a first labeled antibody that binds to periostin (e.g., 25D4) and a second unlabeled antibody that is being tested for its ability to compete with the first antibody for binding to periostin. The second antibody may be present in a hybridoma supernatant. As a control, immobilized periostin is incubated in a solution comprising the first labeled antibody but not the second unlabeled antibody. After incubation under conditions permissive for binding of the first antibody to periostin, excess unbound antibody is removed, and the amount of label associated with immobilized periostin is measured. If the amount of label associated with immobilized periostin is substantially reduced in the test sample relative to the control sample, then that indicates that the second antibody is competing with the first antibody for binding to periostin. See Harlow and Lane (1988) Antibodies: A Laboratory Manual ch. 14 (Cold Spring Harbor Laboratory, Cold Spring Harbor, N.Y.).

Activity Assays

In one aspect, assays are provided for identifying anti-IL-13 antibodies thereof having biological activity. Biological activity may include, e.g., activity in asthma. Antibodies having such biological activity in vivo and/or in vitro are also provided.

In certain embodiments, an antibody of the invention is tested for such biological activity.

Immunoconjugates

The invention also provides immunoconjugates comprising an anti-periostin antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include At211, I131, I125, Y90, Re186, Re188, Sm153, Bi212, P32, Pb212 and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

Methods and Compositions for Diagnostics and Detection

In certain embodiments, any of the anti-periostin antibodies provided herein is useful for detecting the presence of periostin in a biological sample. The term "detecting" as used herein encompasses quantitative or qualitative detection. In certain embodiments, a biological sample comprises a cell or tissue, such as serum, plasma, nasal swabs and sputum.

In one embodiment, an anti-periostin antibody for use in a method of diagnosis or detection is provided. In a further aspect, a method of detecting the presence of periostin in a biological sample is provided. In certain embodiments, the method comprises contacting the biological sample with an anti-periostin antibody as described herein under conditions permissive for binding of the anti-periostin antibody to periostin, and detecting whether a complex is formed between the anti-periostin antibody and periostin. Such method may be an in vitro or in vivo method. In one embodiment, an anti-periostin antibody is used to select subjects eligible for therapy with an anti-13 antibody, or any other TH2 pathway inhibitor, e.g. where periostin is a biomarker for selection of patients.

Exemplary disorders that may be diagnosed using sir antibody of the invention are provided herein.

In certain embodiments, labeled anti-periostin antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes 32P, 14C, 125I, 3H, and 131I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Pharmaceutical Formulations

Pharmaceutical formulations of an anti-IL-13 antibody or other TH2 pathway inhibitors as described herein are prepared by mixing such antibody or molecule having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide a controller with the TH2 pathway inhibitor. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

Therapeutic Methods and Compositions

Eosinophilic inflammation is associated with a variety of illnesses, both allergic and non-allergic (Gonlugur (2006) Immunol. Invest. 35(1):29-45). Inflammation is a restorative response of living tissues to injury. A characteristic of inflammatory reactions is the accumulation of leukocytes in injured tissue due to certain chemicals produced in the tissue itself. Eosinophil leukocytes accumulate in a wide variety of conditions such as allergic disorders, helminthic infections, and neoplastic diseases (Kudlacz et al., (2002) Inflammation 26: 111-119). Eosinophil leukocytes, a component of the immune system, are defensive elements of mucosal surfaces. They respond not only to antigens but to parasites, chemicals, and trauma.

Tissue eosinophilia occurs in skin diseases such as eczema, pemphigus, acute urticaria, and toxic epidermal necrolysis as well as in atopic dermatitis ([Rzany et al., 1996]). Eosinophils accumulate in the tissue and empty granule proteins in IgE-mediated allergic skin reactions ([Nielsen et al., 2001]). Eosinophils combined with mast cells are likely to cause joint inflammation (Miossec et al., 1997). Eosinophilic inflammation sometimes accompanies joint trauma. Synovial fluid eosinophilia can be associated with diseases such as rheumatoid arthritis, parasitic disease, hypereosinophilic syndrome, Lyme disease, and allergic processes, as well as hemarthrosis and arthrography ([Atanes et al., 1996]). Eosinophilic inflammation can affect bones as well ([Yetiser et al., 2002]). Examples of eosinophilic muscle disease include eosinophilic perimyositis, eosinophilic polymyositis, and focal eosinophilic myositis ([Lakhanpal et al., 1988]). Eosinophilic inflammations affecting skeletal muscles may be associated with parasite infections or drugs or features of some systemic disorders of hypereosinophilia (e.g., idiopathic hypereosinophilic syndrome and eosinophilia-myalgia syndrome. Eosinophils participate in the inflammatory response to epitopes recognized by autoimmune antibodies ([Engineer et al., 2001]). Connective tissue diseases may lead to neutrophilic, eosinophilic, or lymphocytic vascular inflammations ([Chen et al., 1996]). Tissue and peripheral blood eosinophilia can occur in active rheumatismal diseases. Elevation of serum ECP levels in ankylosing spondylitis, a kind of connective tissue disease, suggests that eosinophils are also involved in the underlying process (Feltelius et al., 1987). Wegener's granulomatosis can rarely present with pulmonary nodules, pleural effusion, and peripheral blood eosinophilia. ([Krupsky et al., 1993]).

Peripheral blood eosinophilia of at least 400/mm3 can occur in 7% of cases of systemic sclerosis, 31% of cases of localized scleroderma, and 61% of cases of eosinophilic fasciitis ([Falanga and Medsger, 1987]). Scleroderma yields an inflammatory process closely resembling Meissner's and Auerbach's plexuses and consists of mast cells and eosinophil leukocytes in the gastrointestinal system. Eosinophil-derived neurotoxins can contribute to gastrointestinal motor dysfunction, as occurs in scleroderma ([de Schryver Kecskemeti and Clouse, 1989]).

Eosinophils can accompany localized ([Varga and Kahari, 1997]) or systemic ([Bouros et al., 2002]) connective tissue proliferation. They can incite fibrosis by inhibiting proteoglycan degradation in fibroblasts ([Hernnas et al., 1992]), and fibroblasts mediate eosinophil survival by secreting GM-CSF ([Vancheri et al., 1989]). Eosinophils can be found in nasal ([Bachercht et al., 2001]), bronchial ([Arguelles and Blanco, 1983]), and gastrointestinal polyp tissues ([Assarian and Sundareson, 1985]). Likewise, eosinophils can be localized in inflammatory pseudotumors (myofibroblastic tumor). Eosinophils often accompany inflammatory pseudotumors in the orbital region, in which case the condition can mimic angioedema or allergic rhinoconjunctivitis ([Li et al., 1992]).

Eosinophilic inflammation can be found in tissue trauma (e.g., as a result of surgery or injury). Eosinophilic inflammation can also be associated with cardiovascular illnesses (e.g., eosinophilic myocarditis, eosinophilic coronary arteritis, ischemic heart disease, acute myocardial infarction, cardiac rupture). Necrotic inflammatory processes can also involve eosinophililic inflammation (polymyositis, coronary artery dissection, necrotizing lesions of neuro-Behcet's disease, dementia, cerebral infarction).

Provided herein are methods of Identifying Eosinophilic Inflammation Positive (EIP) patients predictive for a response to treatment with a TH2 Pathway Inhibitor (or that will be responsive to) by measuring total serum periostin levels in the patient.

Also provided herein are methods of treating asthma, an Eosinophilic Disorder, an IL-13 mediated Disorder, an IL4 mediated Disorder, an IL9 mediated Disorder, an IL5 mediated Disorder, an IL33 mediated Disorder, an IL25 mediated Disorder, an TSLP mediated Disorder, an IgE-mediated Disorder or Asthma-Like Symptoms comprising administering a TH2 pathway inhibitor to an Eosinophilic Inflammation Positive Patient, wherein the patient was diagnosed as being EIP by measuring total serum periostin levels in the patient.

In certain embodiments, methods of treating asthma, an Eosinophilic Disorder, an IL-13 mediated Disorder, IL-4 mediated Disorder or an IgE-mediated Disorder comprising administering lebrikizumab to a Eosinophilic Inflammation Positive Patient are provided.

In certain embodiments, methods of treating asthma, an Eosinophilic Disorder, an IL-13 mediated Disorder, IL-4 mediated Disorder or an IgE-mediated Disorder comprising administering a 125-500 mg flat dose of lebrikizumab every 4 weeks to the patient suffering from the disorder are provided.

Also provided are methods of treating asthma (or Respiratory Disease) comprising administering a therapeutically effective amount of Lebrikizumab to the asthma patient, wherein the treatment results in a relative change in FEV1 of greater than 5%. In another embodiment, the FEV1 is greater than 6%, 7%, 8%, 9% or 10% FEV1. In another embodiment, the patient has been diagnosed as EIP using a Total Periostin assay. In another embodiment, the asthma patient has been diagnosed with a total serum periostin assay.

In certain embodiments, methods of treating asthma (or Respiratory Disease) comprising administering a therapeutically effective amount of Lebrikizumab to the asthma patient, wherein the treatment results in a reduction in exacerbation rate of greater than 35%, (other embodiments greater than 36%, 37%, 38%, 39%, 40%, 41%, 42%, 43%, 44%, 45%, 46%, 47%, 48%, 49%, 50%, 51%, up to 85%; another embodiment, wherein the patient has been diagnosed as EIP) are provided.

In certain embodiments, methods of treating asthma (or Respiratory Disease) comprising administering a therapeutically effective amount of Lebrikizumab to the asthma patient, wherein the treatment results in a reduction in nocturnal awakenings are provided. In one embodiment, the patient is diagnosed by measuring total serum periostin levels in the patient. In another embodiment, the asthma of the patient is uncontrolled on a corticosteroid. I another embodiment, the patient is diagnosed with EIP.

Also provided are methods of treating asthma (or Respiratory Disease) comprising administering a therapeutically effective amount of Lebrikizumab to the asthma patient, wherein the treatment results in an improvement in asthma control. In one embodiment, the patient is diagnosed by measuring total serum periostin levels in the patient. In another embodiment, the asthma is uncontrolled on a corticosteroid treatment. In another embodiment, the patient is diagnosed with EIP Methods of treating Asthma (or Respiratory Disease) comprising administering a therapeutically effective amount of Lebrikizumab to the asthma patient, wherein the treatment results in a reduction of inflammation in the lungs are provided. In one embodiment, the patient is diagnosed by measuring total serum periostin levels in the patient. In another embodiment, the asthma is uncontrollable on a corticosteroid treatment. In another embodiment, the patient is diagnosed with EIP In certain embodiments, methods of treating an Eosinophilic Disorder in a patient suffering from the Eosinophilic Disorder and being treated with a corticosteroid comprising administering a therapeutically effective amount of Lebrikizumab to the asthma patient, wherein the treatment results in a reduction or elimination of corticosteroid treatment (amount or frequency) used to treat the disease are provided. In one embodiment, the patient is diagnosed by measuring total serum periostin levels in the patient. In another embodiment, the patient's asthma is uncontrollable on a corticosteroid. In another embodiment, the patient is diagnosed with EIP prior to the treatment.

Also provided are methods of treating of a patient suffering from asthma (or Respiratory Disease) comprising diagnosing the patient as EIP using a Total Periostin Assay, administering a therapeutically effective amount of TH2 Pathway Inhibitor to the asthma patient, diagnosing the patients EIP status, and retreating the patient with the TH2 Pathway Inhibitor if the status is EIP. The diagnosis being made using Total Periostin Assay alone or in combination with $FE_{NO}$ levels and optionally in combination other biomarkers selected from: CST1, CST2, CCL26, CLCA1, PRR4, PRB4, SERPINB2, CEACAM5, iNOS, SERPINB4, CST4, and SERPINB10. In yet a further embodiment, the patient to be treated in addition to having elevated expression levels of periostin as described herein, has a $FE_{NO}$ level greater than 21 ppb. In still another embodiment, the patient to be treated in addition to having elevated expression levels of periostin as described herein, has a $FE_{NO}$ level greater than 35 ppb.

In certain embodiments, methods of Identifying Patients that are Eosinophilic Inflammation Negative (EIN), comprising the step of measuring Total Periostin levels in a patient and determining that the patient is EIN are provided.

Any of the TH2 pathway inhibitors provided herein may be used in therapeutic methods described herein, especially asthma. In one embodiment, the asthma patient is being treated with a corticosteroid, and has been diagnosed as responsive a TH2 pathway inhibitor using a periostin assay described herein. In a further embodiment, the asthma patient is suffering from moderate to severe asthma. In another embodiment, the patient is suffering from mild asthma but is not being treated with a corticosteroid.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). However, other dosage regimens may be useful. The progress of this therapy is easily monitored by conventional techniques and assays.

In certain embodiments, an antibody of the invention is administered as a flat dose (i.e., not weight dependent) of 37.5 mg, or a flat dose of 125 mg, or a flat dose of 250 mg. In certain embodiments, the dose is administered by subcutaneous injection once every 4 weeks for a period of time. In certain embodiments, the period of time is 6 months, one year, two years, five years, ten years, 15 years, 20 years, or the lifetime of the patient. In certain embodiments, the asthma is severe asthma and the patient is inadequately controlled or uncontrolled on inhaled corticosteroids plus a second controller medication. In another embodiment, the patient is diagnosed with EIP status using a Total Periostin Assay to determine EIP status and the patient is selected for treatment with an anti-IL13 antibody as described above. In another embodiment, the method comprises treating an asthma patient with an anti-IL13 antibody as described above where the patient was previously diagnosed with EIP status using a Total Periostin Assay to determine EIP status. In one embodiment, the asthma patient is age 18 or older. In one embodiment, the asthma patient is age 12 to 17 and the anti-IL13 is administered in as a flat dose of 250 mg or a flat dose of 125 mg. In one embodiment, the asthma patient is age 6 to 11 and the anti-IL13 antibody is administered in as a flat dose of 125 mg.

It is understood that any of the above formulations or therapeutic methods may be carried out using an immunoconjugate of the invention in place of or in addition to an anti-target antibody or anti-periostin antibody.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-target antibody or anti-periostin antibody

EXAMPLES

Example 1—Allergen Challenge Clinical Study

A Phase II randomized, double-blind, placebo-controlled study; 5 mg/kg lebrikizumab:placebo (1:1 ratio) subcutaneously q4 weeks for 12 weeks. A high level summary of the trial design is in Table 2 and FIG. 1. The primary outcome measure was allergen-induced late asthmatic response (LAR) at Week 13. Patients received an allergen challenge followed by a methacoline challenge 18-24 hours later during the screening period and at week 13. Serum biomarkers were also assessed to demonstrate IL13 pathway inhibition and to identify patients with an increased benefit from lebrikizumab.

TABLE 2

| Design | Randomized, double-blind, placebo controlled, multiple dose study to evaluate effect of MILR1444A vs placebo on airway hyper-responsiveness to allergen challenge |
|---|---|
| Population | 18-55 year old mild asthma patients |
| Sample Size | 24 (12 per cohort) |
| Study Duration | 12 weeks (and 4 months follow-up) |
| Schedule, Dose | subcutaneous formulation (SQ), Q4w, (1 active dose level 5 mg/kg) |
| 1° endpoint | LAR AUC (Allergen Challenge) |
| 2° endpoint | PC20 (allergen challenge), FEV1, PC20 (Methacholine challenge) |

The patients included in the study were mild asthmatics, 18-55 years old, with: (a) Positive skin test (> or =3 mm over negative control) at screening to house dust mite, cat dander, or ragweed; (b) Forced expiry volume in 1 second (FEV1) > or =70% of predicted; and (c) Early asthmatic response of > or =20% reduction in FEV1 in 5-30 minutes following allergen challenge, and a late asthmatic response (LAR) of > or =15% reduction in FEV1 in 2-8 hours post challenge.

Figure 2A:
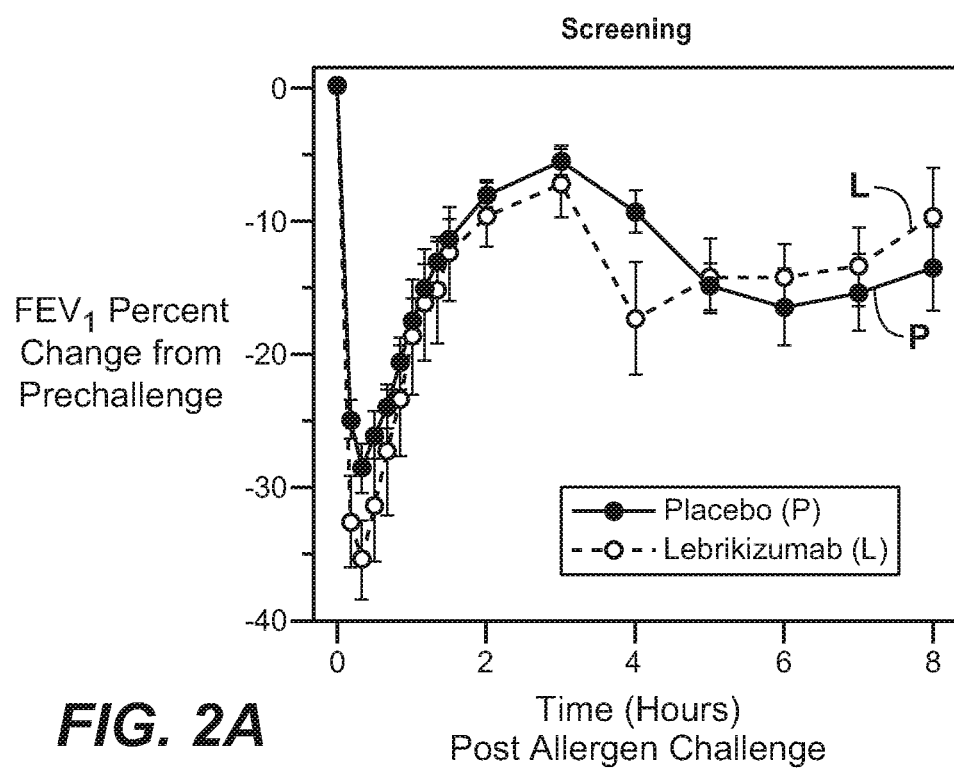
FIGS. 2A-2B show allergen-induced changes in FEV1 following challenges in screening (FIG. 2A) and at week 13 (FIG. 2B). FEV1 was measured every 10 minutes for the first 90 minutes and then every hour from 2-8 hours following allergen challenge. Error bars represent standard errors of the mean.
Figure 2B:
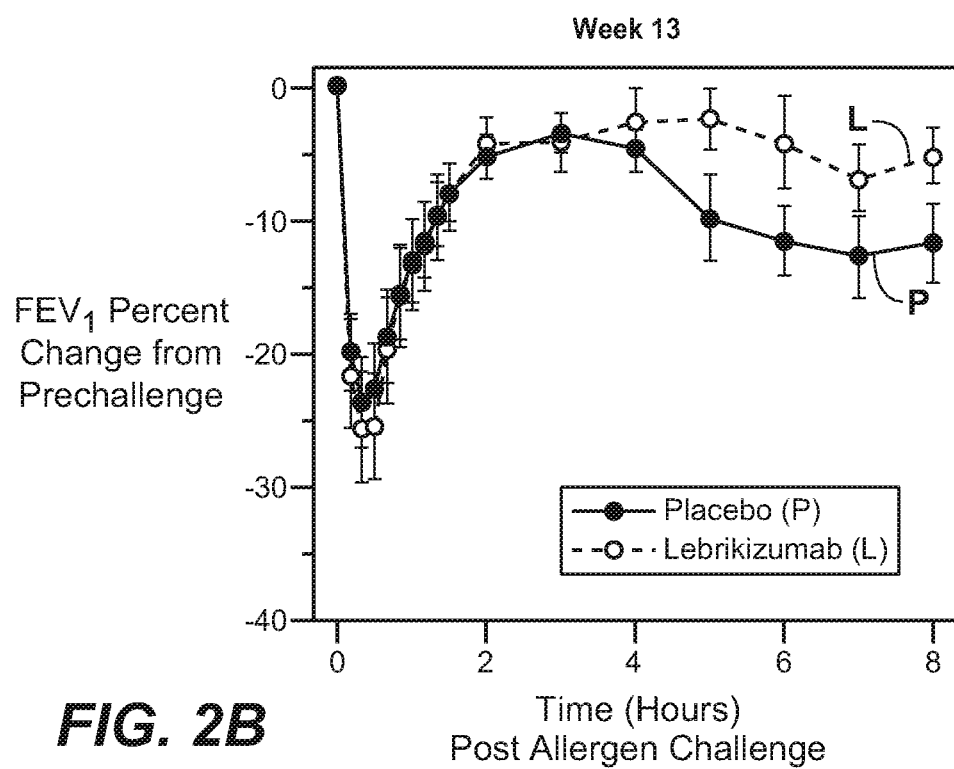

Twenty-eight patients were included in analysis of the primary endpoint (n=16 placebo, 12 lebrikizumab). At Week 13, lebrikizumab inhibited the LAR. The mean AUC (area under the curve) of FEV1 2-8 hours after allergen challenge (LAR) in lebrikizumab-treated patients was reduced by 48% vs. placebo (26.3% vs. 50.5%; 95% CI: −19 to 90%), with no effect on the early phase response (EAR) at week 13. The mean AUC of FEV1 and the maximum reduction in FEV1 0-2 hours post-allergen challenge were similar in the lebrikizumab and placebo groups (27.5% vs. 26.4% for both parameters; Table 3). See also FIGS. 2A-2B. No significant difference between the lebrikizumab and placebo groups was observed on airway hyperresponsiveness to methacholine. The arithmetic mean of the methacholine doubling dose in the lebrikizumab group was 0.33 doubling doses higher than that in the placebo group (1.58 vs. 1.25, 95% CI −0.64 to 1.3), which was not considered a clinically meaningful inhibition.

TABLE 3

| | Screening | | | Week 13 | | |
|---|---|---|---|---|---|---|
| | PB N = 16 | LB N = 12 | (LB − PB)/PB | PB N = 16 | LB N = 12 | (LB − PB)/PB |
| Early Asthmatic Response | | | | | | |
| Max % reduction in FEV1 | 30.3 | 38.0 | 25.4 | 25.5 | 29.6 | 16.1 |
| AUC FEV1 (0-2 h postchallenge), % FEV1 × h | 34.1 | 39.9 | 17.0 | 26.4 | 27.5 | 4.2 |
| Late Asthmatic Response | | | | | | |
| Max % reduction in FEV1 | 24.8 | 30.8 | 24.2 | 16.4 | 13.8 | −15.9 |
| AUC FEV1 (2-8 h postchallenge, % FEV1 × h) | 73.8 | 77.0 | 4.3 | 50.5 | 26.3 | −47.9 |

Figure 3A:
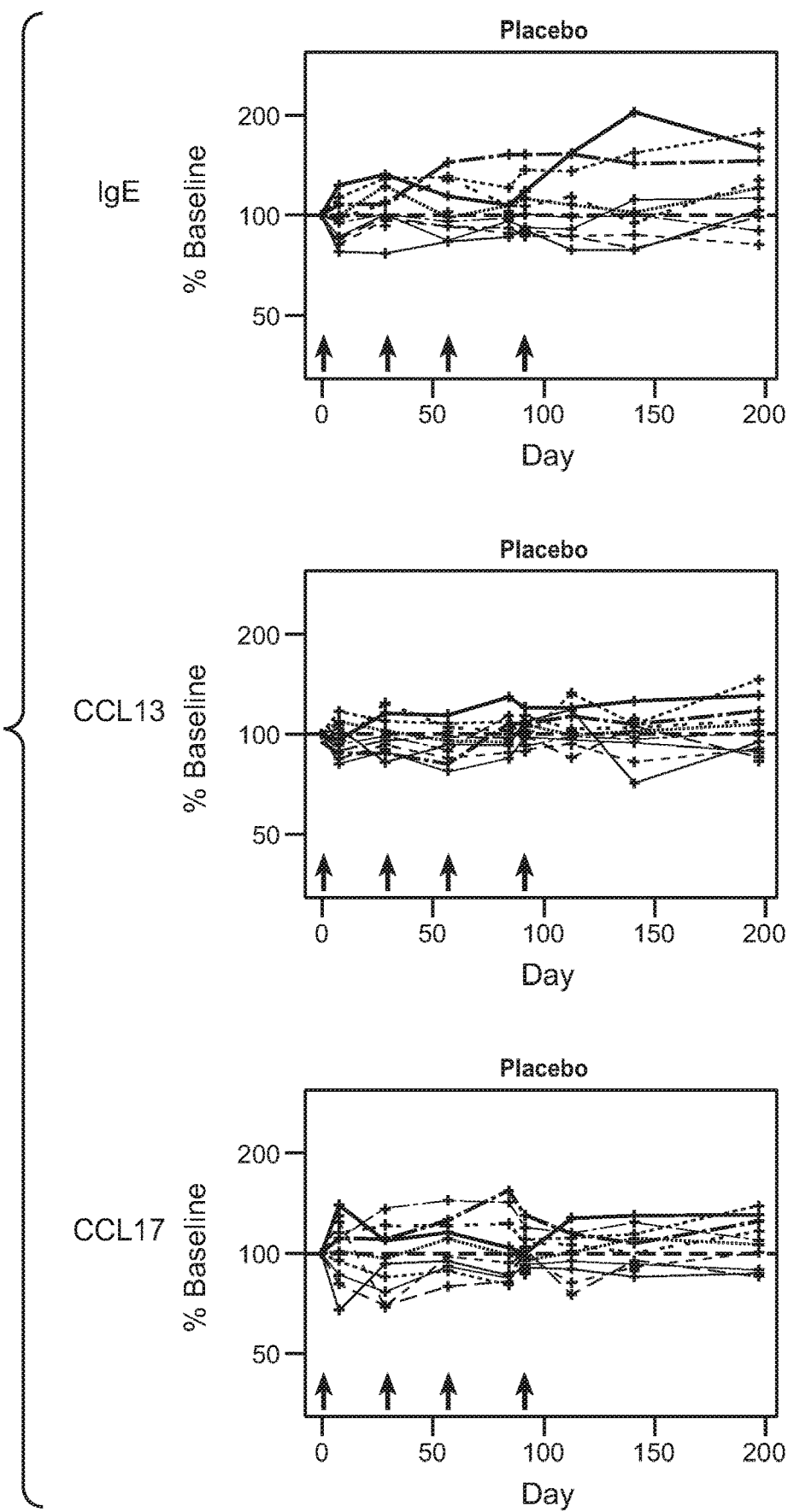
FIGS. 3A-3C show serum levels of IgE, CCL13 (MCP-4), and CCL17 (TARC), (FIG. 3A) Serum levels expressed as % predose levels over time in placebo-treated patients and (FIG. 3B) lebrikizumab-treated patients. Lines represent individual patients; groups medians not indicated. Arrows indicated dosing at weeks 0, 4, 8, and 12 (days 0, 28, 56 and 84).
Figure 3B:
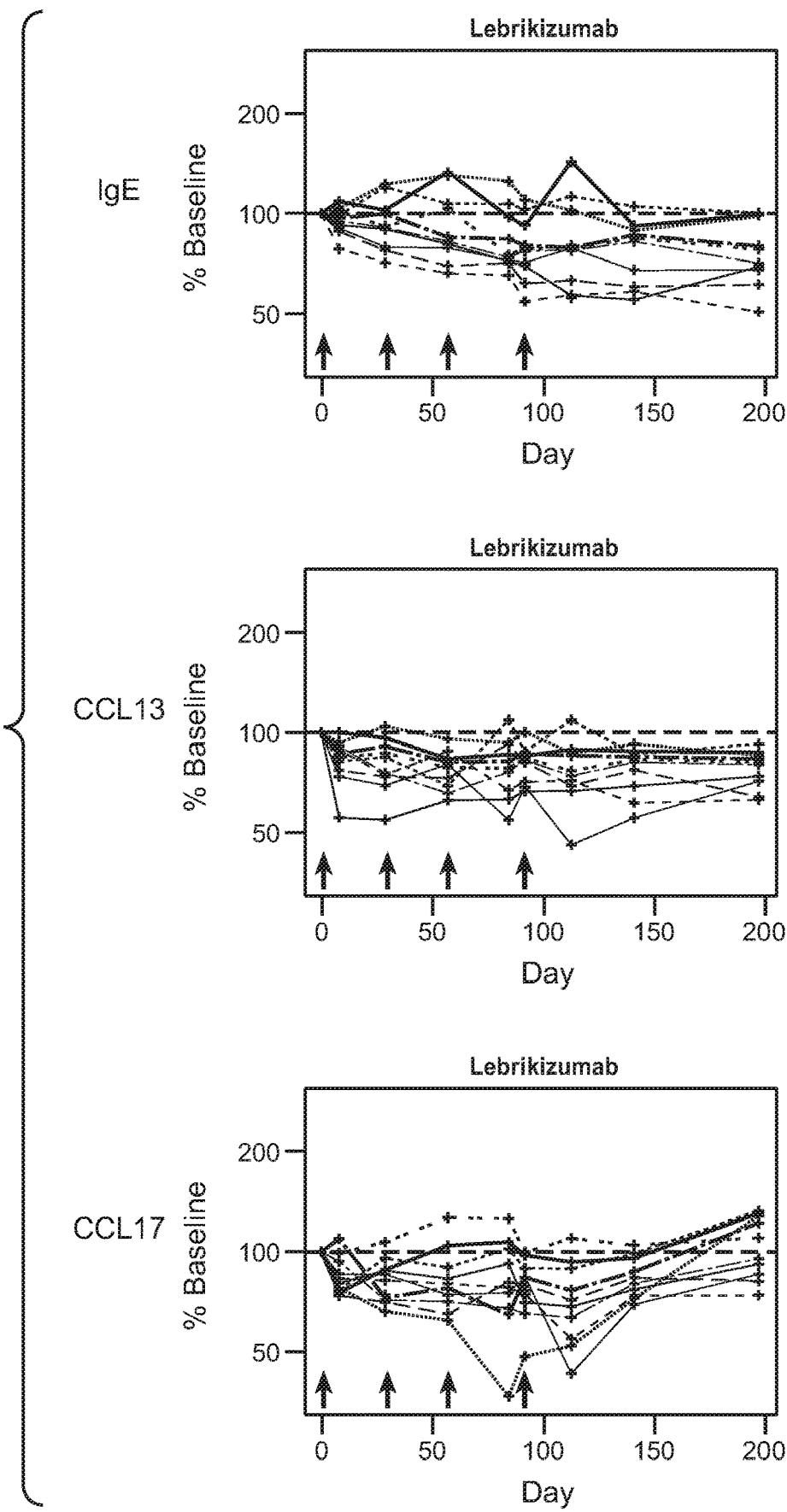
Figure 3C:
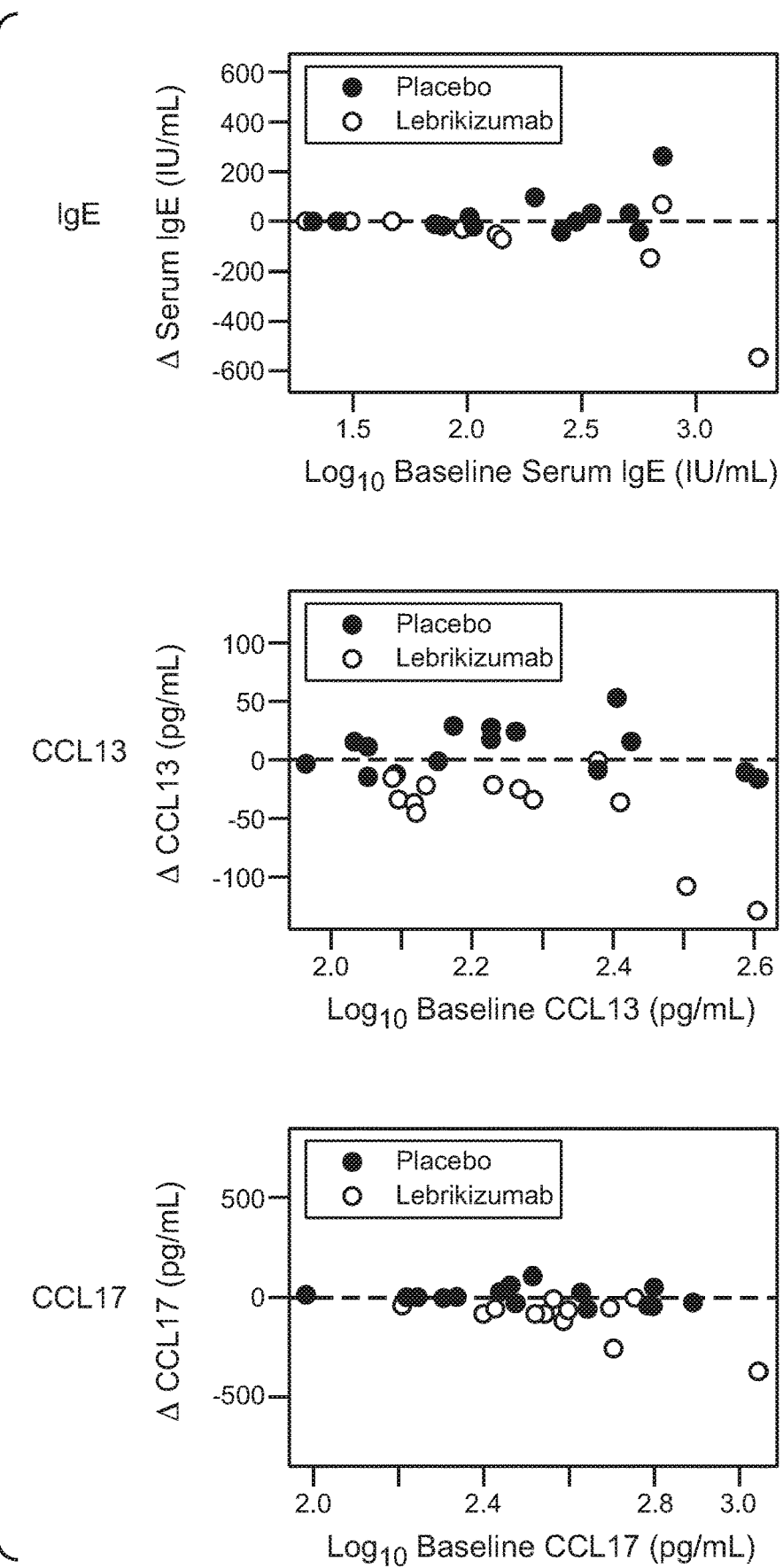

Lebrikizumab treatment clearly exerted systemic effects on markers of Th2 inflammation, with mean placebo-adjusted reductions of 24%, 25% and 26%, in serum IgE, MCP-4/CCL13, and TARC/CCL17, respectively (P<0.01). See FIGS. 3A and 3B. Serum periostin levels were slightly reduced (5-10%) after treatment. Serum IL-13 levels were mostly below level of detection (<150 pg/ml) after treatment. FIG. 3C shows reductions in IgE, CCL13 and CCL17 at week 13 in individual patients relative to baseline levels of those markers. In general, periostin, YKL-40, CEA and blood eosinophils levels did not change significantly after lebrikizumab treatment (data not shown).

Subjects with baseline levels above the median of peripheral blood eosinophils, serum IgE, or serum periostin exhibited a greater placebo-adjusted lebrikizumab dependent reduction in LAR than subjects with baseline levels of these biomarkers below the median. See FIG. 4.

Figure 4:
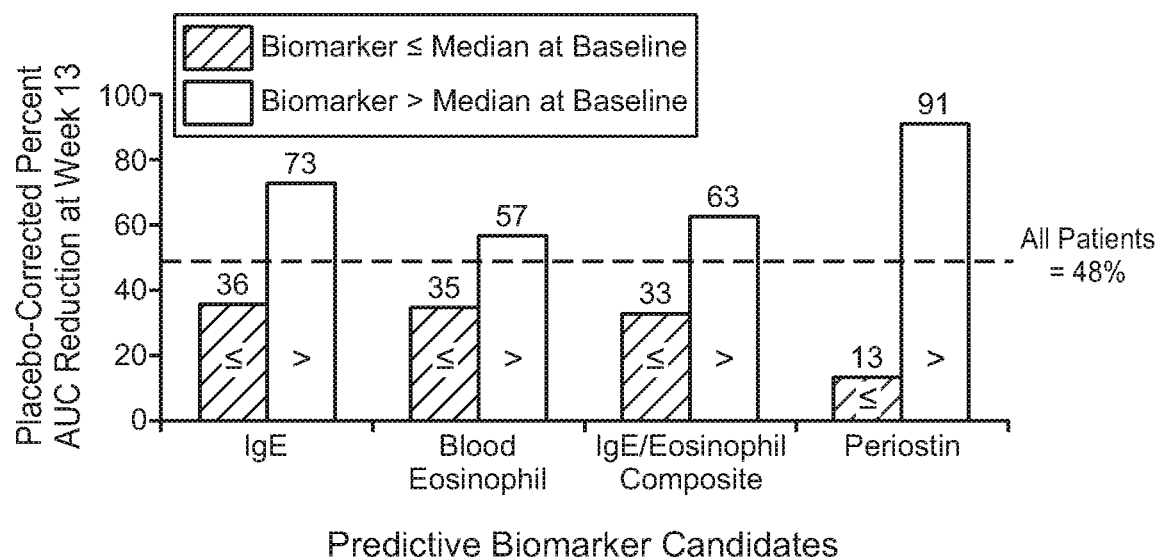
FIG. 4 shows lebrikizumab-induced inhibition of the late asthmatic response (LAR) in biomarker-high and biomarker-low patient subgroups. Data are expressed as placebo-corrected mean reduction in AUC (area under the curve) of the LAR at Week 13 (n=5 to 8 active patients/group).

Patients were categorized as "biomarker-high" or "biomarker-low" based on having higher than or lower than the median levels of inflammatory biomarkers at baseline: serum IgE, CCL13, CCL17, CEA, periostin, YKL-40 and peripheral blood eosiniophils. As shown in FIG. 4, the results for serum IgE, eosinophils, and periostin indicated that patients with elevated (compared to the median) baseline serum IgE, periostin, or increased peripheral blood eosinophils were more likely to respond to IL13 blockade (e.g., by lebrikizumab).

In conclusion, the study met its primary endpoint: 48% reduction (90% CI [−19%, 90%)]) in mean late phase AUC. Lebrikiuzumab significantly reduced LAR compared to placebo. No safety signal was seen in the safety data. Therapeutic blockade of IL13 may be an effective treatment for allergic asthma, particularly in patients with elevated markers of airway TH2 inflammation.

Example 2—Asthma Patient Clinical Study I

A randomized, double-blind, placebo-controlled study was conducted to evaluate the effects of lebrikizumab in patients with asthma who remain inadequately controlled or uncontrolled while on chronic therapy with ICS. Patients continued their standard-of-care therapy which included inhaled corticosteroids (ICS) and could also include a LABA. In this two-arm study, patients were randomly allocated to receive either lebrikizumab or placebo for 6 months. During a 14-20 day run-in period (Visit 1 to Visit 3), patients had to demonstrate compliance with ICS and their ability to use the equipment necessary for daily monitoring throughout the study. Patients were then assessed for study eligibility and randomly allocated (1:1) to study drug (lebrikizumab or placebo) with stratification based on IL-13 signature surrogate status (described further below), LABA use, and study site. The first SC dose occurred within 24 hours of random allocation (Study Day 1, i.e., the day of random allocation, regardless of first study drug administration date). Administration of study drug was repeated once every 4 weeks for the next 20 weeks (for a total of six study drug doses providing a 24-week treatment period). Measures of the efficacy of lebrikizumab were assessed during the treatment period.

Figure 5:
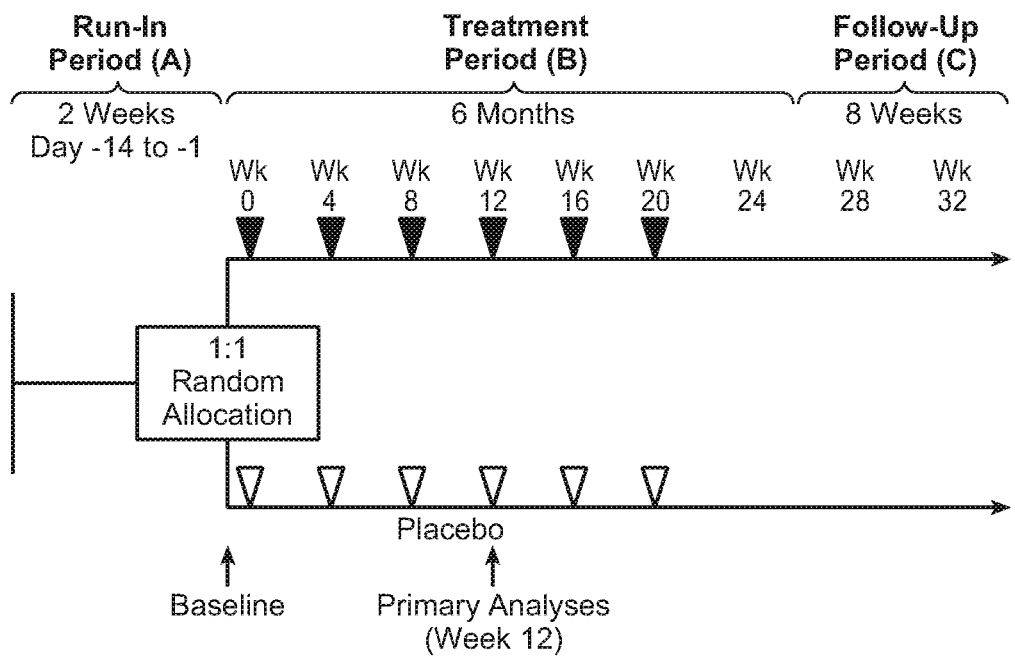
FIG. 5 provides is a schematic of an asthma trial described in Example 2.

Study drug was administered to selected patients by subcutaneous (SC) injection on the following timepoints: Day 1 and at Weeks 4, 8, 12, 16, and 20. Each dose of lebrikizumab was 250 mg. Each placebo dose was 2 mL of the same fluid without lebrikizumab. SC injections were administered in the arm, thigh, or abdomen. A schematic of this trial design can be seen in FIG. 5.

The primary analysis was conducted after all (approximately 200) patients were treated and followed for 24 weeks after random allocation (Day 1). Safety was assessed throughout the study. After the final dose (Week 20) of study drug, patients were monitored for an additional 12 weeks; the first 4 weeks after the final dose were considered part of the (24-week) treatment period, and the final 8 weeks constituted the follow-up period. The 8-week follow-up period, together with the last 4 weeks of the treatment period, allowed for monitoring of patients for 3-4 half-lives following the last dose. Therefore, patients generally participated in the study for a total of approximately 34 weeks. See FIG. 5. Efficacy evaluable patients (n=180) were defined for decision making purposes to exclude subjects for two reasons: (1) not part of target population in key characteristics and (2) unreliable baseline FEV1 from which to measure treatment effect. See FIG. 6 for baseline characteristics of patients participating in this trial.

TABLE 4

| | |
|---|---|
| Design | 1:1 randomized, double-blind, placebo-controlled study to evaluate efficacy and safety of lebrikizumab vs placebo |
| Population | 18-65 year old patients with asthma who are inadequately controlled on inhaled corticosteroids (ICS) |
| Sample Size | Approximately 218 |
| Study Duration | 2 week screening period, 24 week treatment period, 8 week safety follow-up period |
| Dose | 250 mg, every 28 days, for a total of 6 doses |
| 1° endpoint | Relative change in FEV1 from baseline to Week 12 |
| 2° endpoints | Relative change in FEV1 from baseline to Week 24. Relative change in FEV1 from baseline to Week 12 or patients with IL-13 signature surrogate positive status. Rate of asthma exacerbations during the 24-week period. |

Key Inclusion Criteria included the following: Ability to perform spirometry at Visits 1-3 as per study specific Pulmonary Function Test (PFT) Manual; Chest radiograph within 12 months of Visit 1 with no evidence of a clinically significant abnormality; Ability to complete study materials as measured by compliance with diary completion and PEF measurements between Visits 1-3; Uncontrolled asthma selected on all the following criteria:

Diagnosis of asthma >12 months
Bronchodilator response at Visit 1 or 2
Prebronchodilator FEV1≥40% and 80% predicted at Visits 1 and 3
Use of ICS≥200 µg and ≤1000 µg total daily dose of fluticasone propionate (FP) or equivalent for at least consecutive 6 months prior to Visit 1
Visit 3 Asthma Control Questionnaire (ACQ) s score ≥1.5 despite ICS compliance.

Key Exclusion Criteria included the following:
Medical conditions:
Asthma exacerbation, significant airflow obstruction, or respiratory infection from Visits 1-3
Known malignancy or current evaluation for a potential malignancy
Known immunodeficiency, including but not limited to HIV infection
Pre-existing lung disease other than asthma, including active infections
Uncontrolled clinically significant medical disease
Exposures:
Current smoker or former smoker with a lifetime smoking history of >10 pack years
Prohibited concomitant medications (Steroids other than ICS, short-acting bronchodilators other then SABA, immunomodulatory agents)
Pregnancy or not willing to use highly effective contraception Given the practical difficulties of measuring IL-13 in the lung itself, eosinophil and IgE levels in peripheral blood were used as a surrogate measure, denoted as "IL-13 signature surrogate." IL-13 signature surrogate-positive patients were defined as patients with total IgE≥100 IU/mL and blood eosinophils ≥0.14×10×e9 cells/L, whereas the IL-13 signature surrogate-negative patients had a total IgE≤100 IU/mL or blood eosinophils <0.14×10×e9 cells/L. The criteria for the IgE and eosinophil levels that determined patients' status for IL-13 signature surrogate were established from patients with asthma in whom IL-13 induced gene expression in the bronchial epithelium (IL-13 signature) was correlated with peripheral blood IgE and eosinophils (Corren et al., N Engl J Med 365:1088-1098 [2011]).

The efficacy of lebrikizumab was assessed using multiple measures of asthma activity, including pulmonary function (i.e., FEV1, peak flow including variability in peak flow, response to methacholine at selected centers, fractional exhaled nitric oxide [$FE_{NO}$]) and measures of disease activity or control (i.e., patient-reported outcomes [PROs], use of rescue medication, rate of exacerbations). Change in FEV1 was the primary outcome. The following markers after treatment with lebrikizumab: TARC (CCL17), MCP-4 (CCL13) and IgE for pharmacodynamic analyses.

Primary Efficacy Outcome Measure

The primary efficacy outcome measure was the relative change in pre-bronchodilator FEV1 (volume) from baseline to Week 12.

Secondary Efficacy Outcome Measures

The secondary efficacy outcome measures were the following: Relative change in pre-bronchodilator FEV1 (volume) from baseline to Week 24; Relative change in pre-bronchodilator FEV1 (volume) from baseline to Week 12 for patients with IL-13 signature surrogate positive status; Change in Asthma Control Questionnaire (ACQ) score from baseline to Week 12; Change in Asthma Symptom Score as measured by the Asthma Control Daily Diary (ACDD) from baseline to Week 12; Change in morning pre-bronchodilator peak flow value from baseline to Week 12; Rate of asthma exacerbations during the 24-week treatment period; Rate of severe asthma exacerbations during the 24-week treatment period; Change in rescue medication use (measured by number of puffs per day of rescue medication or nebulized rescue medication) from baseline to Week 12.

Exploratory Measures:

The following exploratory outcome measures were assessed: Change in the number of days per week with well controlled asthma, as measured by the ACDD from baseline to Week 12; Change in weekly frequency of nocturnal awakening due to asthma from baseline to Week 12; Change in $FE_{NO}$ levels from baseline to Week 12.

Initial Observations

In this study of patients with poorly controlled asthma, lebrikizumab treatment was associated with a statistically significant improvement in pre-bronchodilator FEV1, the primary outcome variable. The improvement in FEV1 occurred soon after the initiation of treatment, indicating that IL-13 inhibition impacted measures of airflow relatively quickly. Although lebrikizumab treatment did not lead to statistically significant reductions in protocol-defined and severe exacerbations using the Elecsys® periostin assay (described below, due to unavailable values to contribute to the analysis), a trend towards a decrease in rates of severe exacerbations, especially for periostin high patients, was observed. However, using the E4 Assay as described below, lebrikizumab treatment did lead to statistically significant reductions in protocol-defined and severe exacerbations (84% in the periostin high subgroup (95% CI 14%, 97%, p=0.03). See also below. Furthermore, the $FE_{NO}$ subgroup analysis did achieve a statistically significant reduction in severe exacerbations (p=0.04). Lebrikizumab treatment did not improve asthma symptoms as measured by the symptom-only version of the ACQ5 (which excluded rescue SABA use and FEV1) or the daily diary measures.

The reduction in serum Th2 chemokines, CCL13 and CCL17, and IgE supports a lebrikizumab-mediated biologic effect that underlies the clinical impact measured in the airway. The slight increase in blood eosinophil count is consistent with an overall reduced trafficking of eosinophils from the blood to the lung compartment following inhibition of eosinophil-attracting chemokines. The finding that lebrikizumab decreased $FE_{NO}$ is consistent with this suggestion. However, lebrikizumab may have decreased $FE_{NO}$ by indirectly inhibiting nitric oxide synthase expression via IL-13 blockade, rather than by modifying eosinophilic inflammation (which is also thought to impact $FE_{NO}$).

The patient eligibility criteria for this study required reversibility of at least 12% to 400 μg of albuterol (with no SABA use for at least 4 hours and no LABA use for at least 12 hours before visits). This was to ensure that patients had "room to move" when looking for an overall relative change of at least 10% in lung function. This simple clinical test may limit the ability to generalize these data to unselected, more general asthma patient populations. Indeed, the most common reason for patient ineligibility was failure of this test (in 92 of 263 patients who failed screening).

In this study, we first hypothesized that the combination of high serum IgE and high blood eosinophil count was a surrogate for identifying patients with increased expression of IL-13 related genes in the lung (IL13 signature surrogate, or Th2 high). While the data were still masked to treatment assignment, we wrote a statistical analysis plan to use differentiation based on serum periostin levels. As described in more detail below, this subgroup analysis showed that the effectiveness of lebrikizumab treatment was enhanced in periostin-high relative to periostin-low patients, as observed with both a more robust increase in FEV1 and a greater decline in $FE_{NO}$, as well as a significant interaction test. These findings suggest that the prespecified marker, serum periostin, could potentially be used to select asthma patients who may be more responsive to lebrikizumab treatment.

The baseline characteristics of the patients participating in the study are shown in FIG. 6. The numbers refer to the mean (SD) unless otherwise noted. Periostin high refers to patients with baseline periostin above 23 ng/ml according to the E4 Assay described below. Periostin low refers to patients with baseline periostin below 23 ng/ml according to the E4 Assay described below.

The relative changes in FEV1 (liters) at 12 weeks and at 24 weeks (95% confidence intervals) for patients treated are shown in FIG. 7. As compared to the IL13 signature positive patients, the periostin positive patients experienced a higher relative change in FEV1.

Figure 8B:
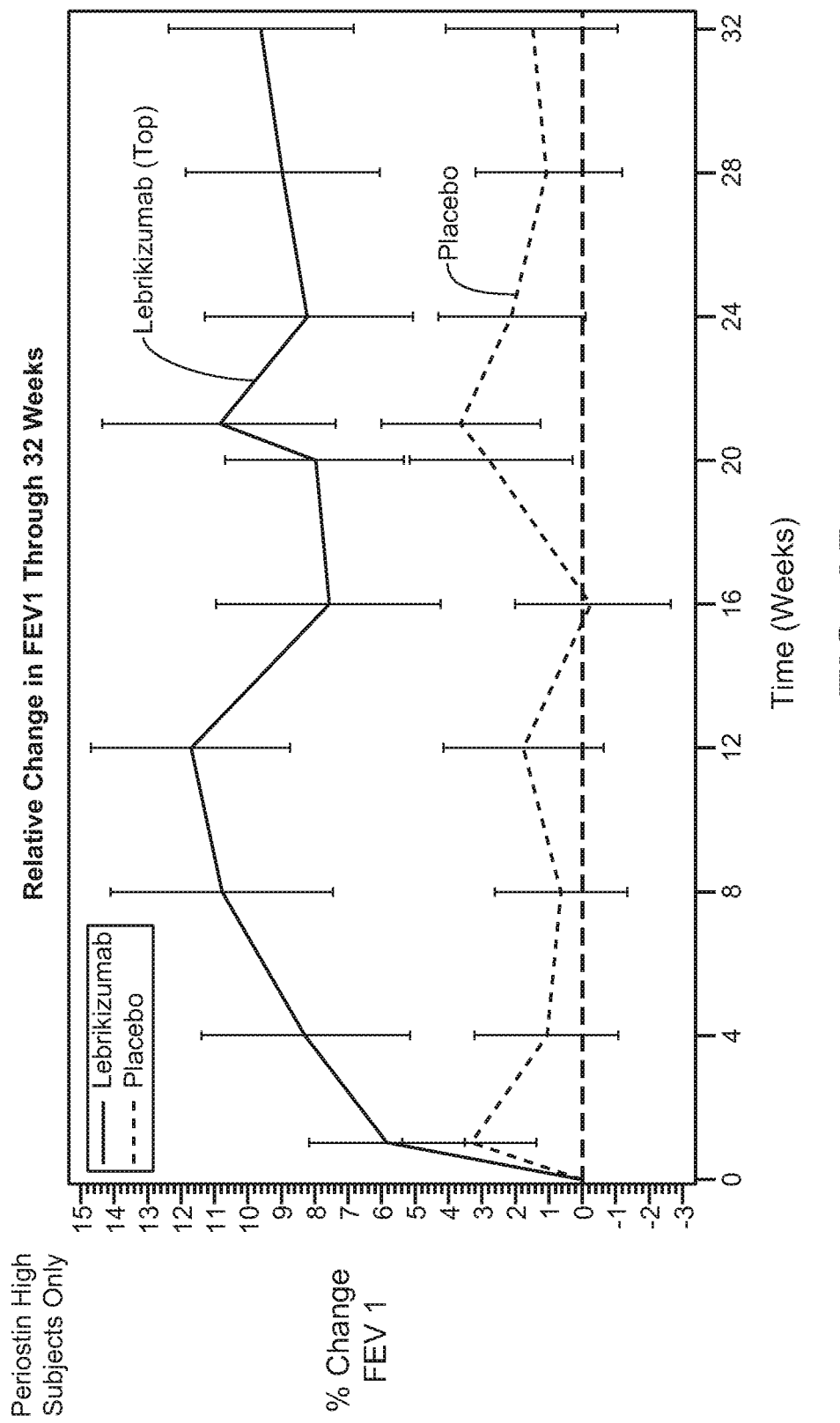

FIG. 7 shows that the placebo corrected relative change in FEV1 from baseline to 12 weeks for all-comers was 5.9% (95% CI 0.9%, 10.9%, p=0.2) and 10% for the periostin high subgroup (95% CI 2.5%, 17.5%, p=0.01)). The placebo corrected relative change in FEV1 from baseline to 24 weeks for all-comers was 4.8% (95% CI 0.3%, 9.3%, p=0.04) and 6.1% for the periostin high subgroup (95% CI -1.4%, 13.6%, p=0.11). FIGS. 8A-8B show the relative change in FEV1 throughout the treatment period (32 weeks) for all efficacy evaluable subjects (FIG. 8A) and for periostin high subjects only (FIG. 8B). The efficacy of lebrikizumab at 32 weeks of treatment did not wane suggesting that it may be possible to decrease the frequency in which lebrikizumab is administered.

We also examined the effect of lebrikizumab treatment on post-bronchodilator FEV1 as an exploratory outcome and an indirect surrogate for airway remodeling. Change in post-bronchodilator FEV1 at 20 weeks was measured after four inhalations of 100 mcg albuterol. At baseline before study drug administration, the mean post-bronchodilator FEV1 was 2.50 liters (0.71) and 2.54 liters (0.73) in the placebo and lebrikizumab groups, respectively. This corresponded to 77.9% predicted in both groups. The overall placebo-corrected change in post-bronchodilator FEV1 was 4.9% (95% CI 0.2% to 9.6%; p=0.04). In the periostin high group, lebrikizumab treatment increased the post-bronchodilator FEV1 at 20 weeks (8.5%; 95% CI 1.1% to 16%; p=0.03). There was no evidence of improvement in post-bronchodilator FEV1 in the periostin low group (1.8%; 95% CI -4.1 to 7.7; p=0.55). In addition, lebrikizumab increased the absolute post-broncbodilator FEV1 in the periostin high group (170 mls; 95% CI 10 to 320 ml). We conclude that lebrikizumab improved post-bronchodilator FEV1 in uncontrolled asthma patients who had evidence of increased Th2 airway inflammation (periostin high). Based upon this data, lebrikizumab may have the potential to reduce airway remodeling in asthma.

Figures 9, 10:
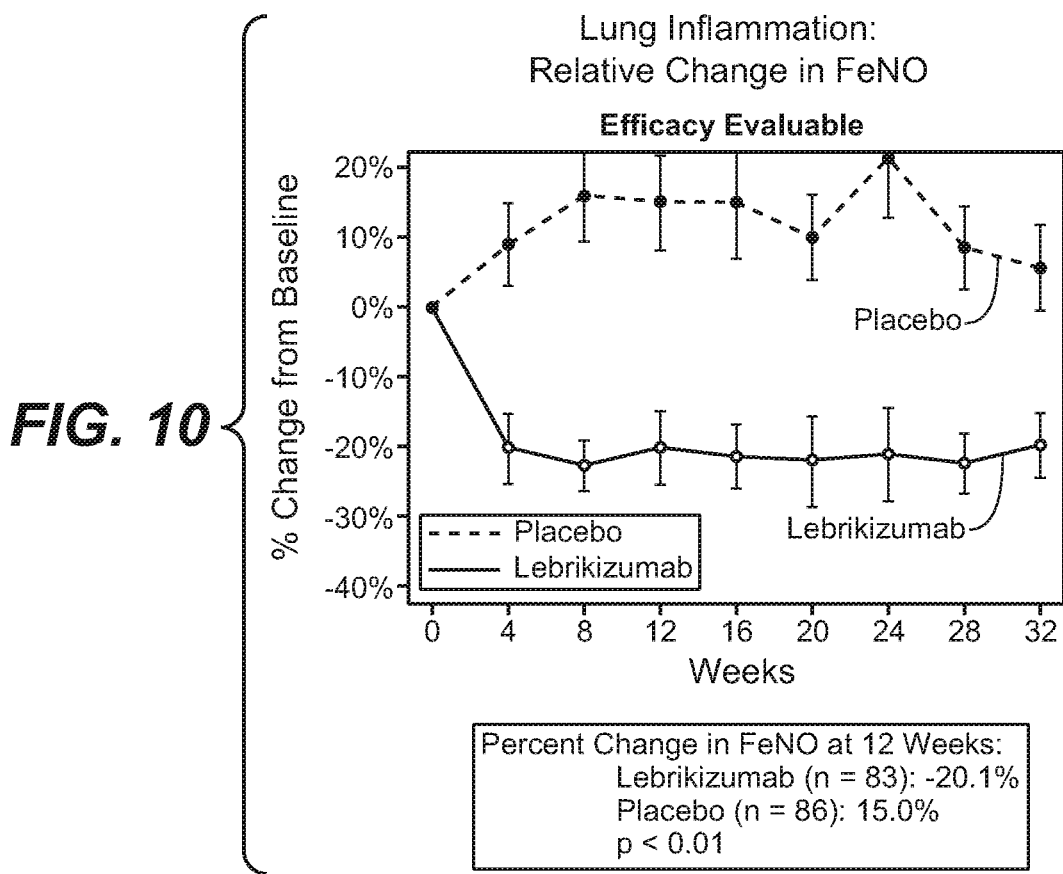
FIG. 9 provides rates of reduction in exacerbations from the asthma trial of Example 2.
FIG. 10 provides percent change of $FE_{NO}$ from asthma trial of Example 2.

FIG. 9 shows the exacerbation rate and severe exacerbation rate observed at 24 weeks of treatment. The exacerbation rate was reduced by 37% in lebrikizumab treated all-comers compared to placebo (95% CI -22%, 67%, p=0.17) and by 61% in the periostin high subgroup (95% CI -6%, 86%, p=0.07). The severe exacerbation rate was reduced by 51% (95% CI -33%, 82%, p=0.16) for all comers and by 84% in the periostin high subgroup (95% CI 14%, 97%, p=0.03). We also examined the rates of severe exacerbations at 32 weeks, the end of the follow-up period, 12 weeks after the final dose of lebrikizumab in the ITT population. As shown in Table 10, severe exacerbation rates across all patients at 32 weeks were significantly reduced by 50% in lebrikizumab treated patients compared with placebo (p=0.03). The rate of severe exacerbations was lowest in periostin-high patients treated with lebrikizumab (0.13); however, the rate reduction from placebo did not reach statistical significance in the subanalyses. We conclude that Lebrikizumab had a significant benefit in reducing severe exacerbations in patients inadequately controlled by ICS. The greatest reduction in severe exacerbations was seen in patients with high periostin levels prior to treatment. The duration of observation to capture events is important in powering studies for this end-point and 32-weeks observation compared to 24 weeks may be needed to detect at least a 50% reduction in approximately 200 subjects.

TABLE 10

Severe exacerbation rate at 32 weeks, 12 weeks post-final dose.

| Group* | Lebrikizumab, severe exacerbation rate | Placebo, severe exacerbation rate | Rate reduction (95% CI) p-value |
|---|---|---|---|
| All patients (n = 218) | 0.17 | 0.34 | 50% (9, 72) p = 0.03 |
| Periostin-high (n = 110) | 0.13 | 0.32 | 61% (-1, 85) p = 0.06 |
| Periostin-low (n = 101) | 0.23 | 0.40 | 43% (-30, 75) p = 0.18 |

Lebrikizumab met its primary endpoint and was very effective in reducing severe exacerbations. The data suggests that the periostin status of a patient can be prognostic of exacerbations events and to a lesser extent FEV1. The data supports the predictive value of periostin levels for determining response to lebrikizumab treatment. For example, using the E4 assay, those patients with serum or plasma periostin levels below 20 ng/ml are less likely to benefit from lebrikizumab whereas those patients with serum or plasma periostin levels above 20 ng/ml are more likely to benefit from lebrikizumab. Furthermore, those patients with serum or plasma periostin levels above 23 ng/ml (as determined by the E4 assay) have even a greater likelihood of benefiting from lebrikizumab treatment.

Patient Reported Outcomes: The ACQ and mini-AQLQ did not demonstrate consistent differences between treatment groups. After several visits, the ACDD data demonstrated some differences in the mean scores between treatment groups in well controlled days, asthma symptoms, nocturnal awakening, and rescue medication use, all favoring lebrikizumab treatment. For all endpoints in the ACDD data (well controlled days, asthma symptoms, nocturnal awakening, and rescue medication use), there was a greater placebo corrected treatment effect in periostin high subjects compared to all subjects; however, none of the differences between treatment groups at 12 weeks were statistically significant.

Lung function: Improvement in lung function (PEF) from baseline was observed for most time points in all lebrikizumab treated subjects and at all time points for periostin high lebrikizumab treated subjects. Placebo treated subjects declined from baseline at all time points.

Lung Inflammation: $FE_{NO}$ declined (improved) throughout the study for both lebrikizumab treated subjects and those in the periostin high subset, while placebo treated subjects had increases in $FE_{NO}$ (worsening). The percent change in $FE_{NO}$ at 12 weeks was −20.1% for lebrikizumab treated subjects (n=83) versus 15% for placebo-treated subjects (n=86) [p<0.01]. The percent change in $FE_{NO}$ at 12 weeks was −24.2% for lebrikizumab treated subjects versus 17.5% for placebo-treated subjects (n=44) [p<0.01]. Differences between treatment groups at 12 weeks were statistically significant. See FIG. 10. In a post hoc analysis, high baseline $FE_{NO}$ was also associated with efficacy in improving FEV1 and a lower severe exacerbation rate compared to placebo. However we noted that baseline $FE_{NO}$ showed greater intra-patient variability during the run-in than did periostin (19.8% versus 5.0%).

We also examined the data to determine whether patients who were both periostin-low and $FE_{NO}$-high benefited from lebrikizumab treatment to the same degree as periostin-high patients. At baseline, we observed a moderate correlation between $FE_{NO}$ and serum periostin (rs=0.31, P<0.001; N=210 with matching data). Using median cutoffs, periostin and $FE_{NO}$ status generally but incompletely overlapped (Table 11). For the data shown in Table 11, the periostin cut-off was 25 ng/mL using the E4 Assay described below and the $FE_{NO}$ cut-off was 21 ppb as measured using standard methodology known in the art. Evaluation of FEV1 based on composite periostin and $FE_{NO}$ status revealed that the placebo-adjusted effect of lebrikizumab at 12 weeks was greatest in the group with high levels of both periostin and $FE_{NO}$ (Table 12). In contrast, the observed treatment benefit in the periostin-low/$FE_{NO}$-high group was marginal (2.3%, P=0.73). Thus, $FE_{NO}$ does not appear to identify a subset periostin-low patients who benefit from lebrikizumab. The relative predictive value of periostin and $FE_{NO}$ for response to lebrikizumab treatment merits further study.

TABLE 11

Distribution of patients according to baseline periostin and $FE_{NO}$ status.

|  |  | $FE_{NO}$ status | |
|---|---|---|---|
|  |  | Low | High |
| Periostin status | Low | 62 | 39 |
|  | High | 42 | 67 | p = 0.0004 by Fisher's exact test (1-sided)

TABLE 12

Mean Relative Change From Baseline $FEV_1$ at 12 Weeks in ITT Patients. The median baseline levels of $FE_{NO}$ or periostin for all patients who met protocol-defined entry criteria were used to define the subsets described in the table (high = median value or higher; low = less than median value).

|  | All Subjects (n = 218) | Periostin-low $FE_{NO}$-low (n = 62) | Periostin-low $FE_{NO}$-high n = 39) | Periostin-high $FE_{NO}$-low (n = 42) | Periostin-high $FE_{NO}$-high (n = 67) |
|---|---|---|---|---|---|
| Lebrikizumab | 9.8% | 2.6% | 9.1% | 8.6% | 16.3% |
| Placebo | 4.3% | 1.5% | 6.8% | 6.3% | 5.4% |
| Difference | 5.5% | 1.1% | 2.3% | 2.3% | 11.2% |
| (95% CI) | (0.8%, 10.2%) | (−4.5%, 6.6%) | (−10.7%, 15.2%) | (−9.3%, 13.9%) | (1.9%, 20.5%) |

The pharmacokinetic characteristics of lebrikizumab were similar to those which had been seen in previous studies. Body weight of the subjects had an impact on the pharmacokinetics of lebrikizumab.

Several markers were evaluated for their ability to provide predictive value in terms of treatment benefit above, in addition to or as an alternative to serum periostin levels. Those markers included CEA, IgE, TARC (CCL17) and MCP-4 (CCL13).

Figure 18A:
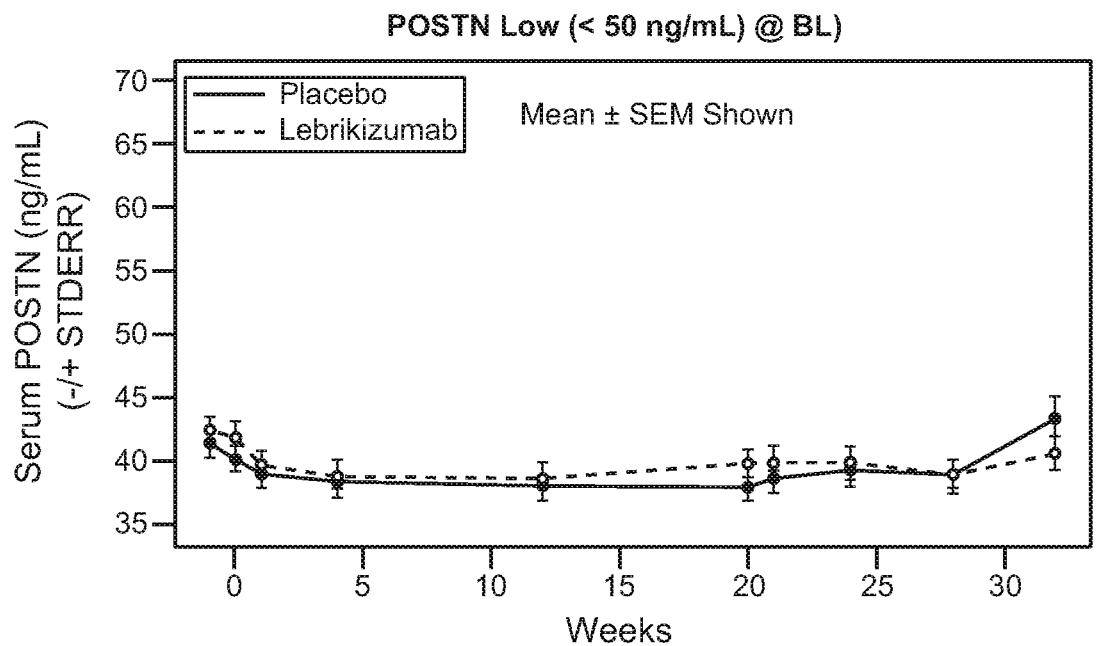
FIGS. 18A-18B show serum periostin pharmacodynamics in periostin-low patients (FIG. 18A) and in periostin-high patients (FIG. 18B) as described in Example 2.
Figure 18B:
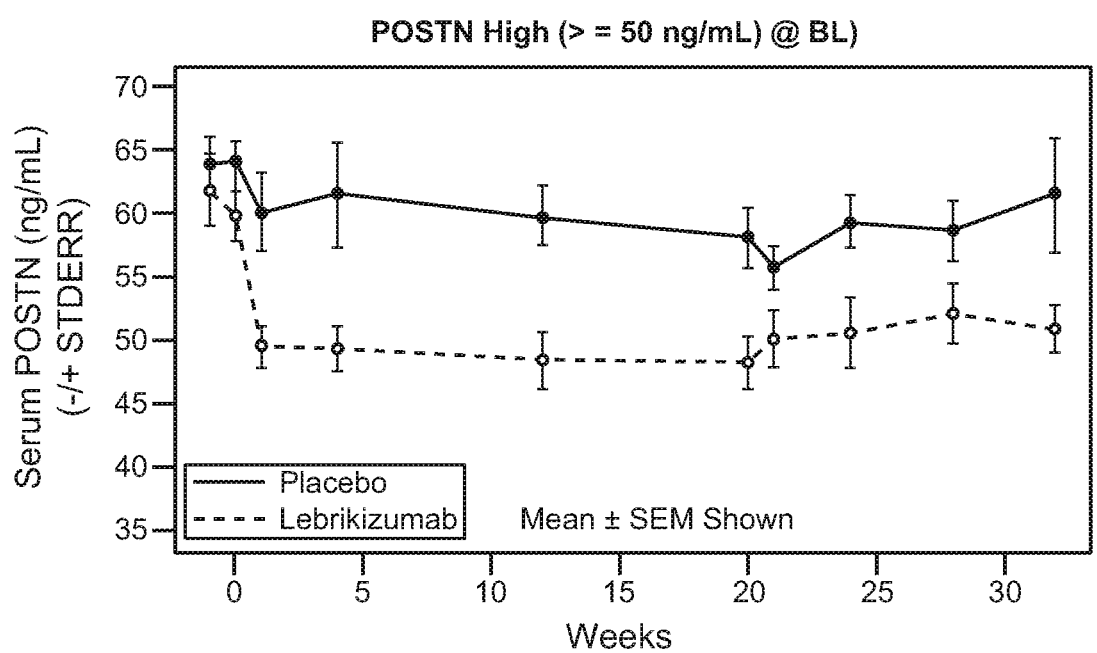

In addition, we hypothesized that the excess serum periostin in periostin-high patients with asthma is due to the effects of IL13. Thus, we sought to assess the relative contribution of IL-13 to total systemic periostin levels in both placebo and lebrikizumab-treated patients with uncontrolled asthma. For these experiments, we measured serum periostin using the Elecsys® periostin assay described in Example 7. As shown in FIGS. 18A-18B and 19, we found that the majority (>90%) patients who were periostin-low at baseline remained low in both arms of the study (FIG. 18A), whereas 72% of periostin-high patients treated with placebo and 40% treated with lebrikizumab remained periostin-high at Week 12 (FIG. 18B). We conclude that in adults with uncontrolled asthma despite ICS, periostin-high patients exhibited a significant reduction in serum periostin levels upon lebrikizumab treatment as compared with placebo, but periostin-low patients exhibited no significant reduction in response to lebrikizumab. These findings suggest that in uncontrolled asthma patients, excess serum periostin is due to the activity of IL-13, and that inhibition of IL-13 with lebrikizumab decreases serum periostin levels.

Figures 11, 12:
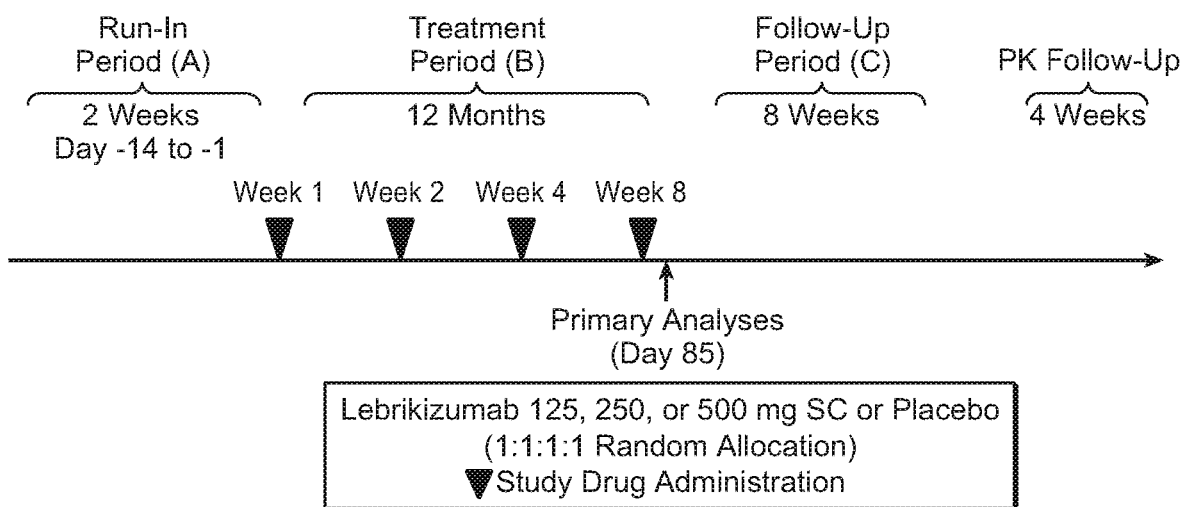
FIG. 11 provides safety results from the asthma trial Example 2.
FIG. 12 provides is a schematic of an asthma trial described in Example 3.

Four lebrikizumab-treated patients experienced serious adverse events (SAEs) (asthma exacerbation [n=2], community-acquired pneumonia, and traumatic pneumothorax related to a car accident). Six placebo patients experienced seven SAEs (asthma exacerbation [n=2], headache, cerebrospinal fluid leak after epidural, shingles, herpes zoster, acute purulent meningitis, and pain medication addiction). See FIG. 11 for safety results from this trial.

The overall frequency of AEs was similar in both treatment arms (lebrikizumab, 74.5%; placebo, 78.6%), as were the frequencies of serious AEs (lebrikizumab, 3.8%; placebo, 5.4%) (Table 9). Musculoskeletal events were more common with lebrikizumab (lebrikizumab, 13.2%; placebo, 5.4%; P=0.045) (Table 9). Twenty-five patients (11.5%) discontinued the study early, including 12 placebo- and 13 lebrikizumab-treated patients.

TABLE 9

| Type of Musculoskeletal or Connective Tissue Disorder | Placebo (n = 112) | Lebrikizumab (n = 106) | All (n = 218) |
|---|---|---|---|
| Arthralgia | 2(1.8) | 3(2.8) | 5(2.3) |
| Back pain | 2(1.8) | 1(0.9) | 3(1.4) |
| Pain in extremity | 1(0.9) | 2(1.9) | 3(1.4) |
| Myalgia | 0 | 2(1.9) | 2(0.9) |
| Neck pain | 2(1.8) | 0 | 2(0.9) |
| Arthritis | 0 | 1(0.9) | 1(0.5) |
| Bone development abnormal | 1(0.9) | 0 | 1(0.5) |
| Bursitis | 0 | 1(0.9) | 1(0.5) |
| Costochondritis | 0 | 1(0.9) | 1(0.5) |
| Exostosis | 0 | 1(0.9) | 1(0.5) |
| Flank pain | 0 | 1(0.9) | 1(0.5) |
| Musculoskeletal chest pain | 0 | 1(0.9) | 1(0.5) |
| Musculoskeletal pain | 0 | 1(0.9) | 1(0.5) |
| Pain in jaw | 1(0.9) | 0 | 1(0.5) |
| Tendinitis | 0 | 1(0.9) | 1(0.5) |
| Musculoskeletal and connective tissue disorders (Total) | 6(5.4) | 14(13.2) | 20(9.2) |

Example 3—Asthma Patient Study II (Dose Ranging Study)

A randomized, double-blind, placebo controlled, four-arm, dose-ranging study was conducted to further evaluate the relationship between the dose of lebrikizumab and the response in terms of the efficacy, safety and tolerability in patients with asthma who were not on inhaled corticosteroids. See FIG. 12 for a schematic design of this trial. Selected patients had as bronchodilator response of at least 15% and a pre-bronchodilator FEV1≥60% and 85% predicted with disease stability demonstrated during the run-in period. Selected patients for the study previously managed with ICS could not have received ICS for a minimum of 30 days prior to the first study visit (Visit 1). The study had no withdrawal period; patients were not to be taken off corticosteroids for the sole purpose of becoming eligible for the study.

The first study-related procedure at Visit 1 began the approximately 2-week run-in period. During the run-in period (Visits 1-3), asthma control (as measured by the Asthma Control Questionnaire [ACQ] score) and pulmonary function were assessed. Patients' asthma was further characterized with skin prick testing and relevant biomarkers including IgE and peripheral blood eosoinophils. The IgE and eosinophil levels were used to classify patients on the basis of their IL-13 signature surrogate status. At the end of the run-in period, eligible patients were randomly allocated (1:1:1:1) to receive one of three doses (500 mg, 250 mg or 125 mg) of lebrikizumab or placebo via SC administration. Study drug was administered four times during the 12-week treatment period. After the final dose of study drug, patients were monitored for an additional 8-week follow-up period. Therefore, most patients participated in the study for a total of approximately 22 weeks after Visit 1, during which time intermittent PK samples were obtained. Intensive PK sampling was performed with additional PK samples obtained during the study and follow-up period as well as an additional PK sample 16 weeks after the last study drug administration, until 70 subjects completed the intensive PK sampling. Therefore, study participation for the patients in the intensive PK sampling group last approximately 26 weeks after Visit 1. Safety was assessed throughout the study and pre-specified thresholds for treatment failure were defined so that patients could be taken off study drug to resume standard therapy if they have a clinically significant deterioration.

Initial Observations

Figure 16:
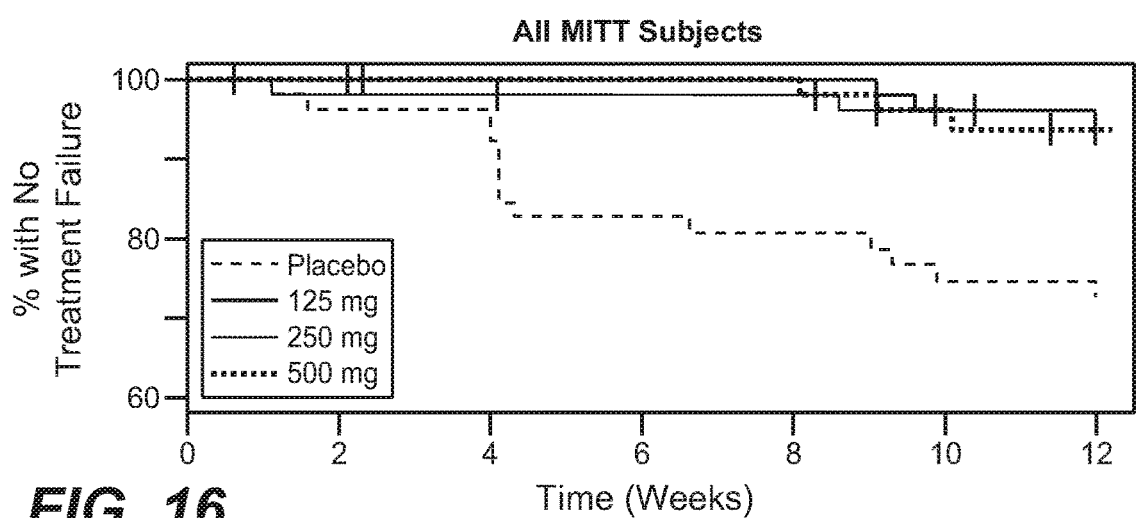
FIG. 16 provides the percentage of patients with no treatment failure in the asthma trial described in Example 3.

Efficacy: The placebo corrected relative change in FEV1 from baseline to 12 weeks for all lebrikizumab treated subjects was 4.1% (95% CI −0.4, 8.6%; p=0.075) improvement. Throughout the 12 week treatment period, the estimated risk of treatment failure in all lebrikizumab treated patients was 75% lower than placebo treated patients (HR 0.25, 95% CI: 0.11, 0.78; p=0.001). These results were considered clinically and statistically significant. There was no evidence of a dose response (see FIG. 16).

Safety: There were no clinically significant imbalances between the lebrikizumab treated and placebo treated patients except for injection site reactions (23% versus 6%, lebrikizumab to placebo respectively).

Example 4—Periostin Assay (E4 Assay)

A periostin capture ELISA assay that is very sensitive (sensitivity 1.88 ng/ml is described below. The antibodies recognize periostin isoforms 1-4 at nM affinity (SEQ ID NOs:5-8)).

Dilute 80 uL of purified monoclonal antibody, 25D4 (Coat Antibody, SEQ ID NOs: 1 and 2 expressed from a hybridoma or a CHO cell line) with phosphate buffered saline to a final concentration of 2 ug/mL. Coat microtiter plates overnight, covered, at 2-8° C. with Coat Antibody 100 µL per well. Wash plate three times with 400 µL wash buffer (PBS/0.05% Tween (polysorbate 20) per well per cycle of wash buffer at room temperature. Add 200 µL per well of blocking buffer to plate. Incubate covered plate at room temp with shaking for 1.5 hours.

Prepare rhuPeriostin standard curve (Standard Stock of rhuPeriostin=rhuPeriostin isoform 1, R&D systems #3548-F2, 5.25 ng/ml, in Assay Diluent (PBS/0.5% bovine serum albumin (BSA)/0.05% polysorbate 20/0.05% ProClin300, pH7.4). Standard curve diluent=PBS/0.5% BSA/0.05% polysorbate 20, 0.05% ProClin300, pH 7.4. For example:

| Std conc (pg/mL) | Procedure |
|---|---|
| 600 | 80 µL rhuPeriostin, 5.25 ng/ml in Assay Diluent + 620 µL standard curve diluent |

| Std conc (pg/mL) | Procedure |
|---|---|
| 300 | 300 µL 600 pg/mL rhuPeriostin + 300 µL standard curve diluent |
| 150 | 300 µL 300 pg/mL rhuPeriostin + 300 µL standard curve diluent |
| 75 | 300 µL 150 pg/mL rhuPeriostin + 300 µL standard curve diluent |
| 37.5 | 300 µL 75 pg/mL rhuPeriostin + 300 µL standard curve diluent |
| 18.75 | 300 µL 37.5 pg/mL rhuPeriostin + 300 µL standard curve diluent |
| 9.38 | 300 µL 18.75 pg/mL rhuPeriostin + 300 µL standard curve diluent |
| 0 | standard curve diluent |

Prepare Controls and samples. Three controls: Spike Source Control (rhuPeriostin full length, isoform 1, R&D Systems #3548-F2), Normal Matrix Control (normal human serum pool, Bioreclamation, Inc.), High Matrix Control (normal human serum pool, plus 100 ng/ml rhuPeriostin spike).

For example:

10 µL Control (or sample) serum+1.99 mL sample/control diluent=1:200

300 µL 1:200 dilution+300 µL sample/control diluent=1:400

300 µL 1:400 dilution+300 µL sample/control diluent=1:800

300 µL 1:800 dilution+300 µL sample/control diluent=1:1600

Each dilution is run in singlicate

Construct Matrix Controls using a normal human serum pool. Use unspiked pooled human serum as the Normal Control. Generate the High Control by spiking 100 ng/ml rhuPOSTN into the pooled serum as described above. Compute mean, standard deviation (SD), and % coefficient of variance (CV, expressed in percent) for the four dilutions for each control on every plate. CV is Quantifies magnitude of variance in replicate measurements with respect to mean of replicates. % CV=100*(SD/mean). Evaluate these mean concentrations across all plates to determine inter-plate precision. This control table is then used to define the Normal and High Control pass/fail criteria, setting allowable variance to ±20% of the mean concentration for each control.

Wash plate three times with 400 µL per well per cycle of wash buffer (PBS/0.05% polysorbate 20). Add diluted standards (duplicate wells), controls (all four dilutions), and samples (all four dilutions) to plate, 100 µL per well. Incubate plate covered, at room temperature with shaking for 2 hours at room temp. Dilute 80 uL detection MAb stock I (biotinylated murine anti-human periostin, MAb 23B9, 7.5 ug/ml in Assay Diluent) to 12 mL with Assay Diluent=50 ng/mL. Wash plate four times with 400 µL per well per cycle of wash buffer. Add diluted detection MAb to plate, 100 µL per well. Incubate covered plate at room temp for one hour with shaking. Dilute 80 uL streptavidin-HRP stock I (AMDEX streptavidin-HRP, GE Healthcare #RPN4401, approximately 1 mg/ml) diluted 1:80 in Assay Diluent to 12 mL with Assay Diluent=1:12 k. Wash plate four times with 400 µL per well per cycle of wash buffer. Add diluted streptavidin-HRP to plate, 100 µL per well. Incubate covered plate at room temp for 45 min. with shaking. Bring Kirkegaard and Perry (KPL) two-step TMB reagents to room temp; do not combine. Wash plate four times with 400 µL per well per cycle of wash buffer. Mix equal volumes of KPL TMB substrate components and add to plate, 100 µL per well. Incubate plate for 20 minutes at room temperature with shaking. Add 1 M phosphoric acid to plate, 100 µL per well. Read plate using 450 nm read wavelength and 650 nm reference wavelength. This assay or an assay similar to the above assay was used in the clinical trial described in Example 3.

A periostin assay using antibodies against isoform 1 (not Total Periostin) was tested on different asthma patient samples using a similar antibody capture format. Preliminary results indicate that periostin isoform 1 is not as robust as a marker for TH2 inflammation as total periostin.

Example 5—Asthma Patient Observational Study (BOBCAT)

We previously reported certain biomarker findings based on our studies of biological samples stored in the Airway Tissue Bank at the University of California, San Francisco (UCSF) that had been collected during bronchoscopy performed for research purposes in healthy and asthmatic volunteers. See, e.g., Intn'l Pub. No. WO2009/124090. To verify these findings in a large cohort of moderate to-severe asthma and generalize them across multiple clinical sites, we conducted a multi-center 3-visit observational study ("BOBCAT") of uncontrolled moderate-to-severe asthmatics (ACQ>1.50 and FEV1 between 40-80%) on high doses of ICS (>1000 µg/day fluticasone DPI or equivalent) with collection of induced sputum, endobronchial biopsies, and peripheral blood. We obtained matched blood and airway data from 59 subjects (see study overview in FIG. 13). Details of the study are provided below.

Figure 13:
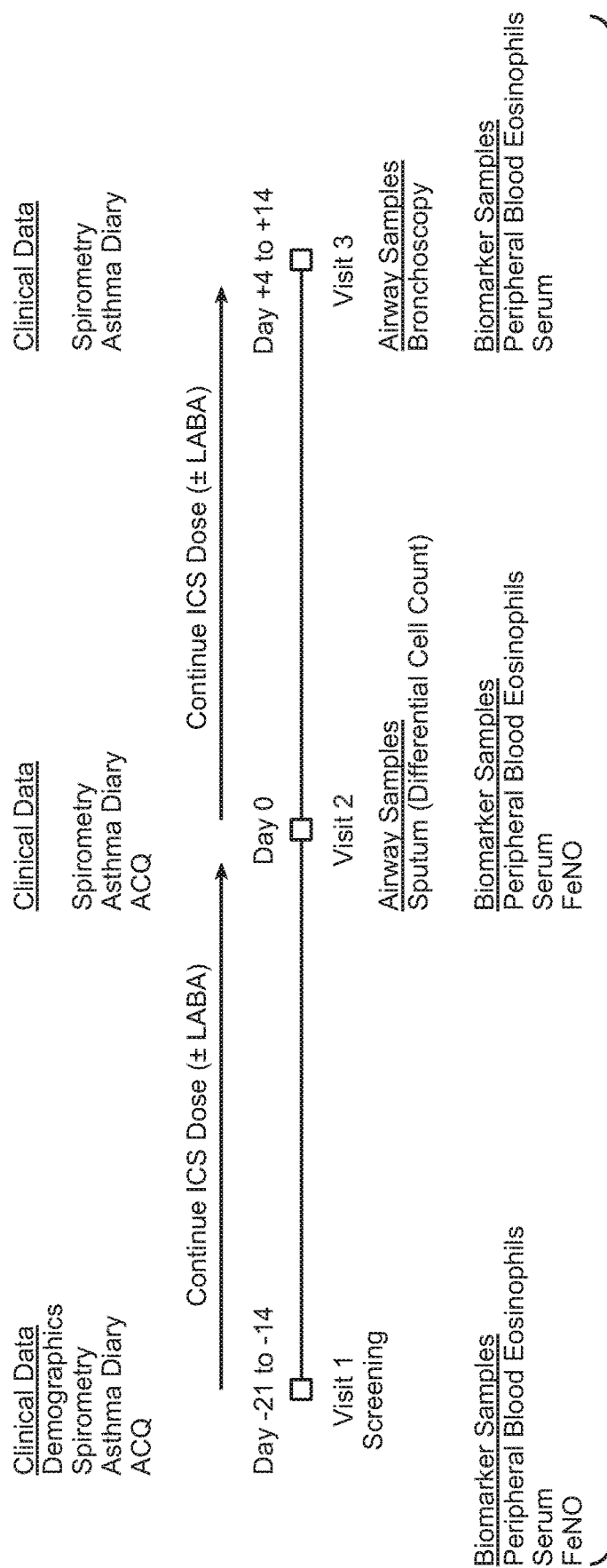
FIG. 13 provides a schematic of an asthma observational study as described in Example 5.
Figure 14A:
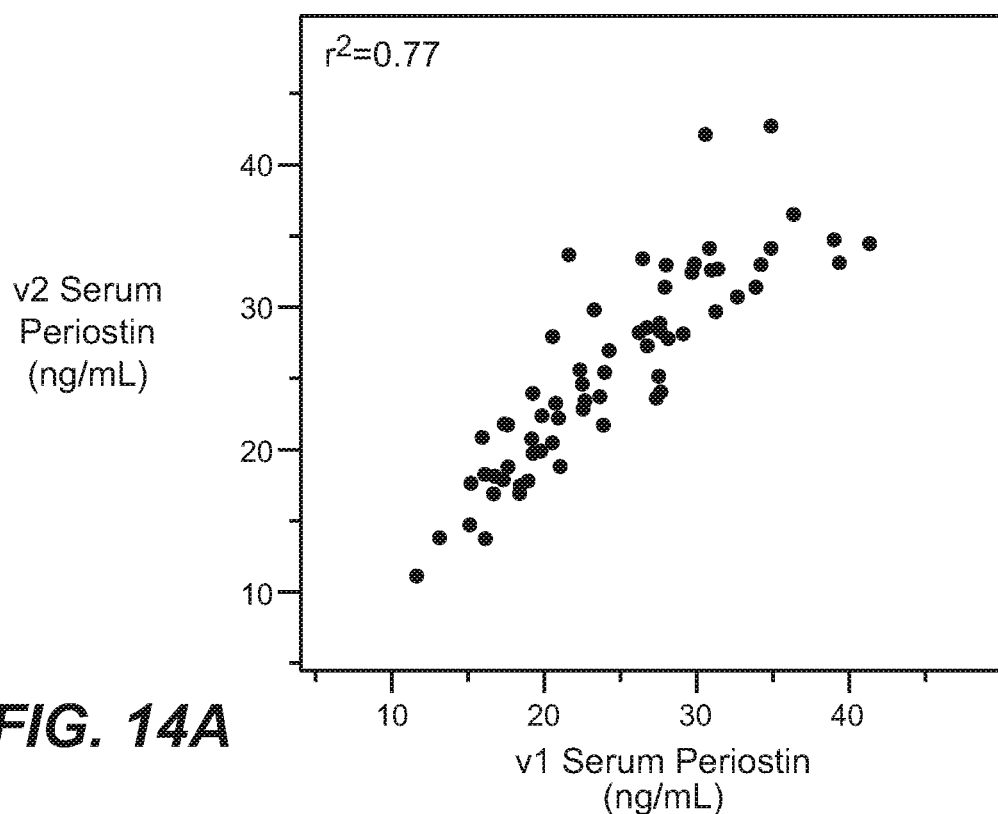
FIGS. 14A-14F show intra-subject correlation between serum periostin levels across multiple visits in the BOBCAT cohort as described in Example 5.
Figure 14B:
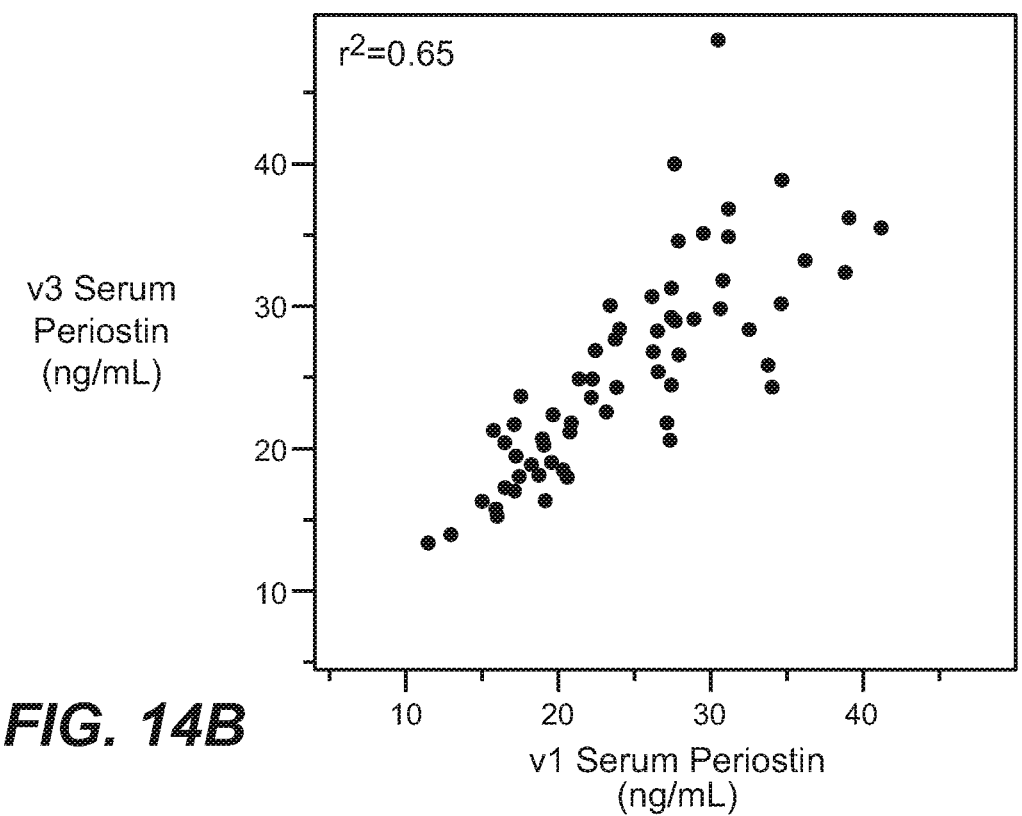
Figure 14C:
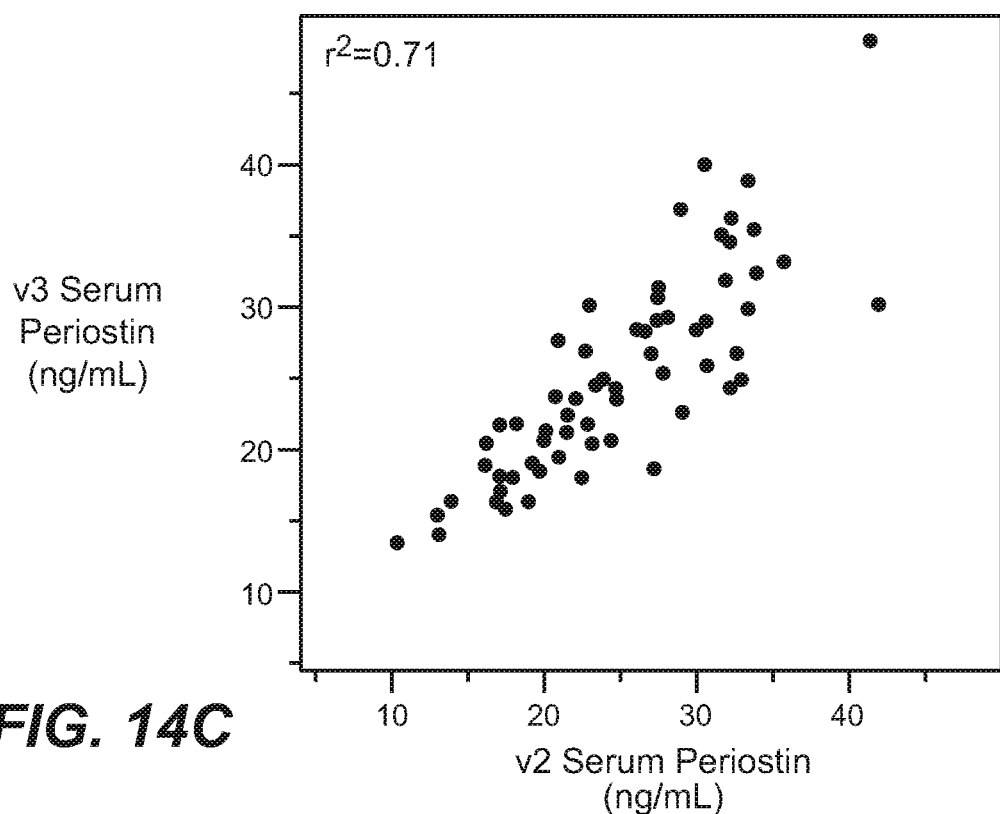
Figure 14D:
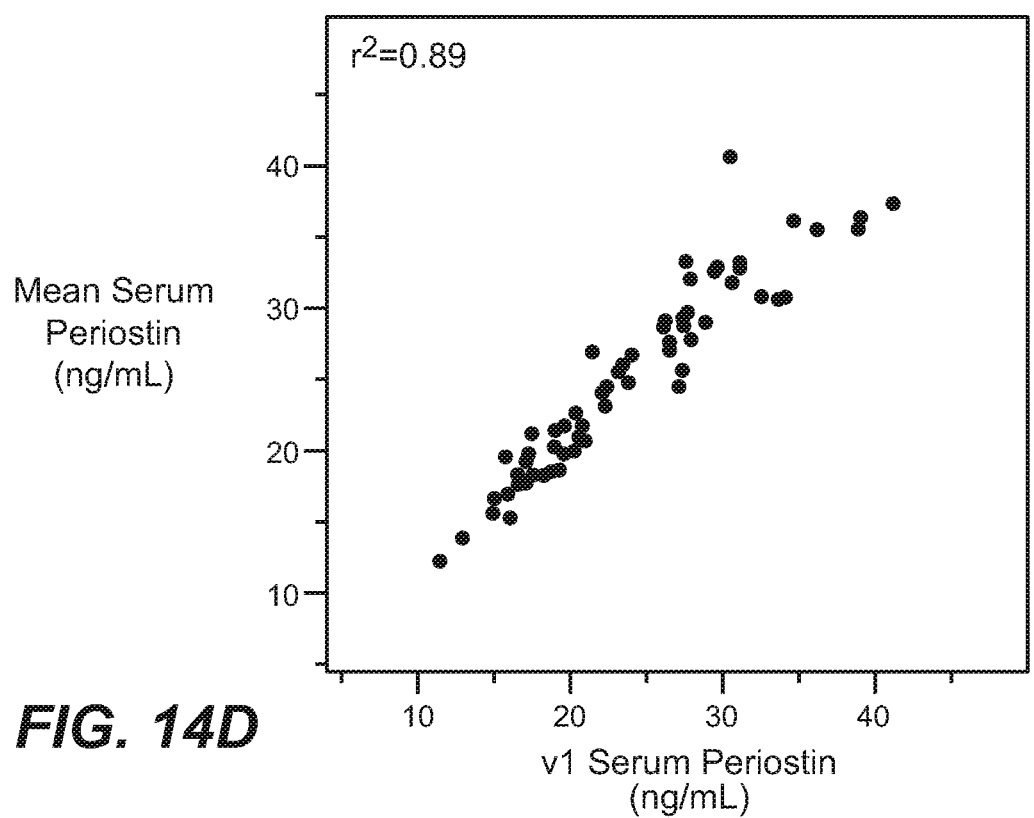
Figure 14E:
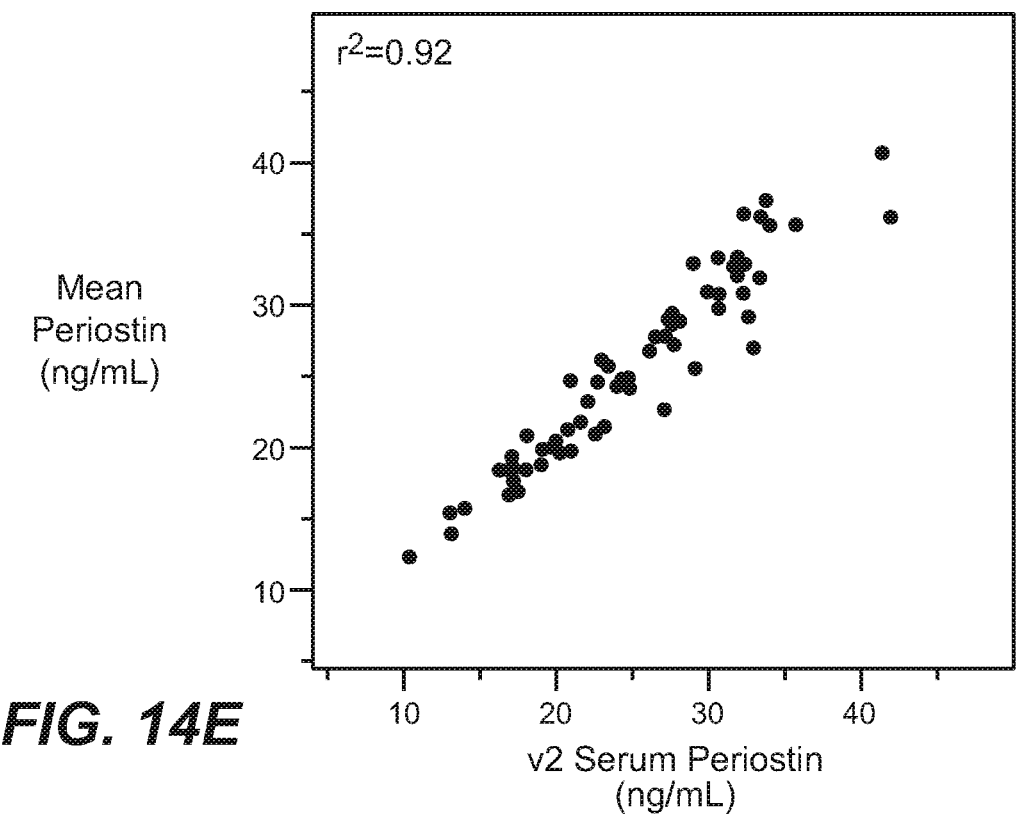
Figure 14F:
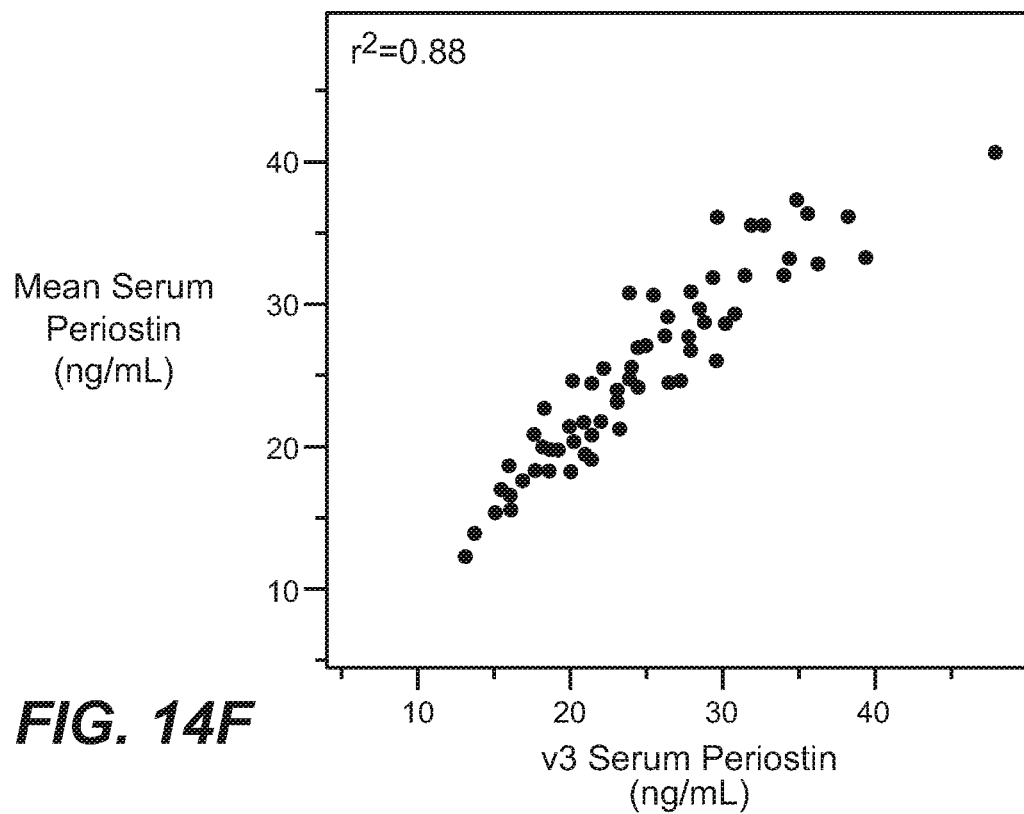

BOBCAT (Bronchoscopic exploratory research study Of Biomarkers in Corticosteroid-refractory AsThma) was a multi-center study conducted in the United States, Canada, and United Kingdom to collect matched airway and blood samples in approximately 60 moderate to severe asthmatics. Inclusion criteria required a diagnosis of moderate to severe asthma (confirmed by an FEV1 between 40-80% of predicted as well as evidence within the past 5 years of >12% reversibility of airway obstruction with a short-acting bronchodilator, or methacholine sensitivity (PC20)<8 mg/ml) that was uncontrolled (as defined by at least 2 exacerbations in the prior year, or a score of >1.50 on the Asthma Control Questionnaire (ACQ) (Juniper, E. F., et al., Respir Med 100, 616-621 (2006)) while on a stable dose regimen (>6 weeks) of high dose ICS (>1000 µg fluticasone or equivalent per day)) with or without a long-acting beta agonist. Permitted concomitant medications also included leukotriene receptor antagonists and oral corticosteroids. BOBCAT study scheme is depicted in FIG. 13.

$FE_{NO}$, bronchoscopy, BAL, induced sputum, and immunohistochemistry for eosinophil counts were performed as previously described (Woodruff, P. G., et al., Am J Respir Crit Care Med 180, 388-395 (2009); Boushey, H. A., et al., N Engl J Med 352, 1519-1528 (2005); Brightling, C. E., et al., Thorax 58, 528-532 (2003); Lemiere, et al., J Allergy Clin Immunol 118, 1033-1039 (2006)). All research protocols were approved by relevant institutional review boards and informed consent was obtained from all subjects prior to enrollment. Patient demographics and lung function data are summarized in Table 5 below.

TABLE 5

BOBCAT demographic and clinical data.

| | UCSF Healthy control | UCSF cohort 1 Mild-moderate asthma, no ICS | UCSF cohort 2 Moderate asthma, on ICS | UCSF cohort 3 Moderate asthma, on ICS | Leicester Healthy control | Leicester Mod-severe asthma, on ICS | BOBCAT Mod-severe asthma, on ICS |
|---|---|---|---|---|---|---|---|
| N subjects | 13 | 15 | 24 | 23 | 10 | 27 | 67 |
| Age | 35 ± 11 | 35 ± 14 | 36 ± 11 | 43 ± 14 | 33 ± 18 | 36 ± 11 | 46 ± 12 |
| Sex (M:F) | 7:6 | 8:7 | 7:17 | 10:13 | 4:6 | 18:9 | 32:35 |
| FEV1 (% predicted) | 99 ± 15 | 85 ± 12 | 84 ± 14 | 75 ± 19 | 99 ± 12 | 79 ± 18 | 60 ± 11 |
| ACQ score | N.D. | N.D. | N.D. | N.D. | N.D. | N.D. | 2.7 ± 0.8 |
| Daily ICS dose (g FPI equivalent*) | 0 | 0 | 250 | N.D. | 0 | 500 (50-1500)** | ≥1000*** |

N.D., not determined
Values presented as mean ± SD or median (range)
*FPI, fluticasone dipropionate. Equivalent ratio of fluticasone:budesonide = 1:1.6
**of these, 6 subjects were also on systemic corticosteroids, receiving between 4-20 mg prednisolone equivalents/day
***of these, 7 subjects were also on systemic corticosteroids, receiving between 5-40 mg prednisolone equivalents/day We used pre-specified cutoff values consistent with previous studies of 3% for sputum eosinophils (Green, R. H., et al., Lancet 360, 1715-1721 (2002); Haldar, P., et al., N Engl J Med 360, 973-984 (2009)) and 22 eosinophils/mm2 total biopsy area (Miranda, C., A. et al., J Allergy Clin Immunol 113, 101-108 (2004); Silkoff, P. E., et al., J Allergy Clin Immunol 116, 1249-1255 (2005)). Serum periostin levels were very stable within individual subjects across the three visits spanning up to 5 weeks (data not shown). Mean periostin levels were significantly higher in "eosinophil high" compared to "eosinophil low" subjects as defined by sputum or tissue eosinophil measurements (data not shown). Subjects stratified by a composite score of 0 for neither, 1 for either, or 2 for both sputum and tissue eosinophilia exhibited a highly significant trend for increasing serum periostin with increasing eosinophil scores (data not shown). Furthermore, non-eosinophilic asthmatics across all cohorts consistently had serum periostin levels below 25 ng/ml using the E4 Assay described above. Using 25 ng/ml serum periostin as a cutoff, "eosinophil-low" and "eosinophil-high" subjects in BOBCAT were effectively differentiated with a positive predictive value of 93% (Table 6). Tissue neutrophil counts were positively correlated with tissue eosinophils and serum periostin levels (data not shown). Taken together, these data show that serum periostin is a systemic biomarker of persistent airway eosinophilia in moderate-to-severe asthmatics despite steroid treatment.

TABLE 6

Contingency table for cutoff values of serum periostin (N = 57) and $FE_{NO}$ (N = 56) vs. composite airway eosinophil status in BOBCAT.

| Test | | Serum Periostin ≥25 ng/ml | | $FE_{NO}$ ≥35 ppb | |
|---|---|---|---|---|---|
| Airway phenotype | | Eosinophil low | Eosinophil high | Eosinophil low | Eosinophil high |
| Test result | − | 11 | 19 | 12 | 26 |
| | + | 2 | 25 | 1 | 17 |
| Sensitivity | | 0.57 | | 0.40 | |
| Specificity | | 0.85 | | 0.92 | |
| PPV | | 0.93 | | 0.94 | |
| NPV | | 0.37 | | 0.32 | |
| p-value | | 0.011 | | 0.042 | |

Eosinophil low: sputum eosinophils <3% AND biopsy eosinophils <22/mm2
Eosinophil high: sputum eosinophils >3% OR biopsy eosinophils >22/mm2
PPV, positive predictive value
NPV, negative predictive value
p-value is Fisher's exact test (2-tailed)

Comparison of Serum Periostin to Fractional Exhaled Nitric Oxide ($FE_{NO}$), Peripheral Blood Eosinophils, Serum IgE, and Serum YKL-40 as Asthma Biomarkers In recent years, other non-invasive biomarkers of asthma severity and airway inflammation have been described. Four markers of particular interest are fractional exhaled nitric oxide ($FE_{NO}$), an exhaled gas produced by the action of the enzyme iNOS (inducible nitric oxide synthase) in inflamed bronchial mucosa (Pavord, I. D. et al., J Asthma 45, 523-531 (2008)); peripheral blood eosinophils; serum IgE; and YKL-40, a chitinase-like protein detectable in peripheral blood (Chupp, G. L., et al., N Engl J Med 357, 2016-2027 (2007)). We measured these biomarkers in our asthmatic cohorts and compared values with airway eosinophilia and other biomarkers.

Neither periostin, $FE_{NO}$, IgE, nor blood eosinophils was significantly correlated with ACQ, FEV1, age, gender, or body mass index (BMI) in BOBCAT. In BOBCAT, $FE_{NO}$ levels, like serum periostin levels, were generally consistent across multiple visits, although $FE_{NO}$ varied more at higher levels (data not shown) whereas blood eosinophils were considerably more variable (r2=0.18 for blood eosinophils between visits 1 and 3, not shown, as compared to r2=0.65 for serum periostin between visits 1 and 3). As shown in FIG. 14A-F, serum periostin levels at visits 1, 2, and 3 were highly correlated with each other and with the mean periostin level across all visits in BOBCAT.

Stratifying for sputum and biopsy eosinophil status as indicated in Table 6, $FE_{NO}$ levels were significantly higher in eosinophilic asthmatics compared to noneosinophilic asthmatics. However, while both $FE_{NO}$ and periostin had a high degree of specificity, exhibiting consistently low values for "eosinophil-low" subjects, $FE_{NO}$ detected fewer subjects with tissue eosinophilia and exhibited greater overlap between "eosinophil-low" and "eosinophil-high" subjects according to each metric employed (FIGS. 15A-D). We fit a logistic regression model incorporating age, sex, BMI, blood eosinophils, serum IgE, $FE_{NO}$, and serum periostin (Table 7), and found that periostin was the most significant single predictor of composite airway eosinophil status (p=0.007).

TABLE 7

Logistic regression model of biomarkers vs. eosinophil status in the BOBCAT study (N = 59).

|  | Estimate | Std. Error | z-score | p-value |
|---|---|---|---|---|
| Age | −0.0396 | 0.039 | −1.015 | 0.31 |
| Sex (male) | −0.2031 | 0.889 | −0.229 | 0.82 |
| Body mass index | −0.1004 | 0.066 | −1.527 | 0.13 |
| Blood eosinophils | 1.7482 | 3.621 | 0.483 | 0.63 |
| Serum IgE | −0.0002 | 0.001 | −0.100 | 0.92 |
| $FE_{NO}$ | 0.0476 | 0.038 | 1.238 | 0.22 |
| Serum periostin | 0.2491 | 0.092 | 2.719 | *0.007* |

Figure 15A:
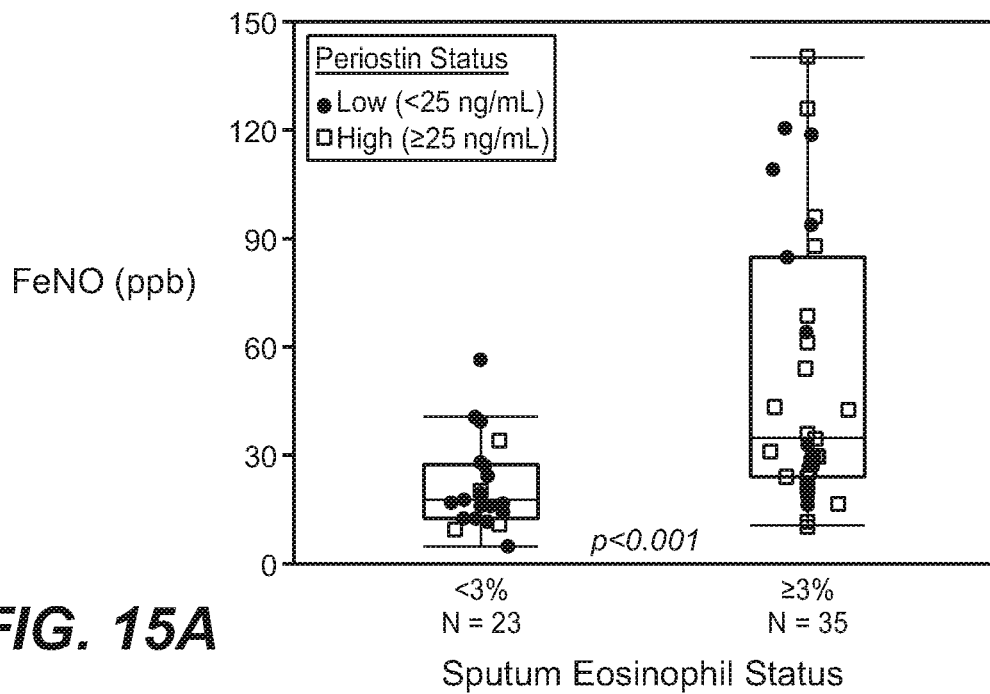
FIGS. 15A-15E show that $FE_{NO}$ differentiates moderate-to-severe uncontrolled asthmatics on high-dose ICS according to airway eosinophilic inflammation (BOBCAT cohort) as described in Example 5.
Figure 15B:
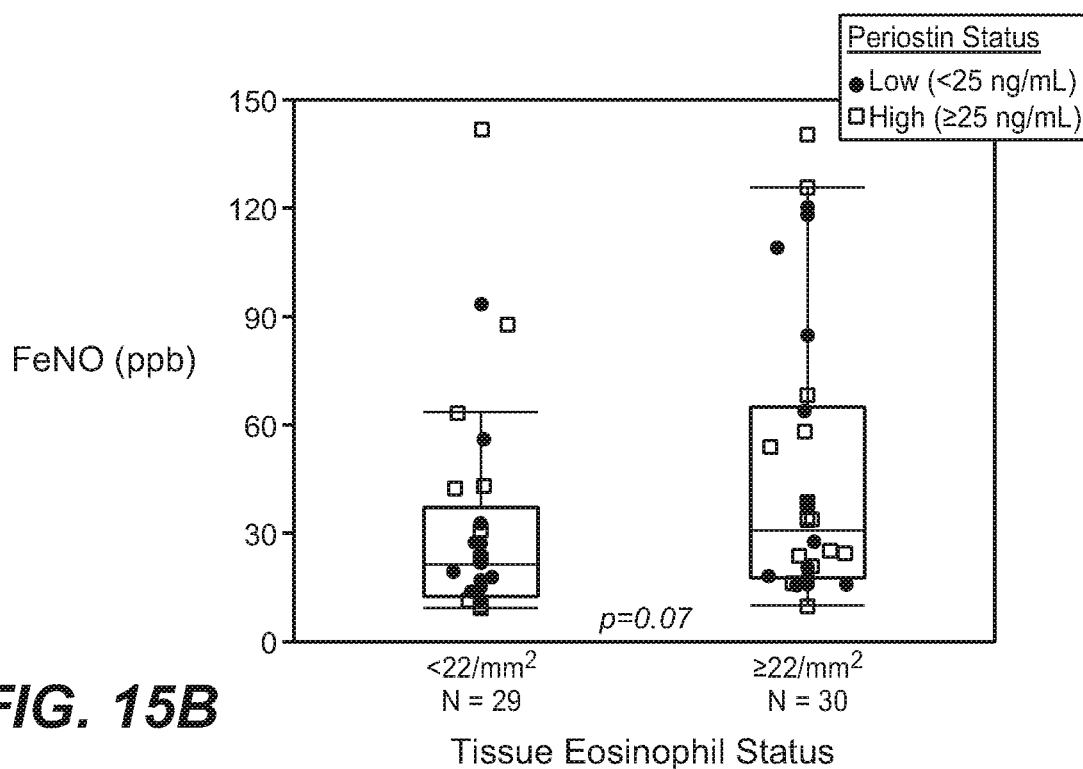
Figure 15C:
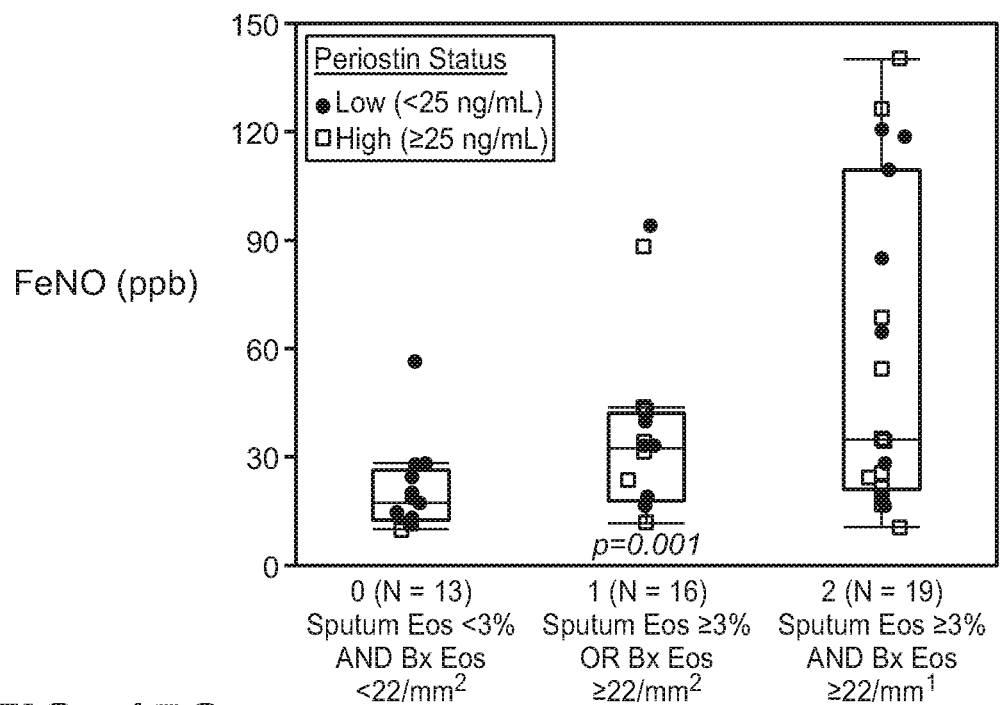
Figure 15D:
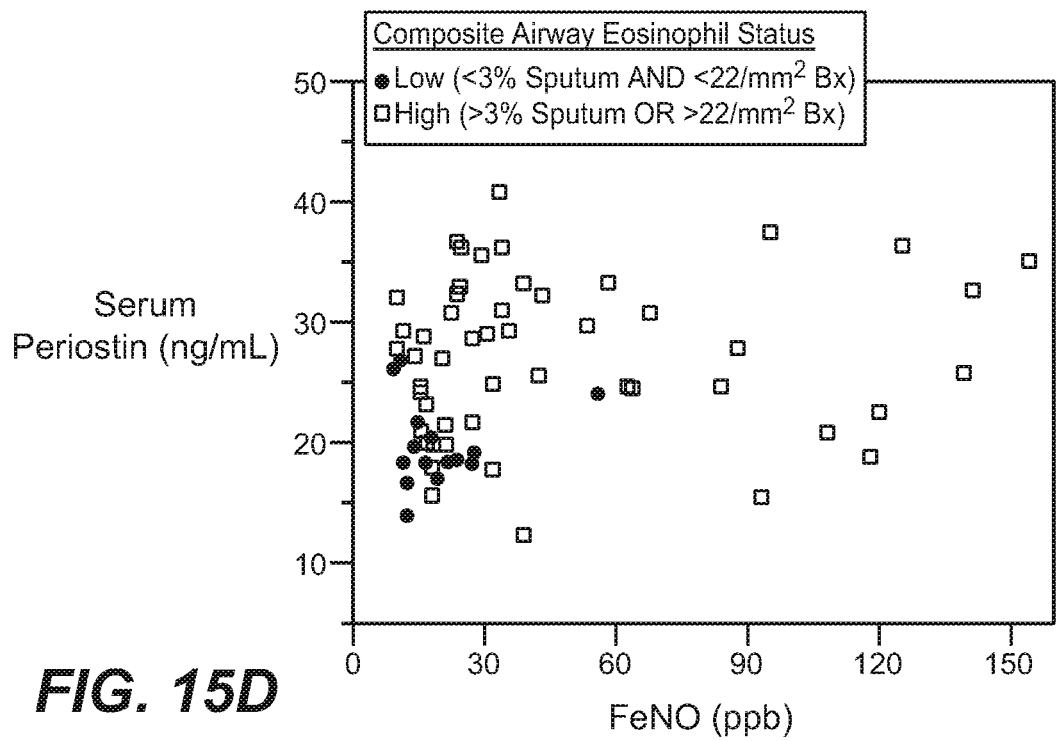
Figure 15E:
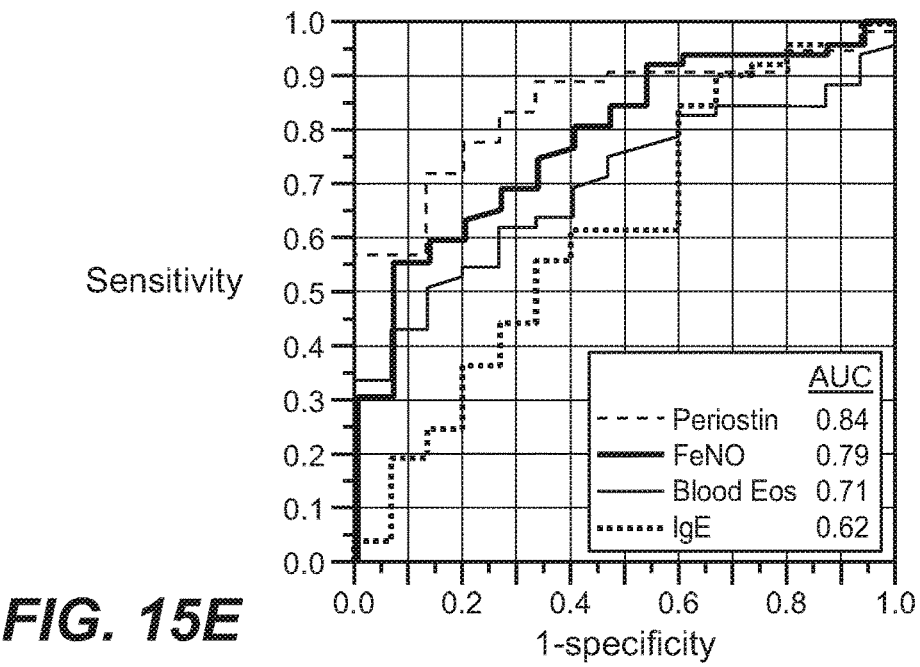

Using a cutoff value of 35 ppb as previously described (Dweik, R. A., et al., Am J Respir Crit Care Med 181, 1033-1041 (2010)), $FE_{NO}$ differentiated "eosinophil-low" and "eosinophil-high" asthmatics with comparable specificity to but lower sensitivity than a periostin cutoff of 25 ng/ml (Table 6). Peripheral blood eosinophils trended higher in "eosinophil-high" asthmatics but did not reach statistical significance (data not shown). To assess the relative performance of each marker on a continuous basis, we performed receiver operating characteristic (ROC) analysis of periostin, $FE_{NO}$, blood eosinophils, and serum IgE vs. composite airway eosinophil status and found that periostin performed favorably to $FE_{NO}$ (AUCs of 0.84 and 0.79 respectively), while blood eosinophils and serum IgE performed substantially less well (FIG. 15E).

YKL-40 showed no significant correlations with periostin nor with any measures of airway or peripheral eosinophilia in any cohort (data not shown). Consistent with these findings of exhaled and blood biomarker levels, we found that bronchial epithelial gene expression levels of periostin and NOS2 (the gene that encodes iNOS) were significantly correlated with each other and with bronchial mucosal expression levels of IL-13 and IL-5 while expression of CHI3L1 (the gene that encodes YKL-40) was not correlated with periostin, IL-13, nor IL-5 (Table 8). Taken together, these data suggest that peripheral blood periostin is a more reliable indicator of airway Th2/eosinophilic inflammation than $FE_{NO}$, blood eosinophils, serum IgE, or YKL-40 in asthmatics across a range of severity and steroid treatment.

Discussion

While asthma is traditionally regarded as an allergic disease mediated by Th2-driven inflammation(1), there is emerging evidence of paths physiological heterogeneity(3-8). We have recently shown that, in mild-to-moderate asthmatics not on steroid treatment, only about half the subjects have evidence of Th2 inflammation in their airways. The "Th2-high" subset is distinguished by elevated markers of allergy, eosinophilic airway inflammation, bronchial fibrosis, and sensitivity to ICS(13). As antagonists of the Th2 cytokines IL-4, IL-5, and IL13 are under active development as asthma therapeutics(35-37), it will become important to identify asthmatics most likely to benefit from these targeted therapies. While bronchoscopy, induced sputum sampling, and measurement of exhaled gases enable the direct characterization of inflammatory pathways in the airways, these modalities can be time consuming, expensive, invasive, and/or are not widely available in primary care settings. Furthermore, assay procedures are not standardized across the relatively few centers equipped to analyze airway samples, which makes implementation in multi-center clinical trials challenging. Thus, to select patients with evidence of Th2-driven eosinophilic inflammation in their airways for targeted therapies, it will be beneficial to develop noninvasive biomarkers of Th2-driven eosinophilic airway inflammation widely available on accessible assay platforms. To address this need, we have used gene expression profiling in asthmatic airway samples to enable the discovery and characterization of clinically useful peripheral biomarkers of Th2-driven eosinophilic airway inflammation.

Periostin is a secreted matricellular protein associated with fibrosis whose expression is upregulated by recombinant IL-4 and IL-13 m cultured bronchial epithelial cells(21, 38) and bronchial fibroblasts(39). It is expressed at elevated levels in vivo in a mouse model of asthma(40), a rhesus model of asthma (unpublished data), and in bronchial epithelial cells(21) and the subepithelial bronchial layers(39) of human asthmatics. In human asthmatics, periostin expression levels correlate with reticular basement membrane thickness, an indicator of subepithelial fibrosis(23). Periostin is also overexpressed in nasal polyps associated with aspirin-sensitive asthma(41, 42) and in the esophageal epithelium of patients with eosinophilic esophagitis in an IL-13 dependent manner(43) and thus may play a role in the tissue infiltration of eosinophils in Th2-driven disease processes(44). Elevated periostin expression has also been observed in several types of epithelial derived cancer(45-49), and elevated levels of soluble periostin have been reported in the serum of some cancer patients(24-26, 45, 46). Whether the local and systemic expression of periostin in asthma or other conditions is due to the direct or indirect actions of IL-13 is as yet unclear and will best be addressed

TABLE 8

Correlation matrix between expression levels of genes encoding biomarkers and Th2 cytokines.

|  | POSTN_210809_s_at | NOS2_210037_s_at | CHI3L1_209395_at |
|---|---|---|---|
| IL-13 | *0.42 (0.014)* | *0.37 (0.029)* | −0.23 (0.198) |
| IL-5 | *0.42 (0.013)* | *0.34 (0.048)* | −0.13 (0.450) |
| POSTN_210809_s_at | — | *0.72 (<0.001)* | −0.24 (0.136) |
| NOS2_210037_s_at | — | — | *−0.34 (0.027)* |

Values given as Spearman's rank correlation (p-value)
IL-13 and IL-5 expression levels determined from endobronchial biopsies by qPCR
Periostin (POSTN_210809_s_at), NOS2 (NOS2_210037_s_at), and CHI3L1 (CHI3L1_209395_at), the gene encoding YKL-40, determined from bronchial epithelial microarray described in Truyen, E., L. et al, *Thorax* 61, 202-208 (2006).

by assessments comparing periostin expression before and after therapeutic blockade of IL13.

Periostin is detectable at considerable systemic concentrations in the peripheral blood of non-asthmatic subjects but is elevated in the peripheral blood of a subset of asthmatics not on ICS treatment. Its expression in bronchial epithelium is suppressed by ICS treatment(13, 21) and its systemic levels are generally lower in moderate asthmatics relatively well-controlled on ICS compared to asthmatics not on ICS, although with considerable heterogeneity. Given that ICS primarily exert their effects locally in the airway and systemic periostin levels (as we previously showed, see e.g., Intn'l Patent Pub. No. WO2009/124090) are suppressed in asthmatics after undergoing ICS treatment, one may conclude that a substantial fraction of systemic periostin originates from the airways in asthmatics and thus differences in systemic periostin levels of 10-20% are clinically meaningful with respect to airway inflammation.

$FE_{NO}$ is associated with airway inflammation and predicts ICS responsiveness in asthmatics of varying severity(11, 34). However, $FE_{NO}$ levels do not reliably reflect airway eosinophilia in severe, steroid-dependent asthma and there are discrepancies between sputum and mucosal eosinophil quantification with respect to $FE_{NO}$(29, 50). Titrating ICS treatment to suppress sputum eosinophil count reduces the rate of severe asthma exacerbations(12), but titrating ICS treatment to $FE_{NO}$ levels does not(51). Serum YKL-40 has been described as a marker of asthmatic airway inflammation, but its levels were not correlated with measures of Th2 inflammation such as IgE or eosinophils(33). Accordingly, in the present study, we found that bronchial epithelial gene expression levels of periostin and NOS2 but not CHI3L1 were correlated with bronchial IL-13 and IL-5 expression (Table 8). While we observed relatively strong positive correlations between bronchial or systemic eosinophilia and serum periostin levels, the correlations between eosinophilia and $FE_{NO}$ were weaker and we failed to observe a correlation between serum YKL-40 and eosinophilic inflammation in the asthmatics studied. Sputum and blood eosinophil counts and $FE_{NO}$ are subject to significant temporal variability depending on allergen exposure, exacerbations, and steroid treatment (50, 52, 53). While the half-life of circulating periostin is presently unknown, it is possible that, if periostin is relatively long-lived in blood, systemic periostin levels may reflect an integration of total airway Th2 inflammation over an extended period of time. Consistent with this possibility, we observed relatively little intra-subject variability in serum periostin in 3 measurements over the course of up to 5 weeks (data not shown). Future studies should be directed at comparatively assessing longitudinal intra-subject variability in serum periostin, airway eosinophilia, $FE_{NO}$, and other candidate biomarkers of Th2 inflammation over longer periods of time.

The standard of care for bronchial asthma that is not well controlled on symptomatic therapy (e.g. β-agonists) is inhaled corticosteroids (ICS). In mild-to-moderate asthmatics with elevated levels of IL-13 in the airway(19) and eosinophilic esophagitis patients with elevated expression levels of IL-13 in esophageal tissue(43), ICS treatment substantially reduces the level of IL-13 and IL-13-induced genes in the affected tissues. In the airway epithelium of asthmatics after one week of ICS treatment and in cultured bronchial epithelial cells, we have shown that corticosteroid treatment substantially reduces IL-13-induced expression levels of Th2 signature genes(13, 21). This downregulation could be the result of ICS-mediated reduction of IL-13 levels, ICS-mediated reduction of target gene expression, or a combination of the two. In severe asthmatics refractory to ICS treatment, a similar fraction of subjects (approximately 40%) was found to have detectable sputum IL-13 levels to those seen in mild, ICS-naïve asthmatics(19), which is comparable to the proportion of subjects with the bronchial epithelial Th2 signature we have described (13). Analogous observations have been reported for persistence in steroid-refractory asthmatics of IL-4 and IL-5 expressing cells in BAL(54) and eosinophilic inflammation in bronchial biopsies and sputum (8). These observations suggest that, although Th2-driven eosinophilic inflammation is suppressed by ICS treatment in moderate asthmatics, it reappears in a subset of severe asthmatics incompletely controlled by steroid treatment. An additional complication is brought on by incomplete adherence to prescribed ICS therapy, which may underlie poor control in some severe asthmatics. Hence, future studies should be directed at assessing blood periostin levels in the context of ICS treatment status, ICS dose, intrinsic steroid sensitivity, and adherence to ICS therapy in controlled and uncontrolled asthmatics.

Currently, there are numerous biological therapeutics in clinical development targeting IL-13 and related factors driving Th2 inflammation in asthma(35-37), including those described herein. It is important that these treatments are targeted to patients with relevant molecular pathology, otherwise important treatment effects may be underestimated; studies of anti-IL5 therapy highlight this point(14, 15, 55). Our findings suggest that approximately half of steroid-naïve mild-to-moderate asthmatics may exhibit activity of the Th2 pathway in their airways, and a similar fraction of moderate-to-severe, steroid-refractory asthmatics exhibits activity of this pathway. Therefore, as described herein, biomarkers that identify asthmatics likely to have Th2 driven inflammation in their airways may aid in the identification and selection of patients most likely to respond to these experimental targeted therapies.

References (Example 5)

1. Galli, S. J., M. Tsai and A. M. Piliponsky, The development of allergic inflammation. *Nature* 454, 445-454 (2008)
2. Haldar, P. and I. D. Pavord, Noneosinophilic asthma: a distinct clinical and pathologic phenotype. *J Allergy Clin Immunol* 119, 1043-1052; quiz 1053-1044 (2007)
3. Anderson, G. P., Endotyping asthma: new insights into key pathogenic mechanisms in a complex, heterogeneous disease. *Lancet* 372, 1107-1119 (2008)
4. Moore, W. C., D. A. Meyers, S. E. Wenzel, W. G. Teague, H. Li, X. Li, R. D'Agostino, Jr., M. Castro, D. Curran-Everett, A. M. Fitzpatrick, B. Gaston, N. N. Jarjour, R. Sorkness, W. J. Calhoun, K. F. Chung, S. A. Comhair, R. A. Dweik, E. Israel, S. P. Peters, W. W. Busse, S. C. Erzurum and E. R. Bleecker, Identification of asthma phenotypes using cluster analysis in the Severe Asthma Research Program. *Am J Respir Crit Care Med* 181, 315-323 (2010)
5. Siddiqui, S. and C. E. Brightling, Airways disease: phenotyping heterogeneity using measures of airway inflammation. *Allergy Asthma Clin Immunol* 3, 60-69 (2007)
6. Simpson, J. L., R. Scott, M. J. Boyle and P. G. Gibson, Inflammatory subtypes in asthma: assessment and identification using induced sputum. *Respirology* 11, 54-61 (2006)

7. Wardlaw, A. J., M. Silverman, R. Siva, I. D. Pavord and R. Green, Multi-dimensional phenotyping: towards a new taxonomy for airway disease. *Clin Exp Allergy* 35, 1254-1262 (2005)
8. Wenzel, S. E., S. J. Szefler, D. Y. Leung, S. I. Sloan, M. D. Rex and R. J. Martin, Bronchoscopic evaluation of severe asthma. Persistent inflammation associated with high dose glucocorticoids. *Am J Respir Crit Care Med* 156, 737-743 (1997)
9. Fahy, J. V., Eosinophilic and neutrophilic inflammation in asthma: insights from clinical studies. *Proc Am Thorac Soc* 6, 256-259 (2009)
10. Fahy, J. V., Identifying clinical phenotypes of asthma: steps in the right direction. *Am J Respir Crit Care Med* 181, 296-297 (2010)
11. Cowan, D. C., J. O. Cowan, R. Palmay, A. Williamson and D. R. Taylor, Effects of steroid therapy on inflammatory cell subtypes in asthma. *Thorax* 65, 384-390 (2010)
12. Green, R. H., C. E. Brightling, S. McKenna, B. Hargadon, D. Parker, P. Bradding, A. J. Wardlaw and I. D. Pavord, Asthma exacerbations and sputum eosinophil counts: a randomised controlled trial. *Lancet* 360, 1715-1721 (2002)
13. Woodruff, P. G., B. Modrek, D. F, Choy, G. Jia, A. R. Abbas, A. Ellwanger, L. L. Koth, J. R. Arron and J. V. Fahy, T-helper type 2-driven inflammation defines major subphenotypes of asthma. *Am J Respir Crit Care Med* 180, 388-395 (2009)
14. Haldar, P., C. E. Brightling, B. Hargadon, S. Gupta, W. Monteiro, A. Sousa, R. P. Marshall, P. Bradding R. H. Green, A. J. Wardlaw and I. D. Pavord, Mepolizumab and exacerbations of refractory eosinophilic asthma. *N Engl J Med* 360, 973-984 (2009)
15. Nair, P., M. M. Pizzichini, M. Kjarsgaard, M. D. Inman, A. Efthimiadis, E. Pizzichini, F. E. Hargreave and P. M. O'Byrne, Mepolizumab for prednisone-dependent asthma with sputum eosinophilia. *N Engl J Med* 360, 985-993 (2009)
16. Hershey, G. K., IL-13 receptors and signaling pathways: an evolving web. *J Allergy Clin Immunol* 677-690; quiz 691 (2003)
17. Berry, M. A., D. Parker, N. Neale, L. Woodman, A. Morgan, P. Monk, P. Bradding, A. J. Wardlaw, I. D. Pavord and C. E. Brightling, Sputum and bronchial submucosal IL-13 expression in asthma and eosinophilic bronchitis. *J Allergy Clin Immunol* 114, 1106-1109 (2004)
18. Humbert, M., S. R. Durham, P. Kimmitt, N. Powell, B. Assoufi, R. Pfister, G. Menz, A. B. Kay and C. J. Corrigan, Elevated expression of messenger ribonucleic acid encoding IL-13 in the bronchial mucosa of atopic and nonatopic subjects with asthma. *J Allergy Clin Immunol* 99, 657-665 (1997)
19. Saha, S. K., M. A. Berry, D. Parker, S. Siddiqui, A. Morgan, R. May, P. Monk, P. Bradding, A. J. Wardlaw, I. D. Pavord and C. E. Brightling, Increased sputum and bronchial biopsy IL-13 expression in severe asthma. *J Allergy Clin Immunol* 121, 685-691 (2008)
20. Truyen, E., L. Coteur, E. Dilissen, L. Overbergh, L. J. Dupont, J. L. Ceuppens and D. M. Bullens, Evaluation of airway inflammation by quantitative Th1/Th2 cytokine mRNA measurement in sputum of asthma patients. *Thorax* 61, 202-208 (2006)
21. Woodruff, P. G., H. A. Boushey, G. M. Dolganov, C. S. Barker, Y. H. Yang, S. Donnelly, A. Ellwanger, S. S. Sidhu, T. P. Dao-Pick, C. Pantoja, D. J. Erle, K. R. Yamamoto and J. V. Fahy, Genome-wide profiling identifies epithelial cell genes associated with asthma and with treatment response to corticosteroids. *Proc Natl Acad Sci USA* 104, 15858-15863 (2007)
22. Winpenny, J. P., Marsey and D. W. Sexton, The CLCA gene family: putative therapeutic target for respiratory diseases. *Inflamm Allergy Drug Targets* 8, 146-160 (2009)
23. Sidhu, S. S., S. Yuan, A. L. Innes, S. Kerr, P. G. Woodruff, L. Hou, S. J. Muller and J. V. Fahy, Roles of epithelial cell-derived periostin in TGF-{beta} activation, collagen production, and collagen gel elasticity in asthma. *Proc Natl Acad Sci USA* (2010)
24. Sasaki, H., M. Dai, D. Auclair, I. Fukai, M. Kiriyama, Y. Yamakawa, Y. Fujii and L. B. Chen, Serum level of the periostin, a homologue of an insect cell adhesion molecule, as a prognostic marker in nonsmall cell lung carcinomas. *Cancer* 92, 843-848 (2001)
25. Sasaki, H., K. M. Lo, L. B. Chen, D. Auclair, Y. Nakashima, S. Moriyama, I. Fukai, C. Tam, M. Loda and Y. Fujii, Expression of Periostin, homologous with an insect cell adhesion molecule, as a prognostic marker in non-small cell lung cancers. *Jpn J Cancer Res* 92, 869-873 (2001)
26. Sasaki, H., C. Y. Yu, M. Dai, C. Tam, M. Loda, D. Auclair, L. B. Chen and A. Elias, Elevated serum periostin levels in patients with bone metastases from breast but not lung cancer. *Breast Cancer Res Treat* 77, 245-252 (2003)
27. Gibson, P. G., Inflammatory phenotypes in adult asthma: clinical applications. *Clin Respir J* 3, 198-206 (2009)
28. Chanez, P., S. E. Wenzel, G. P. Anderson, J. M. Anto, E. H. Bel, L. P. Boulet, C. E. Brightling, W. W. Busse, M. Castro, B. Dahlen, S. E. Dahlen, L. M. Fabbri, S. T. Holgate, M. Humbert, M. Gaga, G. F. Joos, B. Levy, K. F. Rabe, P. J. Sterk, S. J. Wilson and I. Vachier, Severe asthma in adults: what are the important questions? *J Allergy Clin Immunol* 119, 1337-1348 (2007)
29. Lemiere, C., P. Ernst, R. Olivenstein, Y. Yamauchi, K. Govindaraju, M. S. Ludwig, J. G. Martin and Q. Hamid, Airway inflammation assessed by invasive and noninvasive means in severe asthma: eosinophilic and noneosinophilic phenotypes. *J Allergy Clin Immunol* 118, 1033-1039 (2006)
30. Miranda, C., A. Busacker, S. Balzar, J. Trudeau and S. E. Wenzel, Distinguishing severe asthma phenotypes: role of age at onset and eosinophilic inflammation. *J Allergy Clin Immunol* 113, 101-108 (2004)
31. Silkoff P. E., A. M. Lent, A. A. Busacker, R. K. Katial, S. Balzar, M. Strand and S. E. Wenzel, Exhaled nitric oxide identifies the persistent eosinophilic phenotype in severe refractory asthma. *J Allergy Clin Immunol* 116, 1249-1255 (2005)
32. Pavord, I. D. and D. Shaw, The use of exhaled nitric oxide in the management of asthma. *J Asthma* 45, 523-531 (2008)
33. Chupp, G. L., C. G. Lee, N. Jarjour, Y. M. Shim, C. T. Holm, S. He, J. D. Dziura, J. Reed, A. J. Coyle, P. Kiener, M. Cullen, M. Grandsaigne, M. C. Dombret, M. Aubier, M. Pretolani and J. A. Elias, A chitinase-like protein in the lung and circulation of patients with severe asthma. *N Engl J Med* 357, 2016-2027 (2007)
34. Dweik, R. A., R. L. Sorkness, S. Wenzel, J. Hammel, D. Curran-Everett, S. A. Comhair, E. Bleecker, W. Busse, W. J. Calhoun, M. Castro, K. F. Chung, E. Israel, N. Jarjour, W. Moore, S. Peters, G. Teague, B. Gaston and S. C. Erzurum, Use of exhaled nitric oxide measurement to identify a reactive, at-risk phenotype among patients with asthma. *Am J Respir Crit Care Med* 181, 1033-1041 (2010)

35. Barnes, P. J., The cytokine network in asthma and chronic obstructive pulmonary disease. *J Clin Invest* 118, 3546-3556 (2008)
36. Holgate, S. T. and R. Polosa, Treatment strategies for allergy and asthma. *Nat Rev Immunol* 8, 218-230 (2008)
37. Walsh, G. M., Emerging drugs for asthma. *Expert Opin Emerg Drugs* 13, 643-653 (2008)
38. Yuyama, N., D. E. Davies, M. Akaiwa, K. Matsui, Y. Hamasaki, Y. Suminami, N. L. Yoshida, M. Maeda, A. Pandit, J. L. Lordan, Y. Kamogawa, K. Arima, F. Nagumo, M. Sugimachi, A. Berger, I. Richards, S. L. Roberds, T. Yamashita, F. Kishi, H. Kato, K. Arai, K. Ohshima, J. Tadano, N. Hamasaki, S. Miyatake, Y. Sugita, S. T. Holgate and K. Izuhara, Analysis of novel disease-related genes in bronchial asthma. *Cytokine* 19, 287-296 (2002)
39. Takayama, G., K. Arima, T. Kanaji, S. Toda, H. Tanaka, S. Shoji, A. N. McKenzie, H. Nagai, T. Hotokebuchi and K. Izuhara, Periostin: a novel component of subepithelial fibrosis of bronchial asthma downstream of IL-4 and IL-13 signals. *J Allergy Clin Immunol* 118, 98-104 (2006)
40. Hayashi, N., T. Yoshimoto, K. Izuhara, K. Matsui, T. Tanaka and K. Nakanishi, T helper 1 cells stimulated with ovalbumin and IL-18 induce airway hyperresponsiveness and lung fibrosis by IFN-gamma and IL-13 production. *Proc Natl Acad Sci USA* 104, 14765-14770 (2007)
41. Plager, D. A., J. C. Kahl, Y. W. Asmann, A. E. Nilson, J. F. Pallanch, O. Friedman and H. Kita, Gene transcription changes in asthmatic chronic rhinosinusitis with nasal polyps and comparison to those in atopic dermatitis. *PLoS One* 5, e11450 (2010)
42. Stankovic, K. M., H. Goldsztein, D. D. Reh, M. P. Platt and R. Metson, Gene expression profiling of nasal polyps associated with chronic sinusitis and aspirin-sensitive asthma. *Laryngoscope* 118, 881-889 (2008)
43. Blanchard, C., M. K. Mingler, M. Vicario, J. P. Abonia, Y. Y. Wu, T. X. Lu, M. H. Collins, P. E. Putnam, S. I. Wells and M. E. Rothenberg, IL-13 involvement in eosinophilic esophagitis: transcriptome analysis and reversibility with glucocorticoids. *J Allergy Clin Immunol* 120, 1292-1300 (2007)
44. Blanchard, C., M. K. Mingler, M. McBride, P. E. Putnam, M. H. Collins, G. Chang, K. Stringer, J. P. Abonia, J. D. Molkentin and M. E. Rothenberg, Periostin facilitates eosinophil tissue infiltration in allergic lung and esophageal responses. *Mucosal Immunol* 1, 289-296 (2008)
45. Baril, P., R. Gangeswaran, P. C. Mahon, K. Caulee, H. M. Kocher, T. Harada, M. Zhu, H. Kalthoff, T. Crnogorac-Jurcevic and N. R. Lemoine, Periostin promotes invasiveness and resistance of pancreatic cancer cells to hypoxia-induced cell death: role of the beta4 integrin and the PI3k pathway. *Oncogene* 26, 2082-2094 (2007)
46. Ben, Q. W., Z. Zhao, S. F. Ge, J. Zhou, F. Yuan and Y. Z. Yuan, Circulating levels of periostin may help identify patients with more aggressive colorectal cancer. *Int J Oncol* 34, 821-828 (2009)
47. Kudo, Y., I. Ogawa, S. Kitajima, M. Kitagawa, H. Kawai, P. M. Gaffney, M. Miyauchi and T. Takata, Periostin promotes invasion and anchorage-independent growth in the metastatic process of head and neck cancer. *Cancer Res* 66, 6928-6935 (2006)
48. Puglisi, F., C. Puppin, E. Pegolo, C. Andreetta, G. Pascoletti, F. D'Aurizio, M. Pandolfi, G. Fasola, A. Piga, G. Damante and C. Di Loreto, Expression of periostin in human breast cancer. *J Clin Pathol* 61, 494-498 (2008)
49. Siriwardena, B. S., Y. Kudo, I. Ogawa, M. Kitagawa, S. Kitajima, H. Hatano, W. M. Tilakaratne, M. Miyauchi and T. Takata, Periostin is frequently overexpressed and enhances invasion and angiogenesis in oral cancer. *Br J Cancer* 95, 1396-1403 (2006)
50. Nair, P., M. Kjarsgaard, S. Armstrong, A. Efthimiadis, P. M. O'Byrne and F. E. Hargreave, Nitric oxide in exhaled breath is poorly correlated to sputum eosinophils in patients with prednisone-dependent asthma. *J Allergy Clin Immunol* (2010)
51. Shaw, D. E., M. A. Berry, M. Thomas, R. H. Green, C. E. Brightling, A. J. Wardlaw and I. D. Pavord, The use of exhaled nitric oxide to guide asthma management: a randomized controlled trial. *Am J Respir Crit Care Med* 176, 231-237 (2007)
52. Pavord, I. D., P. K. Jeffery, Y. Qiu, J. Zhu, D. Parker, A. Carlsheimer, I. Naya and N. C. Barnes, Airway inflammation in patients with asthma with high-fixed or low-fixed plus as-needed budesonide/formoterol. *J Allergy Clin Immunol* 123, 1083-1089, 1089 e1081-1087 (2009)
53. D'Silva, L., R. J. Cook, Allen, F. E. Hargreave and K. Parameswaran, Changing pattern of sputum cell counts during successive exacerbations of airway disease. *Respir Med* 101, 2217-2220 (2007)
54. Leung, D. Y., R. J. Martin, S. J. Szefler, E. R. Sher, S. Ying, A. B. Kay and Q. Hamid, Dysregulation of interleukin 4, interleukin 5, and interferon gamma gene expression in steroid-resistant asthma. *J Exp Med* 181, 33-40 (1995)
55. Flood-Page, P., C. Swenson, I. Faiferman, J. Matthews, M. Williams, L. Brannick, D. Robinson, S. Wenzel, W. Busse, T. T. Hansel and N. C. Barnes, A study to evaluate safety and efficacy of mepolizumab in patients with moderate persistent asthma. *Am J Respir Crit Care Med* 176, 1062-1071 (2007).

Example 6—Asthma Patient Study III (to Assess Safety, Tolerability and Efficacy)

The study will be a randomized, multicenter, double-blind, placebo-controlled, parallel-group study of lebrikizumab in patients with severe asthma that remains uncontrolled despite daily therapy with ICS (500-2000 µg/day fluticasone propionate dry powder inhaler [DPI] or equivalent) plus a second controller medication, such as a long-acting β-agonist (LABA), leukotriene receptor antagonist (LTRA), long acting muscarinic antagonist (LAMA), or theophylline. This study will also assess the diagnostic value of baseline levels of serum periostin ≥50 ng/mL (as measured by the Elecsys® assay). While continuing their standard of care therapy, which must include ICS and a second controller medication, patients will be randomly assigned to one of three doses of lebrikizumab or placebo for a 52-week placebo-controlled period.

During a 2-week run-in period, also referred to as a screening period, (Visit 1 through Visit 3), patients will be assessed for compliance with their current asthma therapy and their ability to use the equipment necessary for monthly clinic visits throughout the study as well as the degree of asthma control provided by their standard-of-care medications. Patients reporting an Asthma Control Questionnaire (ACQ-5) score ≥1.5 and one or more symptoms of asthma that is not controlled (night time awakening ≥1 time/week, symptoms >2 days/week, SABA use >2 days/week, and/or interference with daily activities) will be considered uncontrolled. Patients whose symptoms remain uncontrolled at Visit 1 or 2 and Visit 3 despite adherence with controller medicines will be eligible to participate. The screening period may be extended by 1 week in the case that adherence data are incomplete and for patients whose ACQ-5 is <1.5 at Visit 3, if the investigator's experience with this patient suggests this week was atypical for their disease. Patients may be eligible for rescreening for selected reasons up to two additional times.

At the end of the run-in (screening) period, eligible patients will be randomly allocated (1:1:1:1) to study drug (either placebo or lebrikizumab 37.5 mg SC monthly, 125 mg SC monthly, or 250 mg SC every 4 weeks). Randomization will be stratified by baseline serum periostin as measured using the Elecsys® assay (<42 ng/mL, ≥42 to <50 ng/mL, ≥50 to <58 ng/mL, ≥58 ng/mL), history of asthma exacerbations in the last 12 months (0, 1-2, ≥3 events), baseline asthma medications (ICS dose ≥1000 μg/day of fluticasone propionate DPI or equivalent plus LABA [yes, no]), and geographical region (United States/Canada, Europe, Asia, rest of world). Patients will continue on stable doses of their standard-of-care therapy, which must include ICS (500 2000 μg/day of fluticasone propionate DPI or equivalent) and a second controller medication, in addition to receiving double-blind study treatment for 52 weeks.

The first SC injection of study treatment will occur on the same day as randomization (Visit 3 [Day 1]), and dosing will be repeated once every 4 weeks over the 52-week placebo controlled period (for a total of 13 study treatment doses). Safety, efficacy, and patient reported outcome (PRO) measures will be assessed throughout the 52 week placebo-controlled period. The primary efficacy endpoint is the rate of asthma exacerbations and will be assessed over the 52-week placebo-controlled period.

Patients who complete the 52-week placebo-controlled period (i.e., patients who have not prematurely discontinued study treatment) will continue into a 52-week active-treatment extension.

All patients who continue into the 52-week active-treatment extension study will receive double blind SC lebrikizumab at a dose of either 125 mg or 250 mg every 4 weeks. Patients assigned to receive either 125 mg or 250 mg lebrikizumab during the 52-week placebo controlled period will remain on their assigned lebrikizumab dose. Patients assigned to receive either placebo or lebrikizumab 37.5 mg SC every 4 weeks during the 52-week placebo controlled period will be randomized in a 1:1 ratio to either SC lebrikizumab 125 mg or 250 mg every 4 weeks for the 52-week active-treatment extension, with randomization stratified by baseline periostin level and prior treatment assignment.

At Week 76 of the 52-week active-treatment extension, each patient will be assessed for asthma control using data from the three most recent visits (Weeks 68, 72, and 76). Patients whose asthma symptoms have been controlled for the 12 consecutive weeks (ACQ 5≤0.75 on each assessment) and who have had no exacerbations within the first half of the active-treatment extension (Weeks 52-76) will discontinue lebrikizumab therapy and enter the follow up period. During follow-up, patients will be followed for safety for 24 weeks after the last dose of study drug. Patients who remain symptomatic (ACQ-5>0.75) at Week 76 or who have experienced an exacerbation event during the first half of the active-treatment extension (Weeks 52-76) will continue on lebrikizumab treatment for an additional 28 weeks. Safety, efficacy, and PRO measures will be assessed throughout the 52-week active-treatment extension.

In the follow-up period, all patients will be followed for safety for 24 weeks (>5 half-lives of the drug) after the last dose of study treatment whenever this may occur, either as scheduled in the protocol or in the event of early discontinuation from study treatment. For patients who complete the study through Visit 23 (Week 76), are well-controlled, and discontinued from study treatment, Visit 23 will replace Safety Follow-up Visit 1. For patients who complete the entire study through Visit 30 (Week 104), Visit 30 will replace Safety Follow-up Visit 1. In both of these cases, the next visit in the follow-up period will be Safety Follow-up Visit 2 at Week 12. For all other patients, the first follow up visit will be Safety Follow-up Visit 1 at Week 4 (approximately 4 weeks after the last dose of study treatment) of the safety follow up period.

Total participation in the study, from randomization at Visit 3 (Day 1), including the 52-week placebo-controlled period, the 52-week active-treatment extension and the safety follow-up period, may be as long as 124 weeks.

Approximately 1400 patients (175 patients per treatment group [SC lebrikizumab 250 mg, 125 mg, 37.5 mg, or placebo] per periostin group [periostin high ≥50 ng/mL, periostin low <50 ng/mL]) will be enrolled in the study at approximately 250 sites located globally. A minimum of 650 patients will be enrolled in the periostin high group (≥50 ng/mL). A minimum of approximately 450 patients who are on ICS fluticasone ≥1000 μg/day DPI or equivalent plus LABA will be enrolled.

The key inclusion criteria include the following: Asthma diagnosis ≥12 months prior to screening; Bronchodilator response/reversibility: Patients must have bronchodilator response ≥12% in response to four puffs of short-acting β-agonist (e.g., albuterol or salbutamol) during the screening period; Pre-bronchodilator FEV1 40%-80% of predicted at both Visit 2 and Visit 3; On ICS≥500 (e.g., 500-2000) μg of fluticasone propionate DPI or equivalent (total daily dose) for ≥6 months prior to screening; On second controller medication (e.g., LABA, LAMA, LTRA, or theophylline within prescribed dosing range) for 6 months prior to screening; Uncontrolled asthma demonstrated both during the screening period (i.e., Visit 1 [Day-14] or Visit 2 [Day-7]) and at the time of randomization (Visit 3 [Day 1]), defined as follows: ACQ-5 score ≥1.5 and at least one of the following symptoms of asthma that is not controlled based upon the National Heart, Lung, and Blood Institute and National Asthma Education and Prevention Program Expert Panel Report 3 (2007) and the Global Initiative for Asthma (2010) guidelines:

Symptoms >2 days/week
Night-time awakenings ≥1 time/week
Use of SABA as rescue medication >2 days/week
Interference with normal daily activities;
Chest X-ray or computed tomography (CT) scan obtained within 12 months prior to Visit 1 or chest X-ray during the screening period confirming the absence of other lung disease; and demonstrated adherence with controller medication of ≥70% during the screening period (Adherence is defined as patients responding affirmatively that they have taken their asthma controller therapy ≥70% of days during the screening period (Visit 1 to Visit 3) as recorded in their peak flow meter device).

Key Exclusion criteria include the following: History of a severe allergic reaction or anaphylactic reaction to a biologic agent or known hypersensitivity to any component of lebrikizumab injection; Maintenance oral corticosteroid therapy, defined as daily or alternate day oral corticosteroid maintenance therapy within the 3 months prior to Visit 1; Asthma exacerbation during the 4 weeks prior to screening (Visit 1) or anytime during screening that required systemic (oral, intravenous (IV) or intramuscular (IM)) corticosteroids for any reason including an acute exacerbation event; A major episode of infection requiring any of the following:
1. Hospitalization for ≥24 hrs within the 4 weeks prior to screening (Visit 1)
2. Treatment with IV antibiotics within the 4 weeks of screening (Visit 1)
3. Oral antibiotics within the 2 weeks prior to screening (Visit 1);

Active parasitic infection within the 6 months prior to Visit 1; tuberculosis requiring treatment within the 12 months prior to screening (patients treated for tuberculosis with no recurrence in the 12 months after completing treatment are permitted); Known immunodeficiency, including but not limited to HIV infection; Current use of an immunomodulatory therapy; Known current malignancy or current evaluation for a potential malignancy; Evidence of active hepatitis B/C or unstable liver disease; Active parasitic infection within the 6 months prior to screening; AST/ALT elevation ≥2.0 the upper limit of normal; History of cystic fibrosis, chronic obstructive pulmonary disease, and/or other clinically significant lung disease other than asthma; Current smoker or history of smoking >10 pack-years; Use of a biologic therapy at any time during the 6 months prior to screening; Female patients of reproductive potential who are not willing to use a highly effective method of contraception for the duration of the study, or who are pregnant or lactating; Other unstable medical disease; Body mass index >38 kg/m²; Body weight <40 kg.

Phase III Dosing Rationale
Population PK Analysis

A preliminary population PK model was developed to describe the PK profile of lebrikizumab in adult patients. A total of 4914 serum concentration-time samples from 333 lebrikizumab-treated patients in the studies described above were used to develop the model. No apparent difference was observed across studies, as evidenced by good agreement between the observed mean PK profile in each study and the profile predicted from historical data.

A two-compartmental model with first-order absorption and elimination kinetics adequately described the serum lebrikizumab concentration-time data. The structural model parameters included clearance (CL), volume of distribution of the central compartment ($V_1$), volume of the peripheral compartment ($V_2$), inter compartmental clearance (Q), as well as first-order rate of absorption ($K_a$) and bioavailability (F) following SC administration. All parameters, except for V2 and Q (which were fixed at population mean values), were assumed to be log normally distributed.

The population mean CL and $V_1$ were estimated to be 0.18 L/day and 3.7 L, respectively. The population mean bioavailability was estimated as 76%. The inter-individual variability of PK parameters was modest, ranging from 15% to 27%. Body weight was found to be a significant covariate for the CL and volumes of distribution of lebrikizumab, with higher weights associated with higher clearances and higher volumes of distribution. Approximately 19% of the inter-individual variability in CL and 11% of inter-individual variability in $V_1$ were explained by body weight. Estimated population PK parameters are summarized in Table 13. The population PK analysis indicated that the PK characteristics of lebrikizumab are consistent with those typical of an IgG monoclonal antibody.

The effect of periostin on PK parameters was assessed by comparing the individual post hoc estimates of PK parameters between patients with baseline periostin levels above and below the median in the Example 2 study and in the Example 3 study. The differences were insignificant (p>0.05) in both studies for CL (p=0.54, 0.11), $V_1$ (p=0.83, 0.79), and F (p=0.74, 0.37).

TABLE 13

Lebrikizumab Population PK Parameters.

| Parameter Description | Population Mean Estimate (% SE) | Inter-Individual Variability (% SE) |
|---|---|---|
| Clearance, CL (L/day) | 0.176 (3.2%) | 24.5% (23.3%) |
| Effect of BW on CL | 0.864 (10.6%) | |
| Volume of distribution in central compartment, $V_1$ (L) | 3.74 (3.4%) | 24.6% (39.6%) |
| Effect of BW on $V_1$ | 0.890 (12.1%) | |
| Volume of distribution in peripheral compartment, $V_2$ (L) | 2.01 (4.9%) | |
| Effect of BW on $V_2$ | 0.316 (34.8%) | |
| Distribution clearance, Q (L/day) | 0.443 (10.2%) | |
| First-order rate of absorption, $K_a$ (1/day) | 0.213 (5.0%) | 26.9% (39.4%) |
| Bioavailability, F (%) | 75.6 (3.7%) | 14.9% (70.9%) |
| Proportional residual error | 13.6% (3.6%) | |
| Additive residual error (μg/mL) | 442 (15.6%) | |

BW = body weight; CL = clearance; PK = pharmacokinetic; Q = inter-compartmental clearance; SE = standard error; $V_1$ = volume of distribution of the central compartment; $V_2$ = volume of distribution of the peripheral compartment.
Note:
BW effect was modeled as power function, $TVP_1 = \theta 1*(BW_i/BW_{Ref})^{\theta 2}$, for which TVP is a typical value of the PK parameter; $BW_i$ refers to body weight for ith individual, $BW_{Ref}$ refers to reference body weight, which is the median body weight of all patients included in the population PK model (82 kg), θ1 refers to the population mean estimate of the PK parameter, and θ2 refers to the effect of body weight on the PK parameter.

Rationale for Flat Dosing

Flat dosing was used in the Phase II studies described above. Given the effect of body weight on the PK profile of lebrikizumab, heavier patients generally had lower drug exposure. However, no correlation was found between body weight and the proportional change in FEV1 from baseline to Week 12 in individual patients treated with lebrikizumab, indicating that the effect of body weight on exposure did not have an impact on efficacy (see FIGS. 20A-20B). Furthermore, the data from these studies indicated no safety concern with flat dosing within the body weight range tested (53-135 kg).

Figure 21:
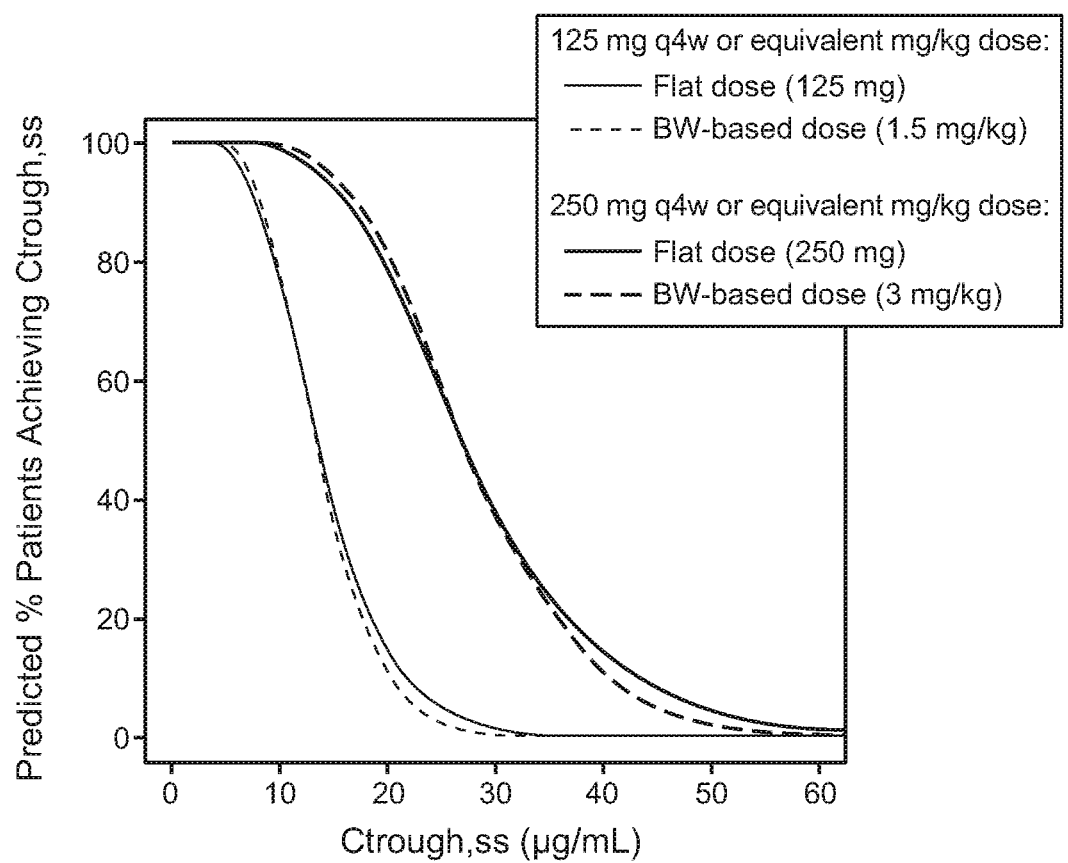
FIG. 21 shows the predicted proportion of patients with steady-state trough concentrations above various levels as described in Example 6.

To evaluate the impact of flat dosing on the overall variability of exposure to lebrikizumab, population PK simulations were performed to compare flat dosing and the equivalent body weight-based (i.e., mg/kg) dosing regimens, assuming a body weight distribution similar to that seen in the Phase II studies described above. The predicted proportion of patients with steady-state trough concentrations above various levels was similar between flat and body weight-based dosing regimens (see FIG. 21), suggesting no clear advantage for dosing based on body weight. Consequently, flat dosing was chosen for the Phase III study given its advantage for reducing the risk of dosing error and operational complexity (e.g., drug preparation) compared with individualized body weight-based dosing.

Rationale for Target Concentrations

Exposure-response analyses using the Phase II data were performed to derive target lebrikizumab concentrations to inform dose selection for the Phase III studies. In both Phase II studies described above, no apparent correlation was found between the placebo-corrected change in FEV1 from baseline and serum trough drug concentration at Week 12 (data not shown) in individual patients treated with lebrikizumab, suggesting that the effect of lebrikizumab on FEV1 is saturated at the range of exposure tested in both studies. Moreover, assessments of the correlation between the change in PD biomarkers (FeNO, IgE, CCL17, and CCL13)

and serum trough drug concentrations in the Phase II studies suggested saturation of these PD responses during the treatment period in both studies. The results were similar in the periostin high group. On the basis of these results, a target serum steady-state trough concentration of 10 µg/mL was proposed to bracket the lower end of the observed $C_{trough,wk12}$ range in both studies (5th-95th percentile: 9.6-50 µg/mL in Example 2 study: 9.4-73 µg/mL in Example 3 study). Furthermore, a serum concentration of 10 µg/mL is expected to maintain a sufficiently high drug level in the lung to neutralize IL 13 in asthma patients, given the assumed serum-to-lung partitioning of lebrikizumab (1:500) and IL-13 levels in the lung based on available data in literature. Therefore, it is anticipated that an effective dose in Phase III will maintain a serum steady-state trough concentration >10 µg/mL.

Figure 22B:
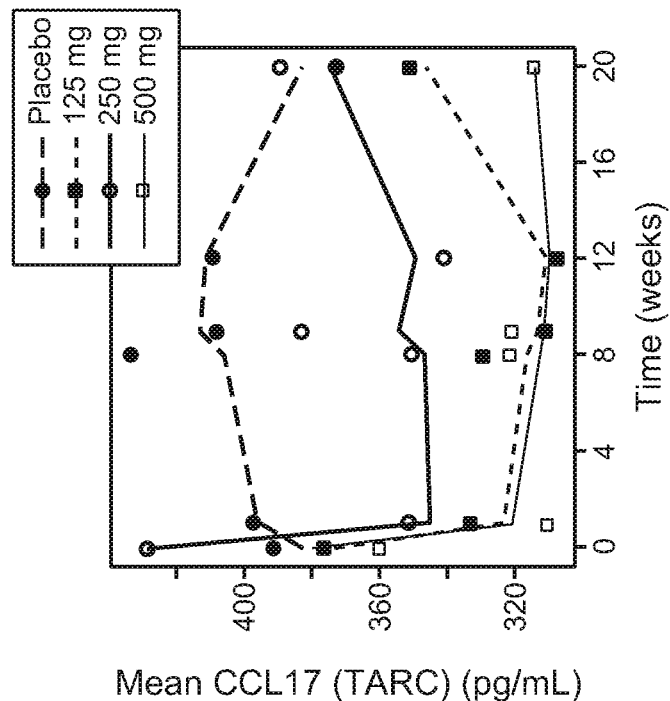
FIGS. 22A-22B show the effect of lebrikizumab on serum CCL17 (TARC) levels over time for the Example 2 study (FIG. 22A) and for the Example 3 study (FIG. 22B) as described in Example 6.
Figure 22A:
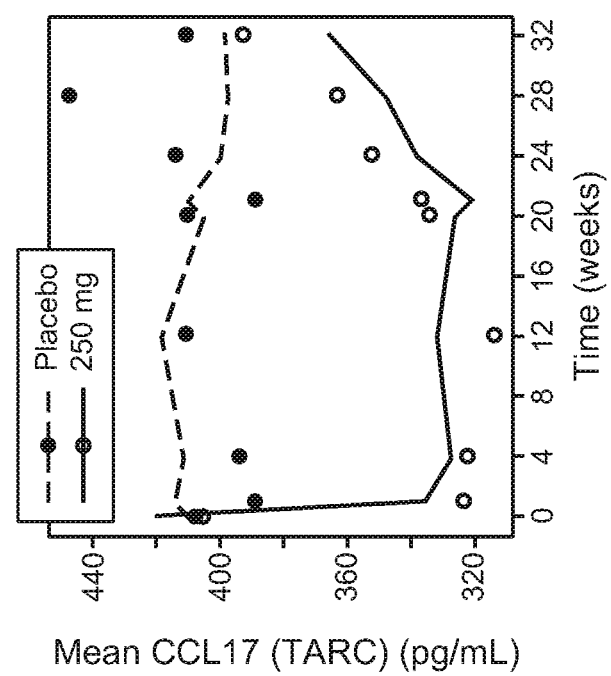

To select a partially effective dose in Phase III, a lower target steady state trough concentration of 5 µg/mL was proposed to ensure no overlap with the observed $C_{trough,wk12}$ range in both Example 2 and Example 3 studies, in which efficacy was observed. Additionally, in both studies, the effect of lebrikizumab on serum CCL17 (TARC) levels returned toward baseline during drug washout (see FIGS. 22A-22B; (FIG. 22A) Example 2 study, (FIG. 22B) Example 3 study), at mean serum lebrikizumab concentrations >5 µg/mL. Although the effect of lebrikizumab on serum CCL17 (TARC) did not directly correlate with efficacy, the recovery of this biomarker suggests suboptimal suppression of IL-13 activity in certain biologic pathways at this concentration. Therefore, a partially effective dose is proposed to maintain a serum steady-state trough concentration <5 µg/mL.

Rationale for the Proposed Phase III Doses

Figure 23:
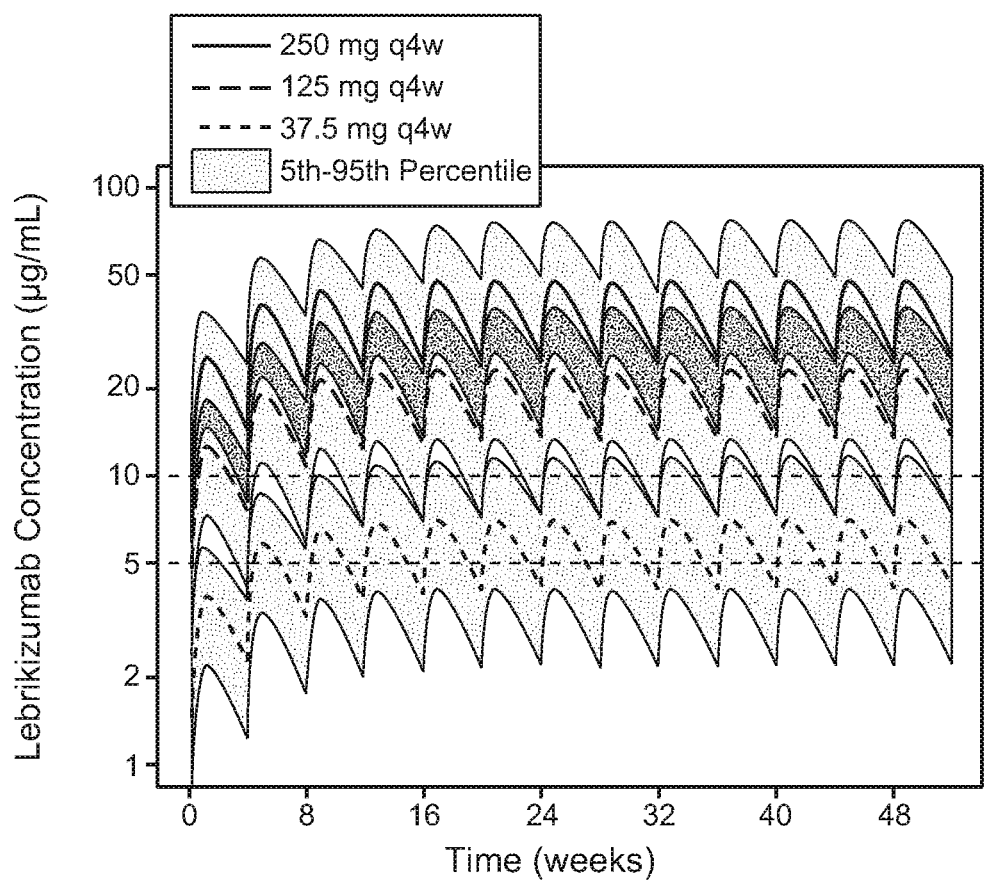
FIG. 23 shows the simulated population PK profiles at each of the Phase III doses, 250 mg every 4 weeks, 125 mg every 4 weeks, and 37.5 mg every 4 weeks as described in Example 6.

Given the lack of a clear dose response in the Example 3 study as described above (i.e. that the doses 125 mg, 250 mg, and 500 mg appeared equally efficacious), the Phase III doses were selected to demonstrate a dose response of lebrikizumab by including both effective and partially effective dose levels. To fulfill this objective, the proposed doses of lebrikizumab for the Phase III program include 250 mg, 125 mg, and 37.5 mg given by SC injection every four weeks (q4 wk). FIG. 23 shows the simulated population PK profiles at these doses, assuming a body weight distribution similar to that seen in the Phase II studies.

The highest dose of 250 mg (two 1-mL SC injections) q4 wk is anticipated to demonstrate clinical efficacy in Phase III. It is the only dose regimen studied in the Phase II proof-of-concept study (Example 2) and showed efficacy in reducing the rate of severe asthma exacerbations in patients whose asthma was uncontrolled despite ICS therapy, the patient population intended for treatment. Example 2 patients had uncontrolled asthma despite treatment with ICS with or without another controller, and ≥90% of patients in Example 2 who were on ICS≥1500 µg/day were also taking a LABA medication. At this dose regimen, almost all (99%) patients are predicted to achieve the target of $C_{trough,ss}$ of 10 µg/mL on the basis of the population PK simulations (see Table 14), which means that maximum efficacy is expected. Therefore, this dose will be tested to replicate the clinical efficacy seen in Phase II.

TABLE 14

Predicted Percentage of Patients with Steady-State Trough Concentration above Target at the Doses Proposed for Phase III.

| Dose | Target Steady-State Trough Concentration | |
|---|---|---|
| (mg every 4 weeks) | >5 µg/mL | >10 µg/mL |
| 250 | 100% | 99% |
| 125 | 99% | 78% |
| 37.5 | 28% | 0.6% |

A middle dose of 125 mg (one 1-mL SC injection) q4 wk is proposed on the basis of the similar magnitudes of FEV1 improvement observed at 125 and 250 mg q4 wk in the Phase II dose-ranging study (Example 3). It is reasonable to expect that the same dose-response relationship holds true in the population of patients with severe asthma for the exacerbation endpoint and thus, the 125 mg dose is anticipated to show efficacy in Phase III. This expectation is further supported by the population PK simulations, which suggest that a majority (78%) of patients will achieve the target $C_{trough,ss}$ of 10 µg/mL with this dose regimen (see Table 14).

The dose of 37.5 mg (one 0.3-mL SC injection) q4 wk is proposed in order to demonstrate a partially effective or clinically ineffective dose of lebrikizumab that is important to establish a dose-response relationship. This dose regimen is chosen taking into account the following considerations:
  Ability to maintain $C_{trough,ss}$ below 5 µg/mL in the majority (72%) of patients and below 10 µg/mL in almost all (99%) patients (see Table 14)
  Reasonable (3.3-fold) separation from the middle dose
  Minimal overlap in the simulated range of serum exposure to lebrikizumab with the middle dose (see Table 14) in order to demonstrate differential clinical responses
  A convenient injection volume (a multiple of 0.1 mL) to reduce possible dosing errors The various outcome measures of this Phase III trial are described below.

Outcome Measures

Each of the following endpoints will be assessed separately in periostin high and periostin low patients. The trial will be considered positive if the primary endpoint is met in the periostin-high group when the 250 mg lebrikizumab group is compared with the placebo group.

Primary Efficacy Outcome Measure

The primary efficacy outcome measure is the rate of asthma exacerbations during the 52-week placebo-controlled period. For this trial, asthma exacerbations will be defined as new or increased asthma symptoms (including, for example, wheeze, cough, dyspnea, or chest tightness or nocturnal awakenings due to these symptoms) that lead to treatment with systemic corticosteroids or to hospitalization. Here, treatment with systemic corticosteroids is defined as treatment with oral (i.e. OCS) or parenteral corticosteroids for ≥3 days or an emergency department visit with one or more doses of parenteral (IV or IM) corticosteroids.

Secondary Efficacy Outcome Measures

The secondary efficacy outcome measures at Week 52 are as follows: Relative change in pre-bronchodilator FEV1 from baseline to Week 52; Time to first asthma exacerbation during the 52-week treatment period; Change in fractional excretion of nitric oxide ($FE_{NO}$) from baseline to Week 52; Change in asthma-specific health-related quality of life, assessed by the Overall Score of the Standardized Version of the Asthma Quality of Life Questionnaire, (AQLQ(S)) from baseline to Week 52; Change in rescue medication use (measured by number of puffs per day of rescue medication or nebulized rescue medication (i.e., SABA)) from baseline to Week 52; Rate of urgent asthma-related health care utilization (i.e., hospitalizations, emergency department visits, and acute care visits) during the 52-week placebo-controlled period.

Exploratory Outcome Measures

Exploratory outcome measures will include the following: Proportion of patients who do not experience a protocol-defined asthma exacerbation during the 52-week placebo-controlled period; Change in morning post-bronchodilator peak flow value (L/min) from baseline to Week 52; Change in post-bronchodilator FEV1 from baseline to Week 52; Time to a 150-mL improvement in pre-bronchodilator $FEV_1$ during the 52-week placebo-controlled period; Relative change in pre-bronchodilator $FEV_1$ (liters) from baseline averaged over Weeks 4 to 52; Relative change in forced vital capacity from baseline to Week 52; rate of exacerbations that are associated with lung function decline, defined as an exacerbation resulting in PEF or FEV1<60% of the highest value during screening period (Visits 1-3) that requires treatment with systemic corticosteroids; Change in work, school and activity impairment as assessed by the Work Productivity and Activity Impairment-Asthma Questionnaire (WPAI-Asthma) from baseline to Week 52; Change in Asthma Control Questionnaire-5 (ACQ-5) score from baseline to Week 52; Change in asthma symptoms, as measured by the Asthma Symptom Utility Index (ASUI) from baseline to Week 52; Change in health utilities, as assessed by the EQ-5D, from baseline to Week 52; Change in the Global Evaluation of Treatment Effectiveness (GETE) from baseline to Week 52.

These exploratory outcome measures may also be assessed during the 52-week active-treatment extension and the 24-week follow-up period. Additional exploratory outcomes measures may include frequency and severity of adverse events in patients exposed to lebrikizumab for >52 weeks; change in interleukin-13 (IL-13)/asthma-related PD biomarkers during the 52-week active-treatment extension or 24-week follow-up period; and serum lebrikizumab concentrations during the 52-week active-treatment extension or 24-week follow-up period.

Patient-Reported Outcomes

Asthma Quality of Life Questionnaire—Standardized (AQLQ(S))

The AQLQ(S) will be used to assess the patients' asthma-specific health-related quality of life (Juniper 2005). The questionnaire contains four domains including activity limitations, symptoms, emotional function, and environmental stimuli. The AQLQ(S) has been validated for use in this study population. The AQLQ(S) has a recall specification of 2 weeks. The AQLQ(S) will be administered to the patient prior to all other non-PRO assessments and before the patient receives any disease status information or study drug during that assessment.

Work, Productivity, and Activity Impairment-Asthma (WPAI-Asthma)

To assess impairment at work, school, and with activities, the WPAI-Asthma questionnaire will be administered (Reilly et al. 1993, 1996). Questionnaire items are adapted from the WPAI-Allergy Specific (WPAI-AS) questionnaire, substituting all occurrences of the term allergy with asthma. The WPAI-AS will be administered to the patient prior to all other non-PRO assessments and before the patient receives any disease status information or study drug during that assessment.

Euro-QOL 5D Questionnaire (EQ-5D)

The EQ-5D is generic preference-based health-related quality of life questionnaire that provides a single index value for health status (The EuroQol Group 1990). The EQ-5D is designed for self-completion by patients. The Eq-5D will be administered to the patient prior to all other non-PRO assessments and before the patient receives any disease-status information or study drug during that assessment.

Asthma Symptom Utility Index (ASUI)

The ASUI (Revicki 1998) is an asthma specific symptom questionnaire measuring cough, wheezing, shortness of breath and night time awakening. The ASUI will be administered to the patient prior to all other non-PRO assessments and before the patient receives any disease-status information or study drug during that assessment.

Example 7—Elecsys® Periostin Assay

The quantitative detection of periostin is assessed in an automated Roche cobas e601 Elecsys® analyzer (Roche Diagnostics GmbH). The test is carried out in the sandwich format wherein the analyte periostin is sandwiched between two monoclonal antibodies binding to two different epitopes on periostin. One antibody is biotinylated and enables the capture of the immune complex to streptavidin-coated magnetic beads. The second antibody bears a complexed ruthenium cation as the signaling moiety that allows a voltage dependent electrochemi-luminescent detection of the bound immuno complex.

In detail, reagents are used as follows:

Beads (M): Streptavidin-coated magnetic microparticles 0.72 mg/mL; preservative.

Reagent 1 (R1): Anti-periostin-antibody-biotin:
This purified mouse monoclonal-antibody corresponds to the coating antibody 25D4 according to example 4 and is used in biotinylated form >1.0 mg/L;
TRIS buffer >100 mmol/L, pH 7.0; preservative.

Reagent 2 (R2): Anti-periostin-antibody-Ru(bpy):
This purified mouse monoclonal anti-periostin antibody corresponds to the detection antibody 23B9 according to example 4 and is used in labeled form (labeled with a (Tris(2,2'-bipyridyl)ruthenium(II)-complex (Ru(bpy)) complex)>1.0 mg/L; TRIS buffer >100 mmol/L, pH 7.0; preservative.

The immunoassay is carried out using two incubations. In the first incubation of about 9 minutes periostin in 20 μL of sample and the biotinylated monoclonal anti-periostin antibody (R1) form a complex. In the second incubation step for further 9 minutes ruthenylated monoclonal anti-periostin antibody (R2) and streptavidin-coated microparticles (M) are added to the vial of the first incubation so that a 3-membered sandwich complex is formed and becomes bound to the solid phase (microparticles) via the interaction of biotin and streptavidin.

The reaction mixture is aspirated into the measuring cell where the microparticles are magnetically captured onto the surface of a platinum electrode. Unbound substances are washed away and the cell flushed with ProCell, a reagent containing Tripropylamine. Application of a voltage to the electrode then induces a chemi-luminescent emission which is measured by a photomultiplier.

Results are determined via an instrument-specific calibration curve which is generated by 2-point calibration and a master curve provided via the reagent barcode. Calibrator 1 is analyte free, whereas calibrator 2 contains 50 ng/mL recombinant human periostin in a buffered matrix. To verify calibration, two controls with approximately 30 and 80 ng/mL periostin are employed.

Example 8—Comparison of E4 Assay and Elecsys® Periostin Assay

Figure 17:
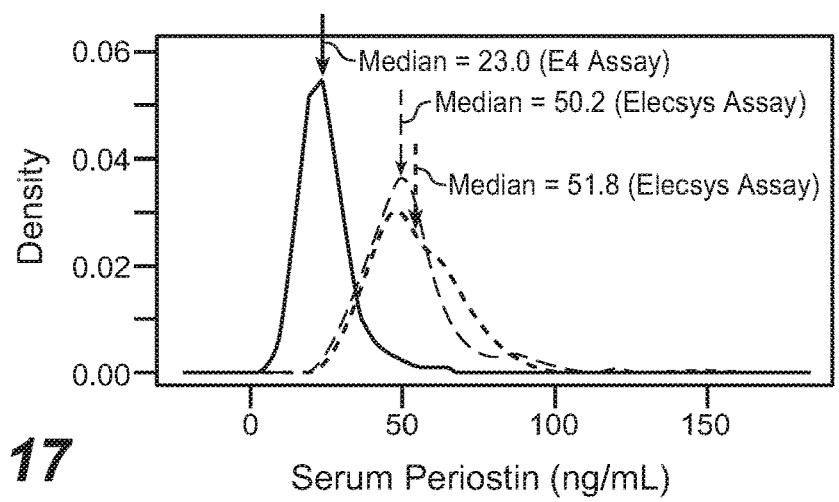
FIG. 17 shows a comparison between serum periostin levels as measured on assays similar to the Example 4 Assay (E4 Assay) or the Elecsys® periostin assay (Example 7) for samples obtained from the clinical trials described in Example 3 and Example 5.

The periostin levels were measured in patient serum samples from the clinical trials described in each of Example 2 and Example 3 using methods similar to the E4 Assay (Example 4) and to the Elecsys® periostin assay (Example 7). Results from samples from both trials showed that the periostin values overlapped. The variability and spread was comparable across the assays. In general, at the median, the Elecsys® assay results were typically = or >2 fold higher than the E4 Assay results. See FIG. 17, i.e., the median was 50-51 ng/ml for the Elecsys® periostin assay and the median was 23 ng/ml for the E4 Assay.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

| SEQUENCE LISTING KEY | |
|---|---|
| SEQ ID NO: | Sequence |
| 1 | QVHLQQSGAELAKPGASVHMSCKASGYTFTTYWMHWVKQRPGQGLEWIGYINPNTGYADY NQKFRDKATLTADKSSSTAYMQLSSLTSEDSTVYFCARRRTGTSYFDYWGQGTTLTVSST KTTPPSV |
| 2 | QTVLSQSPAILSASPGEKVTMTVRASSSVTYMHWYQQKPGSSPKPWIFATSNLASGVPAR FSGSGSGTSYSLTISRVEAEDAATYYCQQWTSNPLTFGAGTK |
| 3 | QVQLQQSGAELVARPGASVKLSCKASGYSFTHYWMQWVKQRPGQGLEWIGAIYPGDGDTR YTQRLKGKATLTADKSSSTAYMELSSLASEDSAVYYCAREGEGNSAMDYWGQGTSVTVSS AKTTPPSV |
| 4 | DIVMTQSQKSMSTSVGDRVSVTCKASQNVGSSVAWFQQKPGQSPKTLIYSASYRDSGVPD RFTGSGSGTDFTLTITNVQSEDLTDYFCLQYGTYPYTFGGGTR |
| 5 | MIPFLPMFSL LLLLIVNPIN ANNHYDKILA HSRIRGRDQG PNVCALQQIL GTKKKYFSTCKNWYKKSICG QKTTVLYECC PGYMRMEGMK GCPAVLPIDH VYGTLGIVGA TTTQRYSDAS KLREEIEGKG SFTYFAPSNE AWDNLDSDIR RGLESNVNVE LLNALHSHMI NKRMLTKDLK NGMIIPSMYN NLGLFINHYP NGVVTVNCAR IIHGNQIATN GVVHVIDRVL TQIGTSIQDF IEAEDDLSSF RAAAITSDIL EALGRDGHFT LFAPTNEAFE KLPRGVLERI MGDKVASEALMKYHILNTLQ CSISIMGGAV FETLEGNTIE IGCDGDSITV NGIKMVNKKD IVTNNGVIHLIDQVLIPDSA KQVIELAGKQ QTTFTDLVAQ LGLASALRPD GEYTLLAPVN NAFSDDTLSMDQRLLKLILQ NHILKVKVGL NELYNGQILE TIGGKQLRVF VYRTAVCIEN SCMEKGSKQGRNGAIHIFRE IIKPAEKSLH EKLKQDKRFS TFLSLLEAAD LKELLTQPGD WTLFVPTNDAFKGMTSEEKE ILIRDKNALQ NIILYHLTPG VFIGKGFEPG VTNILKTTQG SKIFLKEVNDTLLVNELKSK ESDIMTTNGV IHVVDKLLYP ADTPVGNDQL LEILNKLIKY IQIKFVRGST FKEIPVTVYT TKIITKVVEP KIKVIEGSLQ PIIKTEGPTL TKVKIEGEPE FRLIKEGETTTEVIHGEPII KKYTKIIDGV PVEITEKETR EERITTGPEI KYTRSITGGG ETEETLKKLLQEEVTKVTKF IEGGDGHLFE DEEIKRLLQG DTPVRKLQAN KKVQGSRRRL REGRSQ |
| 6 | MIPFLPMFSL LLLLIVNPIN ANNHYDKILA HSRIRGRDQG PNVCALQQIL GTKKKYFSTCKNWYKKSICG QKTTVLYECC PGYMRMEGMK GCPAVLPIDH VYGTLGIVGA TTTQRYSDAS KLREEIEGKG SFTYFAPSNE AWDNLDSDIR RGLESNVNVE LLNALHSHMI NKRMLTKDLKNGMIIPSMYN NLGLFINHYP NGVVTVNCAR IIHGNQIATN GVVHVIDRVL TQIGTSIQDF IEAEDDLSSF RAAAITSDIL EALGRDGHFT LFAPTNEAFE KLPRGVLERI MGDKVASEALMKYHILNTLQ CSESIMGGAV FETLEGNTIE IGCDGDSITV NGIKMVNKKD IVTNNGVIHLIDQVLIPDSA KQVIELAGKQ QTTFTDLVAQ LGLASALRPD GEYTLLAPVN NAFSDDTLSMDQRLLKLILQ NHILKVKVGL NELYNGQILE TIGGKQLRVF VYRTAVCIEN SCMFKGSK QGRNGAIHIFRE IIKPAEKSLH EKLKQDKRFS TFLSLLEAAD LKELLTQPGD WTLFVPTNDAFKGMTSEEKE ILIRDKNALQ NILYHLTPQ VFIGKGFEPG VTNILKTTQG SKIFLKEVNDTLLVNELKSK ESDIMTTNGV IHVVDKLLYP ADTPVGNDQL LEILNKLIKY IQIKFVRGSTFKEIPVTVYK PIIKKYTKII DGVPVEITEK ETREERIITG PEIKYTRIST GGGETEETLK KLLQEEVTKV TKFIEGGDGH LFEDEEIKRL LQGDTPVRKL QANKKVQGSR RRLREGRSQ |
| 7 | MIPFLPMFSLL LLLLIVNPIN ANNHYDKILA HSRISGRDQG PNVCALQQIL GTKKKYFSTCKNWYKKSICG QKTTVLYECC PGYMRMEGMK GCPAVLPIDH VYGTLGIVGA TTTQRYSDAS KLREEIEGKG SFTYFAPSNE AWDNLDSDIR RGLESNVNVE LLNALHSHMI NKRMLTKDLKNGMIIPSMYN NLGLFINHYP NGVVTVNCAR IIHGNQIATN GVVHVIDRVL TQIGTSIQDF IEAEDDLSSF RAAAITSDIL EALGRDGHFT LFAPTNEAFE KLPRGVLERI MGDKVASEALMKYHILNTLQ CSESIMGGAV FETLEGNTIE IGCDGDSITV NGIKMVNKKD IVTNNGVIHLIDQVLIPDSA KQVIELAGKQ QTTFTDLVAQ LGLASALRPD GEYTLLAPVN NAFSDDTLSMDQRLLKLILQ NHILKVKVGL NELYNGQILE TIGGKQLRVF VYRTAVCIEN SCMEKGSKQGRNGAIHIFRE IIKPAEKSLH EKLKQDKRFS TFLSLLEAAD LKELLTQPGD |

| SEQ ID NO: | Sequence |
|---|---|
| | WTLFVPTNDAFKGMTSEEKE ILIRDKNALQ NIILYHLTPG VFIGKGFEPG<br>VTNILKTTQG SKIFLKEVNDTLLVNELKSK ESDIMTTNGV IHVVDKLLYP<br>ADTPVGNDQL LEILNKLIKY IQIKFVRGSTFKEIPVTVYR PTLTKVKIEG<br>EPEFRLIKEG ETITEVIHGE PIIKKYTKII DGVPVEITEK ETREERIITG<br>PEIKYTRIST GGGETEETLK KLLQEDTPVR KLQANKKVQG SRRRLREGRSQ |
| 8 | MIPFLPMFSL LLLLIVNPIN ANNHYDKILA HSRIRGRDQG PNVCALQQIL<br>GTKKKYFSTCKNWYKKSICG QKTTVLYECC PGYMRMEGMK GCPAVLPIDH<br>VYGTLGIVGA TTTQRYSDAS KLREEIEGKG SFTYFAPSNE AWDNLDSDIR<br>RGLESNVNVE LLNALHSHMI NKRMLTKDLKNGMIIPSMYN NLGLFINHYP<br>NGVVTVNCAR IIHGNQIATN GVVHVIDRVL TQIGTSIQDF IEAEDDLSSF<br>RAAAITSDIL EALGRDGHFT LFAPTNEAFE KLPRGVLERI<br>MGDKVASEALMKYHILNTLQ CSESIMGGAV FETLEGNTIE IGCDGDSITV<br>NGIKMVNKKD IVTNNGVIHLIDQVLIPDSA KQVEILAGKQ QTTFTDLVAQ<br>LGLASALRPD GEYTLLAPVN NAFSDDTLSMDQRLLKLILQ NHILKVKVGL<br>NELYNGQILE TIGGKQLRVF VYRTAVCIEN SCMEKGSKQGRNGAIHIFRE<br>IIKPAEKSLH EKLKQDKRFS TFLSLLEAAD LKELLTQPGD<br>WTLFVPTNDAFKGMTSEEKE ILIRDKNALQ NIILYHLTPG VFIGKGFEPG<br>VTNILKTTQG SKIFLKEVNDTLLVNELKSK ESDIMTTNGV IHVVDKLLYP<br>ADTPVGNDQL LEILNKLIKY IQIKFVRGST FKEIPVTVYK PIIKKYTKII<br>DGVPVEITEK ETREERIITG PEIKYTRIST GGGETEETLKKLLQEDTPVR<br>KLQANKKVQG SRRRLREGRS Q |
| 9 | VTLRESGPALVKPTQTLTLTCTVSGFSLSAYSVNWIRQPPGKALEWLAMIWGDGKIVYNS<br>ALKSRLTISKDTSKNQVVLTMTNMDPVDTATYYCAGDGYYPYAMDNWGQGSLVTVSS |
| 11 | AYSVNW |
| 12 | MIWGDGKIVYNSALKS |
| 13 | DGYYPYAMDN |
| 14 | RASKSVDSYGNSFMH |
| 15 | LASNLES |
| 16 | QQNNEDPRT |
| 17 | Asp Ile Gln Leu Thr Gln Ser Pro Ser Ser Leu Ser Ala Ser Val<br>Gly Asp Arg Val Thr Ile Thr Cys Arg Ala Ser Gln Ser Val Asp<br>Tyr Asp Gly Asp Ser Tyr Met Asn Tyr Tyr Gln Gln Lys Pro Gly<br>Lys Ala Pro Lys Leu Leu Ile Tyr Ala Ala Ser Tyr Leu Gln Ser<br>Gly Val Pro Ser Arg Phe Ser Gly Ser Gly Ser Gly Thr Asp Phe<br>Thr Leu Ile Ile Ser Ser Leu Gln Pro Glu Asp Phe Ala Thr Tyr<br>Tyr Cys Gln Gln Ser His Glu Asp Pro Tyr Thr Phe Gly Gln Gly<br>Thr Lys Val Glu Ile Lys Arg Thr Val |
| 18 | Glu Val Gln Leu Val Glu Ser Gly Gly Gly Leu Val Gln Pro Gly<br>Gly Ser Leu Arg Leu Ser Cys Ala Val Ser Gly Tyr Ser Ile Thr<br>Ser Gly Tyr Ser Trp Asn Trp Ile Arg Gln Ala Pro Gly Lys Gly<br>Leu Glu Trp Val Ala Ser Ile Thr Tyr Asp Gly Ser Thr Asn Tyr<br>Asn Pro Ser Val Lys Gly Arg Ile Thr Ile Ser Arg Asp Asp Ser<br>Lys Asn Thr Phe Tyr Leu Gln Met Asn Ser Leu Arg Ala Glu Asp<br>Thr Ala Val Tyr Tyr Cys Ala Arg Gly Ser His Tyr Phe Gly His<br>Trp His Phe Ala Val Trp Gly Gln Gly |
| 19 | MIPFLPMFSLLLLLIVNPINANNHYDKILAHSRIRGRDQGPNVCALQQILGTKKKYFSTC<br>KNWYKKSICGQKTTVLYECCPGYMRMEGMKGCPAVLPIDHVYGTLGIVGATTTQRYSDAS<br>KLREEIEGKGSFTYFAPSNEAWDNLDSDIRRGLESNVNVELLNALHSHMINKRMLTKDLK<br>NGMIIPSMYNNLGLFINHYPNGVVTVNCARIIHGNQIATNGVVHVIDRVLTQIGTSIQDF<br>IEAEDDLSSFRAAAITSDILEALGRDGHFTLFAPTNEAFEKLPRGVLERIMGDKVASEAL<br>MKYHILNTLQCSESIMGGAVFETLEGNTIEIGCDGDSITVNGIKMVNKKDIVTNNGVIHL<br>IDQVLIPDSAKQVIELAGKQQTTFTDLVAQLGLASALRPDGEYTLLAPVNNAFSDDTLSM<br>DQRLLKLILQNHILKVKVGLNELYNGQILETIGGKQLRVGVYRTAVCIENSCMEKGSKQG<br>RNGAIHIFREIIKPAEKSLHEKLKQDKRFSTFLSLLEAADLKELLTQPGDWTLFVPTNDA<br>FKGMTSEEKEILIRDKNALQNIILYHLTPGVFIGKGFEPGVTNILKTTQGSKIFLKEVND<br>TLLVNELKSKESDIMTTNGVIHVVDKLLYPADTPVGNDQLLEILNKLIKYIQIKFVRGST<br>FKEIPVTVYTTKIITKVVEPKIKVIEGSLQPIIKTEGPTLTKVKIEGEPEFRLIKEGETI<br>TEVIHGEPIIKKYTKIIDGVPVEITEKETREERIITGPEIKYTRISTGGGETEETLKKLL<br>QEEVTKVTKFIEGGDGHLFEDEEIKRLLQGDTPVRKLQANKKVQGSRRRLREGRSQ |
| 20 | MIPFLPMFSLLLLLIVNPINANNHYDKILAHSRIRGRDQGPNVCALQQILGTKKKYFSTC<br>KNWYKKSICGQKTTVLYECCPGYMRMRGMKGCPAVLPIDHVYGTLGIVGATTTQRYSDAS<br>KLREEIEGKGSFTYFAPSNEAWDNLDSDIRRGLESNVNVELLNALHSHMINKRMLTKDLK<br>NGMIIPSMYNNLGLFINHYPNGVVTVNCARIIHGNQIATNGVVHVIDRVLTQIGTSIQDF |

| SEQUENCE LISTING KEY | |
|---|---|
| SEQ ID NO: | Sequence |
| | IEAEDDLSSFRAAAITSDILEALGRDGHFTLFAPTNEAFEKLPRGVLERIMGDKVASEAL<br>MKYHILNTLQCSESIMGGAVFETLEGNTIEIGCDGDSITVNGIKMVNKKDIVTNNGVIHL<br>IDQVLIPDSAKQVIELAGKQQTTFTDLVAQLGLASALRPDGEYTLLAPVNNAFSDDTLSM<br>DQRLLKLILQNHILKVKVGLNELYNGQILETIGGKQLRVFVYRTAVCIENSCMEKGSKQG<br>RNGAIHIFREIIKPAEKSLHEKLKQDKRFSTFLSLLEAADLKELLTQPGDWTLFVPTNDA<br>FKGMTSEEKEILIRDKNALQNIILYHLTPGVFIGKGFEPGVTNILKTTQGSKIFLKEVND<br>TLLVNELKSKESDIMTTNGVIHVVDKLLYPADTPVGNDQLLEILNKLIKYIQIKFVRGST<br>FKEIPVTVYKPIIKKYTKIIDGVPVEITEKETREERIITGPEIKYTRISTGGGETEETLK<br>KLLQEEVTKVTKFIEGGDGHLFEDEEIKRLLQGDTPVRKLQANKKVQGSRRRLREGRSQ |
| 21 | MIPFLPMFSLLLLLIVNPINANNHYDKILAHSRIRGRDQGPNVCALQQILGTKKKYFSTC<br>KNWYKKSICGQKTTVLYECCPGYMRMEGMKGCPAVLPIDHVYGTLGIVGATTTQRYSDAS<br>KLREEIEGKGSFTYFAPSNEAWDNLDSDIRRGLESNVNVELLNALHSHMINKRMLTKDLK<br>NGMIIPSMYNNLGLFINHYPNGVVTVNCARIIHGNQAITNGVVHVIDRVLTQIGTSIQDF<br>IEAEDDLSSFRAAAITSDILEALGRDGHFTLFAPTNEAFEKLPRGVLERIMGDKVASEAL<br>MKYHILNTLQCSESIMGGAVFETLEGNTIEIGCDGDSITVNGIKMVNKKDIVTNNGVIHL<br>IDQVLIPDSAKQVIELAGKQQTTFTDLVAQLGLASALRPDGEYTLLAPVNNAFSDDTLSM<br>DQRLLKLILQNHILKVKVGLNELYNGQILETIGGKQLRVFVYRTAVCIENSCMEKGSKQG<br>RNGAIHIFREIIKPAEKSLHEKLKQDKRFSTFLSLLEAADLKELLTQPGDWTLFVPTNDA<br>FKGMTSEEKEILIRDKNALQNIILYIILTPGVFIGKGFEPGVTNILKTTQGSKIFLKEVN<br>DTLLVNELKSKESDIMTTNGVIHVVDKLLYPADTPVGNDQLLEILNKLIKYIQIKFVRGS<br>TFKEIPVTVYRPTLTKVKIEGEPEFRLIKEGETITEVIHGEPIIKKYTKIIDGVPVEITE<br>KETREERIITGPEIKYTRISTGGGETEETLKKLLQEDTPVRKLQANKKVQGSRRRLREGR<br>SQ |
| 22 | MIPFLPMFSLLLLLIVNPINANNHYDKILAHSRIRGRDQGPNVCALQQILGTKKKYFSTC<br>KNWYKKSICGQKTTVLYECCPGYMRMEGMKGCPAVLPIDHVYGTLGIVGATTTQRYSDAS<br>KLREEIEGKGSFTYFAPSNEAWDNLDSDIRRGLESNVNVELLNALHSHMINKRMLTKDLK<br>NGMIIPSMYNNLGLFINHYPNGVVTVNCARIIHGNQAITNGVVHVIDRVLTQIGTSIQDF<br>IEAEDDLSSFRAAAITSDILEALGRDGHFTLFAPTNEAFEKLPRGVLERIMGDKVASEAL<br>MKYHILNTLQCSESIMGGAVFETLEGNTIEIGCDGDSITVNGIKMVNKKDIVTNNGVIHL<br>IDQVLIPDSAKQVIELSAGKQQTTFTDLVAQLGLASALRPDGEYTLLAPVNNAFSDDTLS<br>MDQRLLKLILQNHILKVKVGLNELYNGQILETIGGKQLRVFVYRTAVCIENSCMEKGSKQ<br>GRNGAIHIFREIIKPAEKSLHEKLKQDKRFSTFLSLLEAADLKELLTQPGDWTLFVPTND<br>AFKGMTSEEKEILIRDKNALQNIILYHLTPGVFIGKGFEPGVTNILKTTQGSKIFLKEVN<br>DTLLVNELKSKESDIMTTNGVIHVVDKLLYPADTPVGNDQLLEILNKLIKYIQIKFVRGS<br>TFKEIPVTVYKPIIKKYTKIDGVPVEITEKETREERIITGPEIKYTRISTGGGETEETLK<br>KLLQEDTPVRKLQANKKVQGSRRRLREGRSQ |
| 23 | MIPFLPMFSLLLLLIVNPINANNHYDKILAHSRIRGRDQGPNVCALQQILGTKKKYFSTC<br>KNWYKKSICGQKTTVLYECCPGYMRMEGMKGCPAVLPIDHVYGTLGIVGATTTQRYSDAS<br>KLREEIEGKGSFTYFAPSNEAWDNLDSDIRRGLESNVNVELLNALHSHMINKRMLTKDLK<br>NGMIIPSMYNNLGLFINHYPNGVVTVNCARIIHGNQAITNGVVHVIDRVLTQIGTSIQDF<br>IEAEDDLSSFRAAAITSDILEALGRDGHFTLFAPTNEAFEKLPRGVLERIMGDKVASEAL<br>MKYHILNTLQCSESIMGGAVFETLEGNTIEIGCDGDSITVNGIKMVNKKDIVTNNGVIHL<br>IDQVLIPDSAKQVIELAGKQQTTFTDLVAQLGLASALRPDGEYTLLAPVNNAFSDDTLSM<br>DQRLLKLILQNHILKVKVGLNELYNGQILETIGGKQLRVFVYRTAVCIENSCMEKGSKQG<br>RNGAIHIFREIIKPAEKSLHEKLKQDKRFSTFLSLLEAADLKELLTQPGDWTLFVPTNDA<br>FKGMTSEEKEILIRDKNALQNIILYHLTPGVFIGKGFEPGVTNILKTTQGSKIFLKEVND<br>TLLVNELKSKESDIMTTNGVIHVVDKLLYPADTPVGNDQLLEILNKLIKYIQIKFVRGST<br>FKEIPVTVYSPEIKYTRISTGGGETEETLKKLLQE |
| 24 | EVQLVESGGGLVQPGGSLRLSCAASGFTFSDYGIAWVRQAPGKGLEWVAFISDLAYTIYY<br>ADTVTGRFTISRDNSKNTLYLQMNSLRAEDTAVYYCARDNWDAMDYWGQGTLVTVSS |
| 25 | DIQMTQSPSSLSASVGDRVTITCRSSQSLVHNNANTYLHWYQQKPGKAPKLLIYKVSNRF<br>SGVPSRFSGSGSGTDFTLTISSLQPEDFATYYCSQNTLVPWTFGQGTKVEIK |

The invention claimed is:

1. A method of treating asthma comprising administering an anti-IL-13 antibody comprising hypervariable regions (HVRs) HVRH1, HVRH2, and HVRH3 of the heavy chain variable region, and HVRs HVRL 1, HVRL2, and HVRL3 of the light chain variable region, wherein HVRH1, HVRH2, HVRH3, HVRL 1, HVRL2, and HVRL3 respectively comprise the amino acid sequence of SEQ ID NO: 11, SEQ ID NO: 12, SEQ ID NO: 13, SEQ ID NO: 14, SEQ ID NO: 15, and SEQ ID NO: 16, wherein said antibody is administered to a human patient suffering from asthma at a flat dose of 125 mg or 250 mg every 2-8 weeks, and wherein the anti-IL-13 antibody is administered subcutaneously.

2. The method according to claim 1, wherein the patient is suffering from moderate to severe asthma.

3. The method according to claim 1 or 2, wherein the asthma is uncontrolled on a corticosteroid.

4. The method according to claim 3, wherein the asthma is uncontrolled on an inhaled corticosteroid.

5. The method according to claim 4, wherein the asthma is uncontrolled on a total daily dose of at least 500 mcg fluticasone propionate (FP).

6. The method according to claim 4, wherein the inhaled corticosteroid is triamcinolone, formoterol, beclomethasone dipropionate, budesonide, budesonide and formoterol, flunisolide, fluticasone propionate, fluticasone, fluticasone propionate, or triamcinolone acetonide.

7. The method according to claim 3, wherein the patient is being treated with a second controller medication for asthma.

8. The method according to claim 1, wherein the patient is continuing to be treated with a corticosteroid or an inhaled corticosteroid during the treatment with the anti-IL-13 antibody.

9. The method according to claim 8, wherein the patient is continuing to be treated with a second controller medication for asthma during the treatment with the anti-IL-13 antibody.

10. The method according to claim 9, wherein the second controller medication for asthma is a long acting bronchial dilator.

11. The method according to claim 10, wherein the long acting bronchial dilator is a long-acting beta-2 agonist (LABA), leukotriene receptor antagonist (LTRA), long-acting muscarinic antagonist (LAMA), theophylline, or oral corticosteroids (OCS).

12. The method according to claim 11, wherein the patient has been determined to be Eosinophilic Inflammation Positive (EIP).

13. The method according to claim 1, wherein the patient has been determined to be EIP.

14. The method according to claim 8, wherein the patient has been determined to be EIP.

15. The method according to claim 1, wherein the asthma patient to be treated is 18 years old or older and has serum periostin at ≥50 ng/mL and is uncontrolled on an inhaled corticosteroid and a second controller medication for asthma.

16. The method according to claim 15, wherein the serum periostin is measured using a kit for measuring Total Periostin in a biological sample obtained from a patient, wherein the kit comprises an antibody that binds to Total Periostin.

17. The method of claim 16, further comprising measuring the protein expression levels in a serum sample obtained from the asthma patient for TARC or MCP-4.

18. The method according to claim 1, wherein the anti-IL-13 antibody comprises a VH comprising the amino acid sequence of SEQ ID NO: 9 and a VL comprising the amino acid sequence of SEQ ID NO: 10.

19. The method according to claim 1, wherein the anti-IL-13 antibody is lebrikizumab.

20. The method according to claim 1, wherein the anti-IL-13 antibody is administered using a prefilled syringe or autoinjector device.

21. A method of treating asthma comprising administering an anti-IL-13 antibody, comprising hypervariable regions (HVRs) HVRH1, HVRH2, and HVRH3 of the heavy chain variable region, and HVRs HVRL1, HVRL2, and HVRL3 of the light chain variable region, wherein HVRH1, HVRH2, HVRH3, HVRL1, HVRL2, and HVRL3 respectively comprise the amino acid sequence of SEQ ID NO: 11, SEQ ID NO: 12, SEQ ID NO: 13, SEQ ID NO: 14, SEQ ID NO: 15, and SEQ ID NO: 16, to a human patient suffering from asthma at a flat dose of 125 mg every four weeks or 250 mg every four weeks, wherein the anti-IL-13 antibody is administered subcutaneously.

22. The method of claim 21, wherein a flat dose of 125 mg of the anti-IL-13 antibody is administered to the patient.

23. The method of claim 21, wherein a flat dose of 250 mg of the anti-IL-13 antibody is administered to the patient.

24. The method according to claim 21, wherein the patient is 18 years old or older.

25. The method according to claim 21, wherein the patient is 12 years old or older.

26. The method according to claim 21, wherein the patient is 6 years old or older.

27. The method according to claim 21, wherein the asthma patient is 12 years old or older and uncontrolled on an inhaled corticosteroid and a second controller medication for asthma.

\* \* \* \* \*

UNITED STATES PATENT AND TRADEMARK OFFICE
CERTIFICATE OF CORRECTION

PATENT NO. : 11,226,341 B2
APPLICATION NO. : 15/992115
DATED : January 18, 2022
INVENTOR(S) : Arron et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 8 days.

Signed and Sealed this
Thirty-first Day of January, 2023

*Katherine Kelly Vidal*
Katherine Kelly Vidal
*Director of the United States Patent and Trademark Office*

SEQUENCE LISTING

<160> NUMBER OF SEQ ID NOS: 25

<210> SEQ ID NO 1
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

```
Gln Val His Leu Gln Gln Ser Gly Ala Glu Leu Ala Lys Pro Gly Ala
1               5                   10                  15

Ser Val His Met Ser Cys Lys Ala Ser Gly Tyr Thr Phe Thr Thr Tyr
            20                  25                  30

Trp Met His Trp Val Lys Gln Arg Pro Gly Gln Gly Leu Glu Trp Ile
        35                  40                  45

Gly Tyr Ile Asn Pro Asn Thr Gly Tyr Ala Asp Tyr Asn Gln Lys Phe
50                  55                  60

Arg Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Thr Val Tyr Phe Cys
                85                  90                  95

Ala Arg Arg Arg Thr Gly Thr Ser Tyr Phe Asp Tyr Trp Gly Gln Gly
            100                 105                 110

Thr Thr Leu Thr Val Ser Ser Thr Lys Thr Pro Pro Ser Val
        115                 120                 125
```

<210> SEQ ID NO 2
<211> LENGTH: 102
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Gln Thr Val Leu Ser Gln Ser Pro Ala Ile Leu Ser Ala Ser Pro Gly
1               5                   10                  15

Glu Lys Val Thr Met Thr Cys Arg Ala Ser Ser Ser Val Thr Tyr Met
            20                  25                  30

His Trp Tyr Gln Gln Lys Pro Gly Ser Ser Pro Lys Pro Trp Ile Phe
        35                  40                  45

Ala Thr Ser Asn Leu Ala Ser Gly Val Pro Ala Arg Phe Ser Gly Ser
50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Leu Thr
                85                  90                  95

Phe Gly Ala Gly Thr Lys
            100
```

<210> SEQ ID NO 3
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Ser Phe Thr His Tyr
            20                  25                  30

Trp Met Gln Trp Val Lys Gln Arg Pro Gly Gln Gly Leu Glu Trp Ile
        35                  40                  45
```

Gly Ala Ile Tyr Pro Gly Asp Gly Asp Thr Arg Tyr Thr Gln Arg Leu
        50                  55                  60

Lys Gly Lys Ala Thr Leu Thr Ala Asp Lys Ser Ser Thr Ala Tyr
 65                  70                  75                  80

Met Glu Leu Ser Ser Leu Ala Ser Glu Asp Ser Ala Val Tyr Tyr Cys
                 85                  90                  95

Ala Arg Glu Gly Glu Gly Asn Ser Ala Met Asp Tyr Trp Gly Gln Gly
            100                 105                 110

Thr Ser Val Thr Val Ser Ser Ala Lys Thr Thr Pro Pro Ser Val
        115                 120                 125

<210> SEQ ID NO 4
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Val Met Thr Gln Ser Gln Lys Phe Met Ser Thr Ser Val Gly
 1               5                  10                  15

Asp Arg Val Ser Val Thr Cys Lys Ala Ser Gln Asn Val Gly Ser Ser
            20                  25                  30

Val Ala Trp Phe Gln Gln Lys Pro Gly Gln Ser Pro Lys Thr Leu Ile
        35                  40                  45

Tyr Ser Ala Ser Tyr Arg Asp Ser Gly Val Pro Asp Arg Phe Thr Gly
 50                  55                  60

Ser Gly Ser Gly Thr Asp Phe Thr Leu Thr Ile Thr Asn Val Gln Ser
 65                  70                  75                  80

Glu Asp Leu Thr Asp Tyr Phe Cys Leu Gln Tyr Gly Thr Tyr Pro Tyr
                 85                  90                  95

Thr Phe Gly Gly Gly Thr Arg
            100

<210> SEQ ID NO 5
<211> LENGTH: 836
<212> TYPE: PRT
<213> ORGANISM: Homo sapiens

<400> SEQUENCE: 5

Met Ile Pro Phe Leu Pro Met Phe Ser Leu Leu Leu Leu Leu Ile Val
 1               5                  10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
 50                  55                  60

Lys Lys Ser Ile Cys Gly Gln Lys Thr Thr Val Leu Tyr Glu Cys Cys
 65                  70                  75                  80

Pro Gly Tyr Met Arg Met Glu Gly Met Lys Gly Cys Pro Ala Val Leu
                 85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

```
Lys Gly Ser Phe Thr Tyr Phe Ala Pro Ser Asn Glu Ala Trp Asp Asn
        130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Thr Gln Pro
        515                 520                 525

Gly Asp Trp Thr Leu Phe Val Pro Thr Asn Asp Ala Phe Lys Gly Met
530                 535                 540

Thr Ser Glu Glu Lys Glu Ile Leu Ile Arg Asp Lys Asn Ala Leu Gln
```

```
                545                 550                 555                 560
Asn Ile Ile Leu Tyr His Leu Thr Pro Gly Val Phe Ile Gly Lys Gly
                    565                 570                 575

Phe Glu Pro Gly Val Thr Asn Ile Leu Lys Thr Thr Gln Gly Ser Lys
                580                 585                 590

Ile Phe Leu Lys Glu Val Asn Asp Thr Leu Val Asn Glu Leu Lys
                595                 600                 605

Ser Lys Glu Ser Asp Ile Met Thr Thr Asn Gly Val Ile His Val Val
            610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                    645                 650                 655

Arg Gly Ser Thr Phe Lys Glu Ile Pro Val Thr Val Tyr Thr Thr Lys
                660                 665                 670

Ile Ile Thr Lys Val Val Glu Pro Lys Ile Lys Val Ile Glu Gly Ser
            675                 680                 685

Leu Gln Pro Ile Ile Lys Thr Glu Gly Pro Thr Leu Thr Lys Val Lys
        690                 695                 700

Ile Glu Gly Glu Pro Glu Phe Arg Leu Ile Lys Gly Glu Thr Ile
705                 710                 715                 720

Thr Glu Val Ile His Gly Glu Pro Ile Ile Lys Lys Tyr Thr Lys Ile
                    725                 730                 735

Ile Asp Gly Val Pro Val Glu Ile Thr Glu Lys Glu Thr Arg Glu Glu
                740                 745                 750

Arg Ile Ile Thr Gly Pro Glu Ile Lys Tyr Thr Arg Ile Ser Thr Gly
            755                 760                 765

Gly Gly Glu Thr Glu Thr Leu Lys Lys Leu Leu Gln Glu Glu Val
        770                 775                 780

Thr Lys Val Thr Lys Phe Ile Glu Gly Gly Asp Gly His Leu Phe Glu
785                 790                 795                 800

Asp Glu Glu Ile Lys Arg Leu Leu Gln Gly Asp Thr Pro Val Arg Lys
                    805                 810                 815

Leu Gln Ala Asn Lys Lys Val Gln Gly Ser Arg Arg Arg Leu Arg Glu
                820                 825                 830

Gly Arg Ser Gln
        835

<210> SEQ ID NO 6
<211> LENGTH: 779
<212> TYPE: PRT
<213> ORGANISM: Homo sapiens

<400> SEQUENCE: 6

Met Ile Pro Phe Leu Pro Met Phe Ser Leu Leu Leu Leu Ile Val
1               5                   10                  15

Asn Pro Ile Asn Ala Asn Asn His Tyr Asp Lys Ile Leu Ala His Ser
                20                  25                  30

Arg Ile Arg Gly Arg Asp Gln Gly Pro Asn Val Cys Ala Leu Gln Gln
            35                  40                  45

Ile Leu Gly Thr Lys Lys Lys Tyr Phe Ser Thr Cys Lys Asn Trp Tyr
        50                  55                  60

Lys Lys Ser Ile Cys Gly Gln Lys Thr Thr Val Leu Tyr Glu Cys Cys
65                  70                  75                  80
```

-continued

Pro Gly Tyr Met Arg Met Glu Gly Met Lys Gly Cys Pro Ala Val Leu
            85                  90                  95

Pro Ile Asp His Val Tyr Gly Thr Leu Gly Ile Val Gly Ala Thr Thr
                100                 105                 110

Thr Gln Arg Tyr Ser Asp Ala Ser Lys Leu Arg Glu Glu Ile Glu Gly
            115                 120                 125

Lys Gly Ser Phe Thr Tyr Phe Ala Pro Ser Asn Glu Ala Trp Asp Asn
130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
            195                 200                 205

Ala Arg Ile Ile His Gly Asn Gln Ile Ala Thr Asn Gly Val Val His
            210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
            275                 280                 285

Arg Ile Met Gly Asp Lys Val Ala Ser Glu Ala Leu Met Lys Tyr His
        290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe

```
            500                 505                 510
Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
        530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
                580                 585                 590

Ile Phe Leu Lys Glu Val Asn Asp Thr Leu Leu Val Asn Glu Leu Lys
                595                 600                 605

Ser Lys Glu Ser Asp Ile Met Thr Thr Asn Gly Val Ile His Val Val
        610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Lys Pro Ile
                660                 665                 670

Ile Lys Lys Tyr Thr Lys Ile Ile Asp Gly Val Pro Val Glu Ile Thr
        675                 680                 685

Glu Lys Glu Thr Arg Glu Glu Arg Ile Ile Thr Gly Pro Glu Ile Lys
        690                 695                 700

Tyr Thr Arg Ile Ser Thr Gly Gly Glu Thr Glu Thr Leu Lys
705                 710                 715                 720

Lys Leu Leu Gln Glu Glu Val Thr Lys Val Thr Lys Phe Ile Glu Gly
                725                 730                 735

Gly Asp Gly His Leu Phe Glu Asp Glu Ile Lys Arg Leu Leu Gln
                740                 745                 750

Gly Asp Thr Pro Val Arg Lys Leu Gln Ala Asn Lys Lys Val Gln Gly
        755                 760                 765

Ser Arg Arg Arg Leu Arg Glu Gly Arg Ser Gln
        770                 775

<210> SEQ ID NO 7
<211> LENGTH: 781
<212> TYPE: PRT
<213> ORGANISM: Homo sapiens

<400> SEQUENCE: 7

Met Ile Pro Phe Leu Pro Met Phe Ser Leu Leu Leu Leu Leu Ile Val
1               5                   10                  15

Asn Pro Ile Asn Ala Asn Asn His Tyr Asp Lys Ile Leu Ala His Ser
                20                  25                  30

Arg Ile Arg Gly Arg Asp Gln Gly Pro Asn Val Cys Ala Leu Gln Gln
            35                  40                  45

Ile Leu Gly Thr Lys Lys Lys Tyr Phe Ser Thr Cys Lys Asn Trp Tyr
        50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95
```

```
Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
    450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
```

```
                515                 520                 525
Gly Asp Trp Thr Leu Phe Val Pro Thr Asn Asp Ala Phe Lys Gly Met
    530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
    610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Arg Pro Thr
            660                 665                 670

Leu Thr Lys Val Lys Ile Glu Gly Glu Pro Glu Phe Arg Leu Ile Lys
        675                 680                 685

Glu Gly Glu Thr Ile Thr Glu Val Ile His Gly Glu Pro Ile Ile Lys
    690                 695                 700

Lys Tyr Thr Lys Ile Ile Asp Gly Val Pro Val Glu Ile Thr Glu Lys
705                 710                 715                 720

Glu Thr Arg Glu Glu Arg Ile Ile Thr Gly Pro Glu Ile Lys Tyr Thr
                725                 730                 735

Arg Ile Ser Thr Gly Gly Gly Glu Thr Glu Glu Thr Leu Lys Lys Leu
            740                 745                 750

Leu Gln Glu Asp Thr Pro Val Arg Lys Leu Gln Ala Asn Lys Lys Val
        755                 760                 765

Gln Gly Ser Arg Arg Arg Leu Arg Glu Gly Arg Ser Gln
    770                 775                 780

<210> SEQ ID NO 8
<211> LENGTH: 751
<212> TYPE: PRT
<213> ORGANISM: Homo sapiens

<400> SEQUENCE: 8

Met Ile Pro Phe Leu Pro Met Phe Ser Leu Leu Leu Leu Leu Ile Val
1               5                   10                  15

Asn Pro Ile Asn Ala Asn Asn His Tyr Asp Lys Ile Leu Ala His Ser
                20                  25                  30

Arg Ile Arg Gly Arg Asp Gln Gly Pro Asn Val Cys Ala Leu Gln Gln
            35                  40                  45

Ile Leu Gly Thr Lys Lys Lys Tyr Phe Ser Thr Cys Lys Asn Trp Tyr
        50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110
```

```
Thr Gln Arg Tyr Ser Asp Ala Ser Lys Leu Arg Glu Glu Ile Glu Gly
            115                 120                 125
Lys Gly Ser Phe Thr Tyr Phe Ala Pro Ser Asn Glu Ala Trp Asp Asn
        130                 135                 140
Leu Asp Ser Asp Ile Arg Arg Gly Leu Glu Ser Asn Val Asn Val Glu
145                 150                 155                 160
Leu Leu Asn Ala Leu His Ser His Met Ile Asn Lys Arg Met Leu Thr
                165                 170                 175
Lys Asp Leu Lys Asn Gly Met Ile Ile Pro Ser Met Tyr Asn Asn Leu
            180                 185                 190
Gly Leu Phe Ile Asn His Tyr Pro Asn Gly Val Val Thr Val Asn Cys
        195                 200                 205
Ala Arg Ile Ile His Gly Asn Gln Ile Ala Thr Asn Gly Val Val His
210                 215                 220
Val Ile Asp Arg Val Leu Thr Gln Ile Gly Thr Ser Ile Gln Asp Phe
225                 230                 235                 240
Ile Glu Ala Glu Asp Asp Leu Ser Ser Phe Arg Ala Ala Ile Thr
                245                 250                 255
Ser Asp Ile Leu Glu Ala Leu Gly Arg Asp Gly His Phe Thr Leu Phe
        260                 265                 270
Ala Pro Thr Asn Glu Ala Phe Glu Lys Leu Pro Arg Gly Val Leu Glu
        275                 280                 285
Arg Ile Met Gly Asp Lys Val Ala Ser Glu Ala Leu Met Lys Tyr His
        290                 295                 300
Ile Leu Asn Thr Leu Gln Cys Ser Glu Ser Ile Met Gly Gly Ala Val
305                 310                 315                 320
Phe Glu Thr Leu Glu Gly Asn Thr Ile Glu Ile Gly Cys Asp Gly Asp
                325                 330                 335
Ser Ile Thr Val Asn Gly Ile Lys Met Val Asn Lys Lys Asp Ile Val
            340                 345                 350
Thr Asn Asn Gly Val Ile His Leu Ile Asp Gln Val Leu Ile Pro Asp
        355                 360                 365
Ser Ala Lys Gln Val Ile Glu Leu Ala Gly Lys Gln Gln Thr Thr Phe
    370                 375                 380
Thr Asp Leu Val Ala Gln Leu Gly Leu Ala Ser Ala Leu Arg Pro Asp
385                 390                 395                 400
Gly Glu Tyr Thr Leu Leu Ala Pro Val Asn Asn Ala Phe Ser Asp Asp
                405                 410                 415
Thr Leu Ser Met Asp Gln Arg Leu Leu Lys Leu Ile Leu Gln Asn His
            420                 425                 430
Ile Leu Lys Val Lys Val Gly Leu Asn Glu Leu Tyr Asn Gly Gln Ile
        435                 440                 445
Leu Glu Thr Ile Gly Gly Lys Gln Leu Arg Val Phe Val Tyr Arg Thr
    450                 455                 460
Ala Val Cys Ile Glu Asn Ser Cys Met Glu Lys Gly Ser Lys Gln Gly
465                 470                 475                 480
Arg Asn Gly Ala Ile His Ile Phe Arg Glu Ile Ile Lys Pro Ala Glu
                485                 490                 495
Lys Ser Leu His Glu Lys Leu Lys Gln Asp Lys Arg Phe Ser Thr Phe
            500                 505                 510
Leu Ser Leu Leu Glu Ala Ala Asp Leu Lys Glu Leu Leu Thr Gln Pro
        515                 520                 525
Gly Asp Trp Thr Leu Phe Val Pro Thr Asn Asp Ala Phe Lys Gly Met
```

```
                530                 535                 540
Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
    610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Lys Pro Ile
            660                 665                 670

Ile Lys Lys Tyr Thr Lys Ile Ile Asp Gly Val Pro Val Glu Ile Thr
        675                 680                 685

Glu Lys Glu Thr Arg Glu Glu Arg Ile Ile Thr Gly Pro Glu Ile Lys
    690                 695                 700

Tyr Thr Arg Ile Ser Thr Gly Gly Glu Thr Glu Thr Leu Lys
705                 710                 715                 720

Lys Leu Leu Gln Glu Asp Thr Pro Val Arg Lys Leu Gln Ala Asn Lys
                725                 730                 735

Lys Val Gln Gly Ser Arg Arg Arg Leu Arg Glu Gly Arg Ser Gln
            740                 745                 750

<210> SEQ ID NO 9
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Val Thr Leu Arg Glu Ser Gly Pro Ala Leu Val Lys Pro Thr Gln Thr
1               5                   10                  15

Leu Thr Leu Thr Cys Thr Val Ser Gly Phe Ser Leu Ser Ala Tyr Ser
            20                  25                  30

Val Asn Trp Ile Arg Gln Pro Pro Gly Lys Ala Leu Glu Trp Leu Ala
        35                  40                  45

Met Ile Trp Gly Asp Gly Lys Ile Val Tyr Asn Ser Ala Leu Lys Ser
    50                  55                  60

Arg Leu Thr Ile Ser Lys Asp Thr Ser Lys Asn Gln Val Val Leu Thr
65                  70                  75                  80

Met Thr Asn Met Asp Pro Val Asp Thr Ala Thr Tyr Tyr Cys Ala Gly
                85                  90                  95

Asp Gly Tyr Tyr Pro Tyr Ala Met Asp Asn Trp Gly Gln Gly Ser Leu
            100                 105                 110

Val Thr Val Ser Ser
        115

<210> SEQ ID NO 10
<211> LENGTH: 111
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Val Met Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Arg Thr Phe Gly Gly Gly Thr Lys Val Glu Ile Lys
            100                 105                 110

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Tyr Ser Val Asn Trp
1               5

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Met Ile Trp Gly Asp Gly Lys Ile Val Tyr Asn Ser Ala Leu Lys Ser
1               5                   10                  15

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Gly Tyr Tyr Pro Tyr Ala Met Asp Asn
1               5                   10

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 14

Arg Ala Ser Lys Ser Val Asp Ser Tyr Gly Asn Ser Phe Met His
1               5                   10                  15

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Ala Ser Asn Leu Glu Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Gln Asn Asn Glu Asp Pro Arg Thr
1               5

<210> SEQ ID NO 17
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys Arg
            100                 105                 110

Thr Val

<210> SEQ ID NO 18
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18
```

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Gly
            20                  25                  30

Tyr Ser Trp Asn Trp Ile Arg Gln Ala Pro Gly Lys Gly Leu Glu Trp
        35                  40                  45

Val Ala Ser Ile Thr Tyr Asp Gly Ser Thr Asn Tyr Asn Pro Ser Val
    50                  55                  60

Lys Gly Arg Ile Thr Ile Ser Arg Asp Asp Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Arg Gly Ser His Tyr Phe Gly His Trp His Phe Ala Val Trp Gly
            100                 105                 110

Gln Gly

<210> SEQ ID NO 19
<211> LENGTH: 836
<212> TYPE: PRT
<213> ORGANISM: Homo sapiens

<400> SEQUENCE: 19

Met Ile Pro Phe Leu Pro Met Phe Ser Leu Leu Leu Leu Ile Val
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

```
Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
            275                 280                 285

Arg Ile Met Gly Asp Lys Val Ala Ser Glu Ala Leu Met Lys Tyr His
            290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                    325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
            355                 360                 365

Ser Ala Lys Gln Val Ile Glu Leu Ala Gly Lys Gln Gln Thr Thr Phe
            370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                    405                 410                 415

Thr Leu Ser Met Asp Gln Arg Leu Leu Lys Leu Ile Leu Gln Asn His
                    420                 425                 430

Ile Leu Lys Val Lys Val Gly Leu Asn Glu Leu Tyr Asn Gly Gln Ile
            435                 440                 445

Leu Glu Thr Ile Gly Gly Lys Gln Leu Arg Val Phe Val Tyr Arg Thr
450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                    485                 490                 495

Lys Ser Leu His Glu Lys Leu Lys Gln Asp Lys Arg Phe Ser Thr Phe
                    500                 505                 510

Leu Ser Leu Leu Glu Ala Ala Asp Leu Lys Glu Leu Leu Thr Gln Pro
            515                 520                 525

Gly Asp Trp Thr Leu Phe Val Pro Thr Asn Asp Ala Phe Lys Gly Met
            530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                    565                 570                 575

Phe Glu Pro Gly Val Thr Asn Ile Leu Lys Thr Thr Gln Gly Ser Lys
                    580                 585                 590

Ile Phe Leu Lys Glu Val Asn Asp Thr Leu Leu Val Asn Glu Leu Lys
            595                 600                 605

Ser Lys Glu Ser Asp Ile Met Thr Thr Asn Gly Val Ile His Val Val
            610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                    645                 650                 655

Arg Gly Ser Thr Phe Lys Glu Ile Pro Val Thr Val Tyr Thr Thr Lys
                    660                 665                 670

Ile Ile Thr Lys Val Val Glu Pro Lys Ile Lys Val Ile Glu Gly Ser
```

```
              675                 680                 685
Leu Gln Pro Ile Ile Lys Thr Glu Gly Pro Thr Leu Thr Lys Val Lys
    690                 695                 700

Ile Glu Gly Glu Pro Glu Phe Arg Leu Ile Lys Glu Gly Glu Thr Ile
705                 710                 715                 720

Thr Glu Val Ile His Gly Pro Ile Ile Lys Lys Tyr Thr Lys Ile
                    725                 730                 735

Ile Asp Gly Val Pro Val Glu Ile Thr Glu Lys Glu Thr Arg Glu Glu
                740                 745                 750

Arg Ile Ile Thr Gly Pro Glu Ile Lys Tyr Thr Arg Ile Ser Thr Gly
            755                 760                 765

Gly Gly Glu Thr Glu Thr Leu Lys Lys Leu Leu Gln Glu Glu Val
    770                 775                 780

Thr Lys Val Thr Lys Phe Ile Glu Gly Gly Asp Gly His Leu Phe Glu
785                 790                 795                 800

Asp Glu Glu Ile Lys Arg Leu Leu Gln Gly Asp Thr Pro Val Arg Lys
                805                 810                 815

Leu Gln Ala Asn Lys Lys Val Gln Gly Ser Arg Arg Leu Arg Glu
                820                 825                 830

Gly Arg Ser Gln
        835

<210> SEQ ID NO 20
<211> LENGTH: 779
<212> TYPE: PRT
<213> ORGANISM: Homo sapiens

<400> SEQUENCE: 20

Met Ile Pro Phe Leu Pro Met Phe Ser Leu Leu Leu Leu Ile Val
1                   5                   10                  15

Asn Pro Ile Asn Ala Asn Asn His Tyr Asp Lys Ile Leu Ala His Ser
                20                  25                  30

Arg Ile Arg Gly Arg Asp Gln Gly Pro Asn Val Cys Ala Leu Gln Gln
            35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
                100                 105                 110

Thr Gln Arg Tyr Ser Asp Ala Ser Lys Leu Arg Glu Glu Ile Glu Gly
            115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
                180                 185                 190

Gly Leu Phe Ile Asn His Tyr Pro Asn Gly Val Val Thr Val Asn Cys
            195                 200                 205
```

```
Ala Arg Ile Ile His Gly Asn Gln Ile Ala Thr Asn Gly Val Val His
210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ile Thr
                245                 250                 255

Ser Asp Ile Leu Glu Ala Leu Gly Arg Asp Gly His Phe Thr Leu Phe
                260                 265                 270

Ala Pro Thr Asn Glu Ala Phe Glu Lys Leu Pro Arg Gly Val Leu Glu
                275                 280                 285

Arg Ile Met Gly Asp Lys Val Ala Ser Glu Ala Leu Met Lys Tyr His
290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
                340                 345                 350

Thr Asn Asn Gly Val Ile His Leu Ile Asp Gln Val Leu Ile Pro Asp
                355                 360                 365

Ser Ala Lys Gln Val Ile Glu Leu Ala Gly Lys Gln Gln Thr Thr Phe
370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
                420                 425                 430

Ile Leu Lys Val Lys Val Gly Leu Asn Glu Leu Tyr Asn Gly Gln Ile
                435                 440                 445

Leu Glu Thr Ile Gly Gly Lys Gln Leu Arg Val Phe Val Tyr Arg Thr
450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
                500                 505                 510

Leu Ser Leu Leu Glu Ala Ala Asp Leu Lys Glu Leu Leu Thr Gln Pro
                515                 520                 525

Gly Asp Trp Thr Leu Phe Val Pro Thr Asn Asp Ala Phe Lys Gly Met
530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
                580                 585                 590

Ile Phe Leu Lys Glu Val Asn Asp Thr Leu Leu Val Asn Glu Leu Lys
                595                 600                 605

Ser Lys Glu Ser Asp Ile Met Thr Thr Asn Gly Val Ile His Val Val
610                 615                 620

Asp Lys Leu Leu Tyr Pro Ala Asp Thr Pro Val Gly Asn Asp Gln Leu
```

```
                    625                 630                 635                 640
Leu Glu Ile Leu Asn Lys Leu Ile Lys Tyr Ile Gln Ile Lys Phe Val
                        645                 650                 655

Arg Gly Ser Thr Phe Lys Glu Ile Pro Val Thr Val Tyr Lys Pro Ile
                        660                 665                 670

Ile Lys Lys Tyr Thr Lys Ile Ile Asp Gly Val Pro Val Glu Ile Thr
                        675                 680                 685

Glu Lys Glu Thr Arg Glu Glu Arg Ile Ile Thr Gly Pro Glu Ile Lys
                        690                 695                 700

Tyr Thr Arg Ile Ser Thr Gly Gly Glu Thr Glu Thr Leu Lys
705                     710                 715                 720

Lys Leu Leu Gln Glu Glu Val Thr Lys Val Thr Lys Phe Ile Glu Gly
                        725                 730                 735

Gly Asp Gly His Leu Phe Glu Asp Glu Ile Lys Arg Leu Leu Gln
                        740                 745                 750

Gly Asp Thr Pro Val Arg Lys Leu Gln Ala Asn Lys Lys Val Gln Gly
                        755                 760                 765

Ser Arg Arg Arg Leu Arg Glu Gly Arg Ser Gln
770                     775

<210> SEQ ID NO 21
<211> LENGTH: 781
<212> TYPE: PRT
<213> ORGANISM: Homo sapiens

<400> SEQUENCE: 21

Met Ile Pro Phe Leu Pro Met Phe Ser Leu Leu Leu Leu Leu Ile Val
1               5                   10                  15

Asn Pro Ile Asn Ala Asn Asn His Tyr Asp Lys Ile Leu Ala His Ser
                20                  25                  30

Arg Ile Arg Gly Arg Asp Gln Gly Pro Asn Val Cys Ala Leu Gln Gln
            35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
                100                 105                 110

Thr Gln Arg Tyr Ser Asp Ala Ser Lys Leu Arg Glu Ile Glu Gly
            115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
                180                 185                 190

Gly Leu Phe Ile Asn His Tyr Pro Asn Gly Val Val Thr Val Asn Cys
            195                 200                 205

Ala Arg Ile Ile His Gly Asn Gln Ile Ala Thr Asn Gly Val Val His
    210                 215                 220
```

```
Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ile Thr
            245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
            275                 280                 285

Arg Ile Met Gly Asp Lys Val Ala Ser Glu Ala Leu Met Lys Tyr His
            290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
                340                 345                 350

Thr Asn Asn Gly Val Ile His Leu Ile Asp Gln Val Leu Ile Pro Asp
            355                 360                 365

Ser Ala Lys Gln Val Ile Glu Leu Ala Gly Lys Gln Gln Thr Thr Phe
            370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
                420                 425                 430

Ile Leu Lys Val Lys Val Gly Leu Asn Glu Leu Tyr Asn Gly Gln Ile
            435                 440                 445

Leu Glu Thr Ile Gly Gly Lys Gln Leu Arg Val Phe Val Tyr Arg Thr
            450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
            515                 520                 525

Gly Asp Trp Thr Leu Phe Val Pro Thr Asn Asp Ala Phe Lys Gly Met
530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
            595                 600                 605

Ser Lys Glu Ser Asp Ile Met Thr Thr Asn Gly Val Ile His Val Val
            610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
```

```
                    645                 650                 655
Arg Gly Ser Thr Phe Lys Glu Ile Pro Val Thr Val Tyr Arg Pro Thr
            660                 665                 670
Leu Thr Lys Val Lys Ile Glu Gly Pro Glu Phe Arg Leu Ile Lys
            675                 680                 685
Glu Gly Glu Thr Ile Thr Glu Val Ile His Gly Pro Ile Ile Lys
            690                 695                 700
Lys Tyr Thr Lys Ile Ile Asp Gly Val Pro Val Glu Ile Thr Glu Lys
705                 710                 715                 720
Glu Thr Arg Glu Glu Arg Ile Ile Thr Gly Pro Glu Ile Lys Tyr Thr
                725                 730                 735
Arg Ile Ser Thr Gly Gly Glu Thr Glu Thr Leu Lys Lys Leu
            740                 745                 750
Leu Gln Glu Asp Thr Pro Val Arg Lys Leu Gln Ala Asn Lys Lys Val
            755                 760                 765
Gln Gly Ser Arg Arg Arg Leu Arg Glu Gly Arg Ser Gln
            770                 775                 780

<210> SEQ ID NO 22
<211> LENGTH: 751
<212> TYPE: PRT
<213> ORGANISM: Homo sapiens

<400> SEQUENCE: 22

Met Ile Pro Phe Leu Pro Met Phe Ser Leu Leu Leu Leu Leu Ile Val
1               5                   10                  15

Asn Pro Ile Asn Ala Asn Asn His Tyr Asp Lys Ile Leu Ala His Ser
                20                  25                  30

Arg Ile Arg Gly Arg Asp Gln Gly Pro Asn Val Cys Ala Leu Gln Gln
            35                  40                  45

Ile Leu Gly Thr Lys Lys Lys Tyr Phe Ser Thr Cys Lys Asn Trp Tyr
        50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240
```

```
Ile Glu Ala Glu Asp Asp Leu Ser Ser Phe Arg Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
            275                 280                 285

Arg Ile Met Gly Asp Lys Val Ala Ser Glu Ala Leu Met Lys Tyr His
            290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
            355                 360                 365

Ser Ala Lys Gln Val Ile Glu Leu Ala Gly Lys Gln Gln Thr Thr Phe
370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
                420                 425                 430

Ile Leu Lys Val Lys Val Gly Leu Asn Glu Leu Tyr Asn Gly Gln Ile
            435                 440                 445

Leu Glu Thr Ile Gly Gly Lys Gln Leu Arg Val Phe Val Tyr Arg Thr
450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
                500                 505                 510

Leu Ser Leu Leu Glu Ala Ala Asp Leu Lys Glu Leu Leu Thr Gln Pro
            515                 520                 525

Gly Asp Trp Thr Leu Phe Val Pro Thr Asn Asp Ala Phe Lys Gly Met
            530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
            595                 600                 605

Ser Lys Glu Ser Asp Ile Met Thr Thr Asn Gly Val Ile His Val Val
            610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Lys Pro Ile
```

```
                      660                 665                 670
Ile Lys Lys Tyr Thr Lys Ile Ile Asp Gly Val Pro Val Glu Ile Thr
                675                 680                 685

Glu Lys Glu Thr Arg Glu Arg Ile Ile Thr Gly Pro Glu Ile Lys
            690                 695                 700

Tyr Thr Arg Ile Ser Thr Gly Gly Gly Glu Thr Glu Thr Leu Lys
705                 710                 715                 720

Lys Leu Leu Gln Glu Asp Thr Pro Val Arg Lys Leu Gln Ala Asn Lys
                725                 730                 735

Lys Val Gln Gly Ser Arg Arg Leu Arg Glu Gly Arg Ser Gln
            740                 745                 750

<210> SEQ ID NO 23
<211> LENGTH: 695
<212> TYPE: PRT
<213> ORGANISM: Homo sapiens

<400> SEQUENCE: 23

Met Ile Pro Phe Leu Pro Met Phe Ser Leu Leu Leu Leu Ile Val
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285
```

```
Arg Ile Met Gly Asp Lys Val Ala Ser Glu Ala Leu Met Lys Tyr His
    290             295             300

Ile Leu Asn Thr Leu Gln Cys Ser Glu Ser Ile Met Gly Gly Ala Val
305             310             315             320

Phe Glu Thr Leu Glu Gly Asn Thr Ile Glu Ile Gly Cys Asp Gly Asp
                325             330             335

Ser Ile Thr Val Asn Gly Ile Lys Met Val Asn Lys Lys Asp Ile Val
        340             345             350

Thr Asn Asn Gly Val Ile His Leu Ile Asp Gln Val Leu Ile Pro Asp
    355             360             365

Ser Ala Lys Gln Val Ile Glu Leu Ala Gly Lys Gln Gln Thr Thr Phe
    370             375             380

Thr Asp Leu Val Ala Gln Leu Gly Leu Ala Ser Ala Leu Arg Pro Asp
385             390             395             400

Gly Glu Tyr Thr Leu Leu Ala Pro Val Asn Asn Ala Phe Ser Asp Asp
            405             410             415

Thr Leu Ser Met Asp Gln Arg Leu Leu Lys Leu Ile Leu Gln Asn His
                420             425             430

Ile Leu Lys Val Lys Val Gly Leu Asn Glu Leu Tyr Asn Gly Gln Ile
        435             440             445

Leu Glu Thr Ile Gly Gly Lys Gln Leu Arg Val Phe Val Tyr Arg Thr
    450             455             460

Ala Val Cys Ile Glu Asn Ser Cys Met Glu Lys Gly Ser Lys Gln Gly
465             470             475             480

Arg Asn Gly Ala Ile His Ile Phe Arg Glu Ile Ile Lys Pro Ala Glu
            485             490             495

Lys Ser Leu His Glu Lys Leu Lys Gln Asp Lys Arg Phe Ser Thr Phe
                500             505             510

Leu Ser Leu Leu Glu Ala Ala Asp Leu Lys Glu Leu Leu Thr Gln Pro
        515             520             525

Gly Asp Trp Thr Leu Phe Val Pro Thr Asn Asp Ala Phe Lys Gly Met
    530             535             540

Thr Ser Glu Glu Lys Glu Ile Leu Ile Arg Asp Lys Asn Ala Leu Gln
545             550             555             560

Asn Ile Ile Leu Tyr His Leu Thr Pro Gly Val Phe Ile Gly Lys Gly
            565             570             575

Phe Glu Pro Gly Val Thr Asn Ile Leu Lys Thr Thr Gln Gly Ser Lys
                580             585             590

Ile Phe Leu Lys Glu Val Asn Asp Thr Leu Leu Val Asn Glu Leu Lys
        595             600             605

Ser Lys Glu Ser Asp Ile Met Thr Thr Asn Gly Val Ile His Val Val
    610             615             620

Asp Lys Leu Leu Tyr Pro Ala Asp Thr Pro Val Gly Asn Asp Gln Leu
625             630             635             640

Leu Glu Ile Leu Asn Lys Leu Ile Lys Tyr Ile Gln Ile Lys Phe Val
            645             650             655

Arg Gly Ser Thr Phe Lys Glu Ile Pro Val Thr Val Tyr Ser Pro Glu
                660             665             670

Ile Lys Tyr Thr Arg Ile Ser Thr Gly Gly Glu Thr Glu Glu Thr
        675             680             685

Leu Lys Lys Leu Leu Gln Glu
    690             695
```

```
<210> SEQ ID NO 24
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Ile Ala Trp Val Arg Gln Ala Pro Gly Lys Gly Leu Glu Trp Val
        35                  40                  45

Ala Phe Ile Ser Asp Leu Ala Tyr Thr Ile Tyr Ala Asp Thr Val
    50                  55                  60

Thr Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asn Trp Asp Ala Met Asp Tyr Trp Gly Gln Gly Thr Leu
            100                 105                 110

Val Thr Val Ser Ser
        115

<210> SEQ ID NO 25
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Asn
            20                  25                  30

Asn Ala Asn Thr Tyr Leu His Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Asn
                85                  90                  95

Thr Leu Val Pro Trp Thr Phe Gly Gln Gly Thr Lys Val Glu Ile Lys
            100                 105                 110
```